（12） United States Patent
Planken et al.

(10) Patent No.: US 10,590,115 B2
(45) Date of Patent: Mar. 17, 2020

(54) TETRAHYDROQUINAZOLINE DERIVATIVES USEFUL AS ANTICANCER AGENTS

(71) Applicant: PFIZER INC., New York, NY (US)

(72) Inventors: Simon Planken, San Marcos, CA (US); Hengmiao Cheng, San Diego, CA (US); Michael Raymond Collins, San Diego, CA (US); Jillian Elyse Spangler, San Diego, CA (US); Alexei Brooun, San Diego, CA (US); Andreas Maderna, Escondido, CA (US); Cynthia Palmer, La Mesa, CA (US); Maria Angelica Linton, San Diego, CA (US); Asako Nagata, San Diego, CA (US); Ping Chen, San Diego, CA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 16/265,012

(22) Filed: Feb. 1, 2019

(65) Prior Publication Data

US 2019/0248767 A1    Aug. 15, 2019

Related U.S. Application Data

(60) Provisional application No. 62/782,408, filed on Dec. 20, 2018, provisional application No. 62/651,796, filed on Apr. 3, 2018, provisional application No. 62/628,350, filed on Feb. 9, 2018.

(51) Int. Cl.
| | | |
|---|---|---|
| *C07D 403/14* | (2006.01) | |
| *C07D 487/10* | (2006.01) | |
| *A61P 35/00* | (2006.01) | |
| *C07D 403/04* | (2006.01) | |
| *C07D 239/94* | (2006.01) | |

(52) U.S. Cl.
CPC ............ *C07D 403/14* (2013.01); *A61P 35/00* (2018.01); *C07D 239/94* (2013.01); *C07D 403/04* (2013.01); *C07D 487/10* (2013.01)

(58) Field of Classification Search
CPC ...... C07D 403/14; C07D 487/10; A61P 35/00
See application file for complete search history.

(56) References Cited

U.S. PATENT DOCUMENTS

| | | | |
|---|---|---|---|
| 6,106,864 A | 8/2000 | Dolan et al. | |
| 2002/0025968 A1* | 2/2002 | Pamukcu | A61K 31/517 514/266.3 |

FOREIGN PATENT DOCUMENTS

| | | |
|---|---|---|
| WO | 91/11172 | 8/1991 |
| WO | 94/02518 | 2/1994 |
| WO | 98/55148 | 12/1998 |
| WO | 00/35298 | 6/2000 |
| WO | 20130326900 | *  2/2013 |
| WO | 15/089327 A1 | 6/2015 |
| WO | 2017/087528 A1 | 5/2017 |
| WO | 2017/201161 A1 | 11/2017 |

OTHER PUBLICATIONS

Kenzo SDhirakawa et al., Pyrimidine derivatives. XII.2-(1-Pyrazolyl)pyrimidines. 2, Takeda Res. Lab., Osaka, Japan. Takeda Kenkyusho Nenpo (1963), 22, 27-46.*
International Search Report and the Written Opinion of the International Searching Authority, PCT/IB2019/050993 dated May 8, 2019.
Feramisco, et al., "Transient reversion of ras oncogene-induced cell transformation by antibodies specific for amino acid 12 of ras protein", Nature, 314(18), 639-642 (1985).
Finnin, et al., "Transdermal Penetration Enhancers: Applications, Limitations, and Potential", Journal of Pharmaceutical Sciences, 88(10), 955-958 (1999).
Flaherty, et al., "Inhibition of Mutated, Activated BRAF in Metastatic Melanoma", The New England Journal of Medicine, 363(9), 809-819 (2010).
Haleblian, "Characterization of Habits and Crystalline Modification of Solids and Their Pharmaceutical Applications", Journal of Pharmaceutical Sciences, 64(8), 1269-1288 (1975).
Hunter, et al., "Biochemical and Structural Analysis of Common Cancer-Associated KRAS Mutations", Molecular Cancer Research, 13(9), 1325-1335 (2015).
Janne, et al., "Selumetinib Plus Docetaxel Compared With Docetaxel Alone and Progression-Free Survival in Patients with KRAS-Mutant Advanced Non-Small Cell Lung Cancer. The SELECT-1 Randomized Clinical Trial", JAMA, 317(18), 1844-1853 (2017).
McCormick, "KRAS as a Therapeutic Target", Clinical Cancer Research, 21(8), 1797-1802 (2015).

(Continued)

*Primary Examiner* — Alexander R Pagano
*Assistant Examiner* — Ebenezer O Sackey
(74) *Attorney, Agent, or Firm* — David Rubin

(57) ABSTRACT

Compounds of the general formula:

Formula (I)

processes for the preparation of these compounds, compositions containing these compounds, and the uses of these compounds.

14 Claims, No Drawings

(56) References Cited

OTHER PUBLICATIONS

Ostrem, et al., "K-Ras (G12C) inhibitors allosterically control GTP affinity and effector interactions", Nature, 503, 548-561 (2013).
Prior et al., "A Comprehensive Survey of Ras Mutations in Cancer", Cancer Research, 72(10), 2457-2467 (2012).
Rajalingam et al., "Ras oncogenes and their downstream targets", Biochimica Biophysica Acta, 1773, 1177-1195 (2007).
Turke et al., "MEK inhibition leads to PI3K/AKT activation by relieving a negative feedback on ERBB", Cancer Research, 72(13), 3228-3237 (2012).
Verma et al., "Drug Delivery Technologies and Future Directions", Pharmaceutical Technology On-Line, 25(2), 1-14 (2001).

\* cited by examiner

TETRAHYDROQUINAZOLINE DERIVATIVES USEFUL AS ANTICANCER AGENTS

FIELD OF THE INVENTION

This invention relates to novel tetrahydroquinazoline derivatives useful as inhibitors of the KRAS protein. This invention also relates to a method of using such compounds in the treatment of abnormal cell growth in mammals, especially humans, and to pharmaceutical compositions as anticancer agents.

BACKGROUND OF THE INVENTION

Kirsten Rat Sarcoma Oncogene Homolog (KRAS) is a small GTPase that integrates signals from outside the cell to proliferation and survival signals within the cell. This occurs through growth factor-mediated activation of Guanine Exchange Factors (GEFs), which remove GDP from Ras and allow the entry of GTP, which resides in high concentrations in the cytoplasm. Upon binding of the GTP nucleotide, two disordered switch regions (switch I and switch II) interact with the gamma phosphate of the nucleotide allowing Ras to interact with effector enzymes via a Ras Binding Domain (RBD), which start signalling cascades that alter gene expression. Binding of a GTPase activating protein (GAP) accelerates the intrinsic conversion of GTP to GDP and renders the protein in an inactive state thus terminating the signal (Rajalingam, K., R. Schreck, U. R. Rapp and S. Albert (2007). "Ras oncogenes and their downstream targets." Biochim Biophys Acta 1773(8): 1177-1195.)

Ras is mutated in up to 20% of human tumors at the codon 12, 13, and 61 positions, which serve to promote the GTP bound form of the protein. These include colon, pancreas and lung tumors, the latter of which show KRAS mutation in up to 25-30% of all tumors with 40% of these harboring a G12C mutation thought to be promoted by carcinogens in cigarette smoke. KRAS with G12C mutations activate the Mapk pathway and promote Non-Small Cell Lung Cancer (NSCLC) growth and survival. (Prior, I. A., P. D. Lewis and C. Mattos (2012). "A comprehensive survey of Ras mutations in cancer." Cancer Res 72(10): 2457-2467.)

Since the discovery of KRAS mutations in human tumors and that inhibiting signalling by these proteins caused inhibition of the cancer phenotype there has been a strong desire by both academic groups and industry to find Ras inhibitors (Feramisco, J. R., R. Clark, G. Wong, N. Arnheim, R. Milley and F. McCormick (1985). "Transient reversion of ras oncogene-induced cell transformation by antibodies specific for amino acid 12 of ras protein." Nature 314(6012): 639-642.) and (McCormick, F. (2015). "KRAS as a Therapeutic Target." Clin Cancer Res 21(8): 1797-1801. Specific Inhibitors of the KRAS effector BRaf alone and combined with other inhibitors the Mapk pathway have shown dramatic responses in melanoma where this BRaf is frequently activated via mutation (Flaherty, K. T., I. Puzanov, K. B. Kim, A. Ribas, G. A. McArthur, J. A. Sosman, P. J. O'Dwyer, R. J. Lee, J. F. Grippo, K. Nolop and P. B. Chapman (2010). "Inhibition of mutated, activated BRAF in metastatic melanoma." N Engl J Med 363(9): 809-819.) In contrast, general Mapk inhibitors have not shown dramatic responses in cancers with mutant KRAS potentially because of the lack of an appropriate therapeutic index over normal tissues or compensatory signalling by other Ras pathways (Turk Turke, A. B., Y. Song, C. Costa, R. Cook, C. L. Arteaga, J. M. Asara and J. A. Engelman (2012). "MEK inhibition leads to PI3K/AKT activation by relieving a negative feedback on ERBB receptors." Cancer Res 72(13): 3228-3237.e, Song et al. 2012) and (Janne, P. A., M. M. van den Heuvel, F. Barlesi, M. Cobo, J. Mazieres, L. Crino, S. Orlov, F. Blackhall, J. Wolf, P. Garrido, A. Poltoratskiy, G. Mariani, D. Ghiorghiu, E. Kilgour, P. Smith, A. Kohlmann, D. J. Carlile, D. Lawrence, K. Bowen and J. Vansteenkiste (2017). "Selumetinib Plus Docetaxel Compared With Docetaxel Alone and Progression-Free Survival in Patients With KRAS-Mutant Advanced Non-Small Cell Lung Cancer: The SELECT-1 Randomized Clinical Trial." Jama 317(18): 1844-1853.)

Compounds that selectively bind mutant KRas are highly desirable as they would spare impact on normal tissues and for adequate inhibition of Ras signalling within the tumor to elicit antitumor activity. Recently KRAS G12C has been shown to retain cycling both biochemically and in cancer cells, creating an opportunity to disrupt activation (Hunter, J. C., A. Manandhar, M. A. Carrasco, D. Gurbani, S. Gondi and K. D. Westover (2015). "Biochemical and Structural Analysis of Common Cancer-Associated KRAS Mutations." Mol Cancer Res 13(9): 1325-1335.) Compounds that utilize the cysteine substitution in G12C for binding and prevent the GDP to GTP exchange were described (Ostrem, J. M., U. Peters, M. L. Sos, J. A. Wells and K. M. Shokat (2013). "K-Ras(G12C) inhibitors allosterically control GTP affinity and effector interactions." Nature 503(7477): 548-551.) This makes utilizing G12C binding compounds that lock KRAS in the inactive state an attractive opportunity for cancer treatment.

SUMMARY OF THE INVENTION

Given its role in regulating various biological processes, KRAS is an attractive target for modulation with small molecule inhibitors. To date, few effective KRAS inhibitors have been developed, and few, if any KRAS inhibitors have entered the clinic.

Each of the embodiments of the compounds of the present invention described below can be combined with any other embodiment of the compounds of the present invention described herein not inconsistent with the embodiment with which it is combined. Furthermore, each of the embodiments below describing the invention envisions within its scope pharmaceutically acceptable salts of the compounds of the invention. Accordingly, the phrase "or a pharmaceutically acceptable salt thereof" is implicit in the description of all compounds described herein.

The invention includes embodiments wherein there is provided a compound of Formula (I):

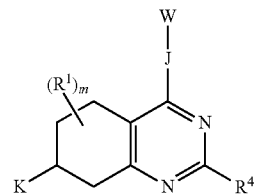

Formula (I)

or a pharmaceutically acceptable salt thereof; wherein:
J is a heterocycle having 3-12 ring atoms, where J is optionally substituted with 1, 2, 3, 4, 5 or 6 $R^2$;
K is $C_6$-$C_{12}$ aryl, or K is heteroaryl having 5-12 ring atoms, where K is optionally substituted with 1, 2, 3, 4, 5, 6 or 7 $R^3$;

W is selected from the group consisting of:

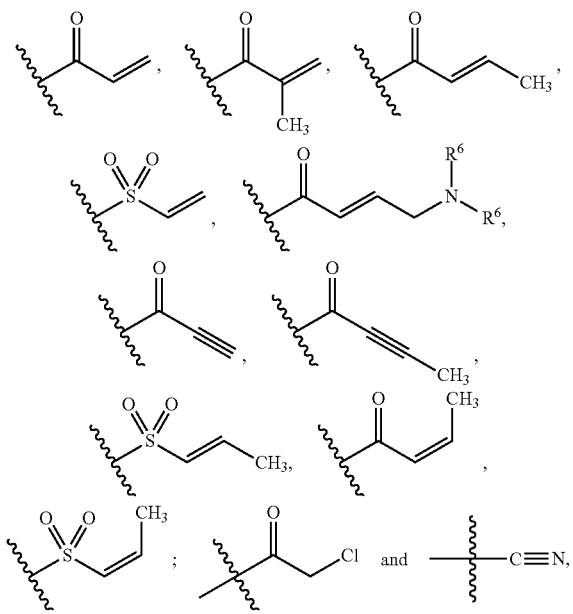

where W is optionally substituted with 1, 2 or 3 $R^5$;

each $R^1$ is independently selected from the group consisting of $C_1$-$C_6$ alkyl, $C_3$-$C_6$ cycloalkyl, $C_1$-$C_6$ alkyl-hydroxy, $C_1$-$C_6$ alkoxy, $C_1$-$C_6$ alkyl-$C_1$-$C_6$alkoxy, hydroxy, $C_2$-$C_6$ alkenyl, $C_2$-$C_6$ alkynyl, halogen, $C_1$-$C_6$ haloalkyl, cyano and —N($R^6$)$_2$, or two $R^1$ optionally join to form a heterocycle having 3-12 ring atoms or a $C_3$-$C_6$ cycloalkyl;

each $R^2$ is independently selected from the group consisting of $C_1$-$C_6$ alkyl, $C_3$-$C_6$ cycloalkyl, hydroxy, $C_1$-$C_6$ alkyl-hydroxy, $C_1$-$C_6$ alkoxy, halogen, $C_1$-$C_6$ haloalkyl, cyano, $C_1$-$C_6$ alkyl-cyano and oxo, or two $R^2$ optionally join to form a heterocycle having 3-12 ring atoms or a $C_3$-$C_6$ cycloalkyl;

each $R^3$ is independently selected from the group consisting of $C_1$-$C_6$ alkyl, $C_3$-$C_6$ cycloalkyl, hydroxy, $C_1$-$C_6$ alkoxy, $C_1$-$C_6$ alkyl-hydroxy, halogen, $C_1$-$C_6$ halo-alkyl, N($R^6$)$_2$, oxo and cyano, or two $R^3$ optionally join to form a heterocycle having 3-12 ring atoms or $C_3$-$C_6$ cycloalkyl;

$R^4$ is —X—Y—Z where:

X is absent or is selected from the group consisting of oxygen, sulfur and —$NR^6$—, Y is absent or $C_1$-$C_6$ alkylenlyl, and Z is selected from H, —N($R^6$)$_2$, —C(O)—N($R^6$)$_2$, —$OR^6$, heterocycle having 3-12 ring atoms, heteroaryl having 5-12 ring atoms, and $C_3$-$C_6$ cycloalkyl, where $R^4$ is optionally substituted with one or more $R^7$;

each $R^5$ is independently selected from the group consisting of: $C_1$-$C_6$ alkyl, hydroxy, $C_1$-$C_6$ alkoxy, halogen and —N($R^6$)$_2$;

each $R^6$ is independently selected from the group consisting of hydrogen, hydroxyl, $C_1$-$C_6$ alkoxy and $C_1$-$C_6$ alkyl, or two $R^6$ optionally join to form heterocycle having 3-12 ring atoms or $C_3$-$C_6$ cycloalkyl;

each $R^7$ is independently $R^{7'}$ or $C_1$-$C_6$ alkyl-$R^{7'}$, where each $R^{7'}$ is independently selected from the group consisting of: $C_1$-$C_6$ alkyl, hydroxy, $C_1$-$C_6$ alkoxy, halogen, —N($R^6$)$_2$, heterocycle having 3-12 ring atoms and oxo; and m is 0, 1, 2, 3, 4, 5, 6 or 7.

The invention includes further embodiments wherein there is provided a compound of Formula (I):

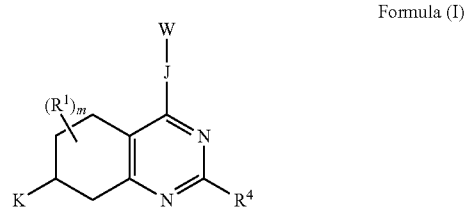

Formula (I)

or a pharmaceutically acceptable salt thereof; wherein:

J is selected from the group consisting of:

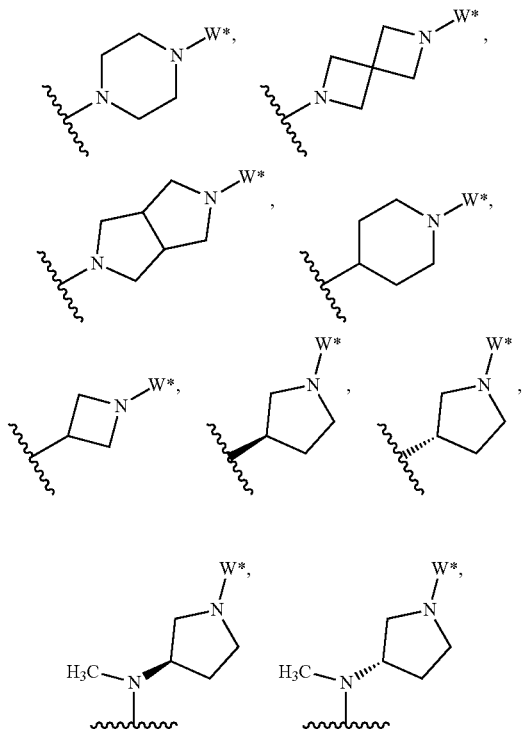

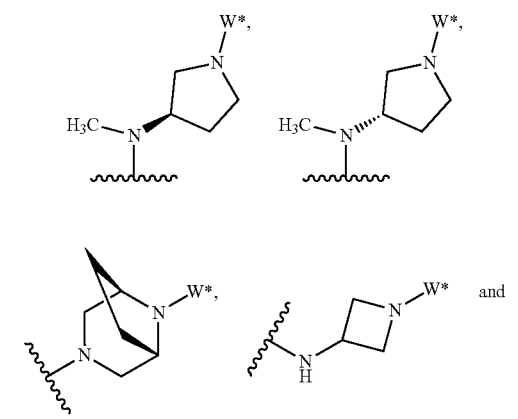

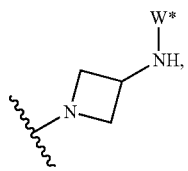

where W* represents the point of attachment to W, and where J is optionally substituted with 1, 2, 3, 4, 5 or 6 $R^2$;

K is selected from the group consisting of:

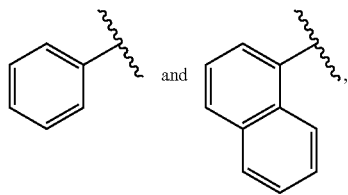 [SMILES: *c1ccccc1 ; *c1cccc2ccccc12]

and or

K is selected from the group consisting of:

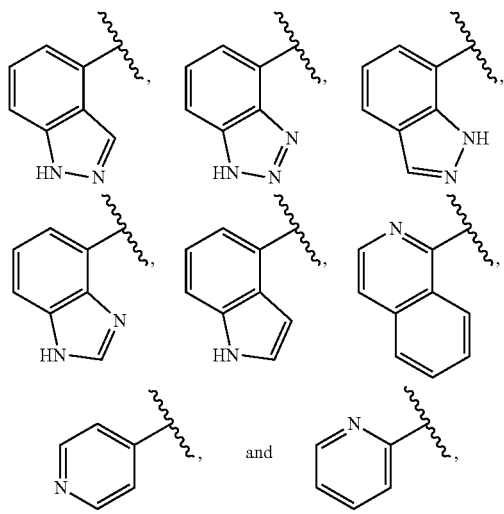

where K is optionally substituted with 1, 2, 3, 4, 5, 6 or 7 $R^3$;

W is selected from the group consisting of:

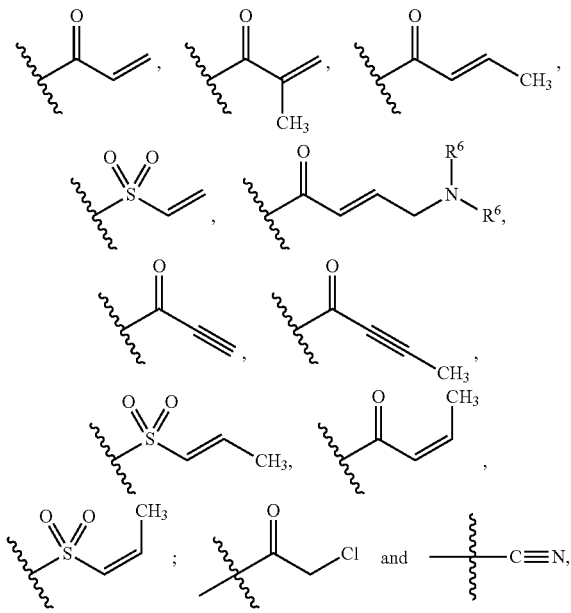

where W is optionally substituted with 1, 2 or 3 $R^5$;

each $R^1$ is independently selected from the group consisting of $C_1$-$C_6$ alkyl, $C_3$-$C_6$ cycloalkyl, $C_1$-$C_6$ alkyl-hydroxy, $C_1$-$C_6$ alkoxy, $C_1$-$C_6$ alkyl-$C_1$-$C_6$alkoxy, hydroxy, $C_2$-$C_6$ alkenyl, $C_2$-$C_6$ alkynyl, halogen, $C_1$-$C_6$ haloalkyl, cyano and —N($R^6$)$_2$, or two $R^1$ optionally join to form a heterocycle having 3-12 ring atoms or a $C_3$-$C_6$ cycloalkyl;

each $R^2$ is independently selected from the group consisting of $C_1$-$C_6$ alkyl, $C_3$-$C_6$ cycloalkyl, hydroxy, $C_1$-$C_6$ alkyl-hydroxy, $C_1$-$C_6$ alkoxy, halogen, $C_1$-$C_6$ haloalkyl, cyano, $C_1$-$C_6$ alkyl-cyano and oxo, or two $R^2$ optionally join to form a heterocycle having 3-12 ring atoms or a $C_3$-$C_6$ cycloalkyl;

each $R^3$ is independently selected from the group consisting of $C_1$-$C_6$ alkyl, $C_3$-$C_6$ cycloalkyl, hydroxy, $C_1$-$C_6$ alkoxy, $C_1$-$C_6$ alkyl-hydroxy, halogen, $C_1$-$C_6$ halo-alkyl, N($R^6$)$_2$, oxo and cyano, or two $R^3$ optionally join to form a heterocycle having 3-12 ring atoms or $C_3$-$C_6$ cycloalkyl;

$R^4$ is —X—Y—Z where:

X is absent or is selected from the group consisting of oxygen, sulfur and —N$R^6$—, Y is absent or $C_1$-$C_6$ alkylenlyl, and Z is selected from H, —N($R^6$)$_2$, —C(O)—N($R^6$)$_2$, —O$R^6$, heterocycle having 3-12 ring atoms, heteroaryl having 5-12 ring atoms, and $C_3$-$C_6$ cycloalkyl, where $R^4$ is optionally substituted with one or more $R^7$;

each $R^5$ is independently selected from the group consisting of: $C_1$-$C_6$ alkyl, hydroxy, $C_1$-$C_6$ alkoxy, halogen and —N($R^6$)$_2$;

each $R^6$ is independently selected from the group consisting of hydrogen, hydroxyl, $C_1$-$C_6$ alkoxy and $C_1$-$C_6$ alkyl, or two $R^6$ optionally join to form heterocycle having 3-12 ring atoms or $C_3$-$C_6$ cycloalkyl;

each $R^7$ is independently $R^{7'}$ or $C_1$-$C_6$ alkyl-$R^{7'}$, where each $R^{7'}$ is independently selected from the group consisting of: $C_1$-$C_6$ alkyl, hydroxy, $C_1$-$C_6$ alkoxy, halogen, —N($R^6$)$_2$, heterocycle having 3-12 ring atoms and oxo; and m is 0, 1, 2, 3, 4, 5, 6 or 7.

The invention includes still further embodiments wherein there is provided a compound of Formula (I):

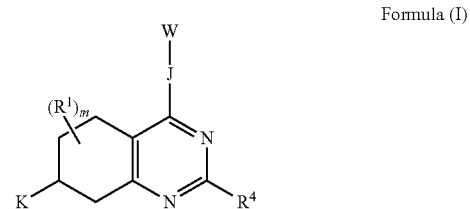

Formula (I)

or a pharmaceutically acceptable salt thereof; wherein:

J is selected from the group consisting of:

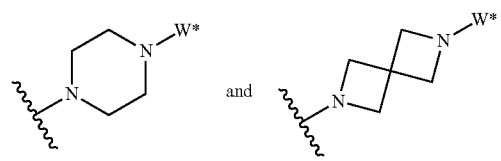

and where W* represents the point of attachment to W, and where J is optionally substituted with $R^2$;

K is selected from the group consisting of:

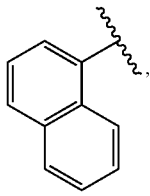 [SMILES: *c1cccc2ccccc12]

or

K is selected from the group consisting of:

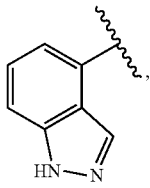

where K is optionally substituted with 1 or 2 $R^3$;
W is selected from the group consisting of:

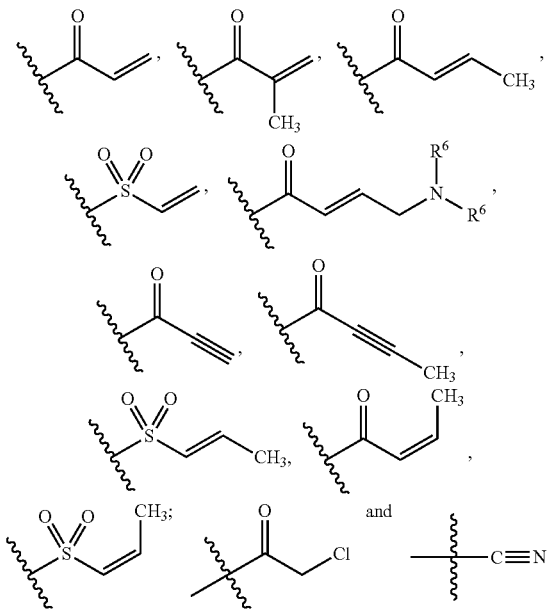

where W is optionally substituted with 1, 2 or 3 $R^5$;
$R^1$ is independently selected from the group consisting of $C_1$-$C_6$ alkyl and $C_1$-$C_6$ alkyl-$C_1$-$C_6$alkoxy;
$R^2$ is $C_1$-$C_6$ alkyl;
each $R^3$ is independently selected from the group consisting of $C_1$-$C_6$ alkyl, hydroxy, halogen, $C_1$-$C_6$ halo-alkyl and $C_1$-$C_6$ alkyl-hydroxy;
$R^4$ is —X—Y—Z where:
X is absent or is oxygen,
Y is absent or $C_1$-$C_6$ alkylenlyl, and
Z is selected from H, —N($R^6$)$_2$, —O$R^6$ and heterocycle having 3-12 ring atoms,
where $R^4$ is optionally substituted with one or more $R^7$;

each $R^5$ is independently selected from the group consisting of: $C_1$-$C_6$ alkyl, hydroxy, $C_1$-$C_6$ alkoxy, halogen and —N($R^6$)$_2$;
each $R^6$ is independently selected from the group consisting of hydrogen and $C_1$-$C_6$ alkyl;
each $R^7$ is independently $R^{7'}$ or $C_1$-$C_6$ alkyl-$R^{7'}$, where each $R^{7'}$ is independently selected from the group consisting of: $C_1$-$C_6$ alkyl and —N($R^6$)$_2$;
m is 0 or 1.

Also included are embodiments of the invention wherein K is selected from the group consisting of:

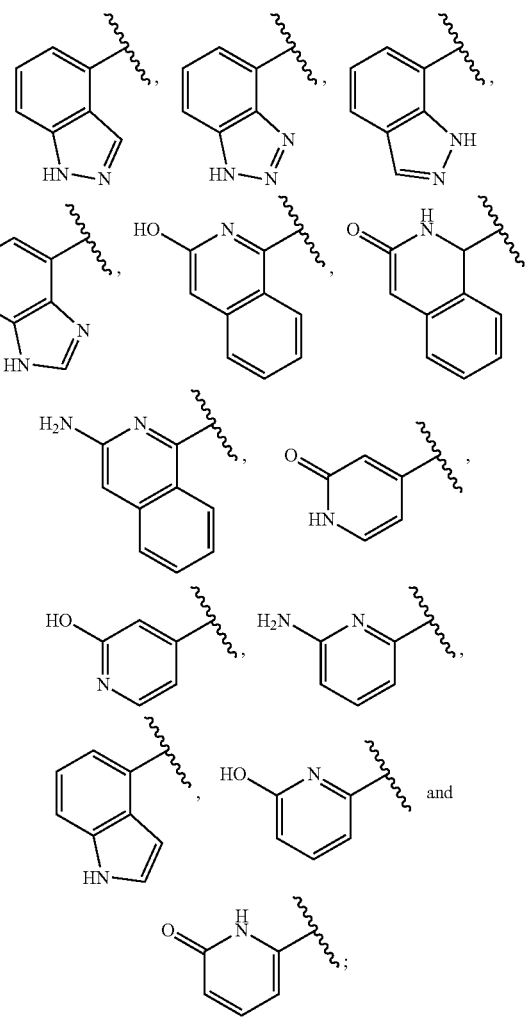

including those embodiments wherein K is selected from the group consisting of:

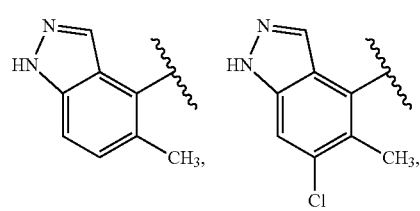

-continued

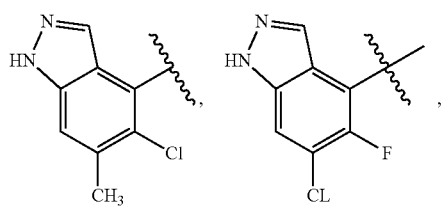

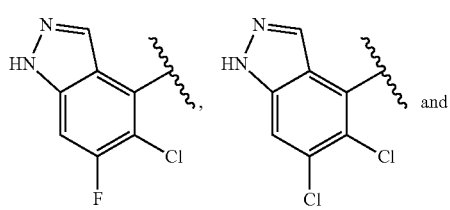

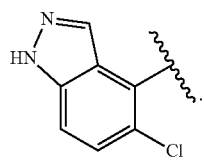

Also included are embodiments of the invention wherein K is selected from the group consisting of:

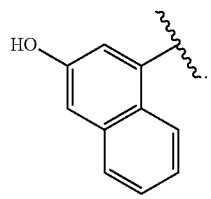 [SMILES: *c1cc(O)cc2ccccc12]

Also included are embodiments of the invention wherein W is:

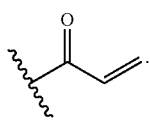 [SMILES: *C(=O)C=C]

Also included are embodiments of the invention wherein J is:

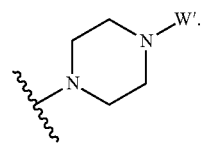

including embodiments wherein J is selected from the group consisting of:

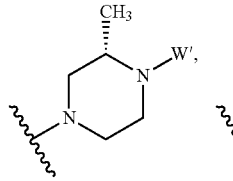 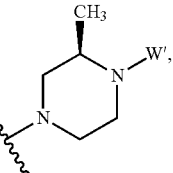

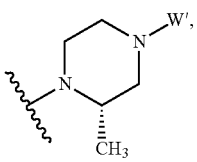 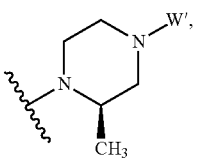

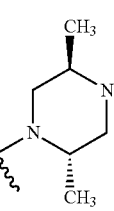 and 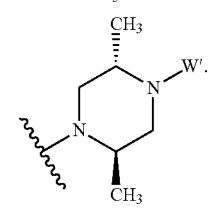

Additionally, the invention includes embodiments wherein $R^4$ is selected from the group consisting of:

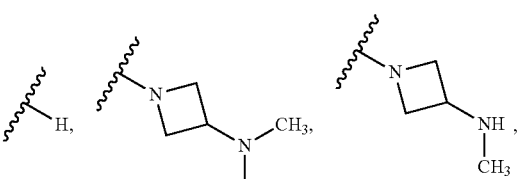

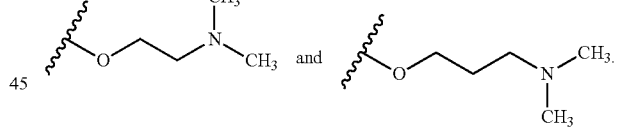

Moreover, embodiments of the invention include compounds selected from the group consisting of:

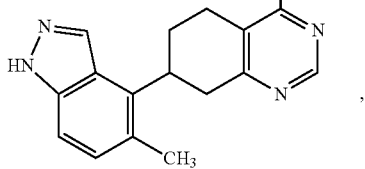

-continued
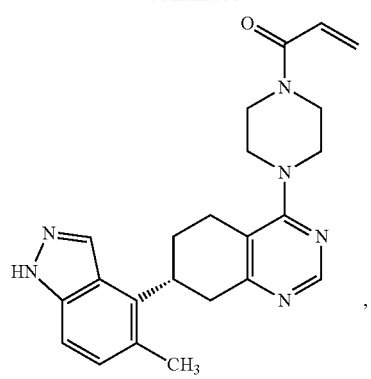
,
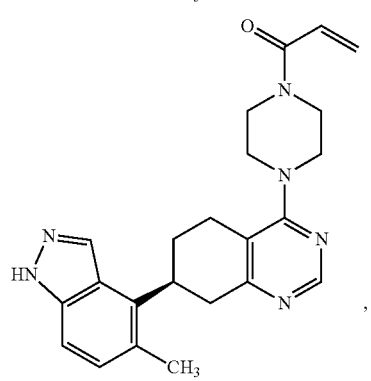
,
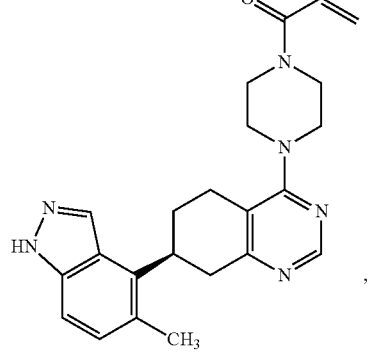
,
-continued
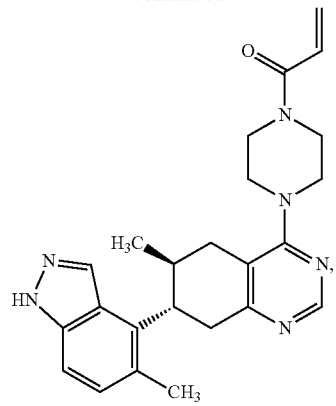
,

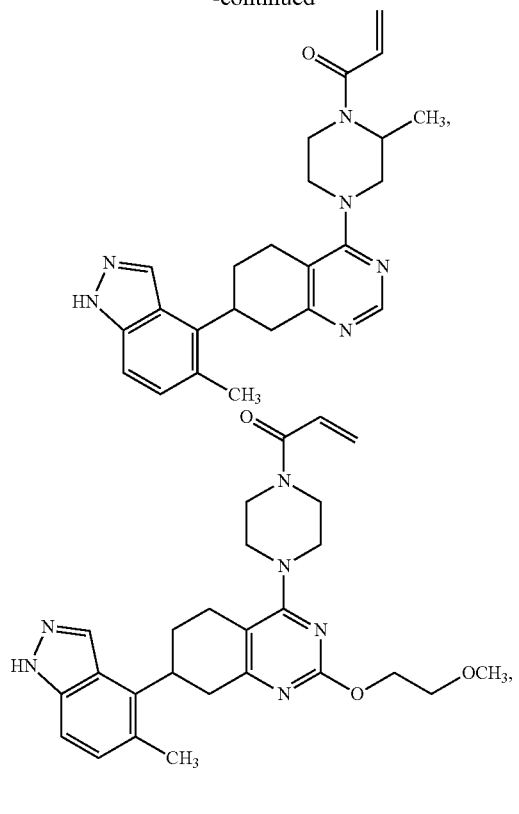
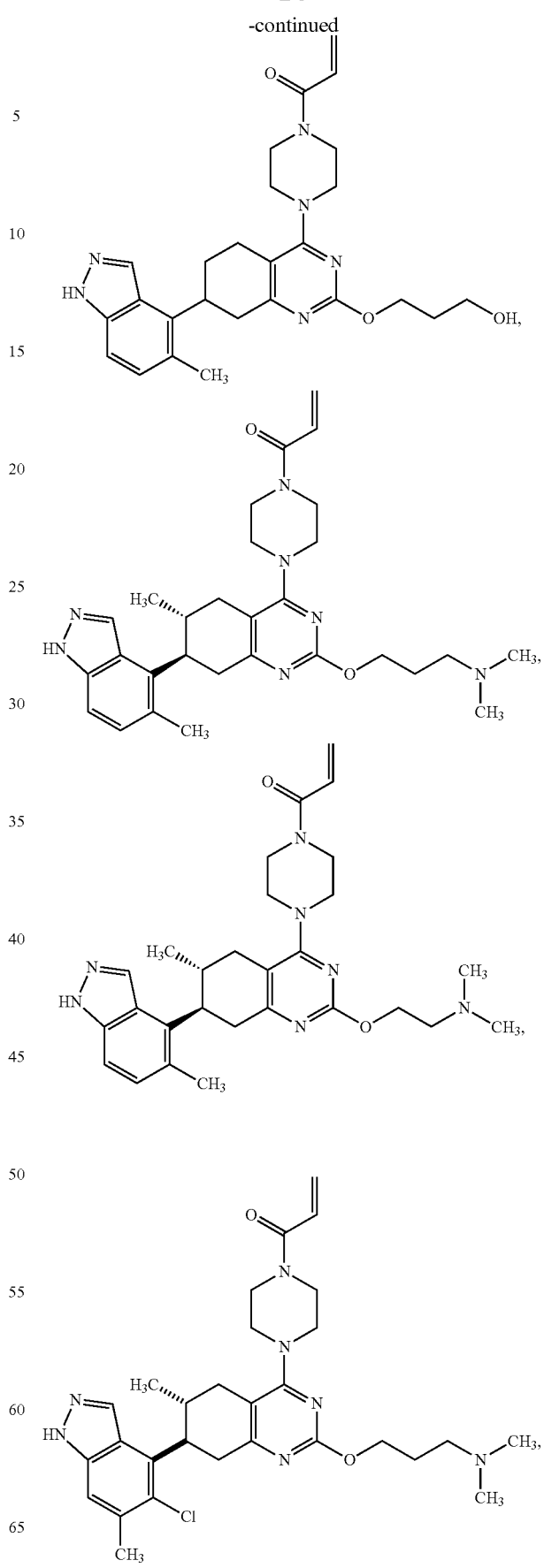

15
-continued

16
-continued

17
-continued
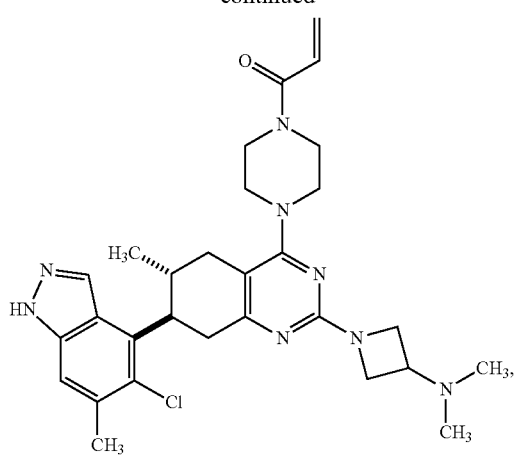
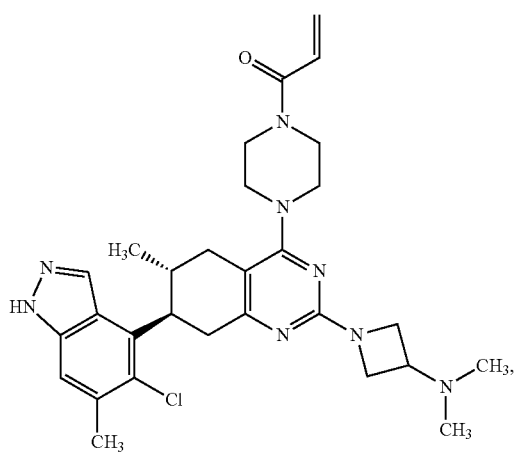
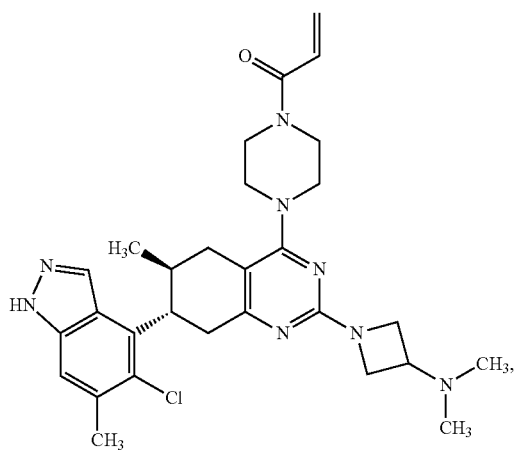
18
-continued
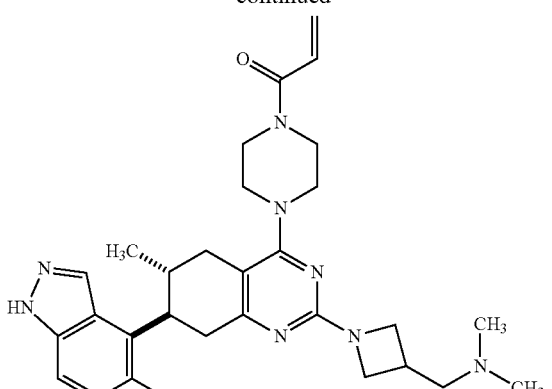
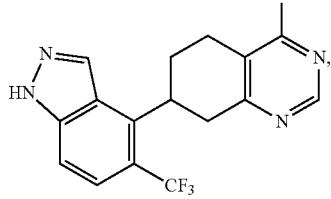
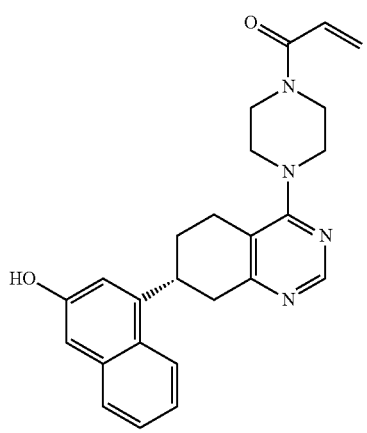
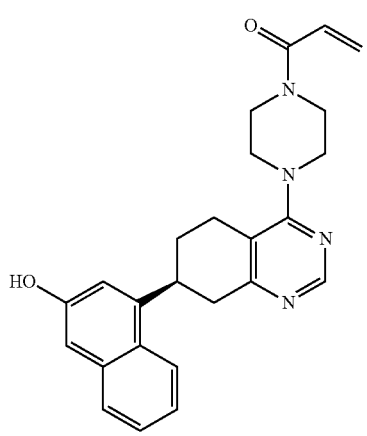

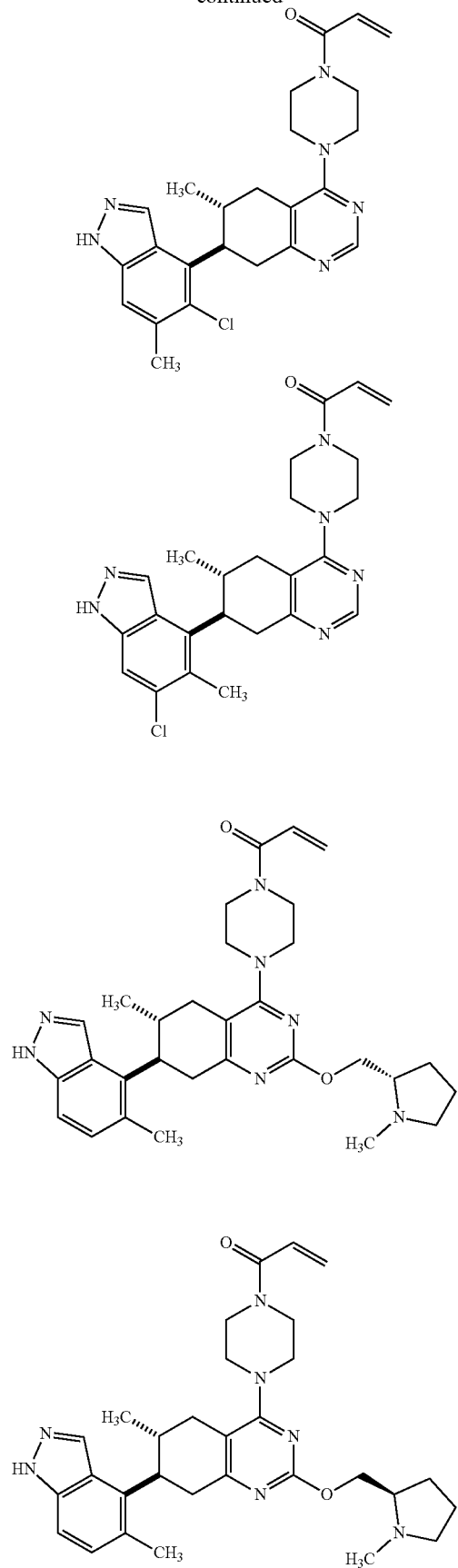

21
-continued
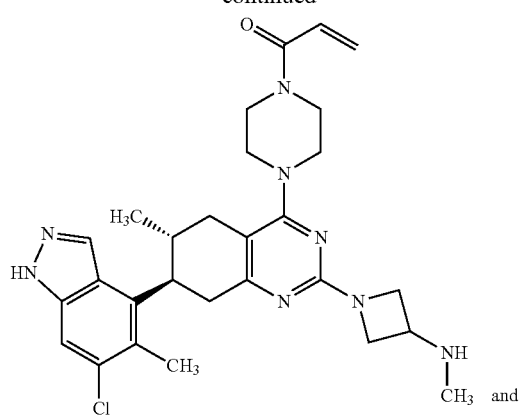
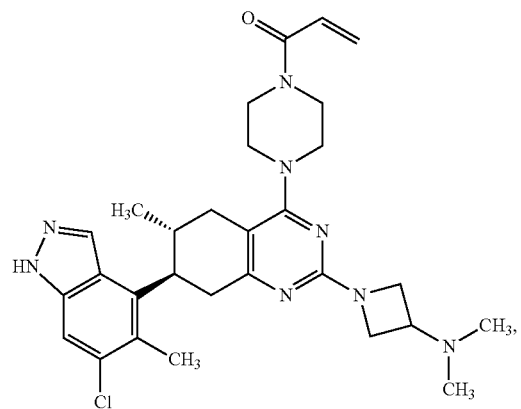
or a pharmaceutically acceptable salt thereof.
Embodiments of the invention preferably include compounds selected from the group consisting of:
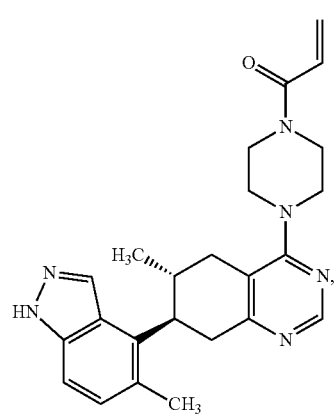
22
-continued
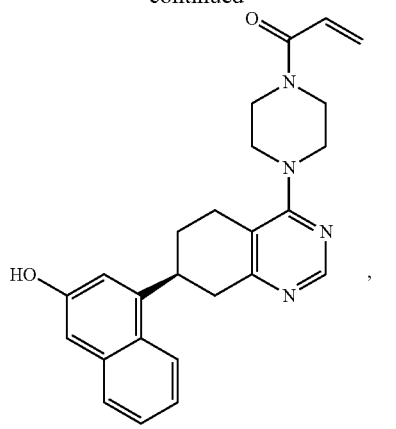
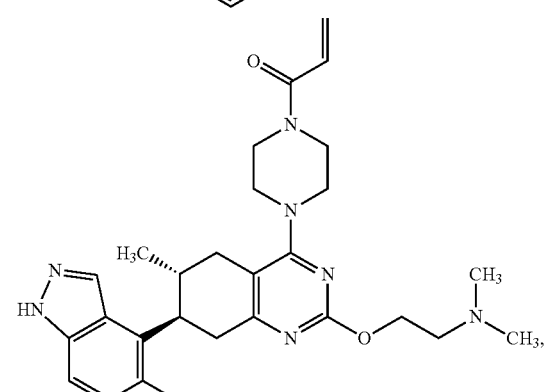
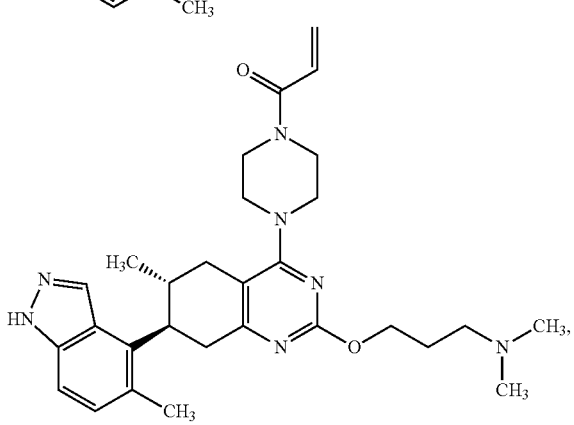
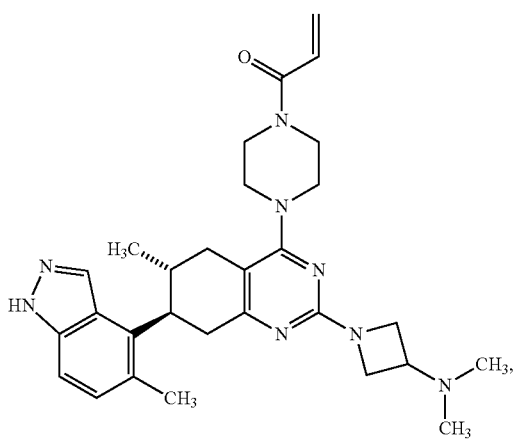

23
-continued
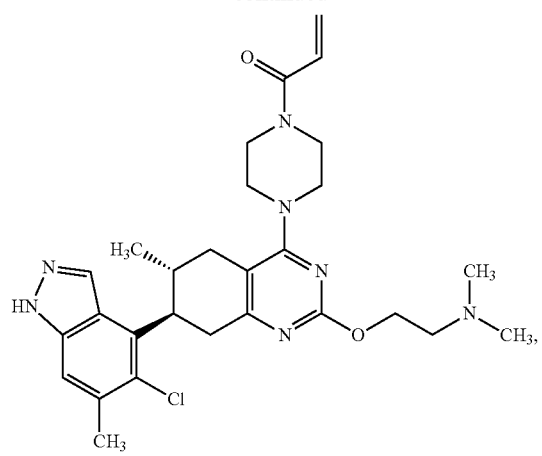
24
-continued
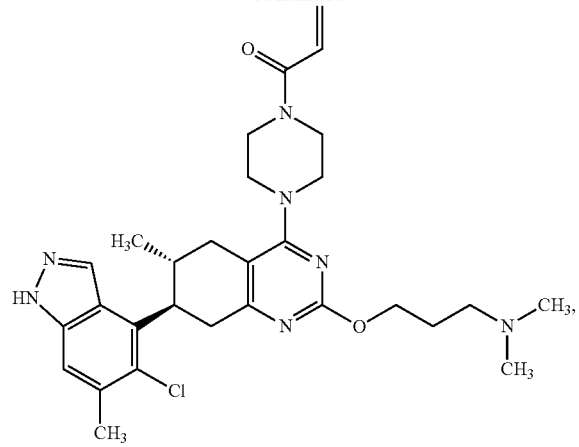
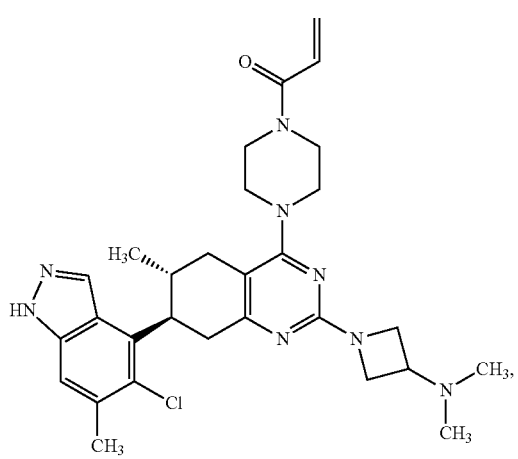
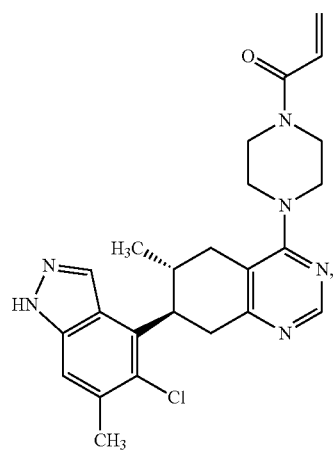
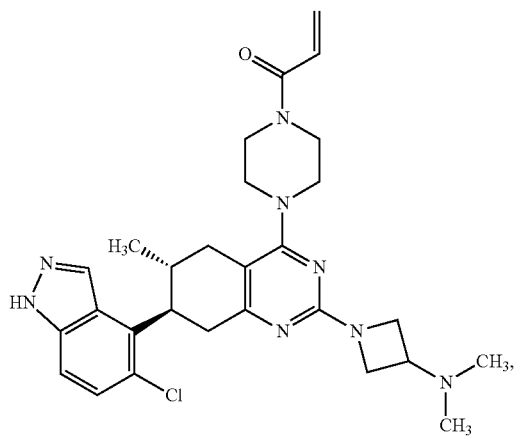
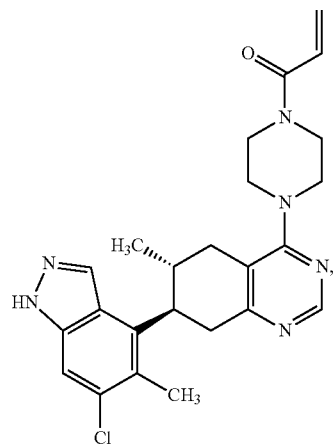

-continued
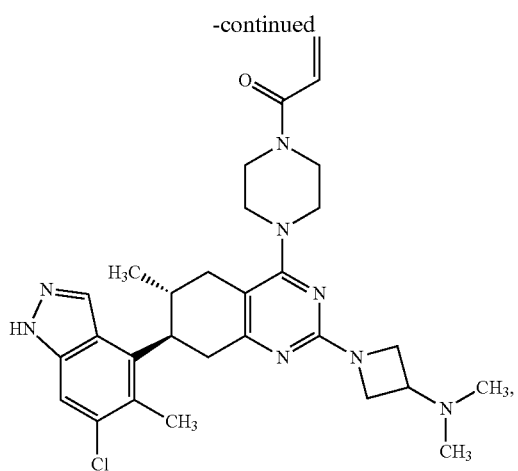
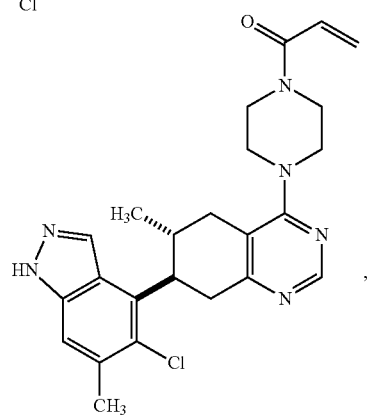
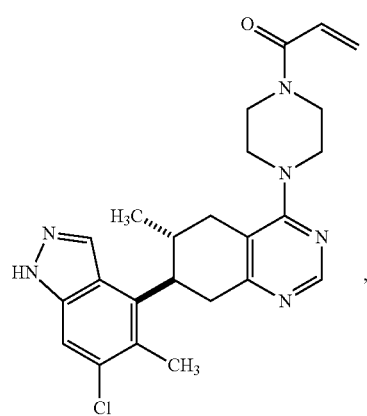
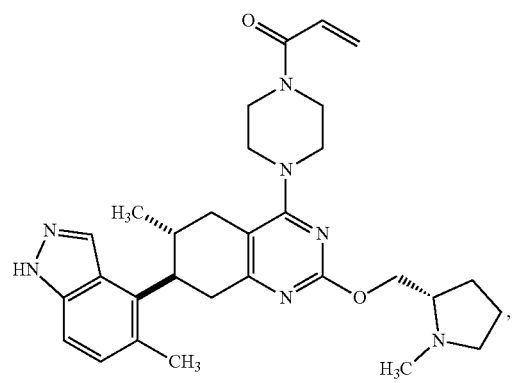
-continued
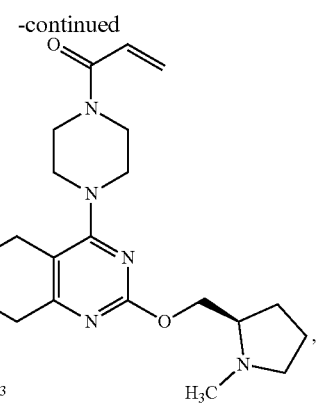
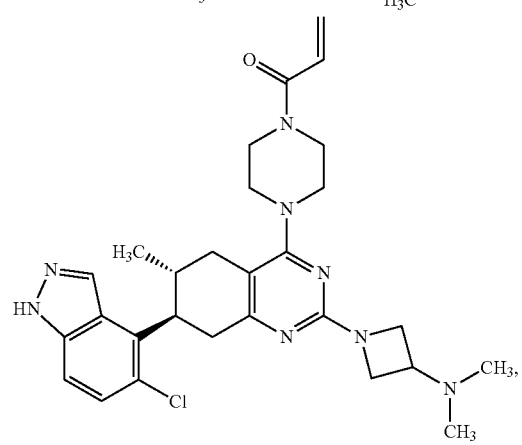
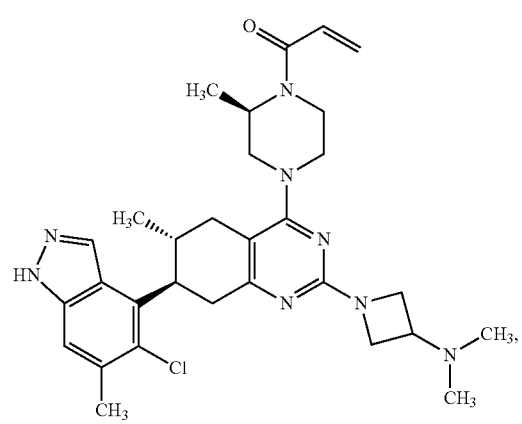
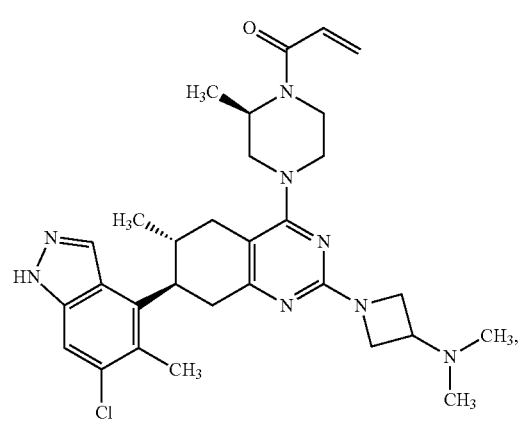

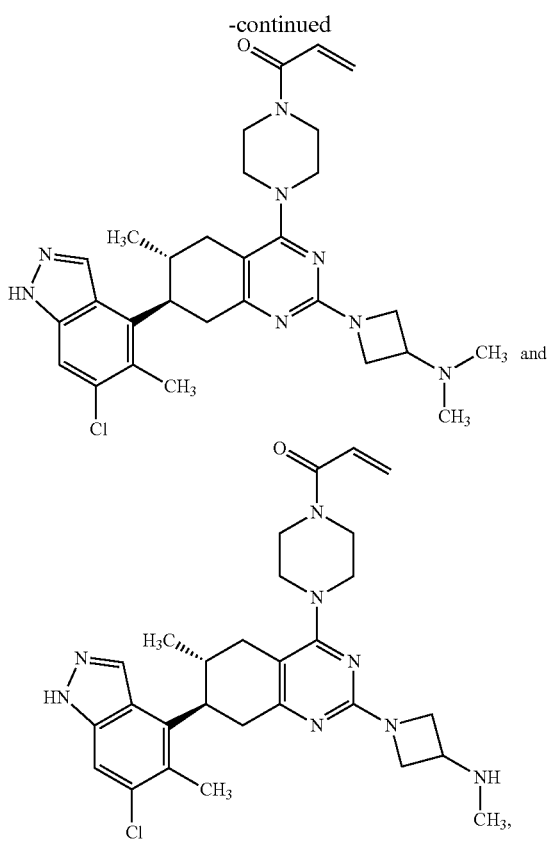

or a pharmaceutically acceptable salt thereof.

Additional embodiments of the invention include pharmaceutical composition comprising a therapeutically effective amount of a compound described herein or a pharmaceutically acceptable salt thereof, and a pharmaceutically acceptable excipient.

Additional embodiments of the invention also include methods for inhibiting KRAS activity in a cell by contacting the cell in which inhibition of KRAS activity is desired with a therapeutically effective amount of a compound described herein, or a pharmaceutically acceptable salt thereof, or a pharmaceutical composition containing said compound or pharmaceutically acceptable salt thereof.

Additional embodiments of the invention also include methods for treating cancer comprising administering to a patient having cancer a therapeutically effective amount of a compound or pharmaceutically acceptable salt thereof as described herein, alone, alone or in combination with one or more pharmaceutically acceptable carrier, excipient or diluent.

Embodiments further include such methods wherein the therapeutically effective amount of the administered compound or pharmaceutically acceptable salt thereof is between about 0.01 to 300 mg/kg per day; or is between about 0.1 to 100 mg/kg per day.

Additional embodiments of the invention also include methods for treating abnormal cell growth in a mammal comprising administering to the mammal a therapeutically effective amount of a compound as described herein or a pharmaceutically acceptable salt thereof. In certain such embodiments, the abnormal cell growth is cancer, and in certain of those embodiments the cancer is lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, or pituitary adenoma. Such cancers may be KRAS associated cancers. Of particular interest are cancers such as lung cancer, colon cancer, pancreatic cancer, and ovarian cancer.

In a further embodiment there is provided a method of treating cancer with the compounds described herein, wherein the cancer is lung cancer, colon cancer, pancreatic cancer, and ovarian cancer.

In a further embodiment there is provided a method of treating cancer with the compounds described herein, wherein the cancer is lung cancer.

In a further embodiment there is provided a method of treating cancer with the compounds described herein, wherein the cancer is pancreatic cancer.

Embodiments of the invention also include the use a compound described herein, or use of a pharmaceutically acceptable salt thereof, for the preparation of a medicament useful in the treatment of abnormal cell growth in a mammal. In certain such embodiments, the abnormal cell growth is cancer, and in certain of those embodiments the cancer is lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, or pituitary adenoma. Such cancers may be KRAS associated cancers.

Also related to cancer treatment, embodiments of the invention include methods for treating cancer in a patient in need thereof comprising: (a) determining that the cancer is associated with a KRAS mutation; and (b) administering to the patient a therapeutically effective amount of a compound or pharmaceutically acceptable salt as described herein, or a pharmaceutical composition thereof. In some embodiments the KRAS mutation is or incorporates a G12C mutation. In some embodiments the KRAS mutation is or incorporates a Ras mutation at codons 12, 13 and/or 61.

Definitions

Unless otherwise stated, the following terms used in the specification and claims have the meanings discussed below. Variables defined in this section, such as R, X, n and the like, are for reference within this section only, and are not meant to have the same meaning as may be used outside of this definitions section. Further, many of the groups defined herein can be optionally substituted. The listing in this definitions section of typical substituents is exemplary and is not intended to limit the substituents defined elsewhere within this specification and claims.

"Alkenyl" refers to an alkyl group, as defined herein, consisting of at least two carbon atoms and at least one carbon-carbon double bond. Representative examples include, but are not limited to, ethenyl, 1-propenyl, 2-propenyl, 1-, 2-, or 3-butenyl, and the like. "Alkenylene" refers to a di-valent form of alkenyl.

"Alkoxy" refers to —O-alkyl where alkyl is preferably $C_1$-$C_8$, $C_1$-$C_7$, $C_1$-$C_6$, $C_1$-$C_5$, $C_1$-$C_4$, $C_1$-$C_3$, $C_1$-$C_2$ or $C_1$ alkyl.

"Alkyl" refers to a saturated aliphatic hydrocarbon radical including straight chain and branched chain groups of 1 to 20 carbon atoms ("($C_1$-$C_{20}$)alkyl"), preferably 1 to 12 carbon atoms ("($C_1$-$C_{12}$)alkyl"), more preferably 1 to 8 carbon atoms ("($C_1$-$C_8$)alkyl"), or 1 to 6 carbon atoms ("($C_1$-$C_6$) alkyl"), or 1 to 4 carbon atoms ("($C_1$-$C_4$)alkyl"). Examples of alkyl groups include methyl, ethyl, propyl, 2-propyl, n-butyl, iso-butyl, tert-butyl, pentyl, neopentyl, and the like. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halogen, carbonyl, thiocarbonyl, O-carbamyl, N-carbamyl, O-thiocarbamyl, N-thiocarbamyl, C-amido, N-amido, C-carboxy, O-carboxy, nitro, silyl, amino and —$NR^xR^y$, where $R^x$ and $R^y$ are for example hydrogen, alkyl, cycloalkyl, aryl, carbonyl, acetyl, sulfonyl, trifluoromethanesulfonyl and, combined, a five- or six-member heteroalicyclic ring. "Haloalkyl" for instance ($C_1$-$C_6$)haloalkyl, refers to an alkyl having one to six carbons and one or more halogen substituents, for instance —$CF_3$ and —$CHF_2$. "Alkylene" refers to a di-valent form of alkyl.

"Alkynyl" refers to an alkyl group, as defined herein, consisting of at least two carbon atoms and at least one carbon-carbon triple bond. Representative examples include, but are not limited to, ethynyl, 1-propynyl, 2-propynyl, 1-, 2-, or 3-butynyl, and the like. "Alkynylene" refers to a di-valent form of alkynyl.

"Amino" refers to an —$NR^xR^y$ group, wherein $R^x$ and $R^y$ are both hydrogen.

"($C_6$-$C_{12}$)aryl" refers to an all-carbon monocyclic or fused-ring polycyclic groups of 6 to 12 carbon atoms having a completely conjugated pi-electron system. Similarly, "($C_5$-$C_{12}$)aryl" refers to an all-carbon monocyclic or fused-ring polycyclic groups of 5 to 12 carbon atoms having a completely conjugated pi-electron system. Examples, without limitation, of aryl groups are phenyl, naphthalenyl and anthracenyl. The aryl group may be substituted or unsubstituted. Typical substituents include halo, trihalomethyl, alkyl, hydroxy, alkoxy, aryloxy, mercapto, alkylthio, arylthio, cyano, nitro, carbonyl, thiocarbonyl, C-carboxy, O-carboxy, O-carbamyl, N-carbamyl, O-thiocarbamyl, N-thiocarbamyl, C-amido, N-amido, sulfinyl, sulfonyl, amino and —$NR^xR^y$, with $R^x$ and $R^y$ as defined above.

"($C_6$-$C_{12}$) aryl" also includes aryl rigs and ring systems as described above which additionally include fused thereto a carbocyclo or heterocycle, for instance:

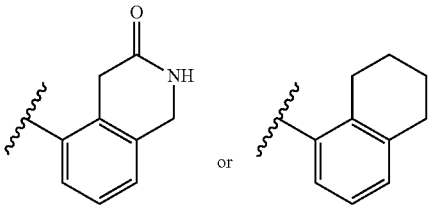 [SMILES: *c1cccc2c1CC(=O)NC2 ; *c1cccc2c1CCCC2]

"Cyano" refers to a —C≡N group. Cyano may be expressed as CN.

"($C_3$-$C_{10}$) cycloalkyl" refers to a 3 to 10 member all-carbon monocyclic ring, a 3 to 10 member all-carbon bicyclic ring, an all-carbon 5-member/6-member or 6-member/6-member fused bicyclic ring, a multicyclic fused ring (a "fused" ring system means that each ring in the system shares an adjacent pair of carbon atoms with each other ring in the system) group wherein one or more of the rings may contain one or more double bonds but none of the rings has a completely conjugated pi-electron system, and a bridged all-carbon ring system. Examples, without limitation, of cycloalkyl groups are cyclopropane, cyclobutane, cyclopentane, cyclopentene, cyclohexane, cyclohexadiene, adamantane, cycloheptane, cycloheptatriene, and the like. A cycloalkyl group may be substituted or unsubstituted. Typical substituent groups include alkyl, aryl, heteroaryl, heteroalicyclic, hydroxy, alkoxy, aryloxy, mercapto, alkylthio, arylthio, cyano, halo, carbonyl, thiocarbonyl, C-carboxy, O-carboxy, O-carbamyl, N-carbamyl, C-amido, N-amido, nitro, amino and —$NR^xR^y$, with $R^x$ and $R^y$ as defined above.

"G12C" refers to a mutation where the amino-acid at position-12 in wild-type KRAS has mutated from a glycine to a cysteine residue.

"Halogen" or the prefix "halo" refers to fluoro, chloro, bromo and iodo. Preferably halogen refers to fluoro or chloro.

"Heteroalkyl" refers to a straight chain or branched chain alkyl group of 1 to 20 carbon atoms, preferably 1 to 12 carbon atoms, more preferably 1 to 8 carbon atoms, or 1 to 6 carbon atoms, or 1 to 4 carbon atoms, wherein one, two or three of which carbon atoms are replaced by a heteroatom selected from $NR^x$, N, O, and $S(O)_n$ (where n is 0, 1 or 2). Typically the heteroatoms, of there are more than one heteroatoms, are not adjacent to one another. Exemplary heteroalkyls include alkyl ethers, secondary and tertiary alkyl amines, amides, alkyl sulfides, and the like. The group may be a terminal group or a bridging group. As used herein, reference to the normal chain when used in the context of a bridging group refers to the direct chain of atoms linking the two terminal positions of the bridging group. As with "alkyl", typical substituent groups on "heteroalkyl" include cycloalkyl, aryl, heteroaryl, heteroalicyclic, hydroxy, alkoxy, aryloxy, mercapto, alkylthio, arylthio, cyano, halogen, carbonyl, thiocarbonyl, O-carbamyl, N-carbamyl, O-thiocarbamyl, N-thiocarbamyl, C-amido, N-amido, C-carboxy, O-carboxy, nitro, silyl, amino and —$NR^xR^y$, where $R^x$ and $R^y$ are for example hydrogen, alkyl, cycloalkyl, aryl, carbonyl, acetyl, sulfonyl, trifluoromethanesulfonyl and, combined, a five- or six-member heteroalicyclic ring. "Heteroalkenyl" refers to a heteroalkyl possessing one or more carbon-carbon double bonds.

"Heteroalkylene" refers to a di-valent form of heteroalkyl. "Heteroalkenylene" refers to a di-valent form of heteroalkenyl.

"Heteroaryl" refers to a monocyclic or fused ring group of 5 to 12 ring atoms containing one, two, three or four ring heteroatoms selected from NR$^x$, N, O, and S(O)$_n$ (where n is 0, 1 or 2) and, in addition, having a completely conjugated pi-electron system. Preferred heteroaryl groups include (C$_2$-C$_7$) heteroaryl in accordance with the definition above. Examples, without limitation, of unsubstituted heteroaryl groups are pyrrole, furan, thiophene, imidazole, oxazole, thiazole, pyrazole, pyridine, pyrimidine, quinoline, isoquinoline, purine, tetrazole, triazine, and carbazole. The heteroaryl group may be substituted or unsubstituted. Typical substituents include alkyl, cycloalkyl, halo, trihalomethyl, hydroxy, alkoxy, aryloxy, mercapto, alkylthio, arylthio, cyano, nitro, carbonyl, thiocarbonyl, sulfonamido, C-carboxy, O-carboxy, sulfinyl, sulfonyl, O-carbamyl, N-carbamyl, O-thiocarbamyl, N-thiocarbamyl, C-amido, N-amido, amino and —NR$^x$R$^y$ with R$^x$ and R$^y$ as defined above. A pharmaceutically acceptable heteroaryl is one that is sufficiently stable to be attached to a compound of the invention, formulated into a pharmaceutical composition and subsequently administered to a patient in need thereof. Examples of typical monocyclic heteroaryl groups include, but are not limited to:

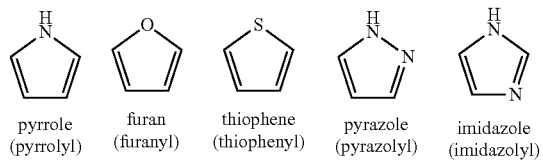

pyrrole (pyrrolyl)   furan (furanyl)   thiophene (thiophenyl)   pyrazole (pyrazolyl)   imidazole (imidazolyl)

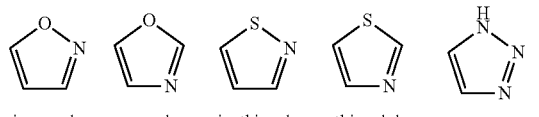

isoxazole (isoxazolyl)   oxazole (oxazolyl)   isothiazole (isothiazolyl)   thiazolyl (thiazolyl)   1,2,3-triazole (1,2,3-triazolyl)

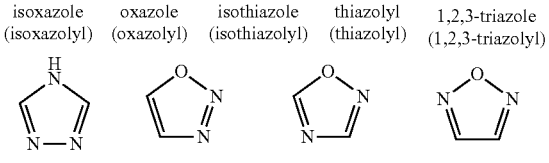

1,3,4-triazole (1,3,4-triazolyl)   1-oxa-2,3-diazole (1-oxa-2,3-diazolyl)   1-oxa-2,4-diazole (1-oxa-2,4-diazolyl)   1-oxa-2,5-diazole (1-oxa-2,5-diazolyl)

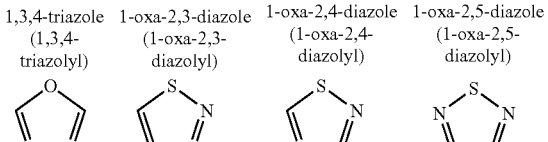

1-oxa-3,4-diazole (1-oxa-3,4-diazolyl)   1-thia-2,3-diazole (1-thia-2,3-diazolyl)   1-thia-2,4-diazole (1-thia-2,4-diazolyl)   1-thia-2,5-diazole (1-thia-2,5-diazolyl)

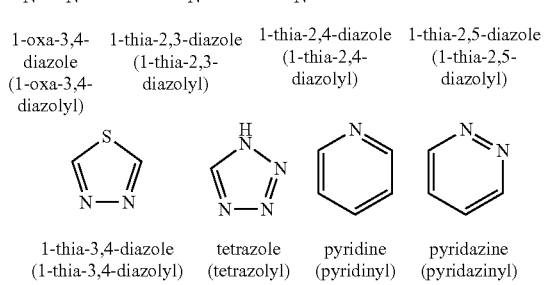

1-thia-3,4-diazole (1-thia-3,4-diazolyl)   tetrazole (tetrazolyl)   pyridine (pyridinyl)   pyridazine (pyridazinyl)

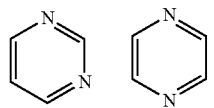

pyrimidine (pyrimidinyl)   pyrazine (pyrazinyl)

Examples of suitable fused ring heteroaryl groups include, but are not limited to:

benzofuran (benzofuranyl)   benzothiophene (benzothiophenyl)   indole (indolyl)

benzimidazole (benzimidazolyl)   indazole (indazolyl)   benzotriazole (benzotriazolyl)

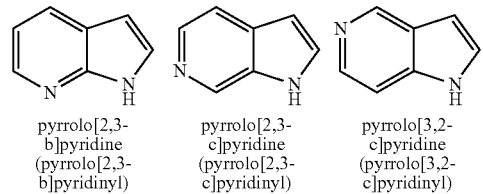

pyrrolo[2,3-b]pyridine (pyrrolo[2,3-b]pyridinyl)   pyrrolo[2,3-c]pyridine (pyrrolo[2,3-c]pyridinyl)   pyrrolo[3,2-c]pyridine (pyrrolo[3,2-c]pyridinyl)

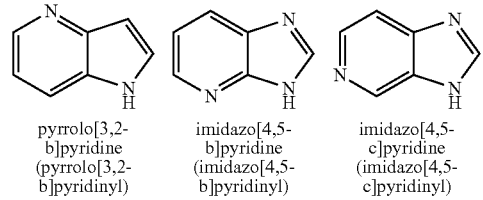

pyrrolo[3,2-b]pyridine (pyrrolo[3,2-b]pyridinyl)   imidazo[4,5-b]pyridine (imidazo[4,5-b]pyridinyl)   imidazo[4,5-c]pyridine (imidazo[4,5-c]pyridinyl)

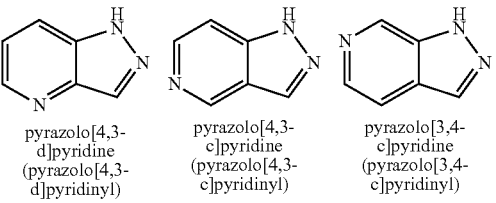

pyrazolo[4,3-d]pyridine (pyrazolo[4,3-d]pyridinyl)   pyrazolo[4,3-c]pyridine (pyrazolo[4,3-c]pyridinyl)   pyrazolo[3,4-c]pyridine (pyrazolo[3,4-c]pyridinyl)

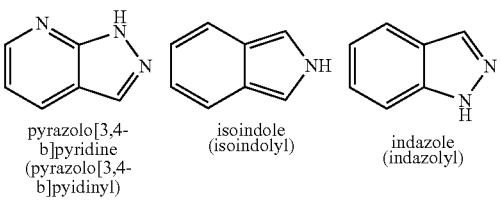

pyrazolo[3,4-b]pyridine (pyrazolo[3,4-b]pyidinyl)   isoindole (isoindolyl)   indazole (indazolyl)

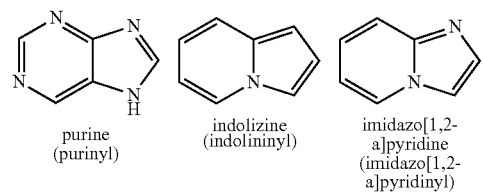

purine (purinyl)   indolizine (indolininyl)   imidazo[1,2-a]pyridine (imidazo[1,2-a]pyridinyl)

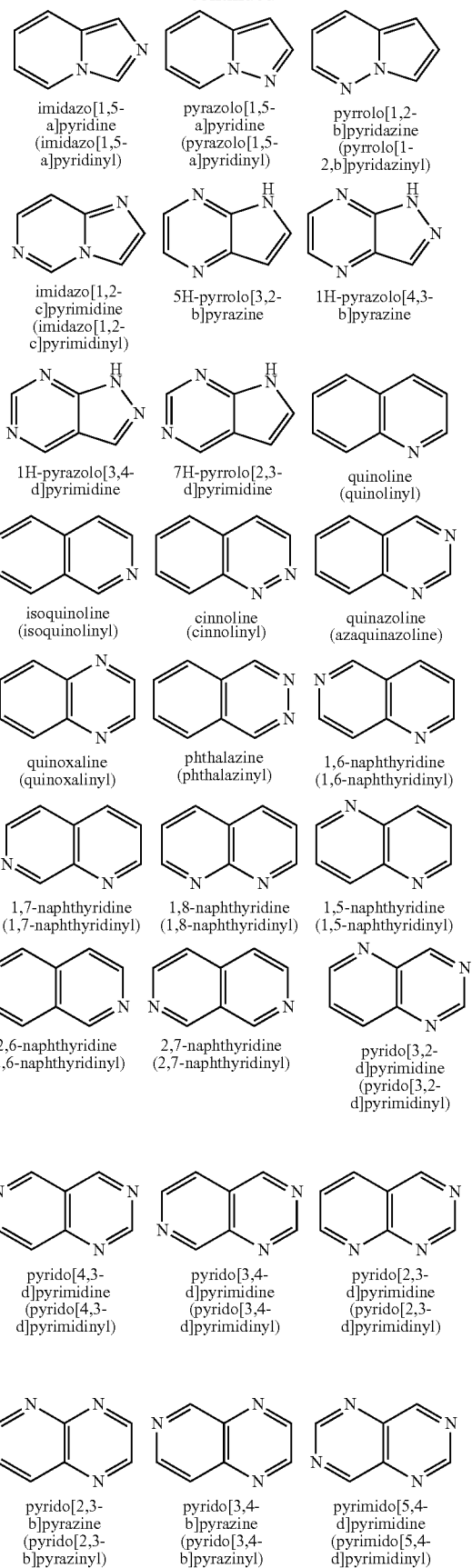

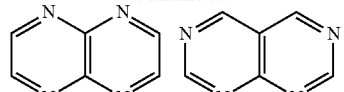

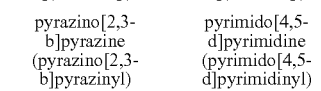

"Heterocyclyl" refers to a monocyclic, spirocyclic or fused ring system having 3 to 12 ring atoms containing one, two, three or four ring heteroatoms selected from N, O, and $S(O)_n$ (where n is 0, 1 or 2), and 1-9 carbon atoms The rings may also have one or more double bonds. However, the rings do not have a completely conjugated pi-electron system. Preferred heterocycles include $(C_2-C_6)$ heterocycles in accordance with the definition above.

Examples of suitable saturated heterocyclic groups include, but are not limited to:

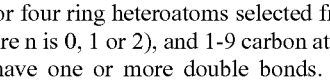

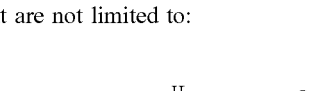

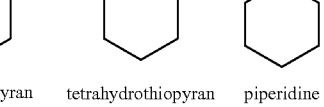

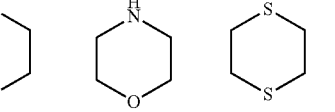

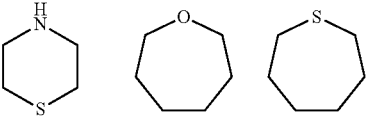

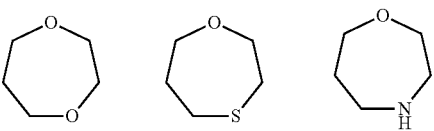

-continued

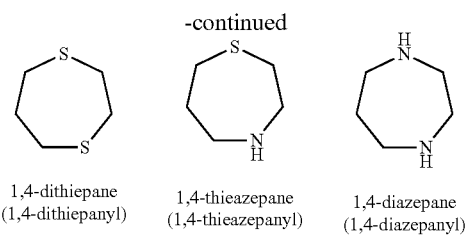

1,4-dithiepane (1,4-dithiepanyl)    1,4-thieazepane (1,4-thieazepanyl)    1,4-diazepane (1,4-diazepanyl)

Examples of suitable partially unsaturated heterocyclic groups include, but are not limited to:

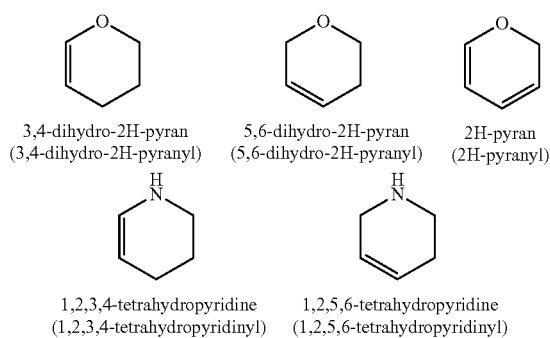

3,4-dihydro-2H-pyran (3,4-dihydro-2H-pyranyl)    5,6-dihydro-2H-pyran (5,6-dihydro-2H-pyranyl)    2H-pyran (2H-pyranyl)

1,2,3,4-tetrahydropyridine (1,2,3,4-tetrahydropyridinyl)    1,2,5,6-tetrahydropyridine (1,2,5,6-tetrahydropyridinyl)

Examples of suitable fused heterocyclic groups include, but are not limited to:

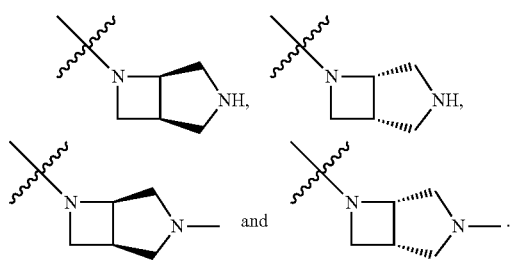

Examples of suitable semi-saturated fused heterocyclic groups include, but are not limited to:

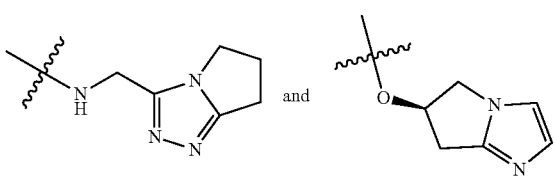 [SMILES: *NCc1nnc2n1CCC2 ; *O[C@@H]1Cc2nccn2C1]

Examples of suitable spirocyclic heterocyclic groups include, but are not limited to:

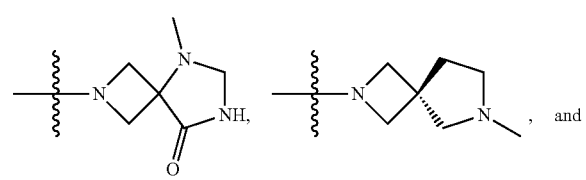

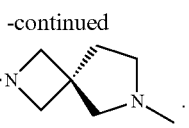

The heterocyclyl group is optionally substituted with one or two substituents independently selected from halo, lower alkyl, lower alkyl substituted with carboxy, ester hydroxy, mono or dialkylamino, or oxo. Moreover, the heterocycle may contain bridging, including bridging between non-adjacent carbons on the heterocycle, with the bridge containing 1-2 carbons and 0-1 heteroatoms selected from selected from $NR^x$, O, and $S(O)_n$ (where n is 0, 1 or 2).

"Hydroxy" or "hydroxyl" refers to an —OH group.

"In vitro" refers to procedures performed in an artificial environment such as, e.g., without limitation, in a test tube or culture medium.

"In vivo" refers to procedures performed within a living organism such as, without limitation, a mouse, rat or rabbit.

"Optional" or "optionally" means that the subsequently described event or circumstance may but need not occur, and that the description includes instances where the event or circumstance occurs and instances in which it does not. For example, "heterocycle group optionally substituted with an alkyl group" means that the alkyl may but need not be present, and the description includes situations where the heterocycle group is substituted with an alkyl group and situations where the heterocycle group is not substituted with the alkyl group.

"Organism" refers to any living entity comprised of at least one cell. A living organism can be as simple as, for example, a single eukariotic cell or as complex as a mammal, including a human being.

A "pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols. As used herein, the term "pharmaceutically acceptable salt" refers to those salts which retain the biological effectiveness and properties of the parent compound. Such salts include: (i) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, citric acid, succinic acid or malonic acid and the like; or (ii) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

A "pharmaceutical composition" refers to a mixture of one or more of the compounds described herein, or physiologically/pharmaceutically acceptable salts, solvates, hydrates or prodrugs thereof, with other chemical components, such as physiologically/pharmaceutically acceptable carriers and excipients. The purpose of a pharmaceutical composition is to facilitate administration of a compound to an organism.

As used herein, a "physiologically/pharmaceutically acceptable carrier" refers to a carrier or diluent that does not cause significant irritation to an organism and does not abrogate the biological activity and properties of the administered compound.

"Therapeutically effective amount" refers to that amount of the compound being administered which will relieve to some extent one or more of the symptoms of the disorder being treated. In reference to the treatment of cancer, a therapeutically effective amount refers to that amount which has at least one of the following effects: reducing the size of the tumor; inhibiting (that is, slowing to some extent, preferably stopping) tumor metastasis; inhibiting to some extent (that is, slowing to some extent, preferably stopping) tumor growth, and relieving to some extent (or, preferably, eliminating) one or more symptoms associated with the cancer.

"Treat", "treating" and "treatment" refer to a method of alleviating or abrogating a methyltransferase mediated cellular disorder and/or its attendant symptoms. With regard particularly to cancer, these terms simply mean that the life expectancy of an individual affected with a cancer will be increased or that one or more of the symptoms of the disease will be reduced.

DETAILED DESCRIPTION

General schemes for synthesizing the compounds of the invention can be found in the Examples section herein.

Unless indicated otherwise, all references herein to the inventive compounds include references to salts, solvates, hydrates and complexes thereof, and to solvates, hydrates and complexes of salts thereof, including polymorphs, stereoisomers, and isotopically labeled versions thereof.

Pharmaceutically acceptable salts include acid addition and base salts (including disalts). Suitable acid addition salts are formed from acids which form non-toxic salts. Examples include the acetate, aspartate, benzoate, besylate, bicarbonate/carbonate, bisulphate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts. For a review on suitable salts, see "Handbook of Pharmaceutical Salts: Properties, Selection, and Use" by Stahl and Wermuth (Wiley-VCH, Weinheim, Germany, 2002), the disclosure of which is incorporated herein by reference in its entirety.

A pharmaceutically acceptable salt of the inventive compounds can be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost non-ionized.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when the solvent is water. Pharmaceutically acceptable solvates in accordance with the invention include hydrates and solvates wherein the solvent of crystallization may be isotopically substituted, e.g. $D_2O$, $d_6$-acetone, $d_6$-DMSO.

Also included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see J Pharm Sci, 64 (8), 1269-1288 by Haleblian (August 1975), the disclosure of which is incorporated herein by reference in its entirety.

Also within the scope of the invention are polymorphs, prodrugs, and isomers (including optical, geometric and tautomeric isomers) of the inventive compounds.

Derivatives of compounds of the invention which may have little or no pharmacological activity themselves but can, when administered to a patient, be converted into the inventive compounds, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association), the disclosures of which are incorporated herein by reference in their entireties. Prodrugs in accordance with the invention can, for example, be produced by replacing appropriate functionalities present in the inventive compounds with certain moieties known to those skilled in the art as 'pro-moieties' as described, for example, in "Design of Prodrugs" by H Bundgaard (Elsevier, 1985), the disclosure of which is incorporated herein by reference in its entirety.

Some examples of prodrugs in accordance with the invention include: (i) where the compound contains a carboxylic acid functionality —(COOH), an ester thereof, for example, replacement of the hydrogen with ($C_1$-$C_8$)alkyl; (ii) where the compound contains an alcohol functionality (—OH), an ether thereof, for example, replacement of the hydrogen with ($C_1$-$C_6$)alkanoyloxymethyl; and (iii) where the compound contains a primary or secondary amino functionality (—$NH_2$ or —NHR where R≠H), an amide thereof, for example, replacement of one or both hydrogens with ($C_1$-$C_{10}$)alkanoyl. Further examples of replacement groups in accordance with the foregoing examples and examples of other prodrug types may be found in the aforementioned references.

Finally, certain inventive compounds may themselves act as prodrugs of other of the inventive compounds.

Compounds of the invention containing one or more asymmetric carbon atoms can exist as two or more stereoisomers. Where the compounds according to this invention have at least one chiral center, they may accordingly exist as enantiomers. Where the compounds possess two or more chiral centers, they may additionally exist as diastereomers. Similarly, where a compound of the invention contains a cyclopropyl group or other cyclic group where chirality exists, and alkenyl or alkenylene group, geometric cis/trans (or Z/E) isomers are possible. Where the compound contains, for example, a keto or oxime group or an aromatic moiety, tautomeric isomerism ('tautomerism') can occur. A single compound may exhibit more than one type of isomerism.

Included within the scope of the invention are all stereoisomers, geometric isomers and tautomeric forms of the inventive compounds, including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC) or supercritical fluid chromatography (SFC).

Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art.

Stereoisomeric conglomerates may be separated by conventional techniques known to those skilled in the art; see, for example, "Stereochemistry of Organic Compounds" by E L Eliel (Wiley, New York, 1994), the disclosure of which is incorporated herein by reference in its entirety.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$. Certain isotopically-labeled compounds of the invention, for example, those incorporating a radioactive isotope, are useful in drug and/or substrate tissue distribution studies. The radioactive isotopes tritium, $^3H$, and carbon-14, $^{14}C$, are particularly useful for this purpose in view of their ease of incorporation and ready means of detection. Substitution with heavier isotopes such as deuterium, $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention intended for pharmaceutical use may be administered as crystalline or amorphous products, or mixtures thereof. They may be obtained, for example, as solid plugs, powders, or films by methods such as precipitation, crystallization, freeze drying, spray drying, or evaporative drying. Microwave or radio frequency drying may be used for this purpose.

The compounds can be administered alone or in combination with one or more other compounds of the invention. Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the invention and methods for their preparation will be readily apparent to those skilled in the art. Such compositions and methods for their preparation can be found, for example, in 'Remington's Pharmaceutical Sciences', 19th Edition (Mack Publishing Company, 1995), the disclosure of which is incorporated herein by reference in its entirety.

Oral Administration: The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001), the disclosure of which is incorporated herein by reference in its entirety.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet.

Other conventional ingredients include anti-oxidants, colorants, flavoring agents, preservatives and taste-masking agents.

Exemplary tablets contain up to about 80 wt % drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tableting. The final formulation may include one or more layers and may be coated or uncoated; or encapsulated.

The formulation of tablets is discussed in detail in "Pharmaceutical Dosage Forms: Tablets, Vol. 1", by H. Lieberman and L. Lachman, Marcel Dekker, N.Y., N.Y., 1980 (ISBN 0-8247-6918-X), the disclosure of which is incorporated herein by reference in its entirety. Solid formulations for oral administration may be formulated to be immediate and/or modified release. Modified release formulations include delayed-, sustained-, pulsed-, controlled-, targeted and programmed release.

Suitable modified release formulations are described in U.S. Pat. No. 6,106,864. Details of other suitable release technologies such as high energy dispersions and osmotic and coated particles can be found in Verma et al, Pharmaceutical Technology On-line, 25(2), 1-14 (2001). The use of chewing gum to achieve controlled release is described in WO 00/35298. The disclosures of these references are incorporated herein by reference in their entireties.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including micro needle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of the invention used in the preparation of parenteral solutions may be increased by the use of appropriate formulation techniques, such as the incorporation of solubility-enhancing agents. Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J Pharm Sci, 88 (10), 955-958 by Finnin and Morgan (October 1999). Other means of topical administration include delivery by electroporation, iontophoresis, phonophoresis, sonophoresis and micro needle or needle-free (e.g. Powderject™, Bioject™, etc.) injection. The disclosures of these references are incorporated herein by reference in their entireties.

Formulations for topical administration may be formulated to be immediate and/or modified release. Modified release formulations include delayed-, sustained-, pulsed-, controlled-, targeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may include a bioadhesive agent, for example, chitosan or cyclodextrin.

The pressurized container, pump, spray, atomizer, or nebulizer contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as 1-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 µg to 20 mg of the compound of the invention per actuation and the actuation volume may vary from 1 µL to 100 µL. A typical formulation includes a compound of the invention, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing a desired mount of the compound of the invention. The overall daily dose may be administered in a single dose or, more usually, as divided doses throughout the day.

Rectal/Intravaginal Administration

Compounds of the invention may be administered rectally or vaginally, for example, in the form of a suppository, pessary, or enema. Cocoa butter is a traditional suppository base, but various alternatives may be used as appropriate. Formulations for rectal/vaginal administration may be formulated to be immediate and/or modified release. Modified release formulations include delayed-, sustained-, pulsed-, controlled-, targeted and programmed release.

Ocular Administration

Compounds of the invention may also be administered directly to the eye or ear, typically in the form of drops of a micronized suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

Compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubilizer. Most commonly used for these purposes are alpha-, beta- and gamma-cyclodextrins, examples of which may be found in PCT Publication Nos. WO 91/11172, WO 94/02518 and WO 98/55148, the disclosures of which are incorporated herein by reference in their entireties.

Dosage

The amount of the active compound administered will be dependent on the subject being treated, the severity of the disorder or condition, the rate of administration, the disposition of the compound and the discretion of the prescribing physician. However, an effective dosage is typically in the range of about 0.001 to about 100 mg per kg body weight per day, preferably about 0.01 to about 35 mg/kg/day, in single or divided doses. For a 70 kg human, this would amount to about 0.07 to about 7000 mg/day, preferably about 0.7 to about 2500 mg/day. In some instances, dosage levels below the lower limit of the aforesaid range may be more than adequate, while in other cases still larger doses may be used without causing any harmful side effect, with such larger doses typically divided into several smaller doses for administration throughout the day.

Kit-of-Parts

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions. Thus the kit of the invention includes two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically includes directions for administration and may be provided with a memory aid.

The following abbreviations may be used herein: Ac (acetyl); AcCl (acetyl chloride); AcOH or HOAc (acetic acid); Ac$_2$O (acetic anhydride); aq. (aqueous); Boc or boc (tert-butoxycarbonyl); BOP ((benzotriazol-1-yloxy)tris(dimethylamino)phosphonium hexafluorophosphate); B$_2$pin$_2$ (bis(pinacolato)diboron); ca. (about or approximately); CDCl$_3$ (deuterated chloroform); CH$_2$Cl$_2$ and/or DCM (dichloromethane); DABCO (1,4-diazabicyclo[2,2,2]pctane); DAST (Diethylaminosulfur trifluoride); DBU (1,8-diazabicyclo[5,4,0]undec-7-ene); DCE (dichloroethane); DEA (diethylamine); DIBAL or DIBAL-H (diisobutylaluminum hydride); DIC (diisopropylcarbodiimide); DIPEA or Hunig's base (N,N-diisopropylethylamine); DHP (dihydropyran); DMA (dimethylacetamide); DMF (dimethylformamide); DME (ethylene glycol); DMP (Dess-Martin Periodinane); DMAP (4-dimethylaminopyridine); DMSO (dimethylsulfoxide); DMSO-d$_6$ (deuterated dimethylsulfoxide); EDC or EDCl (1-ethyl-3-(3-dimethylaminopropyl)-carbodiimide); Et (ethyl); Et$_3$N or TEA (triethylamine); EtOH (ethanol); EtOAc (ethyl acetate); Et$_2$O (diethyl ether); g or gm (gram or grams); HATU (2-(7-aza-1H-benzotriazole-1-yl)-1,1,3,3-tetramethyluronium hexafluorophosphate); HBTU (o-(benzotriazole-1-yl)-1,1,3,3-tetramethyluronium hexafluorophosphate); HFIP (1,1,1,3,3,3-hexafluoro-2-propanol); HMPT (Tris(dimethylamino)phosphine); HPLC (high-performance liquid chromatography); HOBT (1-hydroxy benzotriazole); h or hr (hour or hours, as appropriate); iBu (isobutyl); IPA (iso-propyl alcohol); iPr (isopropyl); iPrOAc (isopropyl acetate); KHMDS (potassium bis(trimethylsilyl)amide); KOAc (potassium acetate); LCMS (liquid chromatography-mass spectrometry); LDA (lithium diisopropylamide); LiHMDS (lithium bis(trimethylsilyl)amide); mCPBA (meta-chloroperoxybenzoic acid); Me (methyl); MeOH (methanol); MeOD (deuterated methanol); MeCN (acetonitrile); m or min (minute or minutes, as appropriate); mg (milligram or milligrams); Ms (methylsulfonyl); MsCl (methanesulfonyl chloride); N (normal); NBS (N-Bromosuccinimide); NCS (N-chlorosuccinimide); NFSI (N-Fluorodibenzenesulfonimide); NMR (nuclear magnetic resonance); nBu (n-butyl); nBuLi (n-butyl lithium); nPr (n-propyl); Pd/C (palladium on carbon); Pd$_2$(dba)$_3$ (tris(dibenzylideneacetone)dipalladium(0)); Pd(dppf)Cl$_2$ ([1,1'-bis(diphenylphosphino)ferrocene]dichloropalladium(II)); Pd[P(o-tol)$_3$]$_2$ (bis[tris(2-methylphenyl)phosphine]palladium); Ph (phenyl); PTSA or pTSA (p-Toluene sulfonic acid); PPTS: (pyridium p-toluenesulfonate); Rt (retention time); rt (room temperature); RuCl(p-cymene)[(R,R)-Ts-DPEN] ([N-[(1R,2R)-2-(Amino-κN)-1,2-diphenylethyl]-4-methylbenzenesulfonamidato-κN]chloro[(1,2,3,4,5,6-η)-1-methyl-4-(1-methylethyl)benzene]-ruthenium); s or sec (second or seconds, as appropriate); Selectfluor (N-Chloromethyl-N'-fluorotriethylenediammonium bis(tetrafluoroborate)); SEM (2-Trimethylsilylethoxymethoxy); SFC (supercritical fluid chromatography); Si-Thiol (silica 1-propanethiol); SK-CCO2-A (2-(dimethylaminomethyl)ferrocene-1-yl-palladium(II) chloride dinorbornylphosphine); T3P (propylphosphonic anhydride); TBAF (tetrabutyl ammonium fluoride); TBDMSCl (t-butyl-dimethylsilyl chloride); TBME or MTBE (tert-butyl methyl ether); t-BuOH (2-methyl-2-propanol, tert-butanol or tert-butyl alcohol); tBu-Xphos (2-di-tert-butylphosphino-2',4',6'-triisopropylbiphenyl); TDA-1 (Tris[2-(2-methoxyethoxy)ethyl]amine or Tris(3,6-dioxaheptyl) amine); TEA, NEt$_3$ or Et$_3$N (triethylamine); TFA (trifluoroacetic acid); THF (tetrahydrofuran); THP (tetrahydropyran); TLC (thin layer chromatography); TMS (trimethylsilyl); TMSCl (trimethylsilyl chloride); TMSCF$_3$ (Trimethyl(trifluoromethyl)silane); Tos or tosyl (4-toluenesulfonyl); TOSMIC (p-Toluenesulfonylmethyl isocyanide); UV (ultraviolet).

EXAMPLES

All of the reactions herein and the preparations of novel starting materials used herein are conventional and appropriate reagents and reaction conditions for their performance or preparation as well as procedures for isolating the desired products will be well-known to those skilled in the art with reference to literature precedents and the examples and preparations hereto.

For some of the steps described it may be necessary to protect potential reactive functions that are not wished to react, and to cleave said protecting groups in consequence. In such a case, any compatible protecting group may be used. In particular methods of protection and deprotection such as those described by T. W. Greene (*Protective Groups in Organic Synthesis*, A. Wiley-Interscience Publication, 1981) or by P. J. Kocienski (*Protecting groups*, Georg Thieme Verlag, 1994), may be used.

General Synthetic Schemes

Scheme I:

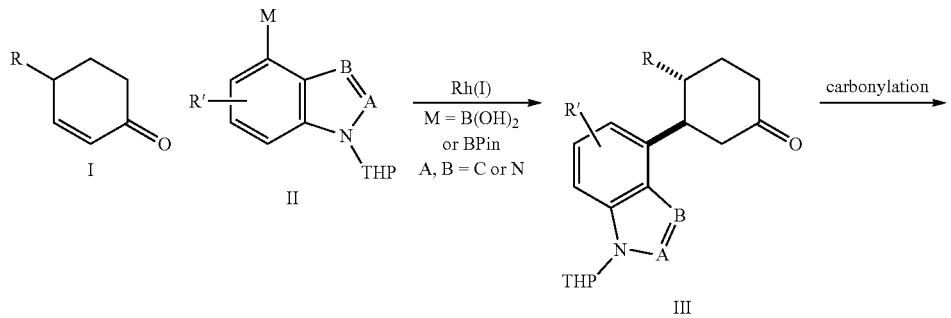

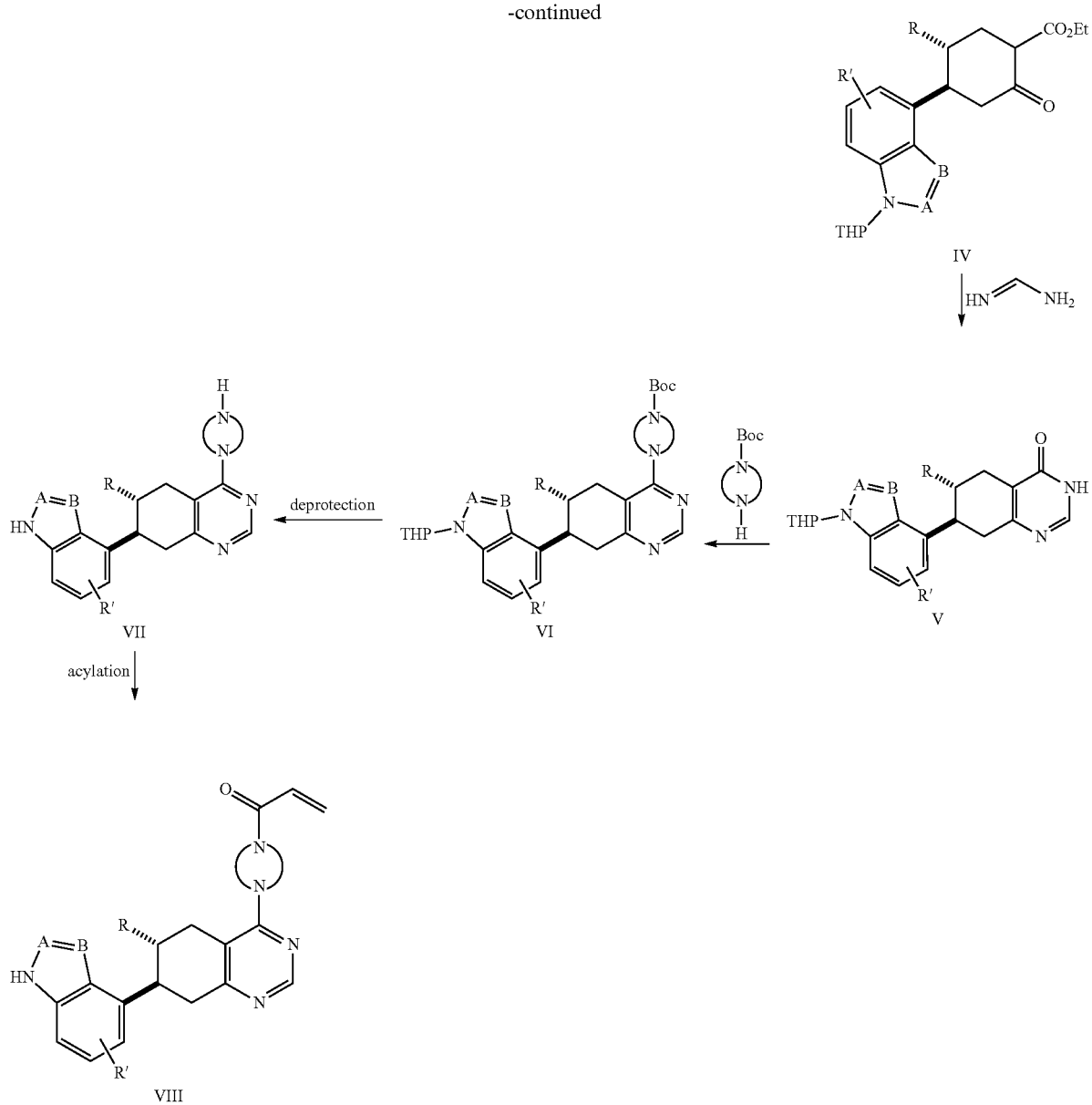

As exemplified in Scheme I, a compound such as I can be purchased or synthesized (*J. Org. Chem.* 2012, 77, 9422-9425) and may be achiral, racemic, or enantiopure. Compounds such as I can undergo a rhodium-catalyzed conjugate addition with an appropriately substituted boronic acid or BPin ester (II) with an appropriate base such as $K_3PO_4$, $KOSiMe_3$ of LiOMe in a solvent such as 1,4-dioxane with or without the addition of $H_2O$ to yield compounds such as III. Compounds such as III can be carbonylated with an appropriate base and cabonylating reagent in an appropriate solvent such as NaH and diethylcarbonate in THF, LDA and methyl cyanoformate in THF, or LHDMS and methyl cyanoformate in toluene to provide compounds such as IV. Compounds such as IV can be condensed with formamidine to provide compounds such as V, typically in an alcoholic solvent with an alkoxide base. Compounds such as V can be coupled with a nucleophilic amine species to provide compounds such as VI. This coupling is typically carried out in one step using BOP reagent and DBU or in two steps by treatment of V with $POCl_3$ followed by addition of the nucleophilic amine species. Compounds such as VI can be deprotected by treatment with acid, typically TFA in DCM or HCl in MeOH, to provide compounds such as VII. Compounds such as VII can be acylated to provide compounds such as VIII, typically by treatment with acryloyl chloride in DCM with TEA as base, EtOAc/$H_2O$ with $NaHCO_3$ as base, or HFIP with $NaHCO_3$ as base. In some cases the species R may contain protecting groups, which can be removed by an additional step in the synthetic sequence. R, R', A and B are defined as in the below embodiments, schemes, examples and claims herein. Compounds at every step may be purified by standard techniques such as column chromatography, crystallization, and reverse phase HPLC or SFC. If necessary, separation of the enantiomers of VIII may be carried out under standard methods known in the art such as chiral SFC or HPLC to afford single enantiomers.

Scheme II:

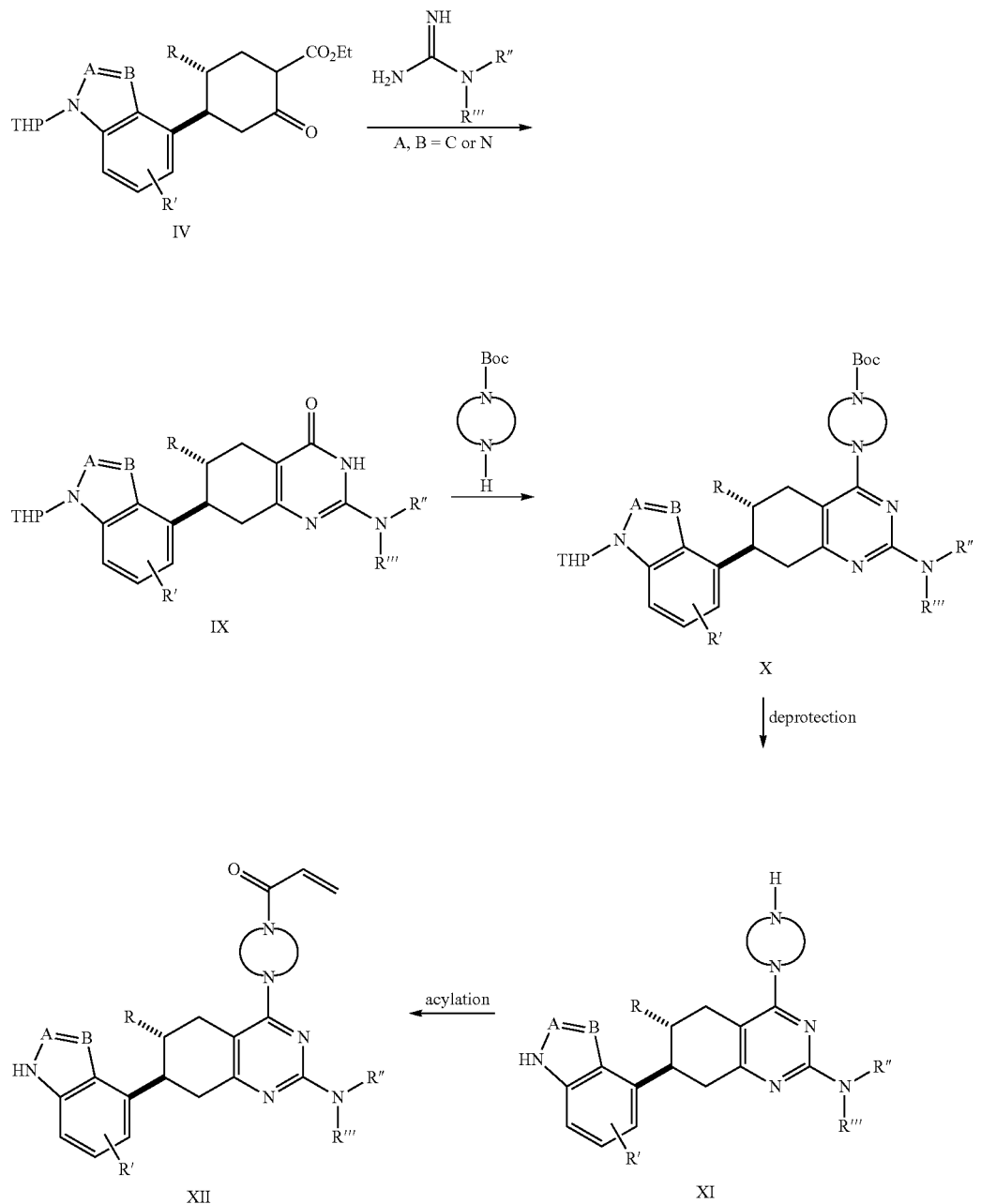

As exemplified in Scheme II, compounds such as IV (prepared according to Scheme I) are condensed with an N,N-dialkylguanidine to provide compounds such as IX. Typically these reactions are run in an alcoholic solvent with an appropriate alkoxide base. Compounds such as IX can be coupled with a nucleophilic amine species to provide compounds such as X. This coupling is typically carried out in one step using BOP reagent and DBU or in two steps by treatment of IX with $POCl_3$ followed by addition of the nucleophilic amine species. Compounds such as X can be deprotected under acidic conditions, typically TFA in DCM or HCl in MeOH, to provide compounds such as XI. Compounds such as XI can be acylated to provide compounds such as XII, typically by treatment with acryloyl chloride in DCM with TEA as base, EtOAc/$H_2O$ with $NaHCO_3$ as base, or HFIP with $NaHCO_3$ as base. R, R', R", R''', A, and B are defined as in the below embodiments, schemes, examples and claims herein. Compounds at every step may be purified by standard techniques such as column chromatography, crystallization, and reverse phase HPLC or SFC. If necessary, separation of the enantiomers of XII may be carried out under standard methods known in the art such as chiral SFC or HPLC to afford single enantiomers.

Scheme III:

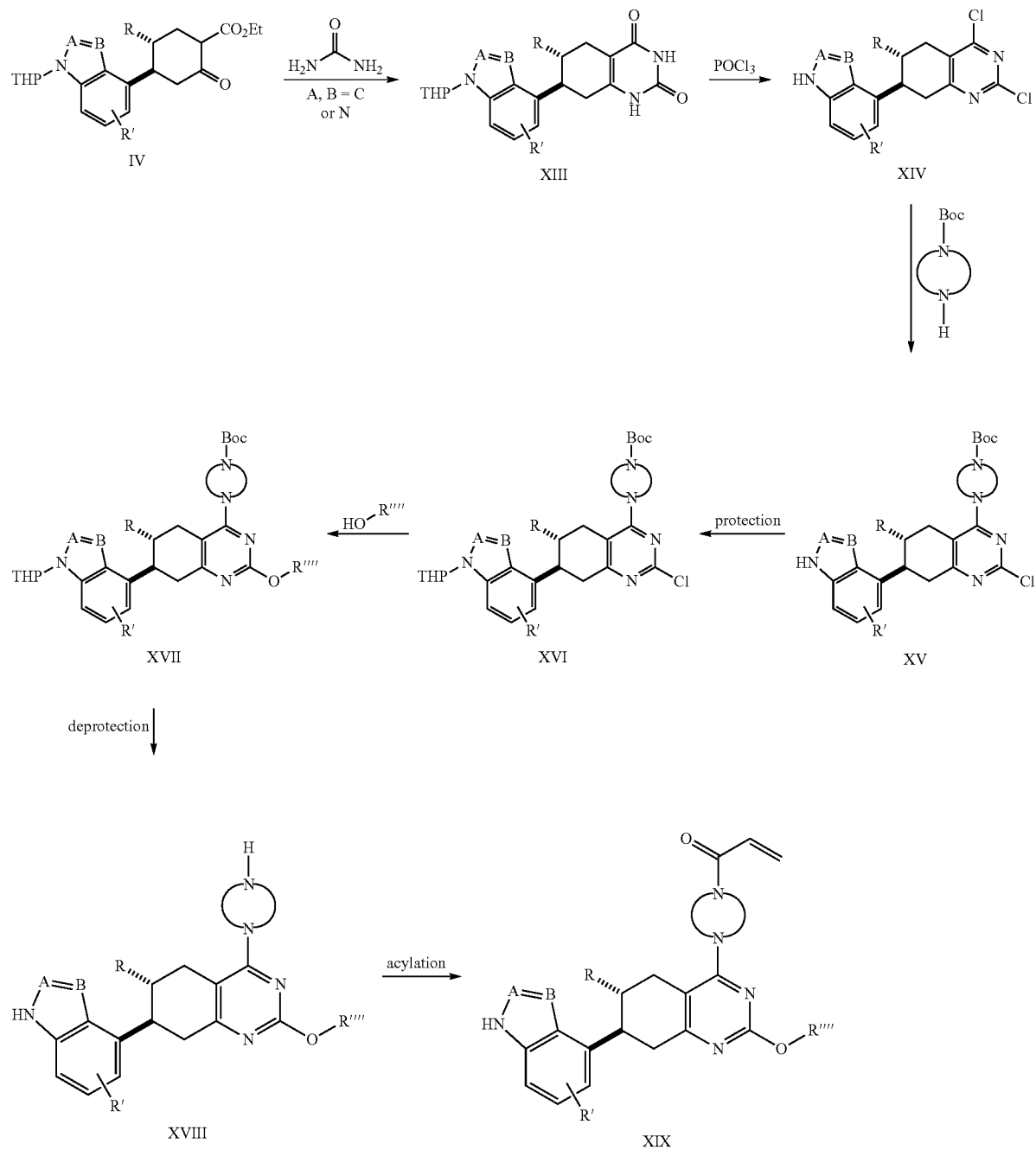

As exemplified in Scheme III, compounds such as IV are condensed with urea to provide compounds such as XIII. Compounds such as XIII are chlorinated, typically with POCl$_3$, to provide compounds such as XIV, which are then coupled with a nucleophilic amine species under basic conditions to provide compounds such as XV. Protection of compounds such as XV, typically with DHP in the presence of mild catalytic acid, provides compounds such as XVI. Coupling of compounds such as XVI with an alcohol under basic conditions provides compounds such as XVII. Deprotection of compounds such as XVII under acidic conditions, typically TFA in DCM or HCl in MeOH, provides compounds such as XVIII. Compounds such as XVIII can be acylated to provide compounds such as XIX, typically by treatment with acryloyl chloride in DCM with TEA as base, EtOAc/H$_2$O with NaHCO$_3$, or HFIP with NaHCO$_3$ as base. R, R', R'''' are defined as in the below embodiments, schemes, examples and claims herein. Compounds at every step may be purified by standard techniques such as column chromatography, crystallization, and reverse phase HPLC or SFC. If necessary, separation of the enantiomers of XIX may be carried out under standard methods known in the art such as chiral SFC or HPLC to afford single enantiomers.

Scheme IV:
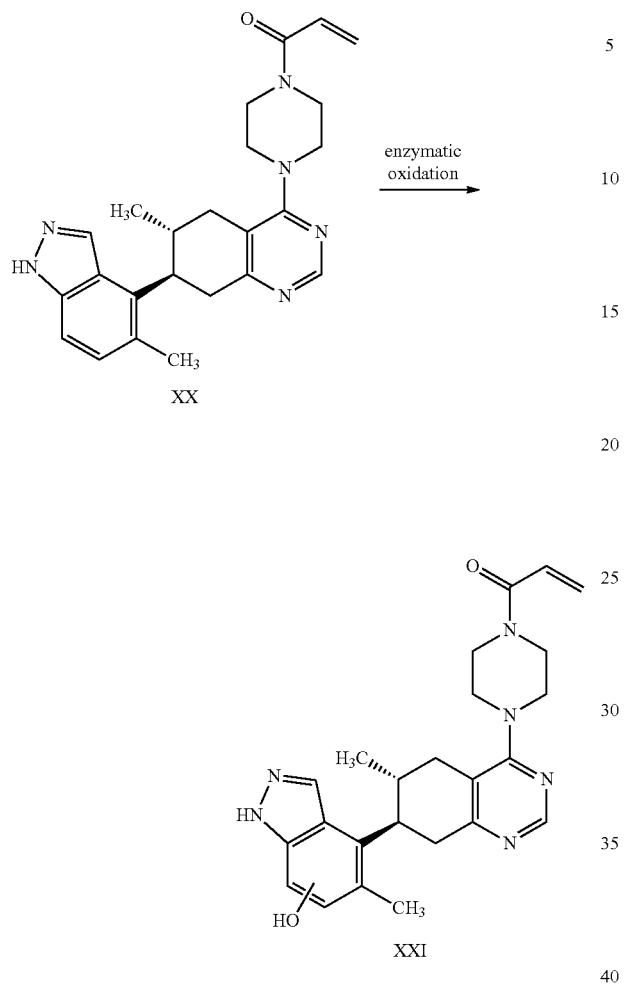
As exemplified in Scheme IV, compounds such as XX are subjected to enzymatic oxidation to provide compounds such as XXI.
Scheme V:
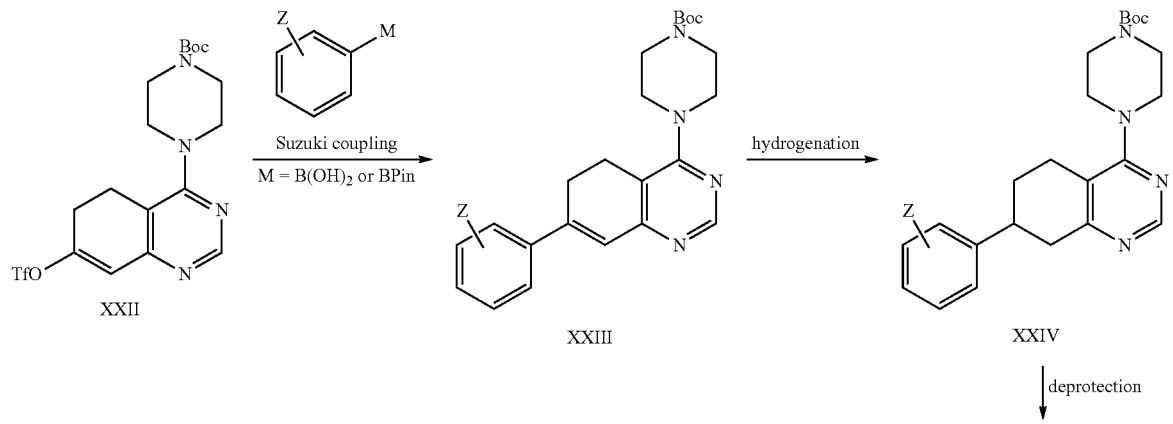

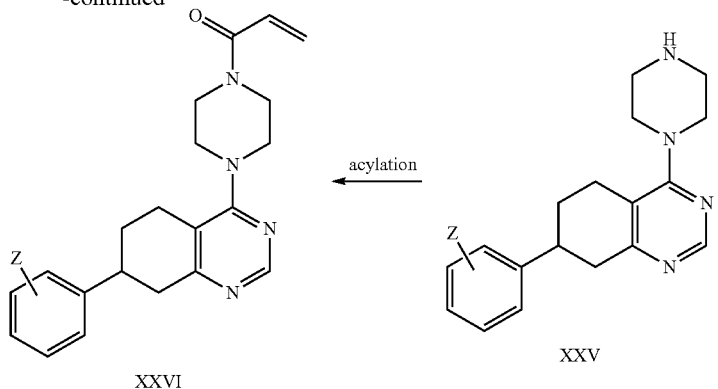

As exemplified in Scheme V, compounds such as XXII are coupled with an appropriate aryl boronic acid or aryl BPin ester under standard Pd-catalyzed Suzuki coupling conditions to provide compounds such as XXIII. Compounds such as XXIII are hydrogenated, typically using catalytic Pd/C or Pt/C in the presence of $H_2$ in a polar solvent such as MeOH, to provide compounds such as XXIV. Compounds such as XXIV are deprotected under acidic conditions, typically TFA in DCM or HCl in MeOH, to provide compounds such as XXV. Compounds such as XXV can be acylated to provide compounds such as XXVI, typically by treatment with acryloyl chloride in DCM with TEA as base, EtOAc/$H_2O$ with $NaHCO_3$ as base, or HFIP with $NaHCO_3$ as base. Z is defined as in the below embodiments, schemes, examples and claims herein, and may contain protecting groups, which can be removed by a subsequent step in the synthetic sequence. Compounds at every step may be purified by standard techniques such as column chromatography, crystallization, and reverse phase HPLC or SFC. If necessary, separation of the enantiomers of XXVI may be carried out under standard methods known in the art such as chiral SFC or HPLC to afford single enantiomers.

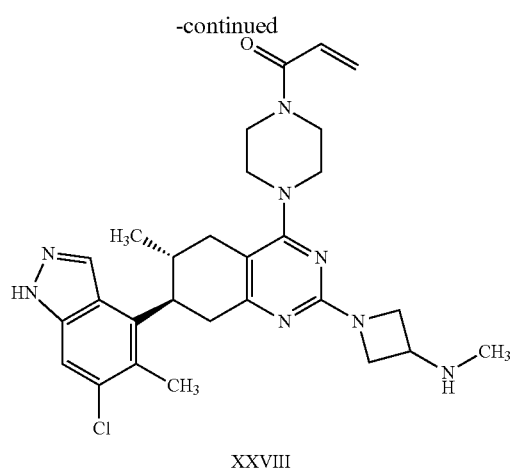

As exemplified in Scheme VII, compounds such as XXVII are subjected to enzymatic oxidation to provide compounds such as XXVIII.

Preparation of Synthetic Intermediates

Preparation of [5-methyl-1-(tetrahydro-2H-pyran-2-yl)-1H-indazol-4-yl]boronic acid (Int-1) as Shown in Scheme 1

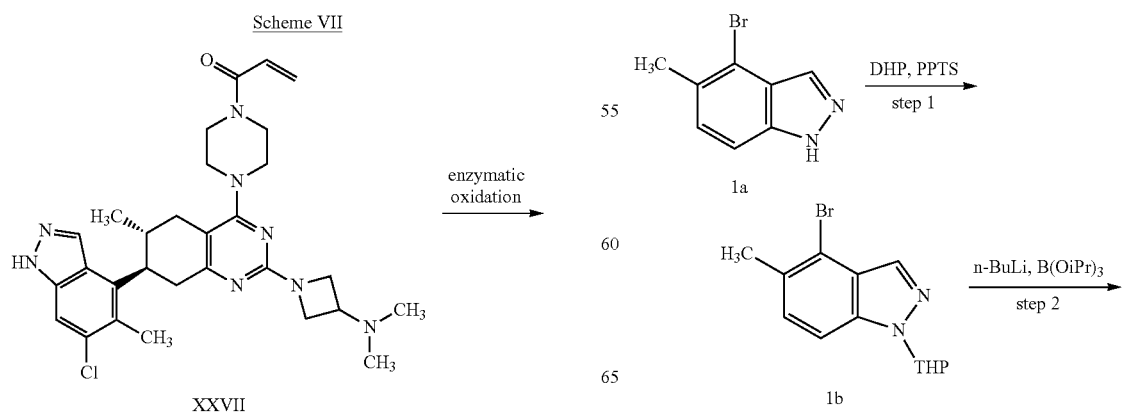

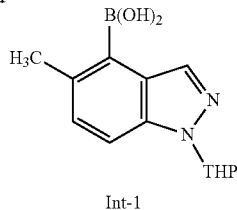

Int-1

Step 1: Synthesis of 4-bromo-5-methyl-1-(tetrahydro-2H-pyran-2-yl)-1H-indazole (1b)

This reaction was run in two parallel batches. To a stirred solution of 4-bromo-5-methyl-1H-indazole (100 g, 474 mmol, 1.0 eq) in DCM (1 L) was added PPTS (11.9 g, 47.4 mmol, 0.1 eq) at 28° C. Then DHP (119.6 g, 1.4 mol, 3.0 eq) was added in one portion. The mixture was stirred at 30° C. for 18 hours. TLC analysis (20% EtOAc/petroleum ether) showed complete consumption of starting material. The two batches were combined together for work-up. The reaction was quenched with $H_2O$ (1.5 L) and the layers were separated. The aqueous layer was extracted with DCM (1 L). The combined organics were washed with $H_2O$ (1 L) and brine (1 L), dried over $Na_2SO_4$, and concentrated to dryness. The residue was triturated with petroleum ether (300 mL) to provide 4-bromo-5-methyl-1-(tetrahydro-2H-pyran-2-yl)-1H-indazole (1 b) as an off-white solid (223 g, 80% yield). $^1$H NMR (400 MHz, DMSO-$d_6$) δ 8.00 (s, 1H), 7.68 (d, J=8.5 Hz, 1H), 7.39 (d, J=8.5 Hz, 1H), 5.84 (dd, J=9.6, 2.5 Hz, 1H), 3.87 (d, J=12.4 Hz, 1H), 3.73 (ddd, J=11.5, 7.7, 6.0 Hz, 1H), 2.45 (s, 3H), 2.43-2.31 (m, 1H), 2.09-1.90 (m, 2H), 1.83-1.66 (m, 1H), 1.57 (dt, J=9.3, 3.9 Hz, 2H). LCMS (ESI) m/z 295, 297 (M+H).

Step 2: Synthesis of [5-methyl-1-(tetrahydro-2H-pyran-2-yl)-1H-indazol-4-yl]boronic acid (Int-1)

The reaction was carried out in two parallel batches. A stirred solution of 4-bromo-5-methyl-1-(tetrahydro-2H-pyran-2-yl)-1H-indazole (210.0 g, 711.44 mmol, 1.0 eq) and B(O-iPr)$_3$ (267.61 g, 1.42 mol, 2.0 eq) in THF (2.0 L) was cooled to −70° C. Then n-BuLi (526.5 mL, 1.32 mol, 1.85 eq) was added dropwise to above solution over a period of 3 hours, maintaining the reaction temperature between −70° C. and −65° C. After addition, the reaction mixture was stirred at −70° C. for 1 hour. TLC analysis (20% EtOAc/petroleum ether) showed consumption of the starting material. The mixture was quenched with a solution of saturated aq. NH$_4$Cl (2.0 L) and diluted with MTBE (2.0 L). The layers were separated and the aqueous layer was extracted with MTBE (1.0 L). The combined organics were washed with brine (1.5 L), dried over anhydrous Na$_2$SO$_4$, filtered, and concentrated at 25° C. The residue was dissolved in MTBE (300 mL). Petroleum ether (1.2 L) was added dropwise to the solution at 20° C. (room temperature). A white solid precipitated during the petroleum ether addition. The resultant suspension was filtered and the filter cake was washed with petroleum ether (800 mL). The filter cake was dried under vacuum to provide [5-methyl-1-(tetrahydro-2H-pyran-2-yl)-1H-indazol-4-yl]boronic acid (Int-1) (280.0 g, 76% yield) as a white solid. $^1$H NMR (400 MHz, DMSO-$d_6$) δ 8.29 (s, 2H), 7.89 (d, J=0.8 Hz, 1H), 7.55 (d, J=8.6 Hz, 1H), 7.19 (d, J=8.6 Hz, 1H), 5.77 (dd, J=9.7, 2.6 Hz, 1H), 3.91-3.83 (m, 1H), 3.72 (ddd, J=11.5, 7.8, 6.2 Hz, 1H), 2.45 (s, 3H), 2.39 (ddd, J=16.2, 8.4, 3.8 Hz, 1H), 2.10-1.97 (m, 1H), 1.91 (dq, J=13.0, 3.4 Hz, 1H), 1.80-1.67 (m, 1H), 1.57 (dq, J=9.0, 4.6 Hz, 2H). LCMS (ESI) m/z 261 (M+H).

Preparation of 5-chloro-1-(tetrahydro-2H-pyran-2-yl)-1H-indazol-4-ol (Int-2) as Shown in Scheme 2

Scheme 2:

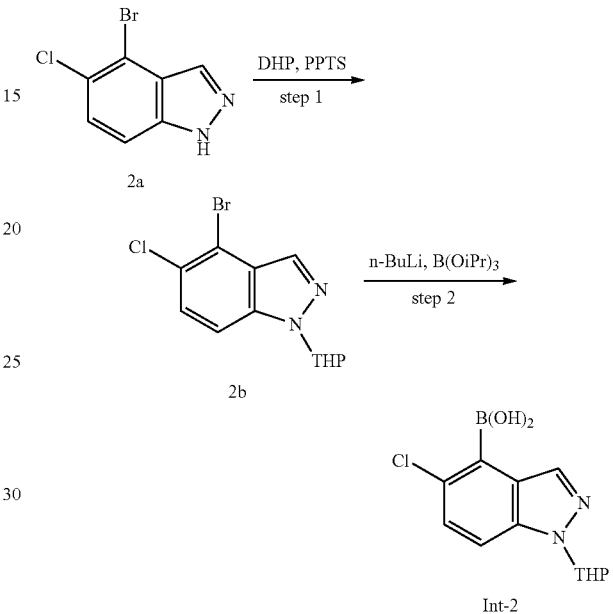

Step 1: Synthesis of 4-bromo-5-chloro-1-(tetrahydro-2H-pyran-2-yl)-1H-indazole (2b)

To a solution of 4-bromo-5-chloro-1H-indazole (2a) (950 mg, 4.10 mmol, 1.0 eq) in THF (50 mL) was added DHP (518 mg, 6.16 mmol, 1.5 eq) and PPTS (103 mg, 0.410 mmol, 0.1 eq). The mixture was stirred at 50° C. for 20 h. Another batch of DHP (173 mg, 2.05 mmol, 0.5 eq) was added and the resulting mixture was stirred at 50° C. for 16 h. LCMS analysis indicated the starting material was consumed to provide the product as a mixture of two regioisomers. The solvent was removed under reduced pressure. The crude product was purified by flash chromatography (SiO$_2$, 20 g, 10% EtOAc/petroleum ether) to provide 4-bromo-5-chloro-1-(tetrahydro-2H-pyran-2-yl)-1H-indazole (2b) as a white solid (850 mg, 66% yield). $^1$H NMR (400 MHz, DMSO-$d_6$) δ 8.11 (s, 1H), 7.84 (d, J=8.9 Hz, 1H), 7.61 (d, J=8.9 Hz, 1H), 5.93-5.88 (m, 1H), 3.87 (d, J=12.2 Hz, 1H), 3.77-3.72 (m, 1H), 2.37-2.32 (m, 1H), 2.01 (t, J=14.0 Hz, 2H), 1.73 (d, J=6.6 Hz, 1H), 1.58 (t, J=6.4 Hz, 2H). LCMS (ESI) m/z 315, 317 (M+H).

Step 2: Synthesis of [5-chloro-1-(tetrahydro-2H-pyran-2-yl)-1H-indazol-4-yl]boronic acid (Int-2)

To the mixture of 4-bromo-5-chloro-1-(tetrahydro-2H-pyran-2-yl)-1H-indazole (2b) (2.27 g, 7.193 mmol 1.0 eq) in THF (20 mL) was added n-BuLi (2.4 M in hexane, 4.5 mL, 10.8 mmol, 1.5 eq) at −70° C. The mixture was stirred at this temperature for 20 min. Trimethyl borate (2.24 g, 22 mmol, 3.0 eq) was added at −70° C. The mixture was stirred at this temperature for 20 min. LCMS analysis showed formation of the desired compound. The reaction was quenched with saturated aq. NH$_4$Cl and then extracted with EtOAc (2×30 mL). The combined organics were washed with brine, dried over anhydrous Na$_2$SO$_4$, concentrated, and purified with flash chromatography (SiO$_2$, 0→50% EtOAc/PE) to provide [5-chloro-1-(tetrahydro-2H-pyran-2-yl)-1H-indazol-4-yl] boronic acid (Int-2) as a white solid (1.42 g, 70% yield). $^1$H NMR (400 MHz, DMSO-d$_6$) δ 8.59 (s, 2H), 7.94 (d, J=0.8 Hz, 1H), 7.70 (dd, J=8.9, 0.9 Hz, 1H), 7.36 (d, J=8.8 Hz, 1H), 5.84 (dd, J=9.6, 2.6 Hz, 1H), 3.94-3.82 (m, 1H), 3.73 (ddd, J=11.5, 7.9, 5.8 Hz, 1H), 2.45-2.28 (m, 1H), 2.08-1.97 (m, 1H), 1.94 (dq, J=13.1, 3.6 Hz, 1H), 1.82-1.65 (m, 1H), 1.58 (tt, J=8.6, 3.7 Hz, 2H). LCMS (ESI) m/z 281 (M+H).

Preparation of 5-chloro-6-methyl-1-(tetrahydro-2H-pyran-2-yl)-4-(4,4,5,5-tetramethyl-1,3,2-dioxaborolan-2-yl)-1H-indazole (Int-3) as Shown in Scheme 3

Step 2: Synthesis of 2-bromo-3-chloro-6-fluoro-4-methylbenzaldehyde (3c)

To a solution of 1-bromo-2-chloro-5-fluoro-3-methylbenzene (3b) (13 g, 58 mmol, 1.0 eq) in THF (100 mL) was added LDA (2.0 M in THF, 35 mL, 1.2 eq) at −78° C. The mixture was stirred for 40 min and then DMF (6.5 mL) was added. The reaction was stirred for at −78° C. 1 hr. The reaction mixture was poured into H$_2$O (50 mL) and extracted with EtOAc (3×40 mL). The combined organics were dried over anhydrous Na$_2$SO$_4$ and concentrated to dryness. The crude residue was purified by flash chromatography (SiO$_2$, 0→15% EtOAc/PE) to provide 2-bromo-3-chloro-6-fluoro-4-methylbenzaldehyde (3c) (8.34 g, 57% yield) as a light yellow solid. $^1$H NMR (400 MHz, CDCl$_3$) δ 10.29 (s, 1H), 7.09 (d, J=10.6 Hz, 1H), 2.51 (s, 3H).

Scheme 3:

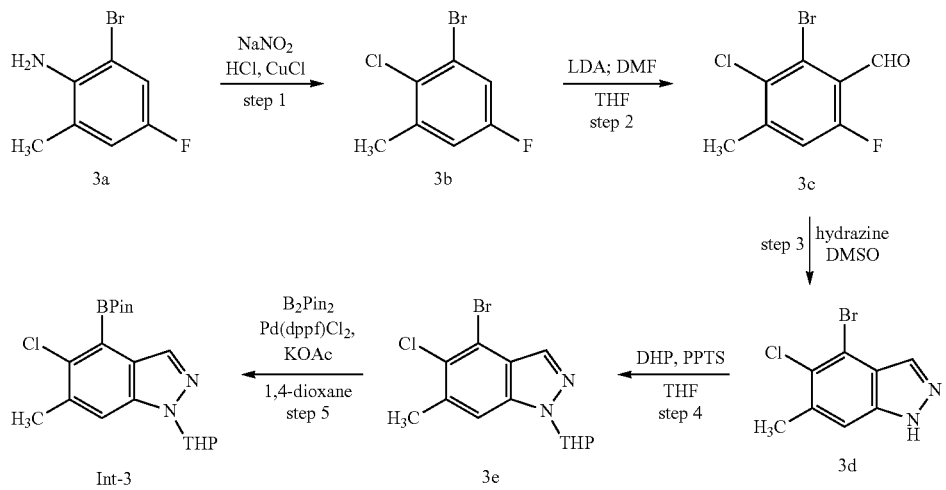

Step 1: Synthesis of 1-bromo-2-chloro-5-fluoro-3-methylbenzene (3b)

2-Bromo-4-fluoro-6-methylaniline (3a) (5 g, 24.5 mmol, 1.0 eq) was added to a solution of concentrated HCl (30 mL) and H$_2$O (30 mL) and the resulting mixture was stirred at 60-70° C. for 1 h. The mixture was cooled to 0-5° C., a solution of NaNO$_2$ (2.03 g, 29.4 mmol, 1.2 eq) in H$_2$O (10 mL) was added, and the reaction was stirred for 15 min. The mixture was added into a solution of CuCl (3.64 g, 36.8 mmol, 1.5 eq) in concentrated HCl (50 mL) and stirred at 70-80° C. for 30 min. The crude reaction mixture was cooled to room temperature and extracted with DCM (3×100 mL). The combined organics were dried over anhydrous Na$_2$SO$_4$, filtered, and concentrated to provide 1-bromo-2-chloro-5-fluoro-3-methylbenzene (3b) as a brown oil (4.5 g, 80% yield), which was taken on without further purification. $^1$H NMR (400 MHz, CDCl$_3$) δ 7.23 (dd, J=7.8, 2.9 Hz, 1H), 6.97-6.91 (m, 1H), 2.43 (s, 3H).

Step 3: Synthesis of 5-bromo-4-methoxy-1H-indazole (3d)

To a mixture of 2-bromo-3-chloro-6-fluoro-4-methylbenzaldehyde (3c) (220 mg, 0.875 mmol, 1.0 eq) in DMSO (5 mL) was added NH$_2$NH$_2$ (516 mg, 10.3 mmol, 12 eq). The mixture was stirred at 130° C. for 3 hrs. The reaction mixture was poured into H$_2$O (35 mL) and extracted with DCM (3×30 mL). The combined organics were dried over anhydrous Na$_2$SO$_4$ and concentrated to dryness. The crude residue was purified by flash chromatography (SiO$_2$, 0→20% EtOAc/PE) to provide 4-bromo-5-chloro-6-methyl-1H-indazole (3d) (108 mg, 50% yield) as a white powder. $^1$H NMR (400 MHz, CDCl$_3$) δ 8.02 (s, 1H), 7.33 (s, 1H), 2.56 (d, J=0.6 Hz, 3H). LCMS (ESI) m/z 245, 247 (M+H).

Step 4: Synthesis of 4-bromo-5-chloro-6-methyl-1H-indazole (3e)

4-Bromo-5-chloro-6-methyl-1-(tetrahydro-2H-pyran-2-yl)-1H-indazole (3e) (2.4 g, 59% yield) was prepared according to the procedure used to prepare 4-bromo-5- methyl-1-(tetrahydro2H-pyran-2-yl)-1H-indazole (1b) except the reaction was run in THF at 50° C. $^1$H NMR (400 MHz, CDCl$_3$) δ 7.94 (s, 1H), 7.43 (s, 1H), 5.66 (dd, J=9.0, 2.6 Hz, 1H), 3.99 (d, J=11.5 Hz, 1H), 3.80-3.64 (m, 1H), 2.56 (s, 3H), 2.54-2.46 (m, 1H), 2.15 (dd, J=8.1, 4.4 Hz, 1H), 2.11-2.03 (m, 1H), 1.79-1.64 (m, 3H). LCMS (ESI) m/z 329, 331 (M+H).

Step 5: Synthesis of 5-chloro-6-methyl-1-(tetrahydro-2H-pyran-2-yl)-4-(4,4,5,5-tetramethyl-1,3,2-dioxaborolan-2-yl)-1H-indazole (Int-3)

A mixture of 4-bromo-5-chloro-6-methyl-1-(tetrahydro-2H-pyran-2-yl)-1H-indazole (3e) (3 g, 9.1 mmol, 1.0 eq), 4,4,4',4',5,5,5',5'-octamethyl-2,2'-bi(1,3,2-dioxaborolane) (4.62 g, 18.2 mmol, 2.0 eq), KOAc (2.68 g, 27.3 mmol, 3.0 eq) and Pd(dppf)Cl$_2$ (0.666 g, 0.910 mmol, 0.1 eq) in 1,4-dioxane (25 mL) was stirred at 80° C. for 16 hrs. LCMS analysis showed complete consumption of the starting material. The reaction was cooled to 25° C. and concentrated to dryness. The residue was diluted with H$_2$O (30 mL) and extracted with EtOAc (3×30 mL). The combined organics were washed with brine (50 mL), dried over anhydrous Na$_2$SO$_4$, and concentrated to dryness. The crude residue was purified by flash chromatography (SiO$_2$, 0→20% EtOAc/PE) to provide 5-chloro-6-methyl-1-(tetrahydro-2H-pyran-2-yl)-4-(4,4,5,5-tetramethyl-1,3,2-dioxaborolan-2-yl)-1H-indazole (Int-3) (2.2 g, yield 63.7% yield) as a light yellow gum. $^1$H NMR (400 MHz, DMSO-d$_6$) δ 8.06 (s, 1H), 7.82 (s, 1H), 6.08-5.29 (m, 1H), 3.92-3.82 (m, 1H), 3.80-3.66 (m, 1H), 2.46 (s, 3H), 2.43-2.33(m, 1H), 2.08-2.00 (m, 1H), 1.97-1.88 (m, 1H), 1.80-1.67 (m, 1H), 1.63-1.53 (s, 2H), 1.38 (s, 12H); LCMS (ESI) m/z 377 (M+H).

Preparation of tert-butyl 4-(7-(((trifluoromethyl)sulfonyl)oxy)-5,6-dihydroquinazolin-4-yl)piperazine-1-carboxylate (Int-4) According to Scheme 4

Scheme 4:

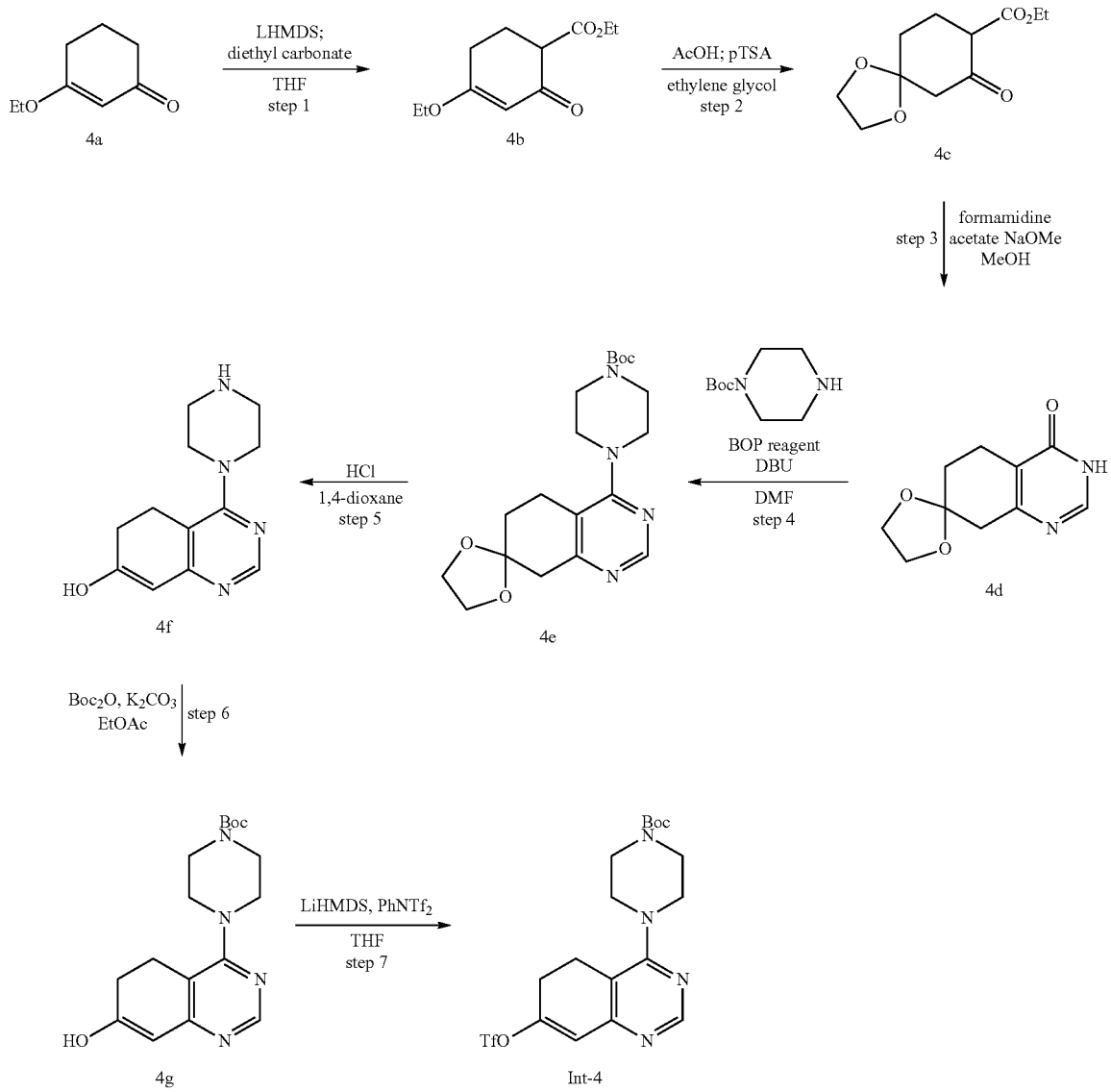

Step 1: Synthesis of ethyl 4-ethoxy-2-oxocyclohex-3-ene-1-carboxylate (4b)

To a solution of 3-ethoxycyclohex-2-en-1-one (4a) (50 g, 356.7 mmol, 1.0 eq) and diethyl carbonate (84.3 g, 713 mmol, 2.0 eq) in THF (600 mL) was added LHMDS (1.0 M in THF, 713 mL, 713 mmol, 2.0 eq) dropwise quickly at −78° C. The mixture was warmed to 20° C. and stirred for 16 h. Additional LHMDS (250 mL, 250 mmol, 1.0 M) was added and the mixture was stirred at 20° C. for 4 h. The mixture was poured into 1N HCl (1 L) and stirred for 1 h. The mixture was extracted with EtOAc (3×500 mL). The combined organics were washed with brine (400 mL) and dried over anhydrous $Na_2SO_4$. After filtration and concentration, the residue was washed with petroleum ether/EtOAc (10/1) to provide ethyl 4-ethoxy-2-oxocyclohex-3-ene-1-carboxylate (4b) as a yellow solid (57 g, 75% yield). $^1$H NMR (400 MHz, $CDCl_3$) δ 5.38 (s, 1H), 4.21 (q, J=7.1 Hz, 2H), 3.91 (qd, J=7.1, 2.2 Hz, 2H), 3.31 (dd, J=8.9, 5.0 Hz, 1H), 2.56 (dt, J=17.0, 5.4 Hz, 1H), 2.51-2.25 (m, 2H), 2.25-2.06 (m, 1H), 1.36 (t, J=7.0 Hz, 3H), 1.28 (t, J=7.1 Hz, 3H). LCMS (ESI) m/z 213 (M+H).

Step 2: Synthesis of 7-oxo-1,4-dioxaspiro[4.5]decane-8-carboxylate (4c)

A solution of ethyl 4-ethoxy-2-oxocyclohex-3-ene-1-carboxylate (4b) (220 g, 1.03 mol, 1.0 eq) in 70% aq. acetic acid (1.5 L) was stirred for 16 h at 60° C. The mixture was concentrated to dryness. The resultant residue was dried by azeotropic distillation from benzene (3×) to provide the crude diketone. To a solution of the diketone in benzene (800 mL) was added ethylene glycol (70 g, 1.13 mmol, 1.1 eq) and p-toluenesulfonic acid monohydrate (19.57 g, 1.03 mmol, 1.0 eq). The flask was capped with a Dean-Stark trap and the mixture was heated to reflux for 2 h. After cooling to room temperature the solution was made basic with saturated aq. $NaHCO_3$. The product was extracted with EtOAc (3×2 L). The combined organics were washed with brine, dried over $Na_2SO_4$, and evaporated to dryness. The crude residue was purified by flash chromatography ($SiO_2$, 2% EtOAc/hexanes) to provide ethyl 7-oxo-1,4-dioxaspiro[4.5]decane-8-carboxylate (4c) as yellow oil (48 g, 21% yield). $^1$H NMR (400 MHz, DMSO-$d_6$) δ 4.19 (q, J=7.1 Hz, 2H), 3.97-3.82 (m, 5H), 2.49-2.42 (m, 2H), 2.27 (t, J=6.5 Hz, 2H), 1.69 (t, J=6.5 Hz, 2H), 1.23 (t, J=7.1 Hz, 3H). LCMS (ESI) m/z 229 (M+H).

Step 3: Synthesis of 5',8'-dihydro-3'H-spiro[1,3-dioxolane-2,7'-quinazolin]-4'(6'H)-one (4d)

A mixture of ethyl 7-oxo-1,4-dioxaspiro[4.5]decane-8-carboxylate (4c) (48 g, 210.5 mmol, 1.0 eq), formamidine acetate (43.78 g, 421 mmol, 2.0 eq) and NaOMe (22.7 g, 421 mmol, 2.0 eq) in MeOH (500 mL) was refluxed for 4 h. The reaction mixture was concentrated to dryness and the residue was purified by flash chromatography ($SiO_2$, DCM/MeOH=20/1) to give 5',8'-dihydro-3'H-spiro[1,3-dioxolane-2,7'-quinazolin]-4'(6'H)-one (4d) as a yellow solid (29 g, 66% yield). $^1$H NMR (400 MHz, DMSO-$d_6$) δ 7.99 (s, 1H), 4.01-3.89 (m, 4H), 2.70 (s, 2H), 2.47 (dd, J=13.8, 7.3 Hz, 2H), 1.78 (t, J=6.6 Hz, 2H). LCMS (ESI) m/z 209 (M+H).

Step 4: Synthesis of tert-butyl 4-(5',8'-dihydro-6'H-spiro[1,3-dioxolane-2,7'-quinazolin]-4'-yl)piperazine-1-carboxylate (4e)

To a mixture of 5',8'-dihydro-3'H-spiro[1,3-dioxolane-2,7'-quinazolin]-4'(6'H)-one (4d) (29 g, 139.4 mmol, 1.0 eq), tert-butyl piperazine-1-carboxylate (38.9 g, 209.1 mmol, 1.5 eq) and BOP reagent (123.2 g, 278.8 mmol, 2.0 eq) in DMF (300 mL) was added DBU (63.56 g, 418.2 mmol, 3.0 eq) and the mixture was stirred at 20° C. for 16 h. EtOAc (500 mL) was added and the mixture was washed with $H_2O$ (3×300 mL). The organic phase was dried over anhydrous $Na_2SO_4$. After filtration and concentration, the residue was purified by flash chromatography ($SiO_2$, petroleum ether/EtOAc=2/3) to provide tert-butyl 4-(5',8'-dihydro-6'H-spiro[1,3-dioxolane-2,7'-quinazolin]-4'-yl)piperazine-1-carboxylate (4e) as yellow oil (25 g, 47.5% yield). $^1$H NMR (400 MHz, DMSO-$d_6$) δ 8.48 (s, 1H), 3.97 (td, J=6.4, 1.9 Hz, 4H), 3.46-3.42 (m, 4H), 3.32-3.27 (m, 4H), 2.92-2.89 (m, 2H), 2.68 (t, J=6.4 Hz, 2H), 1.81 (t, J=6.1 Hz, 2H), 1.42 (s, 9H). LCMS (ESI) m/z 377 (M+H).

Step 5: Synthesis of 4-(piperazin-1-yl)-5,6-dihydroquinazolin-7-ol (4f)

To a solution of tert-butyl 4-(5',8'-dihydro-6'H-spiro[1,3-dioxolane-2,7'-quinazolin]-4'-yl)piperazine-1-carboxylate (4e) (25 g, 66.31 mmol, 1.0 eq) in THF (300 mL) was added HCl (4.0 N in 1,4-dioxane, 60 mL, 240 mmol, 3.6 eq) and the mixture was stirred at 50° C. for 16 h. LCMS analysis showed consumption of the starting material. The mixture was concentrated to dryness to provide 4-(piperazin-1-yl)-5,6-dihydroquinazolin-7-ol (4f), which was taken on without further purification. LCMS (ESI) m/z 233 (M+H).

Step 6: Synthesis of tert-butyl 4-(7-oxo-5,6,7,8-tetrahydroquinazolin-4-yl)piperazine-1-carboxylate (4g)

A solution of crude 4-(piperazin-1-yl)-5,6-dihydroquinazolin-7-ol hydrochloride (40 in THF (300 mL), $H_2O$ (60 mL) and EtOAc (100 mL) was adjusted to pH=7 and $(Boc)_2O$ (15.18 g, 69.62 mmol, 1.05 eq) was added. Then $K_2CO_3$ (9.15 g, 66.31 mmol) was added and the mixture was stirred at 20° C. for 30 min. The mixture was extracted with EtOAc (2×400 mL). The combined organics were washed with brine (400 mL) and dried over anhydrous $Na_2SO_4$. After filtration and concentration, the residue was triturated with EtOAc/petroleum ether (1/40) to provide tert-butyl 4-(7-oxo-5,6,7,8-tetrahydroquinazolin-4-yl)piperazine-1-carboxylate (4g) (16 g, 73% yield, two steps) as a yellow solid. $^1$H NMR (400 MHz, $CDCl_3$) δ 8.62 (s, 1H), 3.68 (s, 2H), 3.57 (dd, J=6.2, 3.9 Hz, 4H), 3.44-3.32 (m, 4H), 2.92 (t, J=6.6 Hz, 2H), 2.65-2.52 (m, 2H), 1.49 (s, 9H). LCMS (ESI) m/z 333 (M+H).

Step 7: Synthesis of tert-butyl 4-(7-(((trifluoromethyl)sulfonyl)oxy)-5,6-dihydroquinazolin-4-yl)piperazine-1-carboxylate (Int-4)

To a 50 mL flask equipped with a magnetic stir bar was added tert-butyl 4-(7-oxo-5,6,7,8-tetrahydroquinazolin-4-yl)piperazine-1-carboxylate (4g) (1.0 g, 3.008 mmol, 1.0 eq) and THF (10 mL). The mixture was cooled to −78° C. LHMDS (1.0 M in THF, 3.01 mL, 3.01 mmol, 1.0 eq) was added. After 10 minutes $PhNTf_2$ (1.02 g, 2.86 mmol, 0.95 eq) was added. The mixture was stirred at −78° C. for 2 hours and then warmed to room temperature overnight. LCMS analysis indicated formation of the desired product and complete consumption of starting material. The mixture was quenched with 1 M aq. $NaHCO_3$ (10 mL) and extracted with EtOAc (3×30 mL). The combined organics were washed with water and brine and then dried over anhydrous MgSO₄. The mixture was filtered and concentrated to dryness to provide a residue, which was purified by flash chromatography (SiO₂, 0→60% EtOAc/heptanes) provide tert-butyl 4-(7-(((trifluoromethyl)sulfonyl)oxy)-5,6-dihydroquinazolin-4-yl)piperazine-1-carboxylate (Int-4) (1.4 g, 100% yield) as light yellow solid. ¹H NMR (400 MHz, CDCl₃) δ 8.66-8.59 (m, 1H), 6.62-6.42 (m, 1H), 3.62-3.49 (m, 4H), 3.38-3.22 (m, 4H), 3.00-2.87 (m, 2H), 2.78-2.65 (m, 2H), 1.49 (s, 9H). LCMS (ESI) m/z 465 (M+H).

Preparation of 6-chloro-5-methyl-1-(tetrahydro-2H-pyran-2-yl)-4-(4,4,5,5-tetramethyl-1,3,2-dioxaborolan-2-yl)-1H-indazole (Int-5) According to Scheme 5

NBS (20.9 g, 117 mmol) at 0° C. Then the mixture was warmed up to 25° C. and stirred for 1 h. LCMS analysis indicated that the starting material was consumed and the desired product was formed. The mixture was quenched with saturated aqueous NaHCO₃ and extracted with ethyl acetate (2×200 mL). The combined organic layers were washed with water and brine, dried over Na₂SO₄, filtered, and concentrated under reduced pressure. The residue was purified by flash chromatography (SiO₂, 120 g, petroleum ether/ethyl acetate=98:2) to provide 2-bromo-4-chloro-6-fluoro-3-methylaniline (5c) as a yellow solid (22.1 g, 79% yield). ¹H NMR (400 MHz, DMSO-d₆) δ 7.30 (d, J=10.9 Hz, 1H), 5.45 (s, 2H), 2.36 (d, J=1.0 Hz, 3H). LCMS (ESI) m/z 238, 240 (M+H).

Scheme 5:

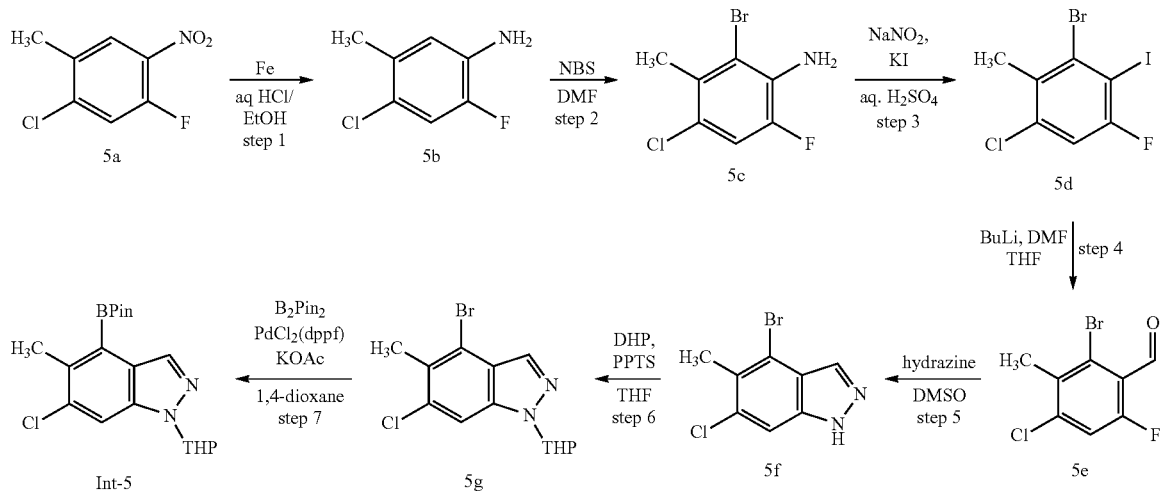

Step 1: Synthesis of 4-chloro-2-fluoro-5-methylaniline (5b)

To a solution of 1-chloro-5-fluoro-2-methyl-4-nitrobenzene (5a) (23.0 g, 121 mmol) in EtOH/H₂O (200 mL, 1:1) was added 12 M HCl (10.1 mL, 121 mmol). The mixture was heated to 80° C. and Fe (23.7 g, 425 mmol) was added slowly over a period of 30 minutes. The mixture was stirred at the same temperature for 1 h. LCMS analysis indicated the starting material was consumed and the desired product was formed. The mixture was cooled to 25° C., diluted with ethyl acetate (300 mL), and basified to pH=8~9 with saturated aqueous NaHCO₃. The layers were filtered separated, and the aqueous layer was extracted with ethyl acetate (2×300 mL). The combined organics were washed with brine, dried over Na₂SO₄, filtered, and concentrated under reduced pressure to provide 4-chloro-2-fluoro-5-methylaniline (5b) as a yellow solid (18.0 g, 93% yield). ¹H NMR (400 MHz, DMSO-d₆) δ 7.08 (d, J=11.1 Hz, 1H), 6.69 (d, J=9.6 Hz, 1H), 5.20 (s, 2H), 2.15 (s, 3H). LCMS (ESI) m/z 160, 162 (M+H).

Step 2: Synthesis of 2-bromo-4-chloro-6-fluoro-3-methylaniline (5c)

To a solution of 4-chloro-2-fluoro-5-methylaniline (5b) (18.7 g, 117 mmol) in DMF (150 mL) was slowly added

Step 3: Synthesis of 3-bromo-1-chloro-5-fluoro-4-iodo-2-methylbenzene (5d)

To a solution of concentrated H₂SO₄ (62 mL) in H₂O (250 mL) was added 2-bromo-4-chloro-6-fluoro-3-methylaniline (5c) (22.1 g, 93 mmol). The mixture was stirred at 25° C. for 10 min and cooled to 5° C. NaNO₂ (7.1 g, 102 mmol) in H₂O (20 mL) was added drop-wise. The resulting mixture was stirred at 5° C. for 20 minutes and added to a solution of KI (62 g, 370 mmol) in H₂O (50 mL), which was stirred at 5° C. for 20 minutes and then warmed to 25° C. for 18 h. TLC analysis (petroleum ether) indicated that the starting material was consumed. The mixture was quenched with water (150 mL) and extracted with ethyl acetate (2×500 mL). The combined organic layers were washed with saturated aqueous Na₂SO₃ and brine, dried over Na₂SO₄, filtered, and concentrated under reduced pressure. The residue was purified by flash chromatography (SiO₂, 120 g, petroleum ether) to provide 3-bromo-1-chloro-5-fluoro-4-iodo-2-methylbenzene (5d) as a light yellow solid (18 g, 56% yield). ¹H NMR (400 MHz, DMSO-d₆) δ 7.60 (d, J=7.8 Hz, 1H), 2.56 (d, J=1.1 Hz, 3H).

Step 4: Synthesis of 2-bromo-4-chloro-6-fluoro-3-methylbenzaldehyde (5e)

To a solution of 3-bromo-1-chloro-5-fluoro-4-iodo-2-methylbenzene (5d) (17.5 g, 50.1 mmol) in THF (100 mL)

was added drop-wise n-BuLi (2.5 M in hexanes, 20 mL, 50 mmol) at −100° C. The mixture was stirred at the same temperature for 30 minutes. Dry DMF (4.0 g, 55 mmol) was added and the mixture was stirred at −100° C. for 20 minutes. TLC (petroleum ether) indicated that almost all of the starting material was consumed and the desired product was formed. The crude reaction mixture was quenched with 1 N HCl. Water was added to the mixture and the aqueous layer was extracted with ethyl acetate (2×150 mL). The combined organic layers were washed with $H_2O$, dried over $Na_2SO_4$, filtered and concentrated under reduced pressure. The crude product was purified by flashchromatography ($SiO_2$, 120 g, petroleum ether/ethyl acetate=97:3) to provide 2-bromo-4-chloro-6-fluoro-3-methylbenzaldehyde (5e) as a yellow solid (8.6 g, 68% yield). $^1$H NMR (400 MHz, DMSO-$d_6$) δ 10.18 (s, 1H), 7.75 (d, J=10.4 Hz, 1H), 2.52-2.50 (m, 3H). LCMS (ESI) m/z 251, 253 (M+H).

Step 5: Synthesis of
4-bromo-6-chloro-5-methyl-1H-indazole (5f)

4-Bromo-6-chloro-5-methyl-1H-indazole (5f) (6.7 g, 80% yield) was prepared according to the procedure used to prepare 5-bromo-4-methoxy-1H-indazole (3d), except the reaction was done at 90° C. for 21 hours. $^1$H NMR (400 MHz, DMSO-$d_6$) δ 13.43 (s, 1H), 8.00 (d, J=0.8 Hz, 1H), 7.73 (s, 1H), 2.53 (s, 3H). LCMS (ESI) m/z 245, 247 (M+H).

Step 6: Synthesis of 4-bromo-6-chloro-5-methyl-1-(tetrahydro-2H-pyran-2-yl)-1H-indazole (5g)

4-Bromo-6-chloro-5-methyl-1-(tetrahydro-2H-pyran-2-yl)-1H-indazole (5g) (5.7 g, 73% yield) was prepared according to the procedure used to prepare 4-bromo-5-methyl-1-(tetrahydro-2H-pyran-2-yl)-1H-indazole (1b) except the reaction was done in THF at 80° C. $^1$H NMR (400 MHz, DMSO-$d_6$) δ 8.05 (s, 1H), 8.01 (s, 1H), 5.88 (dd, J=9.6, 2.4 Hz, 1H), 3.86 (d, J=12.1 Hz, 1H), 3.80-3.73 (m, 1H), 2.54 (s, 3H), 2.38-2.31 (m, 1H), 2.05-1.94 (m, 2H), 1.71 (dd, J=9.1, 3.3 Hz, 1H), 1.57 (dt, J=9.1, 4.6 Hz, 2H). LCMS (ESI) m/z 329, 331 (M+H).

Step 7: Synthesis of 6-chloro-5-methyl-1-(tetrahydro-2H-pyran-2-yl)-4-(4,4,5,5-tetramethyl-1,3,2-dioxaborolan-2-yl)-1H-indazole (Int-5)

A mixture of 4-bromo-6-chloro-5-methyl-1-(tetrahydro-2H-pyran-2-yl)-1H-indazole (7 g, 20 mmol), 4,4,4',4',5,5,5',5'-octamethyl-2,2'-bi(1,3,2-dioxaborolane) (5.93 g, 23.4 mmol), KOAc (6.25 g, 63.7 mmol) and Pd(dppf)Cl$_2$ (0.777 g, 1.06 mmol) in 1,4-dioxane (100 mL) was heated to 85° C. under $N_2$ for 16 hrs. LCMS analysis showed that most of the starting material was consumed. The mixture was cooled to 25° C. and filtered. The filtrate was concentrated. The residue was diluted with $H_2O$ (80 mL) and extracted with EtOAc (3×50 mL). The combined organics were washed with brine (50 mL), dried over anhydrous $Na_2SO_4$, and concentrated. The crude material was purified by flash chromatography ($SiO_2$, 0-10% EtOAc/petroleum ether) to afford 6-chloro-5-methyl-1-(tetrahydro-2H-pyran-2-yl)-4-(4,4,5,5-tetramethyl-1,3,2-dioxaborolan-2-yl)-1H-indazole (Int-5) (7.4 g, 90% yield, 65% purity) as a white solid, which was contaminated with 6-chloro-5-methyl-1-(tetrahydro-2H-pyran-2-yl)-1H-indazole. $^1$H NMR (400 MHz, DMSO) δ 8.19 (s, 1H), 8.01 (s, 1H), 5.85 (dd, J=9.6, 2.5 Hz, 1H), 3.90-3.82 (m, 1H), 3.80-3.68 (m, 1H), 2.59 (s, 3H), 2.44-2.26 (m, 1H), 2.10-1.98 (m, 1H), 1.97-1.86 (m, 1H), 1.79-1.66 (m, 1H), 1.64-1.50 (m, 2H), 1.38 (s, 12H). LCMS (ESI) m/z 377, 379 (M+H).

Preparation of Examples

Example A1 (Scheme A)

1-{4-[7-(5-methyl-1H-indazol-4-yl)-5,6,7,8-tetrahydroquinazolin-4-yl]piperazin-1-yl}prop-2-en-1-one Example A2 (Scheme A)

1-{4-[(7R)-7-(5-methyl-1H-indazol-4-yl)-5,6,7,8-tetrahydroquinazolin-4-yl]piperazin-1-yl}prop-2-en-1-one Example A3 (Scheme A)

1-{4-[(7S)-7-(5-methyl-1H-indazol-4-yl)-5,6,7,8-tetrahydroquinazolin-4-yl]piperazin-1-yl}prop-2-en-1-one Scheme A:

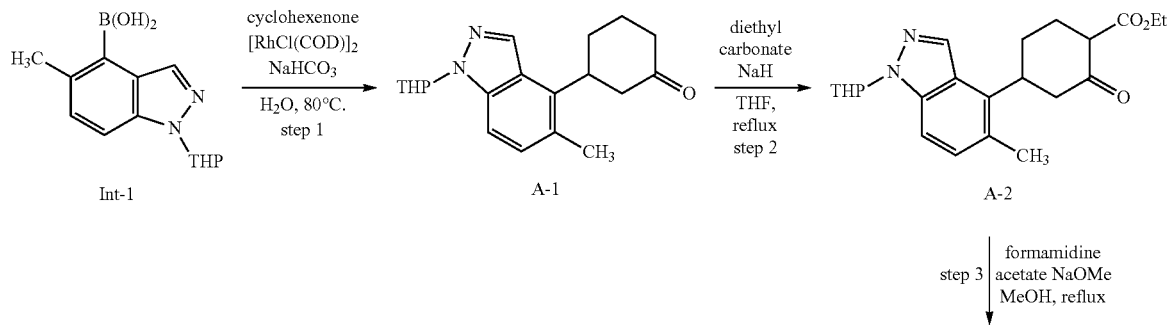

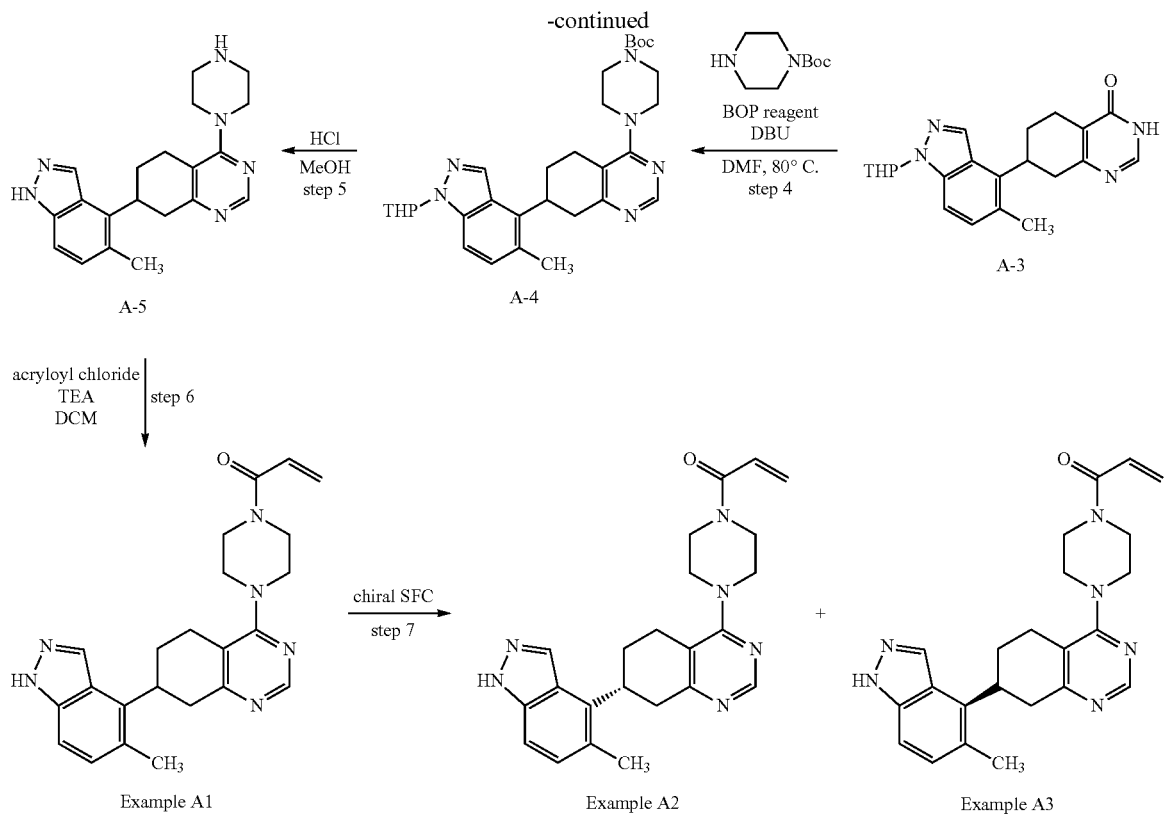

Step 1: Synthesis of 3-[5-methyl-1-(tetrahydro-2H-pyran-2-yl)-1H-indazol-4-yl]cyclohexanone (A-1)

To a 25 mL flask equipped with a magnetic stir bar was added the [5-methyl-1-(tetrahydro-2H-pyran-2-yl)-1H-indazol-4-yl]boronic acid (Int-1) (650 mg, 2.5 mmol, 1.0 eq), [RhCl(COD)]$_2$ (61.6 mg, 0.125 mmol, 0.05 eq) and NaHCO$_3$ (620 mg, 5.0 mmol, 2.0 eq). The flask was purged with nitrogen and then water (12.5 mL) and cyclohexenone (721 mg, 7.5 mmol, 3.0 eq) were added. The mixture was stirred at 80° C. overnight. LCMS analysis indicated complete consumption of the boronic acid. The reaction was cooled to room temperature. The mixture was poured into a separatory funnel and extracted with EtOAc (2×25 mL). The combined organics were dried over anhydrous Na$_2$SO$_4$, filtered and concentrated. Purification by flash chromatography (Biotage, 25 g SiO$_2$, 25% EtOAc/heptanes) provided the 3-[5-methyl-1-(tetrahydro-2H-pyran-2-yl)-1H-indazol-4-yl]cyclohexanone (A-1) (1:1 mixture of diastereoisomers, 680 mg, 87% yield) as clear oil, which solidified to an off-white solid upon standing. $^1$H NMR (400 MHz, CDCl$_3$) δ 8.18 (s, 1H), 7.39 (dd, J=8.5, 3.2 Hz, 1H), 7.22 (d, J=8.6 Hz, 1H), 5.71 (dt, J=9.5, 2.5 Hz, 1H), 4.05 (d, J=12.3 Hz, 1H), 3.84-3.69 (m, 1H), 3.54 (tt, J=13.1, 3.9 Hz, 1H), 3.01 (t, J=13.9 Hz, 1H), 2.68-2.48 (m, 4H), 2.43 (s, 3H), 2.41-2.35 (m, 1H), 2.34-2.22 (m, 1H), 2.19 (s, 1H), 2.12-1.92 (m, 2H), 1.94-1.75 (m, 3H), 1.69 (d, J=3.1 Hz, 1H). LCMS (ESI) m/z 313 (M+H).

Step 2: Synthesis of 3-[5-methyl-1-(tetrahydro-2H-pyran-2-yl)-1H-indazol-4-yl]cyclohexanone (A-2)

To a 50 mL flask equipped with a magnetic stir bar was added 3-[5-methyl-1-(tetrahydro-2H-pyran-2-yl)-1H-indazol-4-yl]cyclohexanone (A-1) (677 mg, 2.2 mmol, 1.0 eq), diethyl carbonate (3 mL) and THF (6 mL). Sodium hydride (60% dispersion in mineral oil, 217 mg, 5.4 mmol, 2.5 eq) was added in one portion. The flask was equipped with a reflux condenser and then the mixture was heated to 70° C. After 1 hour the reaction was checked by LCMS, which indicated consumption of the starting material and formation of the product as a complex mixture of diastereoisomers. The reaction was poured into a separatory funnel, diluted with EtOAc, and washed with saturated aq. NH$_4$Cl. The aqueous layer was extracted with EtOAc. The combined organics were washed with brine, dried over anhydrous MgSO$_4$, filtered, and concentrated. The crude residue was purified by flash chromatography (Biotage, 25 g SiO$_2$, 10→25% EtOAc/heptanes) to provide 3-[5-methyl-1-(tetrahydro-2H-pyran-2-yl)-1H-indazol-4-yl]cyclohexanone (A-2) as a yellow oil (680 mg, 82% yield), which was taken on without further purification. LCMS (ESI) m/z 385 (M+H).

Step 3: Synthesis of 7-[5-methyl-1-(tetrahydro-2H-pyran-2-yl)-1H-indazol-4-yl]-5,6,7,8-tetrahydroquinazolin-4(3H)-one (A-3)

To a 2 dram vial equipped with a magnetic stir bar was added the ethyl 4-[5-methyl-1-(tetrahydro-2H-pyran-2-yl)-1H-indazol-4-yl]-2-oxocyclohexanecarboxylate (A-2) (384 mg, 1.0 mmol, 1.0 eq) and formamidine acetate (521 mg, 5.0 mmol, 5.0 eq). Sodium methoxide (0.5 M in MeOH, 20 mL, 10.0 mmol, 10 eq) was added and the mixture was heated to reflux overnight. The reaction was cooled to room temperature and concentrated to dryness. The residue was dissolved in EtOAc and washed with saturated aq. NH$_4$Cl. The aqueous layer was extracted with EtOAc. The combined organics were dried over anhydrous $Na_2SO_4$, filtered, and concentrated. The residue was purified by flash chromatography (Biotage, 10 g $SiO_2$, 100% EtOAc→15% EtOH/EtOAc) to provide 7-[5-methyl-1-(tetrahydro-2H-pyran-2-yl)-1H-indazol-4-yl]-5,6,7,8-tetrahydroquinazolin-4(3H)-one (A-3) as a white solid (1:1 mixture of diastereoisomers, 364 mg, 48% yield). $^1$H NMR (400 MHz, $CDCl_3$) δ 8.06 (s, 1H), 8.03 (s, 1H), 7.39 (d, J=8.5 Hz, 1H), 7.23 (d, J=8.6 Hz, 1H), 5.70 (dd, J=9.4, 2.7 Hz, 1H), 4.04 (d, J=11.6 Hz, 1H), 3.74 (td, J=11.1, 2.8 Hz, 1H), 3.52 (tdd, J=12.4, 5.2, 2.9 Hz, 1H), 3.24 (dd, J=17.3, 11.7 Hz, 1H), 2.98 (dd, J=17.3, 5.0 Hz, 1H), 2.88 (dd, J=18.4, 4.6 Hz, 1H), 2.67-2.52 (m, 2H), 2.46 (s, 3H), 2.39-2.23 (m, 1H), 2.20-2.02 (m, 3H), 1.81-1.61 (m, 3H). LCMS (ESI) m/z 365 (M+H).

Step 4: Synthesis of tert-butyl 4-{7-[5-methyl-1-(tetrahydro-2H-pyran-2-yl)-1H-indazol-4-yl]-5,6,7,8-tetrahydroquinazolin-4-yl}piperazine-1-carboxylate (A-4)

To a 10 mL flask equipped with a magnetic stir bar was added 7-[5-methyl-1-(tetrahydro-2H-pyran-2-yl)-1H-indazol-4-yl]-5,6,7,8-tetrahydroquinazolin-4(3H)-one (A-3) (364 mg, 1.0 mmol, 1.0 eq), DMF (2.5 mL), DBU (304 mg, 2.0 mmol, 2.0 eq), BOP reagent (464 mg, 1.05 mmol, 1.05 eq) and tert-butyl piperazine-1-carboxylate (233 mg, 1.25 mmol, 1.25 eq). The mixture was heated to 65° C. overnight. LCMS analysis indicated conversion to the desired product as a 1:1 mixture of diastereoisomers. The reaction was cooled to room temperature and water was added. A white solid was formed, which was collected by filtration. The filter cake was washed with water and dried under vacuum. The resultant solid was dissolved in EtOAc (30 mL) and washed with 0.1 N HCl (2×20 mL) and brine. The organic solution was dried over anhydrous $Na_2SO_4$, filtered, and concentrated. Purification by flash chromatography (Biotage, 25 g $SiO_2$, 60→100% EtOAc/heptanes) provided tert-butyl 4-{7-[5-methyl-1-(tetrahydro-2H-pyran-2-yl)-1H-indazol-4-yl]-5,6,7,8-tetrahydroquinazolin-4-yl}piperazine-1-carboxylate as an off-white solid (1:1 mixture of diastereoisomers, 327 mg, 61% yield). $^1$H NMR (400 MHz, $CDCl_3$) δ 8.55 (d, J=1.6 Hz, 1H), 7.93 (s, 1H), 7.32 (t, J=7.9 Hz, 1H), 7.16 (d, J=8.6 Hz, 1H), 5.62 (ddd, J=9.5, 4.2, 2.8 Hz, 1H), 4.00-3.88 (m, 1H), 3.73-3.62 (m, 1H), 3.56 (t, J=3.5 Hz, 3H), 3.43 (d, J=9.9 Hz, 4H), 3.30-3.16 (m, 3H), 3.08 (dd, J=18.8, 6.3 Hz, 1H), 2.81-2.61 (m, 3H), 2.56-2.43 (m, 1H), 2.40 (s, 3H), 2.24-1.99 (m, 4H), 1.75-1.63 (m, 2H), 1.42 (s, 9H). LCMS (ESI) m/z 533 (M+H).

Step 5: Synthesis of 7-(5-methyl-1H-indazol-4-yl)-4-(piperazin-1-yl)-5,6,7,8-tetrahydroquinazoline (A-5)

To a 25 mL flask equipped with a magnetic stir bar was added tert-butyl 4-{7-[5-methyl-1-(tetrahydro-2H-pyran-2-yl)-1H-indazol-4-yl]-5,6,7,8-tetrahydroquinazolin-4-yl}piperazine-1-carboxylate (A-4) (325 mg, 0.61 mmol, 1.0 eq), MeOH (6.1 mL) and HCl (4.0 N in 1,4-dioxane, 3.1 mL, 12.2 mmol, 20 eq). The reaction was left to stir overnight. LCMS analysis indicated formation of the fully deprotected product. The reaction was concentrated to dryness to provide 7-(5-methyl-1H-indazol-4-yl)-4-(piperazin-1-yl)-5,6,7,8-tetrahydroquinazoline (A-5) (214 mg, 100% yield) as a brown oil, which was taken onto the next step without further purification. LCMS (ESI) m/z 349 (M+H).

Step 6: Synthesis of 1-{4-[7-(5-methyl-1H-indazol-4-yl)-5,6,7,8-tetrahydroquinazolin-4-yl]piperazin-1-yl}prop-2-en-1-one (Example A1)

To a 25 mL flask equipped with a magnetic stir bar was added 7-(5-methyl-1H-indazol-4-yl)-4-(piperazin-1-yl)-5,6,7,8-tetrahydroquinazoline (A-5) (34.8 mg, 0.1 mmol, 1.0 eq), DCM (4 mL), TEA (101 mg, 1.0 mmol, 10 eq), and acryloyl chloride (13.6 mg, 0.15 mmol, 1.5 eq). After 2 hours the reaction was checked by LCMS, which showed conversion to the desired product. The reaction was concentrated to dryness and purified by flash chromatography (Biotage, 10 g $SiO_2$, 20% EtOH/EtOAc) to provide 1-{4-[7-(5-methyl-1H-indazol-4-yl)-5,6,7,8-tetrahydroquinazolin-4-yl]piperazin-1-yl}prop-2-en-1-one as a white solid (14.7 mg, 37% yield). $^1$H NMR (400 MHz, $CDCl_3$) δ 8.58 (s, 1H), 7.90 (s, 1H), 7.29 (d, J=9.9 Hz, 1H), 7.14 (d, J=8.5 Hz, 1H), 6.53 (dd, J=16.7, 10.6 Hz, 1H), 6.27 (dd, J=16.8, 1.7 Hz, 1H), 5.74 (dd, J=10.6, 1.7 Hz, 1H), 4.11-3.63 (m, 9H), 3.25-3.15 (m, 2H), 3.01-2.83 (m, 1H), 2.84-2.70 (m, 1H), 2.39 (s, 3H), 2.32-2.06 (m, 2H). LCMS (ESI) m/z 403 (M+H).

Step 7: Synthesis of 1-{4-[(7R)-7-(5-methyl-1H-indazol-4-yl)-5,6,7,8-tetrahydroquinazolin-4-yl]piperazin-1-yl}prop-2-en-1-one (Example A2) and 1-{4-[(7S)-7-(5-methyl-1H-indazol-4-yl)-5,6,7,8-tetrahydroquinazolin-4-yl]piperazin-1-yl}prop-2-en-1-one (Example A3)

To a 25 mL flask equipped with a magnetic stir bar was added 7-(5-methyl-1H-indazol-4-yl)-4-(piperazin-1-yl)-5,6,7,8-tetrahydroquinazoline (214 mg, 0.614 mmol, 0.614 eq), DCM (10 mL), TEA (621 mg, 6.14 mmol, 10 eq), and acryloyl chloride (83.3 mg, 0.92 mmol, 1.5 eq). After 1 hour the reaction was the reaction was concentrated to dryness. The residue was purified by chiral SFC on a Chrialpak AD-3 (4.6 mm×100 mm, 3 micron particle size) column which was eluted with 40% IPA in $CO_2$ held at 25° C. at 120 bar. A flow rate of 4.0 mL/min gave $Rt_{(Peak\ 1)}$=1.62 min, and $Rt_{(Peak\ 2)}$=1.62 min. 1-{4-[(7R)-7-(5-Methyl-1H-indazol-4-yl)-5,6,7,8-tetrahydroquinazolin-4-yl]piperazin-1-yl}prop-2-en-1-one (Example A2) (Peak 1): 36 mg, >99% ee, 15% yield. $^1$H NMR (400 MHz, DMSO-$d_6$) δ 12.94 (s, 1H), 8.52 (s, 1H), 8.11 (s, 1H), 7.30 (d, J=8.4 Hz, 1H), 7.17 (d, J=8.5 Hz, 1H), 6.85 (dd, J=16.7, 10.4 Hz, 1H), 6.15 (dd, J=16.7, 2.4 Hz, 1H), 5.72 (dd, J=10.4, 2.4 Hz, 1H), 3.85-3.70 (m, 2H), 3.69-3.57 (m, 3H), 3.55-3.48 (m, 2H), 3.30-3.23 (m, 2H), 3.20-3.07 (m, 1H), 3.05-2.88 (m, 2H), 2.70 (d, J=16.7 Hz, 1H), 2.43 (s, 3H), 2.36-2.20 (m, 1H), 2.00 (d, J=12.4 Hz, 1H); $[α]_d^{22}$=−44.0° (C=0.1, $CHCl_3$); LCMS (ESI) m/z 403 (M+H). 1-{4-[(7S)-7-(5-Methyl-1H-indazol-4-yl)-5,6,7,8-tetrahydroquinazolin-4-yl]piperazin-1-yl}prop-2-en-1-one (Example A3) (Peak 2): 34.3 mg, ~98% ee, 14% yield. $^1$H NMR (400 MHz, DMSO-$d_6$) δ 12.94 (s, 1H), 8.52 (s, 1H), 8.11 (s, 1H), 7.30 (d, J=8.5 Hz, 1H), 7.17 (d, J=8.5 Hz, 1H), 6.85 (dd, J=16.7, 10.5 Hz, 1H), 6.15 (dd, J=16.7, 2.4 Hz, 1H), 5.72 (dd, J=10.5, 2.4 Hz, 1H), 3.86-3.69 (m, 2H), 3.70-3.57 (m, 3H), 3.57-3.44 (m, 2H), 3.30-3.22 (m, 2H), 3.15 (dd, J=18.3, 11.5 Hz, 1H), 3.04-2.87 (m, 2H), 2.70 (d, J=16.3 Hz, 1H), 2.43 (s, 3H), 2.35-2.19 (m, 1H), 2.00 (d, J=12.3 Hz, 1H); $[α]_d^{22}$=+53.3° (C=0.2, $CHCl_3$); LCMS (ESI) m/z 403 (M+H).

The examples in Table A were prepared using similar chemistry in Scheme A and the procedure used to prepare 1-{4-[7-(5-methyl-1H-indazol-4-yl)-5,6,7,8-tetrahydroquinazolin-4-yl]piperazin-1-yl}prop-2-en-1-one (Example A1) and [(6R,7R)-rel-7-(5-methyl-1H-indazol-4-yl)-4-(piperazin-1-yl)-5,6,7,8-tetrahydroquinazolin-6-yl]methanol (A-7). The following examples were made with non-critical changes or substitutions to the exemplified procedure used to prepare Example A1 that someone who is skilled in the art would be able to realize.

TABLE A

| Example | Structure | Compound name | LCMS m/z | Analytical data |
|---|---|---|---|---|
| A4 | 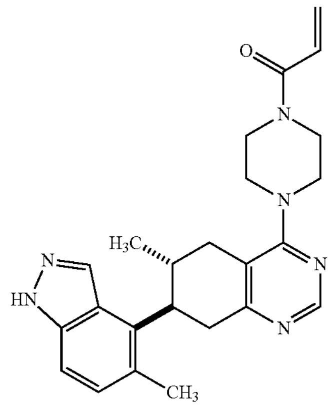 | 1-{4-[(6R,7R)-rel-6-methyl-7-(5-methyl-1H-indazol-4-yl)-5,6,7,8-tetrahydroquinazolin-4-yl]piperazin-1-yl}prop-2-en-1-one | 417 (M + H) | $^1$H NMR (400 MHz, CDCl$_3$) δ 8.63 (s, 1H), 8.02 (s, 1H), 7.30 (d, J = 8.5 Hz, 1H), 7.23 (d, J = 8.5 Hz, 1H), 6.62 (dd, J = 16.8, 10.5 Hz, 1H), 6.35 (dd, J = 16.8, 1.9 Hz, 1H), 5.76 (dd, J = 10.5, 1.9 Hz, 1H), 3.84 (s, 3H), 3.69-3.50 (m, 3H), 3.49-3.26 (m, 4H), 3.23-3.12 (m, 1H), 2.91-2.75 (m, 1H), 2.47 (s, 5H), 0.83 (d, J = 5.2 Hz, 3H). |
| A5 | 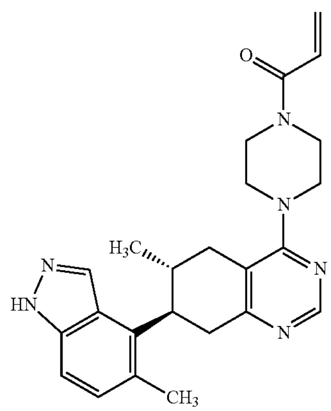 [SMILES: C=CC(=O)N1CCN(c2ncnc3c2C[C@@H](C)[C@H](c2c(C)ccc4[nH]ncc24)C3)CC1] | 1-{4-[(6R,7R)-6-methyl-7-(5-methyl-1H-indazol-4-yl)-5,6,7,8-tetrahydroquinazolin-4-yl]piperazin-1-yl}prop-2-en-1-one | 417 (M + H) | $^1$H NMR (400 MHz, DMSO-d$_6$) δ 12.95 (s, 1H), 8.50 (s, 1H), 8.07 (s, 1H), 7.30 (d, J = 8.4 Hz, 1H), 7.18 (d, J = 8.5 Hz, 1H), 6.85 (dd, J = 16.7, 10.4 Hz, 1H), 6.15 (dd, J = 16.7, 2.4 Hz, 1H), 5.72 (dd, J = 10.4, 2.4 Hz, 1H), 3.85-3.72 (m, 2H), 3.70-3.47 (m, 4H), 3.40 (dd, J = 10.6, 6.5 Hz, 1H), 3.28 (br s, 2H), 3.21-3.07 (m, 1H), 2.98 (dd, J = 18.5, 6.3 Hz, 1H), 2.73 (dd, J = 16.1, 4.3 Hz, 1H), 2.64 (t, J = 13.0 Hz, 1H), 2.43 (s, 4H), 0.72 (d, J = 6.3 Hz, 3H). <br> >99% ee <br> $[α]_d^{22}$ = −38.8° (C = 0.1, CHCl$_3$); |
| A6 | 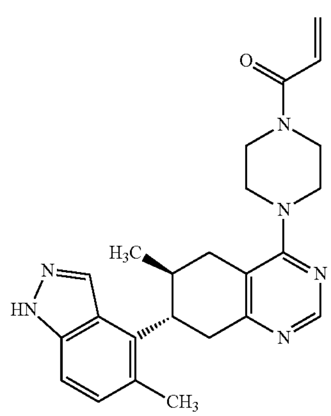 [SMILES: C=CC(=O)N1CCN(c2ncnc3c2C[C@H](C)[C@@H](c2c(C)ccc4[nH]ncc24)C3)CC1] | 1-{4-[(6S,7S)-6-methyl-7-(5-methyl-1H-indazol-4-yl)-5,6,7,8-tetrahydroquinazolin-4-yl]piperazin-1-yl}prop-2-en-1-one | 417 (M + H) | $^1$H NMR (400 MHz, DMSO-d$_6$) δ 12.96 (s, 1H), 8.51 (s, 1H), 8.08 (s, 1H), 7.31 (d, J = 8.4 Hz, 1H), 7.18 (d, J = 8.5 Hz, 1H), 6.86 (dd, J = 16.8, 10.5 Hz, 1H), 6.16 (d, J = 16.8 Hz, 1H), 5.94-5.30 (m, 1H), 3.79 (s, 2H), 3.72-3.46 (m, 4H), 3.46-3.37 (m, 1H), 3.28 (br s, 2H), 3.17 (dd, J = 18.2, 11.9 Hz, 1H), 2.99 (dd, J = 18.9, 6.1 Hz, 1H), 2.74 (d, J = 15.4 Hz, 1H), 2.65 (t, J = 12.8 Hz, 1H), 2.43 (s, 4H), 0.73 (d, J = 6.4 Hz, 3H). <br> ~98% ee <br> $[α]_d^{22}$ = +32.0° (C = 0.1, CHCl$_3$); |

TABLE A-continued

| Example | Structure | Compound name | LCMS m/z | Analytical data |
|---|---|---|---|---|
| A8 | 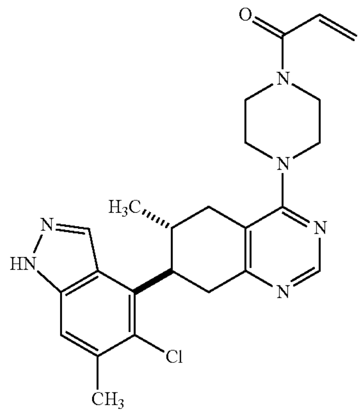 | 1-{4-[(6R,7R)-rel-7-(5-chloro-6-methyl-1H-indazol-4-yl)-6-methyl-5,6,7,8-tetrahydroquinazolin-4-yl]piperazin-1-yl}prop-2-en-1-one | 451 (M + H) | $^1$H NMR (400 MHz, DMSO) δ 13.17 (s, 1H), 8.52 (s, 1H), 8.21 (s, 1H), 7.45 (s, 1H), 6.85 (dd, J = 16.7, 10.5 Hz, 1H), 6.16 (dd, J = 16.7, 2.3 Hz, 1H), 5.73 (dd, J = 10.4, 2.3 Hz, 1H), 3.92-3.71 (m, 3H), 3.71-3.50 (m, 4H), 3.33 (m, 3H), 3.17 (m, 1H), 2.98 (dd, J = 18.4, 6.0 Hz, 1H), 2.81-2.60 (m, 2H), 2.47 (s, J = 10.8 Hz, 3H), 0.76 (m, J = 8.8 Hz, 3H) |
| A9 | 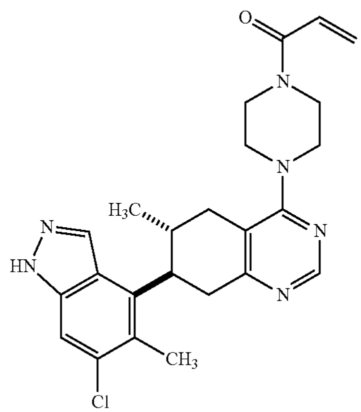 | 1-{4-[(6R,7R)-rel-7-(6-chloro-5-methyl-1H-indazol-4-yl)-6-methyl-5,6,7,8-tetrahydroquinazolin-4-yl]piperazin-1-yl}prop-2-en-1-one | 451 (M + H) | $^1$H NMR (400 MHz, DMSO) δ 13.10 (s, 1H), 8.51 (s, 1H), 8.17 (s, 1H), 7.55 (s, 1H), 6.85 (dd, J = 16.7, 10.5 Hz, 1H), 6.16 (dd, J = 16.7, 2.4 Hz, 1H), 5.73 (dd, J = 10.4, 2.4 Hz, 1H), 3.79 (m, 2H), 3.64 (m, 2H), 3.59-3.46 (m, 3H), 3.30 (m, 3H), 3.16 (m, 1H), 3.02 (m, 1H), 2.78-2.65 (m, 2H), 2.49 (s, 3H), 0.71 (d, J = 6.4 Hz, 3H). |

The intermediate A-6 detailed in the following preparation afford Example A7 according to method A. However, this example fall outside of the synthetic scope of the preceding examples due a required deprotection step and this chemistry is included below for completeness. Subsequent chemistry to afford final examples is similar to the Method A examples, with minimal additions or changes that one skilled in the art can appreciate.

Synthesis of [(6R,7R)-rel-7-(5-methyl-1H-indazol-4-yl)-4-(piperazin-1-yl)-5,6,7,8-tetrahydroquinazolin-6-yl]methanol (A-7)

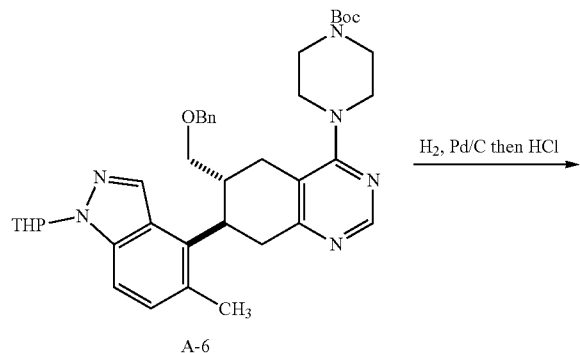

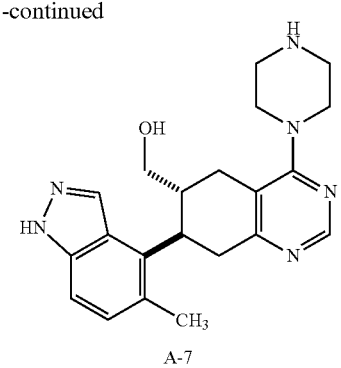

A-7

To a 10 mL stainless steel reaction vessel was added tert-butyl 4-{(6R,7R)-rel-6-[(benzyloxy)methyl]-7-[5-methyl-1-(tetrahydro-2H-pyran-2-yl)-1H-indazol-4-yl]-5,6,7,8-tetrahydroquinazolin-4-yl}piperazine-1-carboxylate (A-6) (340 mg, 0.52 mmol, 1.0 eq), MeOH (5.2 mL), and HCl (4.0 N in 1,4-dioxane, 0.26 mL, 1.0 mmol, 2.0 eq). Pd/C (10% loading, 70 mg) was added and the vessel was pressurized with H$_2$ to 8 bar and heated to 50° C. overnight. LCMS analysis showed complete debenzylation with partial deprotection of the THP and Boc groups. The crude reaction was filtered through a thin pad of celite. The mixture was concentrated on the rotovap and then dissolved in MeOH (6 mL). Additional HCl (4.0 N in 1,4-dioxane, 1.3 mL, 5.2 mmol, 10 eq) was added to induce complete deprotection.

The mixture was left to stir overnight. The mixture was concentrated to dryness to provide [(6R,7R)-rel-7-(5-methyl-1H-indazol-4-yl)-4-(piperazin-1-yl)-5,6,7,8-tetrahydroquinazolin-6-yl]methanol (A-7) as an off-white solid (195 mg, 99% yield), which was taken on without further purification. LCMS (ESI) m/z 379 (M+H).

| A7 | 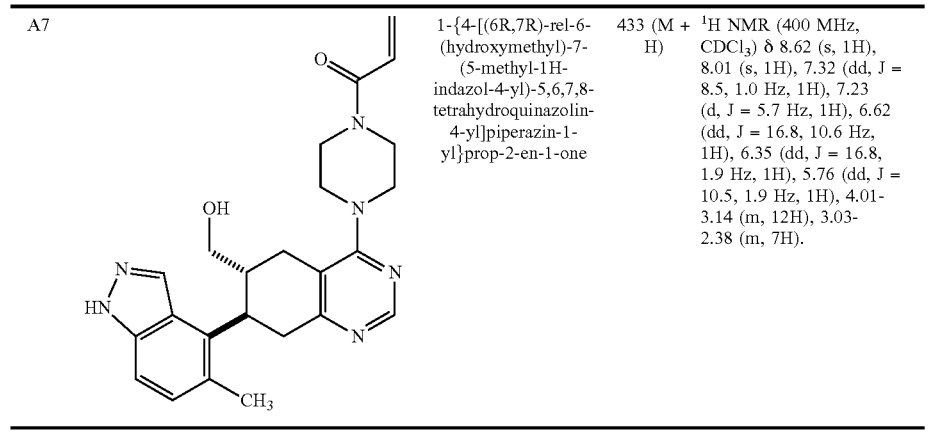 | 1-{4-[(6R,7R)-rel-6-(hydroxymethyl)-7-(5-methyl-1H-indazol-4-yl)-5,6,7,8-tetrahydroquinazolin-4-yl]piperazin-1-yl}prop-2-en-1-one | 433 (M + H) | ¹H NMR (400 MHz, CDCl₃) δ 8.62 (s, 1H), 8.01 (s, 1H), 7.32 (dd, J = 8.5, 1.0 Hz, 1H), 7.23 (d, J = 5.7 Hz, 1H), 6.62 (dd, J = 16.8, 10.6 Hz, 1H), 6.35 (dd, J = 16.8, 1.9 Hz, 1H), 5.76 (dd, J = 10.5, 1.9 Hz, 1H), 4.01-3.14 (m, 12H), 3.03-2.38 (m, 7H). |

Example B1 (Scheme B)

1-{6-[7-(5-methyl-1H-indazol-4-yl)-5,6,7,8-tetrahydroquinazolin-4-yl]-2,6-diazaspiro[3.3]hept-2-yl}prop-2-en-1-one was prepared in library format Scheme B:

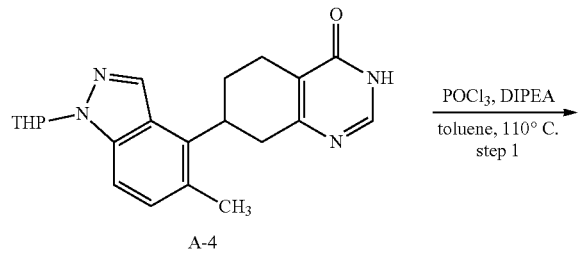

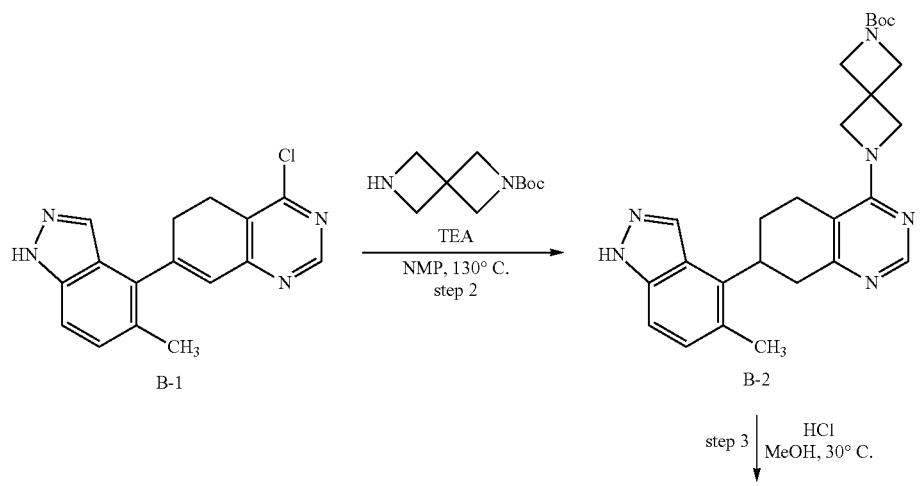

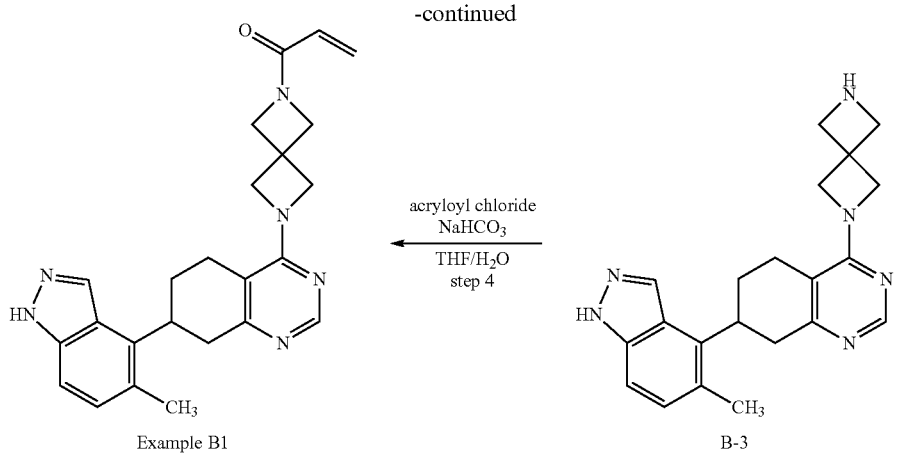

Example B1

B-3

Step 1: Synthesis of 4-chloro-7-(5-methyl-1H-indazol-4-yl)-5,6,7,8-tetrahydroquinazoline (B-1)

To a 40 mL vial was added 7-[5-methyl-1-(tetrahydro-2H-pyran-2-yl)-1H-indazol-4-yl]-5,6,7,8-tetrahydroquinazolin-4(3H)-one (A-4) (300 mg, 0.825 mmol, 1.0 eq), POCl$_3$ (5 mL) and toluene (5 mL). DIPEA (320 mg, 2.475 mmol, 3.0 eq) was added. The vial was capped and shaken at 110° C. for 16 hours. The solvents were removed under reduced pressure to provide 4-chloro-7-(5-methyl-1H-indazol-4-yl)-5,6,7,8-tetrahydroquinazoline (B-1), which was used directly in the next step without purification.

Step 2: Synthesis of tert-butyl 6-[7-(5-methyl-1H-indazol-4-yl)-5,6,7,8-tetrahydroquinazolin-4-yl]-2,6-diazaspiro[3.3]heptane-2-carboxylate (B-2)

To an 8 mL vial was added a solution of tert-butyl 2,6-diazaspiro[3.3]heptane-2-carboxylate (90 μmol, 1.2 eq). TEA (225 μmol, 3.0 eq) was added to the vial followed by a solution of 4-chloro-7-(5-methyl-1H-indazol-4-yl)-5,6,7,8-tetrahydroquinazoline (B-1) (75 μmol, 1.0 eq) in NMP (0.9 mL). The vial was capped and shaken at 130° C. for 16 hours. LCMS analysis shows the reaction was complete. The solvent was removed in vacuo and the resultant residue was purified by preparative TLC to provide tert-butyl 6-[7-(5-methyl-1H-indazol-4-yl)-5,6,7,8-tetrahydroquinazolin-4-yl]-2,6-diazaspiro[3.3]heptane-2-carboxylate (B-2).

Step 3: Synthesis of 4-(2,6-diazaspiro[3.3]hept-2-yl)-7-(5-methyl-1H-indazol-4-yl)-5,6,7,8-tetrahydroquinazoline (B-3)

To an 8 mL vial was added tert-butyl 6-[7-(5-methyl-1H-indazol-4-yl)-5,6,7,8-tetrahydroquinazolin-4-yl]-2,6-diazaspiro[3.3]heptane-2-carboxylate (B-2) and HCl (4.0 M in MeOH, 750 μL). The vial was capped and shaken at 30° C. for 2 hours. LCMS analysis showed that the reaction was complete. The solvent was removed under vacuum to provide 4-(2,6-diazaspiro[3.3]hept-2-yl)-7-(5-methyl-1H-indazol-4-yl)-5,6,7,8-tetrahydroquinazoline (B-3), which was taken on without further purification.

Step 4: Synthesis of 1-{6-[7-(5-methyl-1H-indazol-4-yl)-5,6,7,8-tetrahydroquinazolin-4-yl]-2,6-diazaspiro[3.3]hept-2-yl}prop-2-en-1-one (Example B1)

To a vial containing 4-(2,6-diazaspiro[3.3]hept-2-yl)-7-(5-methyl-1H-indazol-4-yl)-5,6,7,8-tetrahydroquinazoline (B-3) was added saturated aq. NaHCO$_3$ (500 μL), THF (500 μL), and a solution of acryloyl chloride (0.15 M in THF, 500 μL, 75 μmol, 1.0 eq). The vial was capped and shaken at 30° C. for 2 hrs. LCMS analysis showed conversion to the product. The mixture was extracted with EtOAc (3×1.5 mL). The combined organics were dried over anhydrous MgSO$_4$, filtered, and concentrated. The residue was purified by preparative HPLC (Agela Durashell C18, 150×25 mm, 5 μm, 0-35% gradient of acetonitrile and water (0.22% formic acid), 30 mL/min), to provide 1-{6-[7-(5-methyl-1H-indazol-4-yl)-5,6,7,8-tetrahydroquinazolin-4-yl]-2,6-diazaspiro[3.3]hept-2-yl}prop-2-en-1-one (Example B1). LCMS (ESI) m/z 414 (M+H).

The examples in Table B were prepared in library format using similar chemistry in Scheme B and the procedure used to prepare 1-{6-[7-(5-methyl-1H-indazol-4-yl)-5,6,7,8-tetrahydroquinazolin-4-yl]-2,6-diazaspiro[3.3]hept-2-yl}prop-2-en-1-one (Example B1). The following examples were made with non-critical changes or substitutions to the exemplified procedure used to prepare Example B1 that someone who is skilled in the art would be able to realize.

TABLE B

| Example | Structure | Compound name | LCMS m/z |
|---|---|---|---|
| B2 | 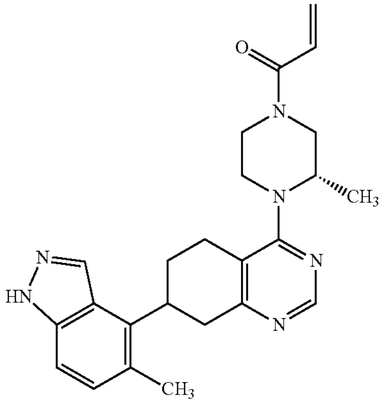 [SMILES: C=CC(=O)N1CCN(c2ncnc3c2CCC(c2c(C)ccc4[nH]ncc24)C3)[C@@H](C)C1] | 1-{(3S)-3-methyl-4-[7-(5-methyl-1H-indazol-4-yl)-5,6,7,8-tetrahydroquinazolin-4-yl]piperazin-1-yl}prop-2-en-1-one | 416 (M + H) |
| B3 | 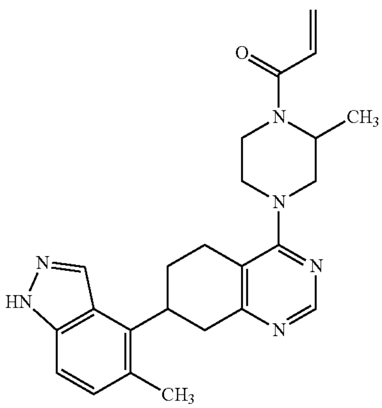 [SMILES: C=CC(=O)N1CCN(c2ncnc3c2CCC(c2c(C)ccc4[nH]ncc24)C3)CC1C] | 1-{2-methyl-4-[7-(5-methyl-1H-indazol-4-yl)-5,6,7,8-tetrahydroquinazolin-4-yl]piperazin-1-yl}prop-2-en-1-one | 416 (M + H) |

Example C1 (Scheme C)

tert-butyl 4-{2-chloro-7-[5-methyl-1-(tetrahydro-2H-pyran-2-yl)-1H-indazol-4-yl]-5,6,7,8-tetrahydroquinazolin-4-yl}piperazine-1-carboxylate Scheme C:

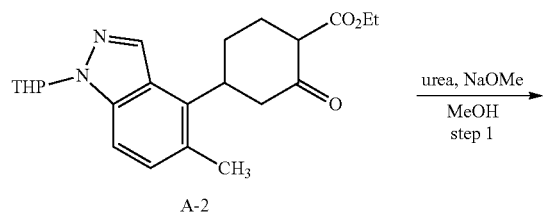

urea, NaOMe
MeOH
step 1

A-2

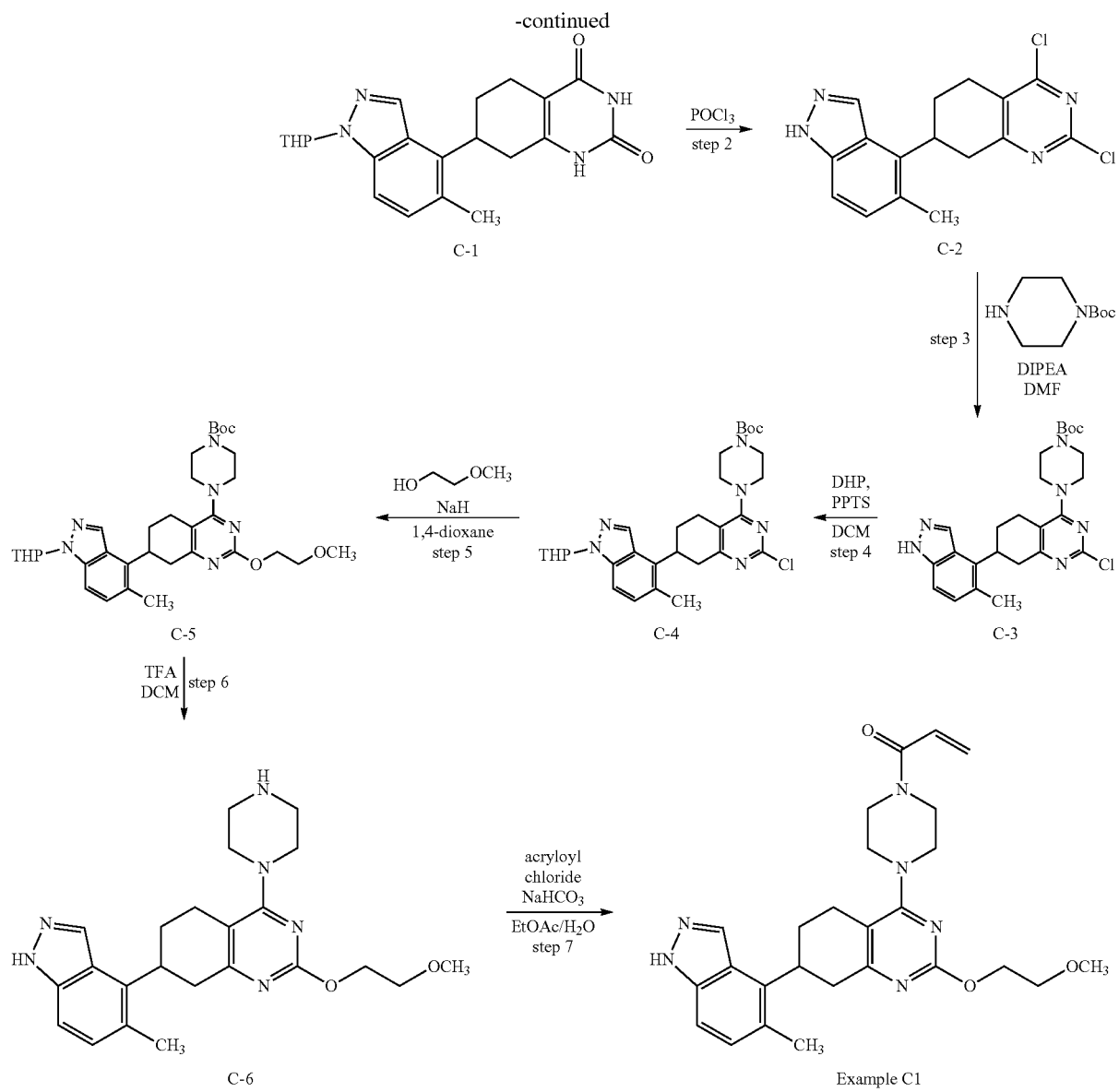

Step 1: Synthesis of ethyl 4-[5-methyl-1-(tetrahydro-2H-pyran-2-yl)-1H-indazol-4-yl]-2-oxocyclohexanecarboxylate (C-1)

To a solution of ethyl 4-(5-methyl-1H-indazol-4-yl)-2-oxocyclohexanecarboxylate (A-2) (11.5 g, 29.9 mmol, 1.0 eq) in MeOH (400 mL) was added urea (3.59 g, 59.8 mmol, 2.0 eq) and NaOMe (3.23 g, 59.8 mmol, 2.0 eq). The reaction was stirred at 80° C. for 16 hours. LCMS analysis showed formation of the desired product. The mixture was concentrated to dryness and the crude residue was purified by column chromatography (SiO$_2$, 10% MeOH/DCM) to provide ethyl 4-[5-methyl-1-(tetrahydro-2H-pyran-2-yl)-1H-indazol-4-yl]-2-oxocyclohexanecarboxylate (C-1) (2.3 g, 20% yield). $^1$H NMR (400 MHz, DMSO-d$_6$) δ 10.95 (s, 1H), 10.69 (d, J=8.1 Hz, 1H), 8.28 (s, 1H), 7.49 (d, J=8.7 Hz, 1H), 7.22 (d, J=8.5 Hz, 1H), 5.79 (dd, J=9.8, 2.5 Hz, 1H), 3.87 (d, J=11.5 Hz, 1H), 3.79-3.65 (m, 1H), 3.45-3.36 (m, 1H), 2.94-2.77 (m, 1H), 2.57-2.47 (m, 1H), 2.46-2.34 (m, 5H), 2.31-2.15 (m, 2H), 2.09-1.97 (m, 1H), 1.93 (dd, J=13.3, 3.2 Hz, 1H), 1.84 (t, J=9.2 Hz, 1H), 1.79-1.65 (m, 1H), 1.62-1.50 (m, 2H). LCMS (ESI) m/z 381 (M+H).

Step 2: Synthesis of 2,4-dichloro-7-(5-methyl-1H-indazol-4-yl)-5,6,7,8-tetrahydroquinazoline (C-2)

A solution of ethyl 4-[5-methyl-1-(tetrahydro-2H-pyran-2-yl)-1H-indazol-4-yl]-2-oxocyclohexanecarboxylate (C-1) (2.3 g, 6.0 mmol) in POCl$_3$ (30 mL) was stirred at 105° C. for 2 hours. LCMS analysis showed complete consumption of the starting material. The mixture was concentrated to dryness. The residue was diluted with DCM (30 mL) and TEA was added to adjust the pH to 8. The solvent was evaporated. The crude residue was purified by column chromatography (SiO$_2$, 33% EtOAc/PE) to provide 2,4-dichloro-7-(5-methyl-1H-indazol-4-yl)-5,6,7,8-tetrahydroquinazoline (C-2) (1 g, 50% yield). LCMS (ESI) m/z 333 (M+H).

Step 3: Synthesis of tert-butyl 4-[2-chloro-7-(5-methyl-1H-indazol-4-yl)-5,6,7,8-tetrahydroquinazolin-4-yl]piperazine-1-carboxylate (C-3)

To a solution of 2,4-dichloro-7-(5-methyl-1H-indazol-4-yl)-5,6,7,8-tetrahydroquinazoline (C-2) (1 g, 3 mmol, 1.0 eq) in DMF (30 mL) was added tert-butyl piperazine-1-carboxylate (671 mg, 3.6 mmol, 1.2 eq) and DIPEA (776 mg, 6 mmol, 2.0 eq). The reaction was stirred at 80° C. for 2 hours. LCMS analysis showed conversion to the desired product. The reaction mixture was cooled to room temperature and poured into a separatory funnel. Water (50 mL) was added and the mixture was extracted with EtOAc (2×30 mL). The combined organics were washed with brine, dried over anhydrous sodium sulfate, filtered, and concentrated to dryness. The crude was purified by column chromatography (SiO$_2$, 25% EtOAc/PE) to provide tert-butyl 4-[2-chloro-7-(5-methyl-1H-indazol-4-yl)-5,6,7,8-tetrahydroquinazolin-4-yl]piperazine-1-carboxylate C-3) (1 g, 70% yield). $^1$H NMR (400 MHz, CDCl$_3$) δ 8.04 (s, 1H), 7.32 (d, J=8.5 Hz, 1H), 7.22 (d, J=8.5 Hz, 1H), 3.72-3.43 (m, 8H), 3.44-3.35 (m, 2H), 3.30 (dd, J=19.2, 11.5 Hz, 1H), 3.14 (dd, J=19.1, 6.4 Hz, 1H), 2.79-2.66 (m, 2H), 2.46 (s, 3H), 2.32-2.02 (m, 2H), 1.49 (s, 9H). LCMS (ESI) m/z 483 (M+H).

Step 4: Synthesis of tert-butyl 4-{2-chloro-7-[5-methyl-1-(tetrahydro-2H-pyran-2-yl)-1H-indazol-4-yl]-5,6,7,8-tetrahydroquinazolin-4-yl}piperazine-1-carboxylate (C-4)

To a solution of tert-butyl 4-[2-chloro-7-(5-methyl-1H-indazol-4-yl)-5,6,7,8-tetrahydroquinazolin-4-yl]piperazine-1-carboxylate (C-3) (520 mg, 1.08 mmol, 1.0 eq) in DCM (400 mL) at 0° C. was added 3,4-dihydro-2H-pyran (272 mg, 3.23 mmol, 3.0 eq) and pridinium 4-toluenesulfonate (27.1 mg, 0.108 mmol, 0.1 eq). The reaction was warmed to 20° C. and stirred for 18 hours. LCMS analysis showed conversion to the desired product. The mixture was concentrated to dryness and the crude residue was purified by column chromatography (SiO$_2$, 50% EtOAc/PE) to provide tert-butyl 4-{2-chloro-7-[5-methyl-1-(tetrahydro-2H-pyran-2-yl)-1H-indazol-4-yl]-5,6,7,8-tetrahydroquinazolin-4-yl}piperazine-1-carboxylate (C-4) (500 mg, 82% yield). LCMS (ESI) m/z 567 (M+H).

Step 5: Synthesis of tert-butyl 4-{2-(2-methoxyethoxy)-7-[5-methyl-1-(tetrahydro-2H-pyran-2-yl)-1H-indazol-4-yl]-5,6,7,8-tetrahydroquinazolin-4-yl}piperazine-1-carboxylate (C-5)

To a solution of tert-butyl 4-{2-chloro-7-[5-methyl-1-(tetrahydro-2H-pyran-2-yl)-1H-indazol-4-yl]-5,6,7,8-tetrahydroquinazolin-4-yl}piperazine-1-carboxylate (C-4) (200 mg, 0.353 mmol, 1.0 eq) in 1,4-dioxane (20 mL) was added 2-methoxyethan-1-ol (107 mg, 1.41 mmol, 4.0 eq) and NaH (60% dispersion in mineral oil, 70.5 mg, 1.76 mmol, 5.0 eq). The reaction was stirred at 90° C. for 16 hours. LCMS analysis showed conversion to the desired product. The reaction was quenched by addition of water (10 mL). The mixture was poured into a separatory funnel and extracted with EtOAc (2×20 mL). The combined organics were washed with brine, dried over anhydrous sodium sulfate, filtered, and concentrated to dryness. The crude residue was purified by column chromatography (SiO$_2$, 50% EtOAc/PE) to provide tert-butyl 4-{2-(2-methoxyethoxy)-7-[5-methyl-1-(tetrahydro-2H-pyran-2-yl)-1H-indazol-4-yl]-5,6,7,8-tetrahydroquinazolin-4-yl}piperazine-1-carboxylate (C-5) (200 mg, 94% yield). LCMS (ESI) m/z 607 (M+H).

Step 6: Synthesis of 2-(2-methoxyethoxy)-7-(5-methyl-1H-indazol-4-yl)-4-(piperazin-1-yl)-5,6,7,8-tetrahydroquinazoline (C-6)

A solution of tert-butyl 4-{2-(2-methoxyethoxy)-7-[5-methyl-1-(tetrahydro-2H-pyran-2-yl)-1H-indazol-4-yl]-5,6,7,8-tetrahydroquinazolin-4-yl}piperazine-1-carboxylate (C-5) (200 mg, 0.33 mmol, 1.0 eq) in 25% TFA in DCM (20 mL) was stirred at 20° C. for 2 hours. LCMS analysis showed conversion to the desired product. The reaction mixture was concentrated to dryness to provide 2-(2-methoxyethoxy)-7-(5-methyl-1H-indazol-4-yl)-4-(piperazin-1-yl)-5,6,7,8-tetrahydroquinazoline (C-6) (120 mg, 86% yield), which was taken without further purification. LCMS (ESI) m/z 423 (M+H).

Step 7: 1-{4-[2-(2-methoxyethoxy)-7-(5-methyl-1H-indazol-4-yl)-5,6,7,8-tetrahydroquinazolin-4-yl]piperazin-1-yl}prop-2-en-1-one (Example C1)

To a solution of 2-(2-methoxyethoxy)-7-(5-methyl-1H-indazol-4-yl)-4-(piperazin-1-yl)-5,6,7,8-tetrahydroquinazoline (C-6) (120 mg, 0.284 mmol, 1.0 eq) in EtOAc (10 mL) was added a solution of saturated NaHCO$_3$ (10 mL). A solution of acryloyl chloride (31 mg, 0.341 mmol, 1.2 eq) in EtOAc was added and the reaction was stirred at 20° C. for 20 minutes. LCMS analysis showed conversion to the desired product. The reaction mixture was poured into a separatory funnel and extracted with EtOAc (2×20 mL). The combined organics were washed with brine, dried over anhydrous sodium sulfate, filtered, and concentrated to dryness. The crude residue was purified by preparative HPLC (Gemini 5u C18, 150×21.2 mm, 40-50% acetonitrile, 20 mL/min) to provide 1-{4-[2-(2-methoxyethoxy)-7-(5-methyl-1H-indazol-4-yl)-5,6,7,8-tetrahydroquinazolin-4-yl]piperazin-1-yl}prop-2-en-1-one (Example C1) (25.7 mg, 19% yield). $^1$H NMR (400 MHz, CDCl$_3$) δ 8.14-7.94 (m, 1H), 7.30 (d, J=7.7 Hz, 1H), 7.22 (d, J=8.4 Hz, 1H), 6.60 (dd, J=16.7, 10.6 Hz, 1H), 6.35 (d, J=16.8 Hz, 1H), 5.76 (d, J=10.5 Hz, 1H), 4.46 (s, 2H), 4.07-3.88 (m, 1H), 3.78 (d, J=32.0 Hz, 4H), 3.63 (s, 4H), 3.52-3.08 (m, 7H), 2.75 (s, 2H), 2.47 (s, 3H), 2.21 (d, J=32.3 Hz, 2H). LCMS (ESI) m/z 477 (M+H).

The examples in Table C were prepared using similar chemistry in Scheme C and the procedure used to prepare 1-{4-[2-(2-methoxyethoxy)-7-(5-methyl-1H-indazol-4-yl)-5,6,7,8-tetrahydroquinazolin-4-yl]piperazin-1-yl}prop-2-en-1-one (Example C1). The following examples were made with non-critical changes or substitutions to the exemplified procedure used to prepare Example C1 that someone who is skilled in the art would be able to realize.

TABLE C

| Example | Structure | Compound name | LCMS m/z | Analytical data |
|---|---|---|---|---|
| C2 | 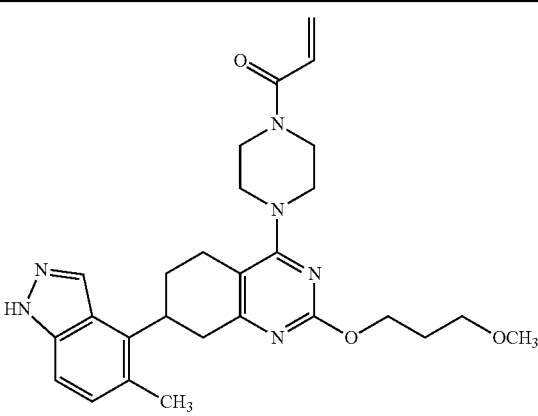 | 1-{4-[2-(3-methoxypropoxy)-7-(5-methyl-1H-indazol-4-yl)-5,6,7,8-tetrahydroquinazolin-4-yl]piperazin-1-yl}prop-2-en-1-one | 491 (M + H) | $^1$H NMR (400 MHz, CDCl$_3$) δ 10.09 (s, 1H), 8.06 (s, 1H), 7.29 (d, J = 8.5 Hz, 1H), 7.22 (d, J = 8.5 Hz, 1H), 6.61 (dd, J = 16.8, 10.5 Hz, 1H), 6.34 (dd, J = 16.8, 1.9 Hz, 1H), 5.75 (dd, J = 10.6, 1.9 Hz, 1H), 4.37 (t, J = 6.4 Hz, 2H), 3.82 (s, 3H), 3.69-3.52 (m, 6H), 3.48-3.38 (m, 1H), 3.34 (s, 4H), 3.24 (dd, J = 18.9, 11.6 Hz, 1H), 3.08 (dd, J = 18.9, 6.4 Hz, 1H), 2.82-2.66 (m, 2H), 2.48 (s, 3H), 2.31-2.12 (m, 2H), 2.06 (p, J = 6.4 Hz, 2H). |
| C3 | 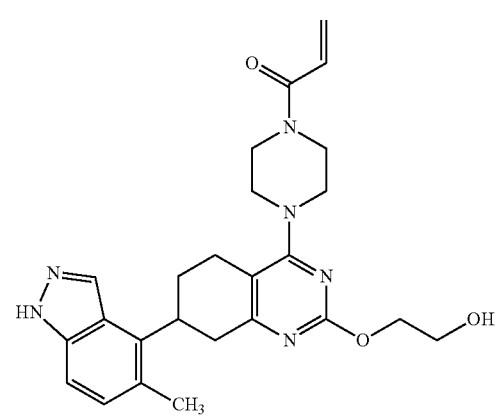 [SMILES: C=CC(=O)N1CCN(c2nc(OCCO)nc3c2CCC(c2c(C)ccc4[nH]ncc24)C3)CC1] | 1-{4-[2-(2-hydroxyethoxy)-7-(5-methyl-1H-indazol-4-yl)-5,6,7,8-tetrahydroquinazolin-4-yl]piperazin-1-yl}prop-2-en-1-one | 463 (M + H) | $^1$H NMR (400 MHz, DMSO-d$_6$) δ 12.95 (s, 1H), 8.12 (s, 1H), 7.30 (d, J = 8.6 Hz, 1H), 7.17 (d, J = 8.5 Hz, 1H), 6.84 (dd, J = 16.7, 10.5 Hz, 1H), 6.15 (dd, J = 16.7, 2.4 Hz, 1H), 5.73 (dd, J = 10.4, 2.5 Hz, 1H), 4.84 (s, 1H), 4.25 (s, 2H), 3.87-3.51 (m, 10H), 3.09 (dd, J = 18.3, 11.7 Hz, 1H), 2.89 (dd, J = 18.4, 5.1 Hz, 2H), 2.72-2.59 (m, 1H), 2.43 (s, 4H), 2.22 (dt, J = 11.8, 6.8 Hz, 1H), 1.98 (d, J = 12.3 Hz, 1H). |
| C4 | 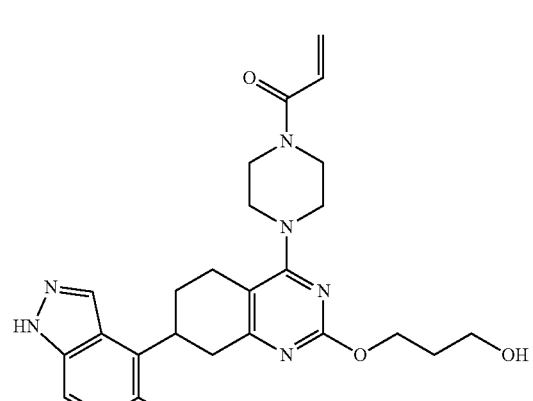 | 1-{4-[2-(3-hydroxypropoxy)-7-(5-methyl-1H-indazol-4-yl)-5,6,7,8-tetrahydroquinazolin-4-yl]piperazin-1-yl}prop-2-en-1-one | 477 (M + H) | $^1$H NMR (400 MHz, DMSO-d$_6$) δ 12.95 (s, 1H), 8.11 (s, 1H), 7.30 (d, J = 8.4 Hz, 1H), 7.16 (d, J = 8.5 Hz, 1H), 6.85 (dd, J = 16.7, 10.5 Hz, 1H), 6.15 (dd, J = 16.7, 2.5 Hz, 1H), 5.72 (dd, J = 10.4, 2.4 Hz, 1H), 4.51 (t, J = 5.1 Hz, 1H), 4.25 (t, J = 6.5 Hz, 2H), 3.86-3.68 (m, 2H), 3.65-3.57 (m, 3H), 3.52 (q, J = 6.1 Hz, 4H), 3.30 (s, 2H), 3.07 (dd, J = 18.3, 11.7 Hz, 1H), 2.87 (dt, J = 21.2, 10.1 Hz, 2H), 2.64 (t, J = 12.9 |

TABLE C-continued

| Example | Structure | Compound name | LCMS m/z | Analytical data |
|---|---|---|---|---|
| | | | | Hz, 1H), 2.42 (s, 3H), 2.24 (ddd, J = 23.5, 11.7, 3.8 Hz, 1H), 1.97 (d, J = 12.2 Hz, 1H), 1.82 (p, J = 6.3 Hz, 2H). |
| C5 | 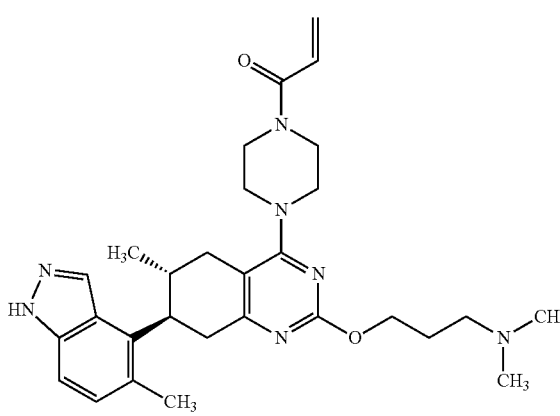 [SMILES: C=CC(=O)N1CCN(c2nc(OCCCN(C)C)nc3c2C[C@@H](C)[C@H](c2c(C)ccc4[nH]ncc24)C3)CC1] | 1-{4-[(6R,7R)-2-[3-(dimethylamino)propoxy]-6-methyl-7-(5-methyl-1H-indazol-4-yl)-5,6,7,8-tetrahydroquinazolin-4-yl]piperazin-1-yl}prop-2-en-1-one | 518 (M + H) | ¹H NMR (400 MHz, CDCl₃) δ 10.04 (s, 1H), 7.31 (d, J = 8.6 Hz, 1H), 7.25 (d, J = 8.6 Hz, 1H), 6.64 (dd, J = 16.8, 10.6 Hz, 1H), 6.37 (dd, J = 16.8, 1.9 Hz, 1H), 5.78 (dd, J = 10.6, 1.9 Hz, 1H), 4.35 (t, J = 6.6 Hz, 2H), 3.85 (s, 3H), 3.71-3.52 (m, 3H), 3.51-3.20 (m, 4H), 3.10 (dd, J = 18.6, 6.0 Hz, 1H), 2.79 (d, J = 11.3 Hz, 1H), 2.58-2.34 (m, 7H), 2.26 (s, 5H), 2.605-1.88 (m, 2H), 0.83 (d, J = 5.3 Hz, 3H). >99% ee [α]$_d^{22}$ = +28.0° (C = 0.1, MeOH); |
| C6 | 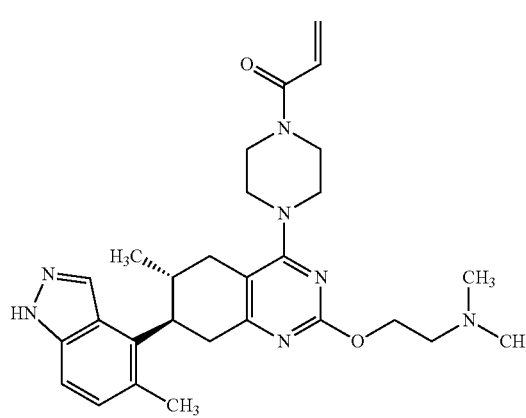 [SMILES: C=CC(=O)N1CCN(c2nc(OCCN(C)C)nc3c2C[C@@H](C)[C@H](c2c(C)ccc4[nH]ncc24)C3)CC1] | 1-{4-[(6R,7R)-2-[2-(dimethylamino)ethoxy]-6-methyl-7-(5-methyl-1H-indazol-4-yl)-5,6,7,8-tetrahydroquinazolin-4-yl]piperazin-1-yl}prop-2-en-1-one | 504 (M + H) | ¹H NMR (400 MHz, CDCl₃) δ 8.03 (s, 1H), 7.29 (d, J = 8.6 Hz, 1H), 7.21 (d, J = 8.5 Hz, 1H), 6.61 (dd, J = 16.8, 10.5 Hz, 1H), 6.34 (dd, J = 16.8, 1.9 Hz, 1H), 5.75 (dd, J = 10.5, 1.9 Hz, 1H), 4.42 (t, J = 6.1 Hz, 2H), 3.82 (s, 3H), 3.67-3.54 (m, 3H), 3.47-3.21 (m, 4H), 3.06 (dd, J = 18.7, 6.0 Hz, 1H), 2.81-2.67 (m, 3H), 2.46 (s, 3H), 2.44-2.37 (m, 2H), 2.34 (s, 6H), 0.80 (d, J = 5.3 Hz, 3H). >99% ee [α]$_d^{22}$ = +22.0° (C = 0.1, MeOH); |

TABLE C-continued

| Example | Structure | Compound name | LCMS m/z | Analytical data |
|---|---|---|---|---|
| C7 | 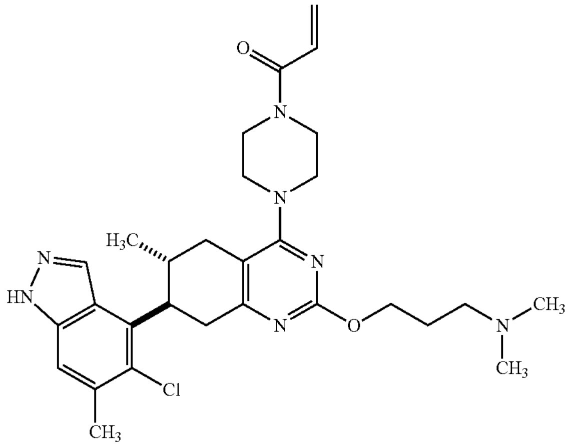 | 1-(4-{(6R,7R)-rel-7-(5-chloro-6-methyl-1H-indazol-4-yl)-2-[3-(dimethyl-amino)propoxy]-6-methyl-5,6,7,8-tetrahydroquinazolin-4-yl}piperazin-1-yl)prop-2-en-1-one | 552 (M + H) | H NMR (400 MHz, MeOD) δ 8.06 (s, 1H), 7.42 (s, 1H), 6.81 (dd, J = 16.8, 10.6 Hz, 1H), 6.26 (dd, J = 16.8, 1.9 Hz, 1H), 5.80 (dd, J = 10.6, 1.9 Hz, 1H), 4.43 (t, J = 8.0 Hz, 2H), 4.04-3.83 (m, 3H), 3.80-3.66 (m, 4H), 3.55-3.42 (m, 2H), 3.28-3.21 (m, 2H), 3.20-3.13 (m, 1H), 3.08-2.96 (m, 1H), 2.87 (s, 6H), 2.84-2.76 (m, 1H), 2.65-2.55 (m, 1H), 2.53 (s, 3H), 2.50-2.35 (m, 1H), 2.24-2.06 (m, 2H), 0.85 (d, J = 6.3 Hz, 3H). |
| C8 | 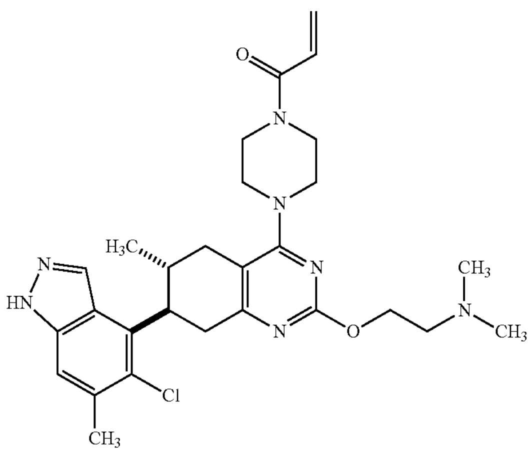 | 1-(4-{(6R,7R)-rel-7-(5-chloro-6-methyl-1H-indazol-4-yl)-2-[2-(dimethyl-amino)ethoxy]-6-methyl-5,6,7,8-tetrahydroquinazolin-4-yl}piperazin-1-yl)prop-2-en-1-one | 538 (M + H) | $^1$H NMR (400 MHz, Methanol-d$_4$) δ 8.53 (s, 1H), 8.08 (s, 1H), 7.42 (s, 1H), 6.82 (dd, J = 16.8, 10.6 Hz, 1H), 6.26 (dd, J = 16.8, 2.0 Hz, 1H), 5.80 (dd, J = 10.6, 2.0 Hz, 1H), 4.53 (t, J = 5.5 Hz, 2H), 4.01-3.84 (m, 4H), 3.79-3.67 (m, 4H), 3.49 (t, J = 8.9 Hz, 2H), 3.18 (dd, J = 18.9, 11.7 Hz, 1H), 3.10-2.95 (m, 3H), 2.81 (dd, J = 15.3, 3.8 Hz, 1H), 2.65-2.39 (m, 11H), 0.85 (d, J = 6.3 Hz, 3H). |
| C9 | 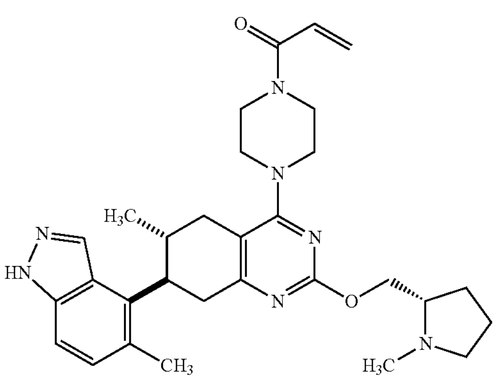 | 1-{4-[(6R,7R)-6-methyl-7-(5-methyl-1H-indazol-4-yl)-2-{[(2S)-1-methylpyrrolidin-2-yl]methoxy}-5,6,7,8-tetrahydroquinazolin-4-yl]piperazin-1-yl}prop-2-en-1-one | 530 (M + H) | $^1$H NMR (400 MHz, DMSO) δ 12.96 (s, 1H), 8.08 (s, 1H), 7.30 (d, J = 8.4 Hz, 1H), 7.18 (d, J = 8.4 Hz, 1H), 6.85 (dd, J = 16.7, 10.5 Hz, 1H), 6.16 (dd, J = 16.7, 2.1 Hz, 1H), 5.73 (dd, J = 10.5, 2.0 Hz, 1H), 4.30-4.20 (m, 1H), 4.01 (dt, J = 10.6, 7.1 Hz, 1H), 3.89-3.48 (m, 7H), 3.33-3.26 (m, 2H), 3.09 (dd, J = 18.2, 12.0 Hz, 1H), 2.98-2.80 (m, 2H), 2.62 (dd, J = 38.4, 11.4 Hz, 2H), 2.42 (s, 4H), 2.32 (s, 3H), 2.15 (q, J = 8.6 Hz, 1H), 1.90 (dd, J = 19.3, 8.7 Hz, 1H), |

TABLE C-continued

| Example | Structure | Compound name | LCMS m/z | Analytical data |
|---|---|---|---|---|
| | | | | 1.74-1.49 (m, 3H), 1.24 (s, 1H), 0.70 (d, J = 5.7 Hz, 3H). |
| C10 | 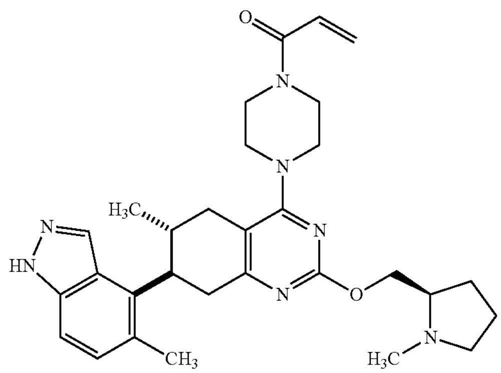 | 1-{4-[(6R,7R)-rel-6-methyl-7-(5-methyl-1H-indazol-4-yl)-2-{[(2R)-1-methylpyrrolidin-2-yl]methoxy}-5,6,7,8-tetrahydroquinazolin-4-yl]piperazin-1-yl}prop-2-en-1-one | 530 (M + H) | $^1$H NMR (400 MHz, DMSO) δ 12.96 (s, 1H), 8.08 (s, 1H), 7.30 (d, J = 8.4 Hz, 1H), 7.17 (d, J = 8.5 Hz, 1H), 6.85 (dd, J = 16.6, 10.5 Hz, 1H), 6.15 (dd, J = 16.7, 2.3 Hz, 1H), 5.72 (dd, J = 10.5, 2.3 Hz, 1H), 4.30-4.18 (m, 1H), 4.00 (dt, J = 10.7, 7.1 Hz, 1H), 3.86-3.48 (m, 7H), 3.09 (dd, J = 18.4, 11.7 Hz, 1H), 2.97-2.84 (m, 2H), 2.62 (dd, J = 38.0, 11.0 Hz, 3H), 2.42 (s, 3H), 2.32 (d, J = 1.4 Hz, 3H), 2.15 (dd, J = 17.1, 8.7 Hz, 1H), 2.03-1.83 (m, 2H), 1.74-1.47 (m, 4H), 1.23 (s, 1H), 0.70 (d, J = 6.0 Hz, 3H). |

Example D1 (Scheme D)

1-(4-{(6R,7R)-7-[5-(hydroxymethyl)-1H-indazol-4-yl]-6-methyl-5,6,7,8-tetrahydroquinazolin-4-yl}piperazin-1-yl)prop-2-en-1-one Scheme D:

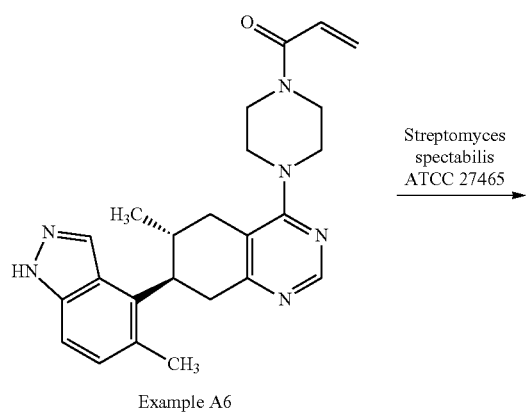

Example A6

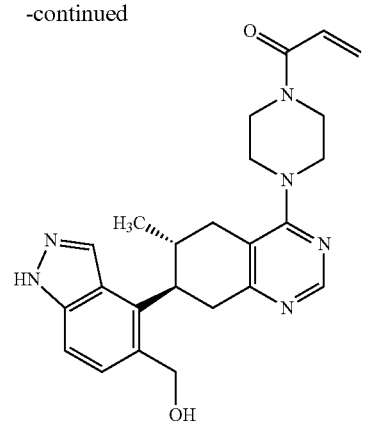

Example D1

To each of two sterile 250 mL Nalgene flasks (baffled, vented) was added 25 mL sterile Iowa medium (dextrose (20 g), Nutrisoy flour (5 g), NaCl (5 g), yeast extract (5 g), K$_2$HPO$_4$ (5 g), P2000 antifoam (1 mL), deionized water (1000 mL). The pH was adjusted to 7.0 with 1N HCl and the solution was autoclaved to sterilize (121° C., 25 min/L)). A solution of *Streptomyces spectabilis* ATCC 27465 in thawed vegetative stock (0.25 mL) was added to each flask. The flasks were capped and incubated on a 2″ throw rotary shaker (Innova 4900, 210 rpm) at 30° C. for two days. A solution of 1-{4-[(6R,7R)-6-methyl-7-(5-methyl-1H-indazol-4-yl)-5,6,7,8-tetrahydroquinazolin-4-yl]piperazin-1-yl}prop-2-en-1-one (Example A6) (5 mg, 12 μmol) in DMSO (1 mL) was added to each flask. The flasks were capped and incubated as above. After 5 days the two flasks for each culture were combined and poured into a separatory funnel. The solution was extracted with EtOAc (2×50 mL) and the combined organics were filtered through a pad of anhydrous MgSO$_4$. The filter cake was washed with EtOAc (20 mL) and the combined organics were concentrated to dryness. The crude material was purified by preparative SFC on a Princeton Methane Sulfonamide (10 mm×250 mm, 5 micron particle size) column which was eluted with 60% MeOH in CO$_2$ held at 25° C. at 100 bar with a flow rate of 10 mL/min to provide 1-(4-{(6R,7R)-7-[5-(hydroxymethyl)-1H-indazol-4-yl]-6-methyl-5,6,7,8-tetrahydroquinazolin-4-yl}piperazin-1-yl)prop-2-en-1-one (Example D1) (11 μg, 0.2% yield). LCMS (ESI) m/z 433 (M+H).

Example E1 (Scheme E)

1-{4-[(6R,7R)-7-(7-hydroxy-5-methyl-1H-indazol-4-yl)-6-methyl-5,6,7,8-tetrahydroquinazolin-4-yl]piperazin-1-yl}prop-2-en-1-one Scheme E:

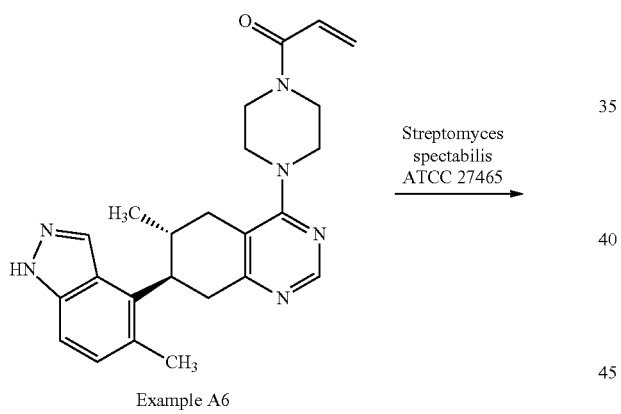

Example A6

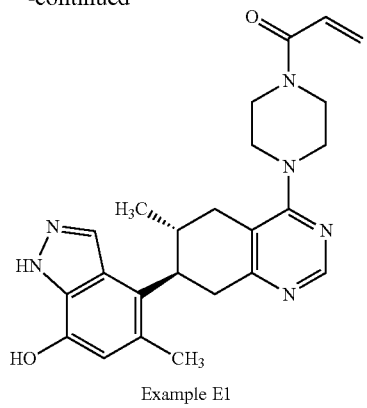

Example E1

1-{4-[(6R,7R)-7-(7-hydroxy-5-methyl-1H-indazol-4-yl)-6-methyl-5,6,7,8-tetrahydroquinazolin-4-yl]piperazin-1-yl}prop-2-en-1-one (Example E1) (26 μg, 0.5% yield) was prepared according to the general procedure for Example D1 except that *Streptomyces spectabilis* ATCC 13273 was used as the cell line. LCMS (ESI) m/z 433 (M+H).

Example F1 (Scheme F)

1-{4-[(6R,7R)-rel-2-[3-(dimethylamino)azetidin-1-yl]-6-methyl-7-(5-methyl-1H-indazol-4-yl)-5,6,7,8-tetrahydroquinazolin-4-yl]piperazin-1-yl}prop-2-en-1-one Example F2 (Scheme F)

1-{4-[(6S,7S)-2-[3-(dimethylamino)azetidin-1-yl]-6-methyl-7-(5-methyl-1H-indazol-4-yl)-5,6,7,8-tetrahydroquinazolin-4-yl]piperazin-1-yl}prop-2-en-1-one Example F3 (Scheme F)

1-{4-[(6R,7R)-2-[3-(dimethylamino)azetidin-1-yl]-6-methyl-7-(5-methyl-1H-indazol-4-yl)-5,6,7,8-tetrahydroquinazolin-4-yl]piperazin-1-yl}prop-2-en-1-one Scheme F:
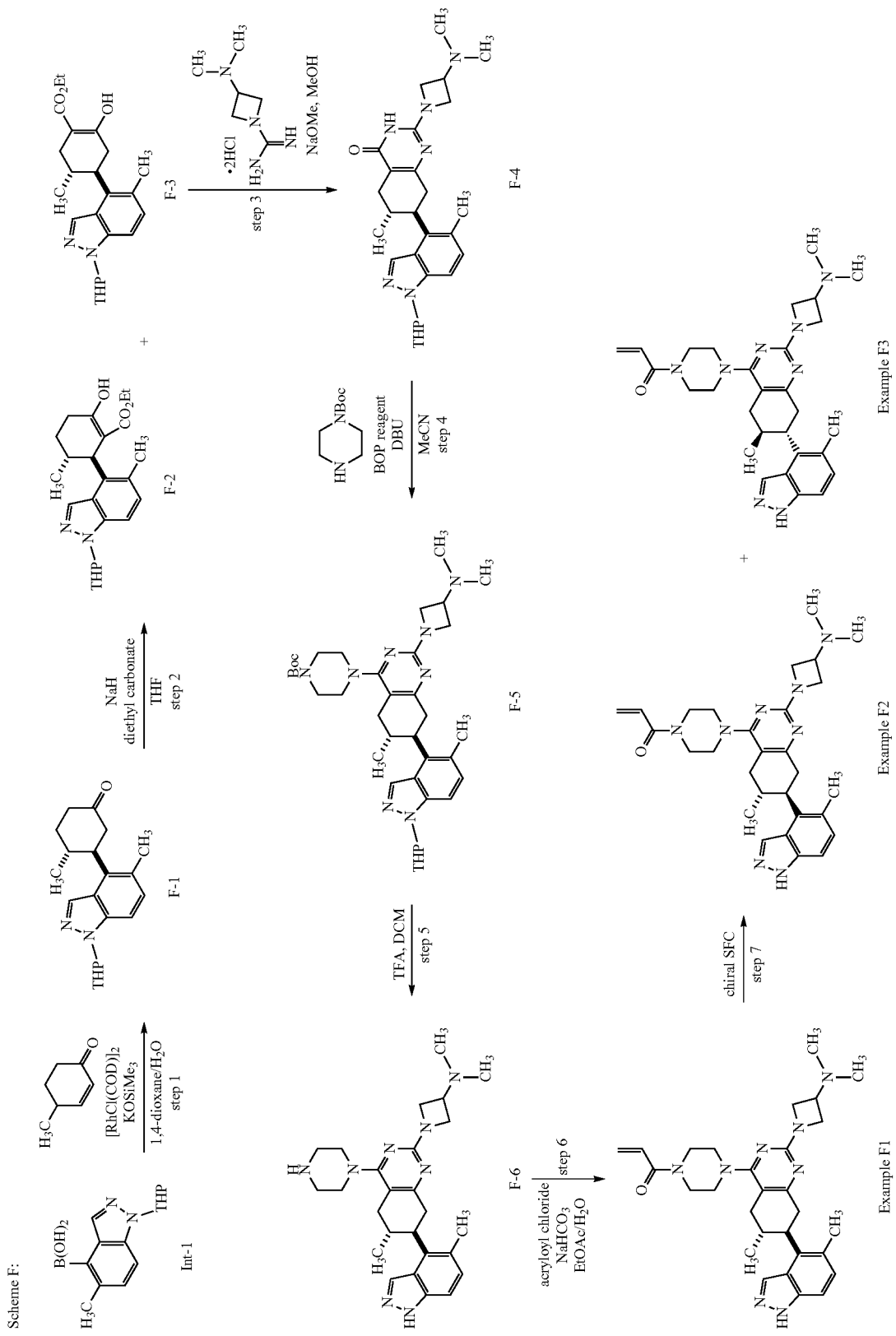

Step 1: Synthesis of (3R,4R)-rel-4-methyl-3-[5-methyl-1-(tetrahydro-2H-pyran-2-yl)-1H-indazol-4-yl]cyclohexanone (F-1)

(3R,4R)-rel-4-methyl-3-[5-methyl-1-(tetrahydro-2H-pyran-2-yl)-1H-indazol-4-yl]cyclohexanone (F-1) (118 g, 90% yield, >20:1 dr) was prepared according to the procedure for the synthesis of 3-[5-methyl-1-(tetrahydro-2H-pyran-2-yl)-1H-indazol-4-yl]cyclohexanone (A-1) except that KOSiMe$_3$ was used as the base in a solvent mixture of 1,4-dioxane/H$_2$O (20:1) to provide the desired product as a yellow gum. LCMS (ESI) m/z 327 (M+H).

Step 2: Synthesis of ethyl (4R,5R)-rel-5-methyl-4-[5-methyl-1-(tetrahydro-2H-pyran-2-yl)-1H-indazol-4-yl]-2-oxocyclohexanecarboxylate (F-2) and ethyl (2S,3R)-rel-3-methyl-2-[5-methyl-1-(tetrahydro-2H-pyran-2-yl)-1H-indazol-4-yl]-6-oxocyclohexanecarboxylate (F-3)

The ~1:1 mixture of ethyl (4R,5R)-rel-5-methyl-4-[5-methyl-1-(tetrahydro-2H-pyran-2-yl)-1H-indazol-4-yl]-2-oxocyclohexanecarboxylate (F-3) and ethyl (2S,3R)-rel-3-methyl-2-[5-methyl-1-(tetrahydro-2H-pyran-2-yl)-1H-indazol-4-yl]-6-oxocyclohexanecarboxylate (F-2) (86.8 g, 44.02% yield) was prepared according to the general procedure used to synthesize 3-[5-methyl-1-(tetrahydro-2H-pyran-2-yl)-1H-indazol-4-yl]cyclohexanone (A-2) to provide the product as an off-white solid. LCMS (ESI) m/z 399 (M+H).

Step 3: Synthesis of (6R,7R)-rel-2-[3-(dimethylamino)azetidin-1-yl]-6-methyl-7-[5-methyl-1-(tetrahydro-2H-pyran-2-yl)-1H-indazol-4-yl]-5,6,7,8-tetrahydroquinazolin-4(3H)-one (F-4)

To a stirred solution of the ~1:1 mixture of ethyl (4R,5R)-rel-5-methyl-4-[5-methyl-1-(tetrahydro-2H-pyran-2-yl)-1H-indazol-4-yl]-2-oxocyclohexanecarboxylate (F-3) and ethyl (2S,3R)-rel-3-methyl-2-[5-methyl-1-(tetrahydro-2H-pyran-2-yl)-1H-indazol-4-yl]-6-oxocyclohexanecarboxylate (F-2) (885 mg, 1.11 mmol, 1.0 eq) and 3-(dimethylamino)azetidine-1-carboximidamide hydrochloride (411 mg, 2.89 mmol, 2.6 eq) (WO15089327) in dry EtOH (5 mL) was added a solution of NaOEt [prepared by added Na metal (204 mg, 8.88 mmol) to ethanol (5 mL)]. The resulting mixture was stirred at 25° C. for 4 hrs. LCMS showed consumption of only ethyl (4R,5R)-rel-5-methyl-4-[5-methyl-1-(tetrahydro-2H-pyran-2-yl)-1H-indazol-4-yl]-2-oxocyclohexanecarboxylate. The mixture was filtered and the cake was washed with EtOH (2×3 mL). The combined filtrates were concentrated. The crude residue was purified by flash chromatography (SiO$_2$, 0→10% MeOH/DCM) to provide (6R,7R)-rel-2-[3-(dimethylamino)azetidin-1-yl]-6-methyl-7-[5-methyl-1-(tetrahydro-2H-pyran-2-yl)-1H-indazol-4-yl]-5,6,7,8-tetrahydroquinazolin-4(3H)-one (F-4) (300 mg, 57% yield) as a gummy white solid. $^1$H NMR (400 MHz, CDCl$_3$) δ 8.05 (s, 1H), 7.34 (t, J=7.6 Hz, 1H), 7.20 (d, J=8.6 Hz, 1H), 5.81-5.57 (m, 1H), 4.18 (t, J=8.1 Hz, 2H), 4.04 (t, J=12.6 Hz, 3H), 3.75 (t, J=9.9 Hz, 1H), 3.33 (s, 1H), 3.21 (s, 1H), 3.16-3.03 (m, 1H), 2.87 (dd, J=17.3, 4.6 Hz, 1H), 2.70 (dd, J=18.1, 4.4 Hz, 1H), 2.56 (s, 1H), 2.42 (s, 4H), 2.28 (s, 6H), 2.09 (dd, J=28.1, 10.2 Hz, 3H), 1.81-1.60 (m, 3H), 0.74 (s, 3H). LCMS (ESI) m/z 477 (M+H).

Step 4: Synthesis of tert-butyl 4-{(6R,7R)-rel-2-[3-(dimethylamino)azetidin-1-yl]-6-methyl-7-[5-methyl-1-(tetrahydro-2H-pyran-2-yl)-1H-indazol-4-yl]-5,6,7,8-tetrahydroquinazolin-4-yl}piperazine-1-carboxylate (F-5)

To a 250 mL flask equipped with a magnetic stir bar was added (6R,7R)-2-[3-(dimethylamino)azetidin-1-yl]-6-methyl-7-[5-methyl-1-(tetrahydro-2H-pyran-2-yl)-1H-indazol-4-yl]-5,6,7,8-tetrahydroquinazolin-4(3H)-one (F-4) (1 g, 2.1 mmol, 1.0 eq), tert-butyl piperazine-1-carboxylate (1.95 g, 10.5 mmol, 5.0 eq) and BOP reagent (1.4 g, 3.15 mmol, 1.5 eq). MeCN (21 mL) and DBU (639 mg, 4.2 mmol, 2.0 eq) were added and the mixture was heated to 60° C. After 48 hours the reaction was checked by LCMS, which showed conversion to the desired product. The reaction mixture was cooled to room temperature and poured into a separatory funnel. The mixture was partitioned between TBME (50 mL) and water (20 mL). The organic layer was washed with water (20 mL) and brine (20 mL), dried over anhydrous sodium sulfate, filtered, and concentrated. The crude residue was purified by flash chromatography (Biotage, 25 g SiO$_2$, 40→60% EtOAc/heptanes +2% NEt$_3$) to provide tert-butyl 4-{(6R,7R)-rel-2-[3-(dimethylamino)azetidin-1-yl]-6-methyl-7-[5-methyl-1-(tetrahydro-2H-pyran-2-yl)-1H-indazol-4-yl]-5,6,7,8-tetrahydroquinazolin-4-yl}piperazine-1-carboxylate (F-5) as an off-white solid (1.33 g, 99% yield). $^1$H NMR (400 MHz, CDCl$_3$) δ 7.98 (d, J=4.6 Hz, 1H), 7.34 (dd, J=15.0, 8.6 Hz, 1H), 7.23-7.15 (m, 1H), 5.68 (ddd, J=12.6, 9.7, 2.6 Hz, 1H), 4.16-3.86 (m, 5H), 3.75 (dd, J=10.8, 8.1 Hz, 1H), 3.62 (t, J=8.5 Hz, 2H), 3.46 (d, J=11.2 Hz, 3H), 3.34-3.03 (m, 6H), 2.70 (d, J=12.8 Hz, 1H), 2.64-2.50 (m, 1H), 2.43 (s, 3H), 2.32 (q, J=11.9, 11.0 Hz, 2H), 2.21 (s, 6H), 2.15 (s, 1H), 2.06 (d, J=12.3 Hz, 1H), 1.80-1.72 (m, 3H), 1.49 (s, 9H), 0.76 (d, J=5.6 Hz, 3H). LCMS (ESI) m/z 645 (M+H).

Step 5: Synthesis of N,N-dimethyl-1-[(6R,7R)-rel-6-methyl-7-(5-methyl-1H-indazol-4-yl)-4-(piperazin-1-yl)-5,6,7,8-tetrahydroquinazolin-2-yl]azetidin-3-amine (F-6)

To a stirred solution of tert-butyl 4-{(6R,7R)-rel-2-[3-(dimethylamino)azetidin-1-yl]-6-methyl-7-[5-methyl-1-(tetrahydro-2H-pyran-2-yl)-1H-indazol-4-yl]-5,6,7,8-tetrahydroquinazolin-4-yl}piperazine-1-carboxylate (F-5) (125 mg, 0.194 mmol, 1.0 eq) in DCM (8 mL) was added TFA (2 mL). The resulting solution was stirred at 25° C. for 72hrs. LCMS analysis showed conversion to the product. Solvent was removed under reduced pressure to provide N,N-dimethyl-1-[(6R,7R)-rel-6-methyl-7-(5-methyl-1H-indazol-4-yl)-4-(piperazin-1-yl)-5,6,7,8-tetrahydroquinazolin-2-yl]azetidin-3-amine (F-6) (89 mg, 100% yield) as a brown oil, which was taken on without further purification. LCMS (ESI) m/z 461 (M+H).

Step 6: Synthesis of 1-{4-[(6R,7R)-rel-2-[3-(dimethylamino)azetidin-1-yl]-6-methyl-7-(5-methyl-1H-indazol-4-yl)-5,6,7,8-tetrahydroquinazolin-4-yl]piperazin-1-yl}prop-2-en-1-one (Example F1)

To a stirred mixture of N,N-dimethyl-1-[(6R,7R)-rel-6-methyl-7-(5-methyl-1H-indazol-4-yl)-4-(piperazin-1-yl)-5,6,7,8-tetrahydroquinazolin-2-yl]azetidin-3-amine (F-6) (89 mg, 0.19 mmol, 1.0 eq) in EtOAc (50 mL) and saturated NaHCO$_3$ (50 mL) was added dropwise a solution of acryloyl chloride (17.5 mg, 0.193 mmol, 1.0 eq) in EtOAc (5 mL) at 0-5° C. The resulting mixture was stirred at the same temperature for 20 mins. LCMS analysis showed consumption of the starting material. The organic layer was separated. The aqueous layer was extracted with EtOAc (2×30 mL). The combined organics were dried over anhydrous Na$_2$SO$_4$ and concentrated. The crude material was purified by flash chromatography (SiO$_2$, 0→5% MeOH/DCM) to provide 1-{4-[(6R,7R)-rel-2-[3-(dimethylamino)azetidin-1-yl]-6-methyl-7-(5-methyl-1H-indazol-4-yl)-5,6,7,8-tetrahydroquinazolin-4-yl]piperazin-1-yl}prop-2-en-1-one (Example F1) (26 mg, 27% yield) as a white solid. $^1$H NMR (400 MHz, DMSO-d$_6$) δ 12.94 (s, 1H), 8.05 (s, 1H), 7.28 (d, J=8.5 Hz, 1H), 7.16 (d, J=8.5 Hz, 1H), 6.84 (dd, J=16.7, 10.5 Hz, 1H), 6.14 (dd, J=16.7, 2.4 Hz, 1H), 5.71 (dd, J=10.4, 2.4 Hz, 1H), 3.95 (t, J=7.9 Hz, 2H), 3.85-3.75 (m, 1H), 3.76-3.67 (m, 3H), 3.64-3.57 (m, 2H), 3.49-3.40 (m, 2H), 3.29-3.15 (m, 3H), 3.12-2.94 (m, 2H), 2.81 (dd, J=18.3, 6.2 Hz, 1H), 2.69-2.61 (m, 1H), 2.60-2.51 (m, 1H), 2.45-2.34 (m, 4H), 2.09 (s, 6H), 0.68 (d, J=6.1 Hz, 3H). LCMS (ESI) m/z 515 (M+H).

Step 7: Synthesis of 1-{4-[(6S,7S)-2-[3-(dimethylamino)azetidin-1-yl]-6-methyl-7-(5-methyl-1H-indazol-4-yl)-5,6,7,8-tetrahydroquinazolin-4-yl]piperazin-1-yl}prop-2-en-1-one (Example F2) and 1-{4-[(6R,7R)-2-[3-(dimethylamino)azetidin-1-yl]-6-methyl-7-(5-methyl-1H-indazol-4-yl)-5,6,7,8-tetrahydroquinazolin-4-yl]piperazin-1-yl}prop-2-en-1-one (Example F3)

1-{4-[(6R,7R)-rel-2-[3-(dimethylamino)azetidin-1-yl]-6-methyl-7-(5-methyl-1H-indazol-4-yl)-5,6,7,8-tetrahydroquinazolin-4-yl]piperazin-1-yl}prop-2-en-1-one (218 mg) was purified by chiral SFC on a Chrialpak AD-3 (4.6 mm×100 mm, 3 micron particle size) column which was eluted with 30% IPA +10 mM NH$_3$ in CO$_2$ held at 25° C. at 120 bar. A flow rate of 4.0 mL/min gave Rt$_{(Peak\ 1)}$=2.53 min, and Rt$_{(Peak\ 2)}$=4.58 min. 1-{4-[(6R,7R)-2-[3-(dimethylamino)azetidin-1-yl]-6-methyl-7-(5-methyl-1H-indazol-4-yl)-5,6,7,8-tetrahydroquinazolin-4-yl]piperazin-1-yl}prop-2-en-1-one (Example F2) (Peak 1): 29.8 mg, >99% ee, 14% yield. $^1$H NMR (600 MHz, DMSO-d$_6$) δ 8.03 (s, 1H), 7.28 (d, J=8.4 Hz, 1H), 7.16 (d, J=8.4 Hz, 1H), 6.83 (ddd, J=14.9, 10.0, 4.1 Hz, 1H), 6.14 (dd, J=16.6, 2.3 Hz, 1H), 5.71 (dt, J=10.7, 1.8 Hz, 1H), 3.94 (t, J=7.5 Hz, 2H), 3.78 (s, 1H), 3.73-3.68 (m, 3H), 3.60 (s, 2H), 3.41-3.34 (m, 3H), 3.27-3.14 (m, 1H), 3.08-2.96 (m, 2H), 2.81 (dd, J=18.5, 6.6 Hz, 1H), 2.67-2.61 (m, 2H), 2.49-2.34 (m, 5H), 2.07 (s, 6H), 0.68 (s, 3H); [α]$_d^{22}$=−27.3° (C=0.1, MeOH); LCMS (ESI) m/z 515 (M+H). 1-{4-[(6S,7S)-2-[3-(dimethylamino)azetidin-1-yl]-6-methyl-7-(5-methyl-1H-indazol-4-yl)-5,6,7,8-tetrahydroquinazolin-4-yl]piperazin-1-yl}prop-2-en-1-one (Example F3) (Peak 2): 32.7 mg, ~99% ee, 15% yield. $^1$H NMR (600 MHz, DMSO-d$_6$) δ 8.04 (s, 1H), 7.28 (d, J=8.3 Hz, 1H), 7.16 (d, J=8.5 Hz, 1H), 6.94-6.72 (m, 1H), 6.25-5.97 (m, 1H), 5.71 (dt, J=10.5, 1.9 Hz, 1H), 3.94 (t, J=7.4 Hz, 2H), 3.79 (d, J=17.9 Hz, 1H), 3.74-3.67 (m, 3H), 3.61 (s, 2H), 3.41-3.34 (m, 3H), 3.31-3.13 (m, 1H), 3.08-2.97 (m, 2H), 2.81 (dd, J=18.5, 5.8 Hz, 1H), 2.63 (d, J=15.4 Hz, 2H), 2.49-2.34 (m, 5H), 2.07 (s, 6H), 0.68 (d, J=6.3 Hz, 3H); [α]$_d^{22}$=51.2° (C=0.1, MeOH); LCMS (ESI) m/z 515 (M+H).

Example F14 (Scheme F')

1-(4-{(6R,7R)-7-(6-chloro-5-methyl-1H-indazol-4-yl)-2-[3-(dimethylamino)azetidin-1-yl]-6-methyl-5,6,7,8-tetrahydroquinazolin-4-yl}piperazin-1-yl)prop-2-en-1-one Scheme F:
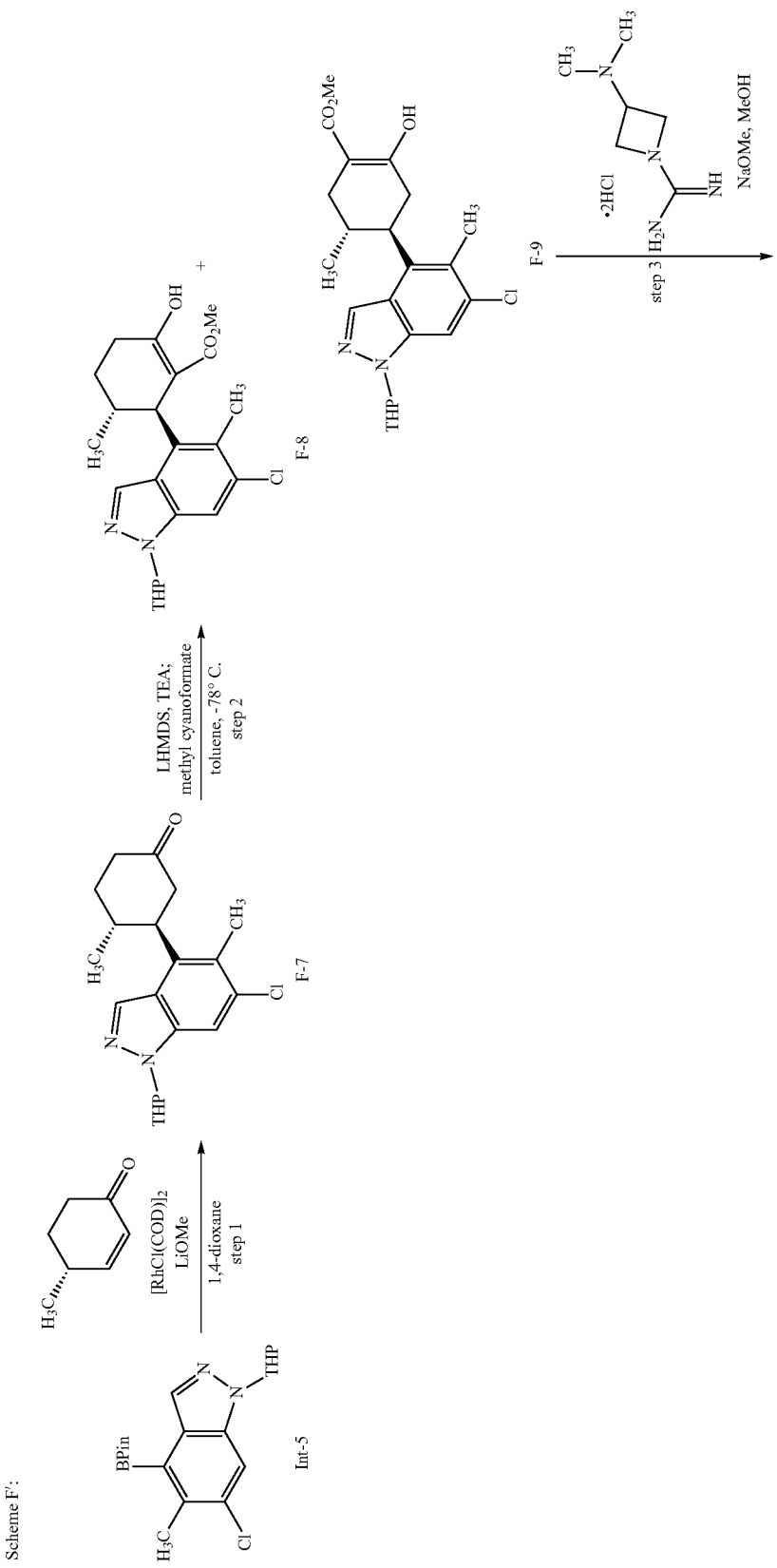

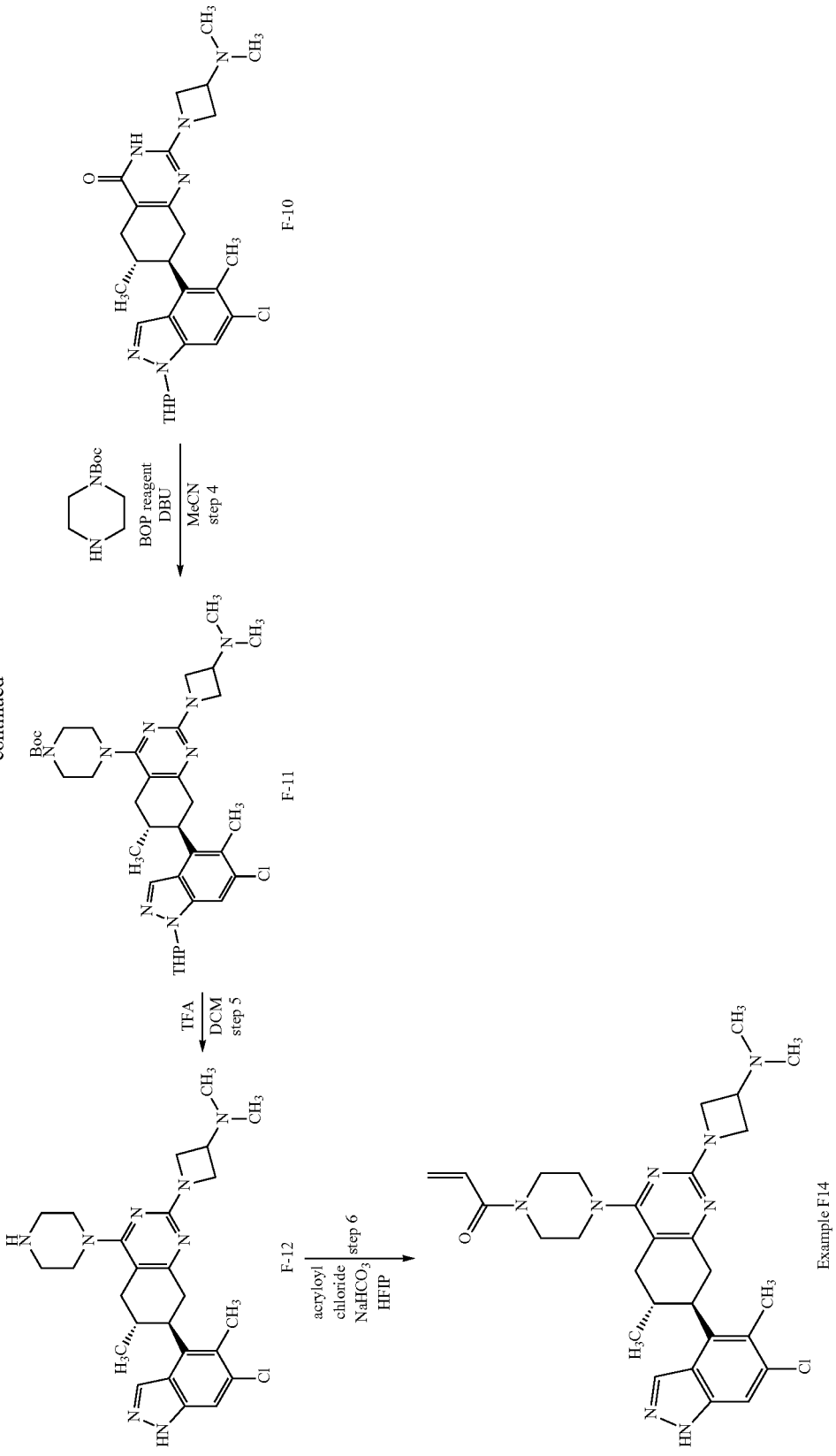

Step 1: Synthesis of (3R,4R)-3-[6-chloro-5-methyl-1-(oxan-2-yl)-1H-indazol-4-yl]-4-methylcyclohexan-1-one (F-7)

To an oven-dried flask equipped with a magnetic stir bar was added 6-chloro-5-methyl-1-(tetrahydro-2H-pyran-2-yl)-4-(4,4,5,5-tetramethyl-1,3,2-dioxaborolan-2-yl)-1H-indazole (9.4 mg, 25 mmol), LiOMe (1.1 g, 30.0 mmol), and [RhCl(COD)]$_2$ (247 mg, 0.50 mmol). The flask was thoroughly purged with N$_2$. Degassed 1,4-dioxane (sparged with N$_2$ for 1 h) and (4R)-4-methylcyclohex-2-en-1-one (3.58 g, 32.5 mmol) were added. The reaction was heated to 40° C. and stirred at this temperature for 48 h. LCMS analysis showed consumption of the starting material with formation of the desired product mass. The reaction was transferred to a separatory funnel and partitioned between EtOAc and saturated aqueous NH$_4$Cl. The organic layer was washed with brine, dried over anhydrous Na$_2$SO$_4$, filtered and concentrated. The residue was purified by flash chromatography (Biotage, 50 g SiO$_2$,15-25% EtOAc/heptanes) to provide (3R,4R)-3-[6-chloro-5-methyl-1-(oxan-2-yl)-1H-indazol-4-yl]-4-methylcyclohexan-1-one (F-7) (6.15 g, 68% yield) as a white foam that solidified upon standing. $^1$H NMR (400 MHz, CDCl$_3$) δ 8.25-8.09 (m, 1H), 7.59 (d, J=7.7 Hz, 1H), 5.64 (td, J=9.7, 2.7 Hz, 1H), 4.13-3.93 (m, 1H), 3.86-3.68 (m, 1H), 3.30 (ddd, J=14.3, 11.0, 4.3 Hz, 1H), 3.10-2.83 (m, 1H), 2.69-2.37 (m, 8H), 2.31-2.03 (m, 3H), 1.90-1.56 (m, 4H), 0.73 (dd, J=6.5, 3.6 Hz, 3H). LCMS (ESI) m/z 361 (M+H).

Step 2: Synthesis of methyl (4R,5R)-4-[6-chloro-5-methyl-1-(oxan-2-yl)-1H-indazol-4-yl]-2-hydroxy-5-methylcyclohex-1-ene-1-carboxylate (F-9) and methyl (5R,6R)-6-[6-chloro-5-methyl-1-(oxan-2-yl)-1H-indazol-4-yl]-2-hydroxy-5-methylcyclohex-1-ene-1-carboxylate (F-8)

To an oven-dried vial flask equipped with a magnetic stir bar was added toluene (39.6 ml, c=0.14 M), LHMDS (1.0 M in PhMe, 11.1 mL, 11.1 mmol), and TEA (6.73 g, 9.27 mL, 66.5 mmol). The mixture was cooled to −78° C. A solution of (3R,4R)-3-[6-chloro-5-methyl-1-(oxan-2-yl)-1H-indazol-4-yl]-4-methylcyclohexan-1-one (F-7) (2.0 g, 5.54 mmol) in toluene (10 mL) was added dropwise and the mixture was stirred at −78° C. A bright yellow reaction solution was produced. A solution of methyl cyanoformate (566 mg, 0.54 ml, 6.65 mmol) in toluene (10 mL) was added dropwise. The mixture was stirred for 5 min. LCMS analysis showed consumption of the starting material with formation of the desired product mass. The reaction was quenched by addition of saturated aqueous NH$_4$Cl and the mixture was transferred to a separatory funnel. The reaction was partitioned between EtOAc and water. The organic layer was washed with brine, dried over anhydrous Na$_2$SO$_4$, filtered and concentrated (2.3 g) to a white foam. $^1$H NMR analysis showed that the crude material was a complex mixture of diastereoisomers with methyl (4R,5R)-4-[6-chloro-5-methyl-1-(oxan-2-yl)-1H-indazol-4-yl]-2-hydroxy-5-methylcyclohex-1-ene-1-carboxylate (F-9) as the major regioisomer and methyl (5R,6R)-6-[6-chloro-5-methyl-1-(oxan-2-yl)-1H-indazol-4-yl]-2-hydroxy-5-methylcyclohex-1-ene-1-carboxylate (F-8) as the minor regioisomer. LCMS (ESI) m/z 419 (M+H).

Step 3: Synthesis of (6R,7R)-7-[6-chloro-5-methyl-1-(oxan-2-yl)-1H-indazol-4-yl]-2-[3-(dimethylamino)azetidin-1-yl]-6-methyl-5,6,7,8-tetrahydroquinazolin-4(3H)-one (F-10)

To a flask equipped with a magnetic stir bar was added the crude mixture containing methyl (4R,5R)-4-[6-chloro-5-methyl-1-(oxan-2-yl)-1H-indazol-4-yl]-2-hydroxy-5-methylcyclohex-1-ene-1-carboxylate (F-9) (2.3 g, 5.5 mmol), 3-(dimethylamino)azetidine-1-carboximidamide bis-hydrochloride (WO15089327) (1.2 g, 5.5 mmol) under nitrogen. A solution of NaOMe (1 M in MeOH, 16.6 mL, 16.6 mmol) was added and the mixture was stirred at ambient temperature for 2 h. LCMS analysis indicated selective and complete consumption of F-9 with formation of the desired product mass. The reaction was quenched with saturated aqueous NaHCO$_3$ and extracted with DCM (3×). The combined organic extracts were dried over Na$_2$SO$_4$, filtered, and concentrated to a yellow solid. The crude residue was purified by flash chromatography (Isco, 40 g SiO$_2$, 0-15% MeOH/DCM +2% TEA) to provide (6R,7R)-7-[6-chloro-5-methyl-1-(oxan-2-yl)-1H-indazol-4-yl]-2-[3-(dimethylamino)azetidin-1-yl]-6-methyl-5,6,7,8-tetrahydroquinazolin-4(3H)-one (F-10) (1.4 g, 49% yield) as an off-white solid. $^1$H NMR (400 MHz, DMSO-d$_6$) δ 11.24 (s, 1H), 8.27 (s, 1H), 7.78 (s, 1H), 5.94-5.74 (m, 1H), 3.98 (td, J=8.0, 7.3, 1.9 Hz, 2H), 3.91-3.82 (m, 1H), 3.75 (td, J=11.1, 9.0, 6.2 Hz, 3H), 3.40-3.19 (m, 2H), 3.15-3.03 (m, 1H), 2.94 (td, J=14.6, 11.6, 6.8 Hz, 1H), 2.70 (dt, J=17.5, 4.3 Hz, 1H), 2.56-2.47 (m, 1H, under DMSO), 2.47-2.29 (m, 4H), 2.06 (s, 9H), 1.80-1.65 (m, 1H), 1.57 (dq, J=10.4, 6.2, 4.8 Hz, 2H), 0.63 (dd, J=9.0, 6.4 Hz, 3H). LCMS (ESI) m/z 511 (M+H).

Step 4: Synthesis of tert-butyl 4-{(6R,7R)-7-[6-chloro-5-methyl-1-(oxan-2-yl)-1H-indazol-4-yl]-2-[3-(dimethylamino)azetidin-1-yl]-6-methyl-5,6,7,8-tetrahydroquinazolin-4-yl}piperazine-1-carboxylate (F-11)

To a round bottom flask equipped with a magnetic stir bar was added (6R,7R)-7-[6-chloro-5-methyl-1-(oxan-2-yl)-1H-indazol-4-yl]-2-[3-(dimethylamino)azetidin-1-yl]-6-methyl-5,6,7,8-tetrahydroquinazolin-4(3H)-one (F-10) (1.4 g, 2.6 mmol) and tert-butyl piperazine-1-carboxylate (3.5 g, 18.6 mmol). The flask was purged with nitrogen and MeCN (6.63 mL, c=0.4 M), DBU (0.8 mL, 5.3 mmol), and BOP reagent (1.8 g, 4.0 mmol) were added. The reaction was heated to 50° C. and stirred at this temperature for 24 h. LCMS analysis showed consumption of the starting material with formation of the desired product mass. The reaction was cooled to room temperature and then poured into water. The mixture was stirred for 1 h and then extracted with MTBE (2×). The combined organic layers were washed with water, dried over anhydrous Na$_2$SO$_4$, and concentrated to provide a yellow residue. The material was purified by flash chromatography (Isco, SiO$_2$, 10-15% MeOH/DCM+2% TEA) to provide tert-butyl 4-{(6R,7R)-7-[6-chloro-5-methyl-1-(oxan-2-yl)-1H-indazol-4-yl]-2-[3-(dimethylamino)azetidin-1-yl]-6-methyl-5,6,7,8-tetrahydroquinazolin-4-yl}piperazine-1-carboxylate (F-11) (1.8 g, 82% yield) as an off-white solid. $^1$H NMR (400 MHz, DMSO-d$_6$) δ 8.19 (d, J=2.6 Hz, 1H), 7.79 (d, J=2.6 Hz, 1H), 5.84 (dd, J=9.4, 2.4 Hz, 1H), 3.93 (t, J=7.7 Hz, 2H), 3.85 (s, 1H), 3.76 (q, J=7.1, 6.0 Hz, 1H), 3.70 (dd, J=8.5, 5.7 Hz, 2H), 3.52 (d, J=9.5 Hz, 2H), 3.39 (dd, J=18.6, 10.3 Hz, 5H), 3.22-3.10 (m, 2H), 3.03 (q, J=6.2 Hz, 1H), 2.99-2.91 (m, 1H), 2.86 (td, J=11.2, 5.8 Hz, 1H), 2.69-2.54 (m, 1H), 2.48 (s, 3H), 2.39 (dd, J=22.2, 11.5 Hz, 2H), 2.07 (s, 8H), 1.82-1.63 (m, 1H), 1.57 (s, 2H), 1.42 (s, 9H), 0.67 (dd, J=8.7, 6.0 Hz, 3H). LCMS (ESI) m/z 679 (M+H).

Step 5: Synthesis of 1-[(6R,7R)-7-(6-chloro-5-methyl-1H-indazol-4-yl)-6-methyl-4-(piperazin-1-yl)-5,6,7,8-tetrahydroquinazolin-2-yl]-N,N-dimethylazetidin-3-amine (F-12)

A vial equipped with a magnetic stir bar was charged with tert-butyl 4-{(6R,7R)-7-[6-chloro-5-methyl-1-(oxan-2-yl)-

1H-indazol-4-yl]-2-[3-(dimethylamino)azetidin-1-yl]-6-methyl-5,6,7,8-tetrahydroquinazolin-4-yl}piperazine-1-carboxylate (F-11) (1.1 g, 1.5 mmol). DCM (5.1 mL, c=0.3 M), and TFA (7.4 g, 5.0 mL, 66 mmol) were added. The mixture was stirred for 3 h, which showed consumption of the starting material with formation of the desired product mass. The reaction mixture was carefully poured into aqueous saturated NaHCO$_3$ (gas evolution) and extracted with DCM (4×). The combined organic extracts were dried over anhydrous Na$_2$SO$_4$, filtered and concentrated to provide 1-[(6R,7R)-7-(6-chloro-5-methyl-1H-indazol-4-yl)-6-methyl-4-(piperazin-1-yl)-5,6,7,8-tetrahydroquinazolin-2-yl]-N,N-dimethylazetidin-3-amine (F-12) (786 mg, 100% yield), which was taken on without further purification. LCMS (ESI) m/z 495 (M+H).

Step 6: 1-(4-{(6R,7R)-7-(6-chloro-5-methyl-1H-indazol-4-yl)-2-[3-(dimethylamino)azetidin-1-yl]-6-methyl-5,6,7,8-tetrahydroquinazolin-4-yl}piperazin-1-yl)prop-2-en-1-one (Example F14)

To a vial equipped with a magnetic stir bar was charged with 1-[(6R,7R)-7-(6-chloro-5-methyl-1H-indazol-4-yl)-6-methyl-4-(piperazin-1-yl)-5,6,7,8-tetrahydroquinazolin-2-yl]-N,N-dimethylazetidin-3-amine (F-12) (1.1 g, 2.2 mmol) and HFIP (11 mL, c=0.2 M). The mixture was stirred until the solid dissolved. NaHCO$_3$ (1.1 g, 13.2 mmol and acryloyl chloride (234 mg, 0.21 mL, 2.6 mmol) were added. After 5 min LCMS analysis showed formation of the desired product mass with ~20% remaining starting material. Additional acryloyl chloride (0.035 mL, 0.43 mmol) was added. After 5 min the reaction was diluted with MTBE, transferred to a separatory funnel, and washed with H$_2$O. The aqueous layer was extracted with MTBE. The combined organics were dried over anhydrous Na$_2$SO$_4$, filtered and concentrated to provide a yellow residue. The crude product was taken up in DMSO and purified by preparative HPLC with a Phenomenex Luna Omega Polar C18 column (250×50 mm, 5 μm particle size), which was eluted with 5-30% MeCN/H$_2$O (+0.1% AcOH) with a flow rate of 85 mL/min to provide 1-(4-{(6R,7R)-7-(6-chloro-5-methyl-1H-indazol-4-yl)-2-[3-(dimethylamino)azetidin-1-yl]-6-methyl-5,6,7,8-tetrahydroquinazolin-4-yl}piperazin-1-yl)prop-2-en-1-one (Example F14) (588 mg, 47% yield) as an off-white solid. $^1$H NMR (400 MHz, DMSO-d$_6$) δ 13.06 (s, 1H), 8.13 (s, 1H), 7.53 (s, 1H), 6.84 (dd, J=16.7, 10.5 Hz, 1H), 6.14 (dd, J=16.7, 2.4 Hz, 1H), 5.71 (dd, J=10.4, 2.4 Hz, 1H), 3.94 (dd, J=8.7, 7.0 Hz, 2H), 3.86-3.67 (m, 4H), 3.61 (s, 2H), 3.50-3.37 (m, 3H), 3.24 (d, J=26.7 Hz, 2H), 3.08-2.94 (m, 2H), 2.84 (dd, J=18.3, 6.3 Hz, 1H), 2.63 (dd, J=15.0, 3.5 Hz, 1H), 2.47 (s, 5H), 2.08 (s, 6H), 0.68 (d, J=6.0 Hz, 3H). LCMS (ESI) m/z 549 (M+H).

Example F5 (Scheme F''')

1-(4-{(6R,7R)-rel-7-(5-chloro-1H-indazol-4-yl)-2-[3-(dimethylamino)azetidin-1-yl]-6-methyl-5,6,7,8-tetrahydroquinazolin-4-yl}piperazin-1-yl)prop-2-en-1-one Example F10 (Scheme F''')

1-(4-{(6R,7R)-7-(5-chloro-1H-indazol-4-yl)-2-[3-(dimethylamino)azetidin-1-yl]-6-methyl-5,6,7,8-tetrahydroquinazolin-4-yl}piperazin-1-yl)prop-2-en-1-one Example F11 (Scheme F''')

1-(4-{(6S,7S)-7-(5-chloro-1H-indazol-4-yl)-2-[3-(dimethylamino)azetidin-1-yl]-6-methyl-5,6,7,8-tetrahydroquinazolin-4-yl}piperazin-1-yl)prop-2-en-1-one

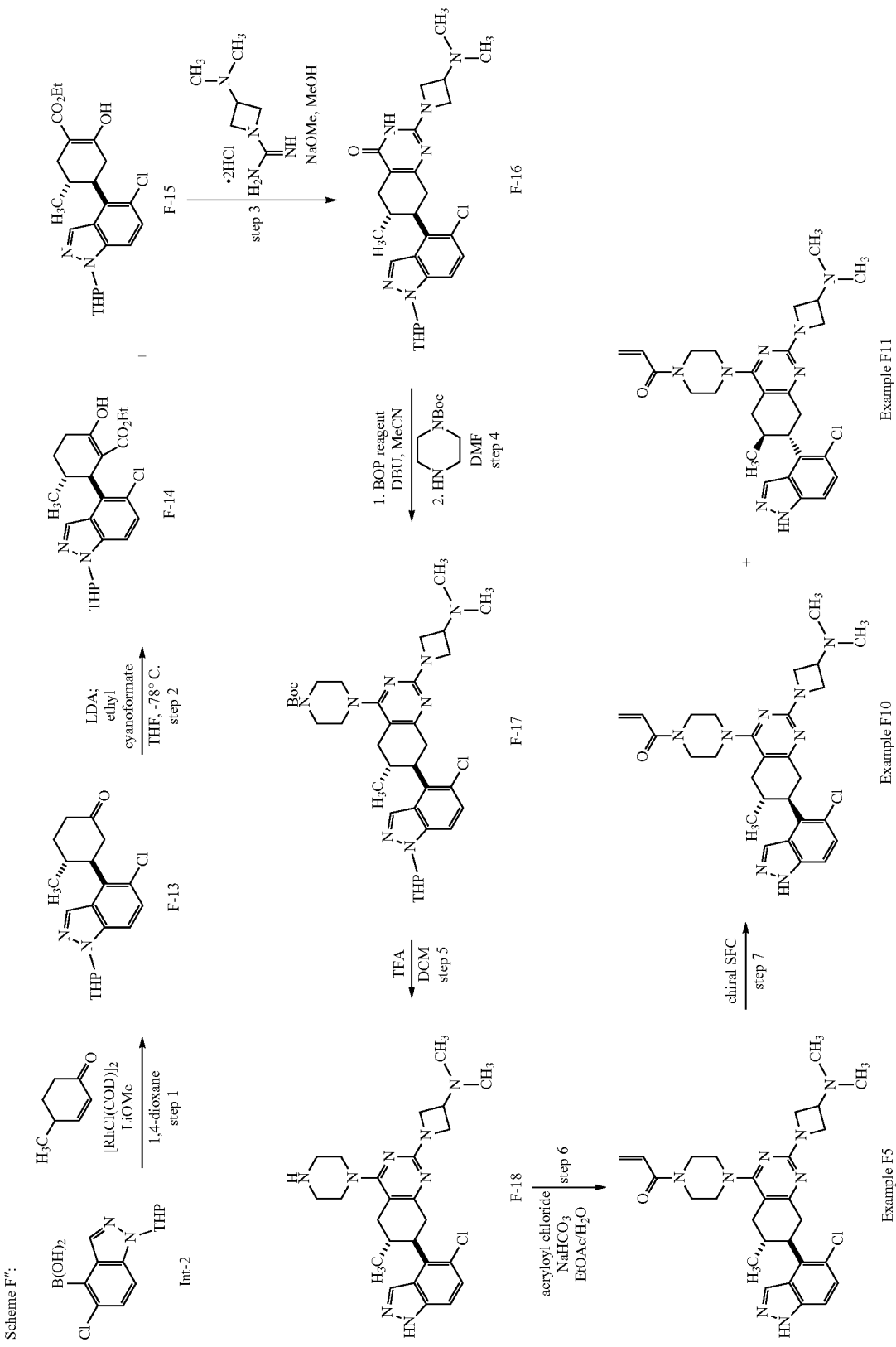
Scheme F':

Step 1: Synthesis of (3R,4R)-rel-3-[5-chloro-1-(oxan-2-yl)-1H-indazol-4-yl]-4-methylcyclohexan-1-one (F-13)

To a stirred solution of (5-chloro-1-(tetrahydro-2H-pyran-2-yl)-1H-indazol-4-yl)boronic acid (Int-2) (1.8 g, 6.43 mmol), 4-methylcyclohex-2-en-1-one (1.06 g, 9.63 mmol) and $K_3PO_4$ (4.09 g, 19.3 mmol) in a mixture of 1,4-dioxane (40 mL) and $H_2O$ (9 mL) was added [Rh(COD)Cl]$_2$ (160 mg, 0.321 mmol) under an inert atmosphere. The resulting mixture was stirred at 40° C. under $N_2$ for 16 h. LCMS analysis showed consumption of the starting material with formation of the desired product mass. The reaction was quenched by addition of brine (50 mL) and the mixture was extracted with EtOAc (3×50 mL). The combined organics were washed with brine (50 mL), dried over $Na_2SO_4$, filtered and concentrated. Purification by flash chromatography (SiO$_2$, 0-30% EtOAc/petroleum ether) provided (3R,4R)-rel-3-[5-chloro-1-(oxan-2-yl)-1H-indazol-4-yl]-4-methylcyclohexan-1-one (F-13) (955 mg, 43% yield) as a white solid. $^1$H NMR (400 MHz, DMSO-d$_6$) δ 8.66 (s, 1H), 7.66 (dd, J=9.0, 2.4 Hz, 1H), 7.44 (d, J=8.9 Hz, 1H), 5.94-5.77 (m, 1H), 3.87 (d, J=10.3 Hz, 1H), 3.75 (dq, J=11.5, 6.3, 5.4 Hz, 1H), 3.50 (ddd, J=13.6, 11.2, 4.2 Hz, 1H), 3.11 (td, J=13.9, 6.8 Hz, 1H), 2.92 (td, J=14.1, 6.1 Hz, 1H), 2.72-2.54 (m, 1H), 2.46-1.91 (m, 6H), 1.75 (dd, J=12.5, 8.0 Hz, 1H), 1.64-1.44 (m, 3H), 0.64 (dd, J=8.7, 6.4 Hz, 3H). LCMS (ESI) m/z 347 (M+H).

Step 2: Synthesis of methyl (5R,6S)-rel-6-[5-chloro-1-(oxan-2-yl)-1H-indazol-4-yl]-2-hydroxy-5-methylcyclohex-1-ene-1-carboxylate (F-14) and methyl (4R,5R)-4-[5-chloro-1-(oxan-2-yl)-1H-indazol-4-yl]-2-hydroxy-5-methylcyclohex-1-ene-1-carboxylate (F-15)

To a solution of (3R,4R)-rel-3-[5-chloro-1-(oxan-2-yl)-1H-indazol-4-yl]-4-methylcyclohexan-1-one (F-13) (950 mg, 2.74 mmol) in THF (30 mL) was added LDA (2 M in THF, 2.74 mL, 5.48 mmol) dropwise at −78° C. The mixture was stirred for 30 min at −78° C. Then ethyl cyanoformate (407 mg, 4.11 mmol) was added and the mixture was stirred for 2 h at −78° C. LCMS showed no starting material. The mixture was quenched with saturated aqueous NH$_4$Cl and extracted with EtOAc (3×40 mL). The combined organics were dried over Na$_2$SO$_4$, filtered, and concentrated. The residue was purified by flash chromatography (SiO$_2$, petroleum ether/EA=3/2) to provide ethyl (5R,6S)-rel-6-[5-chloro-1-(oxan-2-yl)-1H-indazol-4-yl]-2-hydroxy-5-methylcyclohex-1-ene-1-carboxylate (F-14) and ethyl (4R,5R)-4-[5-chloro-1-(oxan-2-yl)-1H-indazol-4-yl]-2-hydroxy-5-methylcyclohex-1-ene-1-carboxylate (F-15) (1.0 g, 87% yield, 1:1 mixture) as a complex mixture of diastereoisomers as a yellow oil. LCMS (ESI) m/z 419 (M+H).

Step 3: Synthesis of (6R,7R)-rel-7-[5-chloro-1-(oxan-2-yl)-1H-indazol-4-yl]-2-[3-(dimethylamino)azetidin-1-yl]-6-methyl-5,6,7,8-tetrahydroquinazolin-4(3H)-one To a mixture of ethyl (5R,6S)-rel-6-[5-chloro-1-(oxan-2-yl)-1H-indazol-4-yl]-2-hydroxy-5-methylcyclohex-1-ene-1-carboxylate (F-14) and ethyl (4R,5R)-4-[5-chloro-1-(oxan-2-yl)-1H-indazol-4-yl]-2-hydroxy-5-methylcyclohex-1-ene-1-carboxylate (F-15) (1.0 g, 2.4 mmol) and 3-(dimethylamino)azetidine-1-carboximidamide (679 mg, 4.77 mmol) in EtOH (20 mL) was added NaOMe (258 mg, 4.77 mmol) and the mixture was stirred at reflux for 16 h. LCMS analysis showed complete and selective consumption of F-15 with formation of the desired product mass. The mixture was concentrated to dryness and purified by flash chromatography (SiO$_2$, DCM/MeOH=1:1) to provide (6R,7R)-rel-7-[5-chloro-1-(oxan-2-yl)-1H-indazol-4-yl]-2-[3-(dimethylamino)azetidin-1-yl]-6-methyl-5,6,7,8-tetrahydroquinazolin-4(3H)-one (F-16) (400 mg, 34% yield) as a yellow solid. LCMS (ESI) m/z 497 (M+H).

Step 4: Synthesis of tert-butyl 4-{(6R,7R)-rel-7-[5-chloro-1-(oxan-2-yl)-1H-indazol-4-yl]-2-[3-(dimethylamino)azetidin-yl]-6-methyl-5,6,7,8-tetrahydroquinazolin-4-yl}piperazine-1-carboxylate (F-17)

To a mixture of (6R,7R)-rel-7-[5-chloro-1-(oxan-2-yl)-1H-indazol-4-yl]-2-[3-(dimethylamino)azetidin-1-yl]-6-methyl-5,6,7,8-tetrahydroquinazolin-4(3H)-one (F-16) (400 mg, 0.805 mmol), tert-butyl piperazine-1-carboxylate (300 mg, 1.61 mmol) and BOP reagent (711 mg, 1.61 mmol) in MeCN (10 mL) was added DBU (245 mg, 1.61 mmol) and the mixture was stirred at 20° C. for 16 h. LCMS analysis showed formation of the HOBt adduct. The mixture was concentrated and the residue was purified by flash chromatography (SiO$_2$, DCM/MeOH=7/3) to give 1-{(6R,7R)-4-[(1H-benzotriazol-1-yl)oxy]-7-[5-chloro-1-(oxan-2-yl)-1H-indazol-4-yl]-6-methyl-5,6,7,8-tetrahydroquinazolin-2-yl}-N,N-dimethylazetidin-3-amine (400 mg, 82% yield). To this intermediate (400 mg, 0.651 mmol) and tert-butyl piperazine-1-carboxylate (243 mg, 1.3 mmol) in DMF (10 ml) was added DBU (198 mg, 1.3 mmol) and the mixture was stirred at 90° C. for 16 h. LCMS analysis showed consumption of the starting material with formation of the desired product. The mixture was concentrated and the residue was purified by flash chromatography (SiO$_2$, DCM/MeOH=20/1) to provide tert-butyl 4-{(6R,7R)-rel-7-[5-chloro-1-(oxan-2-yl)-1H-indazol-4-yl]-2-[3-(dimethylamino)azetidin-1-yl]-6-methyl-5,6,7,8-tetrahydroquinazolin-4-yl}piperazine-1-carboxylate (F-17) (300 mg, 69% yield) as a brown oil. LCMS (ESI) m/z 665 (M+H).

Step 5: Synthesis of 1-[(6R,7R)-rel-7-(5-chloro-1H-indazol-4-yl)-6-methyl-4-(piperazin-1-yl)-5,6,7,8-tetrahydroquinazolin-2-yl]-N,N-dimethylazetidin-3-amine (F-18)

To a solution of tert-butyl 4-{(6R,7R)-rel-7-[5-chloro-1-(oxan-2-yl)-1H-indazol-4-yl]-2-[3-(dimethylamino)azetidin-1-yl]-6-methyl-5,6,7,8-tetrahydroquinazolin-4-yl}piperazine-1-carboxylate (F-17) (300 mg, 0.451 mmol) in DCM (5 mL) was added HCl (4 M in 1,4-dioxane, 3 mL). The mixture was stirred at 20° C. for 2 h. LCMS analysis showed consumption of the starting material with formation of the desired product mass. The mixture was filtered and concentrated to provide 1-[(6R,7R)-rel-7-(5-chloro-1H-indazol-4-yl)-6-methyl-4-(piperazin-1-yl)-5,6,7,8-tetrahydroquinazolin-2-yl]-N,N-dimethylazetidin-3-amine (F-18) (233 mg, 100% yield) as a brown solid, which was taken on without further purification. LCMS (ESI) m/z 481 (M+H).

Step 6: Synthesis of 1-(4-{(6R,7R)-rel-7-(5-chloro-1H-indazol-4-yl)-2-[3-(dimethylamino)azetidin-1-yl]-6-methyl-5,6,7,8-tetrahydroquinazolin-4-yl}piperazin-1-yl)prop-2-en-1-one (Example F5)

To a solution of 1-[(6R,7R)-rel-7-(5-chloro-1H-indazol-4-yl)-6-methyl-4-(piperazin-1-yl)-5,6,7,8-tetrahydroquinazolin-2-yl]-N,N-dimethylazetidin-3-amine (F-18) (233 mg, 0.45 mmol) in EtOAc (40 mL) and saturated aqueous NaHCO₃ (40 mL) was added acryloyl chloride (45 mg, 0.495 mmol). The mixture was stirred for 30 min at ambient temperature. The mixture was extracted with EA (3×40 mL). The combined organic extracts were washed with brine (20 mL), dried over Na₂SO₄, filtered and concentrated. The residue was purified by preparative HPLC with a Gemini-18 column (100×21.2 mm, 5 μm particle size), which was eluted with 45-55% MeCN/H₂O (+0.05% NH₃) to provide 1-(4-{(6R,7R)-rel-7-(5-chloro-1H-indazol-4-yl)-2-[3-(dimethylamino)azetidin-1-yl]-6-methyl-5,6,7,8-tetrahydroquinazolin-4-yl}piperazin-1-yl) prop-2-en-1-one (Example F5) (28 mg, 12% yield) as a white solid. ¹H NMR (400 MHz, MeOD) δ 8.13 (s, 1H), 7.45-7.39 (m, 2H), 6.81 (dd, J=16.8, 10.6 Hz, 1H), 6.26 (d, J=1.9 Hz, 1H), 5.81-5.75 (m, 1H), 4.12-4.09 (m, 2H), 3.91-3.78 (m, 4H), 3.71-3.60 (m, 4H), 3.42-3.33 (m, 2H), 3.25-3.05 (m, 3H), 3.00-2.94 (m, 1H), 2.76 (d, J=12.8 Hz, 1H), 2.54-2.40 (m, 2H), 2.21 (s, 6H), 0.82 (d, J=5.7 Hz, 3H). LCMS (ESI) m/z 535, (M+H).

Step 7: Synthesis of 1-(4-{(6R,7R)-7-(5-chloro-1H-indazol-4-yl)-2-[3-(dimethylamino)azetidin-1-yl]-6-methyl-5,6,7,8-tetrahydroquinazolin-4-yl}piperazin-1-yl)prop-2-en-1-one (Example F10) and 1-(4-{(6S,7S)-7-(5-chloro-1H-indazol-4-yl)-2-[3-(dimethylamino)azetidin-1-yl]-6-methyl-5,6,7,8-tetrahydroquinazolin-4-yl}piperazin-1-yl)prop-2-en-1-one (Example F11)

1-(4-{(6R,7R)-rel-7-(5-chloro-1H-indazol-4-yl)-2-[3-(dimethylamino)azetidin-1-yl]-6-methyl-5,6,7,8-tetrahydroquinazolin-4-yl}piperazin-1-yl)prop-2-en-1-one (18.2 mg) (Example F5) was purified by preparative SFC with a Phenomenex Lux Amylose-1 column (100×4.6 mm column, 3 μm), which was eluted with 5-60% IPA in CO₂ (+10 mM NH₃). A flow rate of 4 mL/min gave Rt$_{(Peak\ 1)}$=2.84 min and Rt$_{(Peak\ 2)}$=3.36 min. 1-(4-{(6R,7R)-7-(5-chloro-1H-indazol-4-yl)-2-[3-(dimethylamino)azetidin-1-yl]-6-methyl-5,6,7,8-tetrahydroquinazolin-4-yl}piperazin-1-yl)prop-2-en-1-one (Example F10) (Peak 1): 6.02 mg, >99% ee, 33% yield. ¹H NMR (600 MHz, DMSO-d₆) δ 13.35 (s, 1H), 8.28 (s, 1H), 7.50 (d, J=8.8 Hz, 1H), 7.41 (d, J=8.8 Hz, 1H), 6.88 (dd, J=16.7, 10.5 Hz, 1H), 6.19 (dd, J=16.7, 2.4 Hz, 1H), 5.76 (dd, J=10.4, 2.4 Hz, 1H), 3.99 (ddd, J=9.8, 7.1, 3.2 Hz, 2H), 3.87-3.58 (m, 8H), 3.52-3.47 (m, 2H), 3.31-3.23 (m, 2H), 3.15-3.02 (m, 2H), 2.85 (dd, J=18.3, 6.2 Hz, 1H), 2.70 (d, J=12.3 Hz, 1H), 2.50 (d, J=12.9 Hz, 1H), 2.12 (s, 6H), 0.76 (d, J=5.4 Hz, 3H); [α]$_d^{22}$=−45.5° (c=0.1, MeOH); LCMS (ESI) m/z 535 (M+H). 1-(4-{(6S,7S)-7-(5-chloro-1H-indazol-4-yl)-2-[3-(dimethylamino)azetidin-1-yl]-6-methyl-5,6,7,8-tetrahydroquinazolin-4-yl}piperazin-1-yl)prop-2-en-1-one (Example F11) (Peak 2): 6.38 mg, >99% ee, 35% yield. ¹H NMR (600 MHz, DMSO-d₆) δ 13.35 (s, 1H), 8.28 (s, 1H), 7.49 (s, 1H), 7.41 (d, J=8.8 Hz, 1H), 6.89 (dd, J=16.7, 10.4 Hz, 1H), 6.19 (dd, J=16.7, 2.4 Hz, 1H), 5.76 (dd, J=10.5, 2.3 Hz, 1H), 4.08-3.92 (m, 2H), 3.88-3.59 (m, 8H), 3.51-3.46 (m, 2H), 3.32-3.21 (m, 2H), 3.15-3.04 (m, 2H), 2.85 (dd, J=18.3, 6.1 Hz, 1H), 2.70 (d, J=12.3 Hz, 1H), 2.50 (d, J=13.0 Hz, 1H), 2.12 (s, 6H), 0.76 (d, J=5.4 Hz, 3H); [α]$_d^{22}$=+78.9° (c=0.1, MeOH); LCMS (ESI) m/z 535 (M+H).

The examples in Table F were prepared using similar chemistry in Scheme F, Scheme F', and Scheme F" and the procedures used to prepare 1-{4-[(6R,7R)-rel-2-[3-(dimethylamino)azetidin-1-yl]-6-methyl-7-(5-methyl-1H-indazol-4-yl)-5,6,7,8-tetrahydroquinazolin-4-yl]piperazin-1-yl}prop-2-en-1-one (Example F1), 1-{4-[(6S,7S)-2-[3-(dimethylamino)azetidin-1-yl]-6-methyl-7-(5-methyl-1H-indazol-4-yl)-5,6,7,8-tetrahydroquinazolin-4-yl]piperazin-1-yl}prop-2-en-1-one (Example F2), 1-{4-[(6R,7R)-2-[3-(dimethylamino)azetidin-1-yl]-6-methyl-7-(5-methyl-1H-indazol-4-yl)-5,6,7,8-tetrahydroquinazolin-4-yl]piperazin-1-yl}prop-2-en-1-one (Example F3), 1-(4-{(6R,7R)-7-(6-chloro-5-methyl-1H-indazol-4-yl)-2-[3-(dimethylamino)azetidin-1-yl]-6-methyl-5,6,7,8-tetrahydroquinazolin-4-yl}piperazin-1-yl)prop-2-en-1-one (Example F14), 1-(4-{(6R,7R)-rel-7-(5-chloro-1H-indazol-4-yl)-2-[3-(dimethylamino)azetidin-1-yl]-6-methyl-5,6,7,8-tetrahydroquinazolin-4-yl}piperazin-1-yl)prop-2-en-1-one (Example F5), 1-(4-{(6R,7R)-7-(5-chloro-1H-indazol-4-yl)-2-[3-(dimethylamino)azetidin-1-yl]-6-methyl-5,6,7,8-tetrahydroquinazolin-4-yl}piperazin-1-yl)prop-2-en-1-one (Example F10), 1-(4-{(6S,7S)-7-(5-chloro-1H-indazol-4-yl)-2-[3-(dimethylamino)azetidin-1-yl]-6-methyl-5,6,7,8-tetrahydroquinazolin-4-yl}piperazin-1-yl)prop-2-en-1-one (Example F11). The following examples were made with non-critical changes or substitutions to the exemplified procedure used to prepare Example F1 that someone who is skilled in the art would be able to realize.

TABLE F

| Example | Structure | Compound name | LCMS m/z | Analytical data |
|---|---|---|---|---|
| F4 | 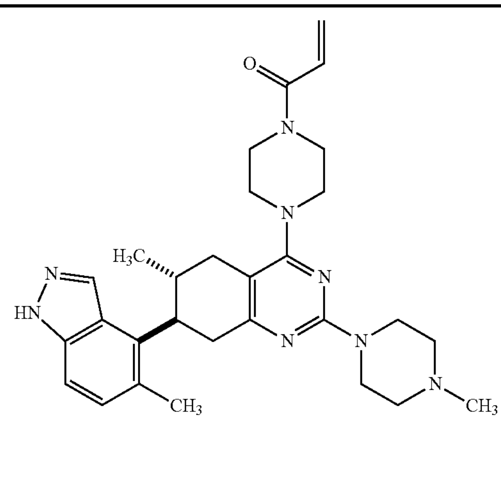 | 1-{4-[(6R,7R)-rel-6-methyl-7-(5-methyl-1H-indazol-4-yl)-2-(4-methylpiperidin-1-yl)-5,6,7,8-tetrahydroquinazolin-4-yl]piperazin-1-yl}prop-2-en-1-one | 515 (M + H) | ¹H NMR (400 MHz, DMSO-d₆) δ 12.97 (s, 1H), 8.03 (s, 1H), 7.29 (d, J = 8.4 Hz, 1H), 7.17 (d, J = 8.5 Hz, 1H), 6.84 (dd, J = 16.7, 10.5 Hz, 1H), 6.15 (dd, J = 16.7, 2.4 Hz, 1H), 5.72 (dd, J = 10.4, 2.4 Hz, 1H), 3.87-3.45 (m, 8H), 3.30-3.15 (m, 6H), 3.11-2.98 (m, 3H), 2.91-2.79 (m, 2H), 2.75-2.60 (m, 4H), 2.44-2.26 (m, 5H), 0.70 (d, J = 6.1 Hz, 3H). |

TABLE F-continued

| Example | Structure | Compound name | LCMS m/z | Analytical data |
|---|---|---|---|---|
| F6 | 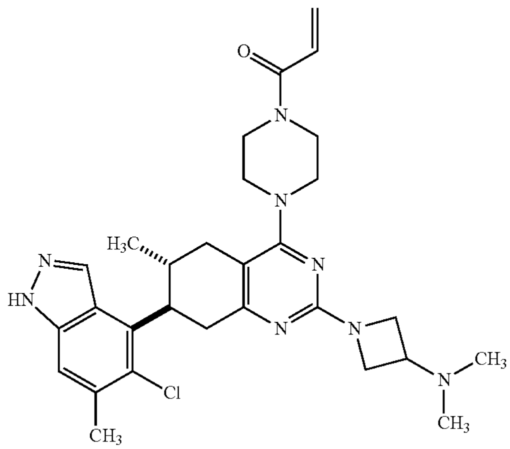 | 1-(4-{(6R,7R)-rel-7-(5-chloro-6-methyl-1H-indazol-4-yl)-2-[3-(dimethyl-amino)azetidin-1-yl]-6-methyl-5,6,7,8-tetrahydroquinazolin-4-yl}piperazin-1-yl)prop-2-en-1-one | 549 (M + H) | $^1$H NMR (400 MHz, DMSO-d$_6$) δ 13.14 (s, 1H), 8.16 (s, 1H), 7.43 (s, 1H), 6.84 (dd, J = 16.7, 10.5 Hz, 1H), 6.14 (dd, J = 16.7, 2.4 Hz, 1H), 5.72 (dd, J = 10.4, 2.4 Hz, 1H), 3.96 (t, J = 7.8 Hz, 2H), 3.87-3.66 (m, 5H), 3.60 (s, 2H), 3.52-3.40 (m, 2H), 3.28-3.15 (m, 3H), 3.02 (dd, J = 18.1, 11.8 Hz, 1H), 2.80 (dd, J = 18.2, 6.0 Hz, 1H), 2.69-2.65 (m, 1H), 2.48 (s, 3H), 2.48-2.39 (m, 3H), 2.12 (s, 6H), 0.71 (d, J = 5.5 Hz, 3H). |
| F7 | 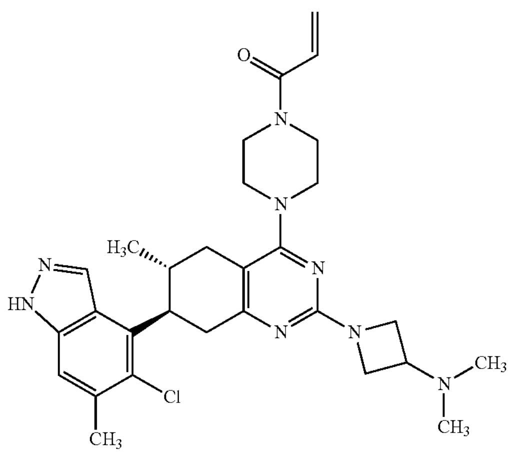 [SMILES: C=CC(=O)N1CCN(c2nc(N3CC(N(C)C)C3)nc3c2C[C@@H](C)[C@H](c2c(Cl)c(C)cc4[nH]ncc24)C3)CC1] | 1-(4-{(6R,7R)-7-(5-chloro-6-methyl-1H-indazol-4-yl)-2-[3-(dimethyl-amino)azetidin-1-yl]-6-methyl-5,6,7,8-tetrahydroquinazolin-4-yl}piperazin-1-yl)prop-2-en-1-one | 549 (M + H) | $^1$H NMR (700 MHz, DMSO-d$_6$) δ 7.80 (s, 1H), 7.11 (s, 1H), 6.48 (dd, J = 16.7, 10.6 Hz, 1H), 5.81 (dd, J = 16.7, 2.2 Hz, 1H), 5.40 (dd, J = 10.4, 2.2 Hz, 1H), 3.62 (q, J = 7.0 Hz, 1H), 3.51-3.28 (m, 9H), 3.17-3.10 (m, 1H), 2.96-2.87 (m, 2H), 2.77 (p, J = 6.1 Hz, 1H), 2.66 (dd, J = 18.4, 11.9 Hz, 1H), 2.49 (dd, J = 18.3, 6.2 Hz, 1H), 2.33 (dd, J = 15.1, 3.6 Hz, 1H), 2.16-2.05 (m, 5H), 1.76 (s, 6H), 0.39 (d, J = 6.2 Hz, 3H).<br>~99% ee, [α]$_d^{22}$ = –+71.5° (C = 0.1, MeOH) |
| F8 | 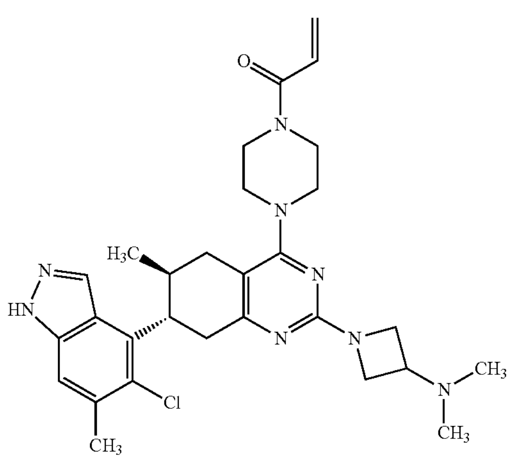 [SMILES: C=CC(=O)N1CCN(c2nc(N3CC(N(C)C)C3)nc3c2C[C@H](C)[C@@H](c2c(Cl)c(C)cc4[nH]ncc24)C3)CC1] | 1-(4-{(6S,7S)-7-(5-chloro-6-methyl-1H-indazol-4-yl)-2-[3-(dimethyl-amino)azetidin-1-yl]-6-methyl-5,6,7,8-tetrahydroquinazolin-4-yl}piperazin-1-yl)prop-2-en-1-one | 549 (M + H) | $^1$H NMR (700 MHz, DMSO-d$_6$) δ 8.12 (s, 1H), 7.68 (d, J = 21.0 Hz, 1H), 7.43 (s, 1H), 6.80 (dd, J = 14.3, 10.7 Hz, 1H), 6.16-6.04 (m, 1H), 5.76-5.64 (m, 1H), 3.94 (s, 1H), 3.69 (s, 9H), 3.45 (s, 1H), 3.24 (d, J = 26.9 Hz, 2H), 3.08 (s, 1H), 3.04-2.91 (m, 1H), 2.81 (d, J = 19.2 Hz, 1H), 2.64 (d, J = 15.3 Hz, 1H), 2.48-2.35 (m, 5H), 2.08 (s, 6H), 0.90-0.79 (m, 3H).<br>>99% ee, [α]$_d^{22}$ = −60.5° (C = 0.1, MeOH) |

TABLE F-continued

| Example | Structure | Compound name | LCMS m/z | Analytical data |
|---|---|---|---|---|
| F9 | 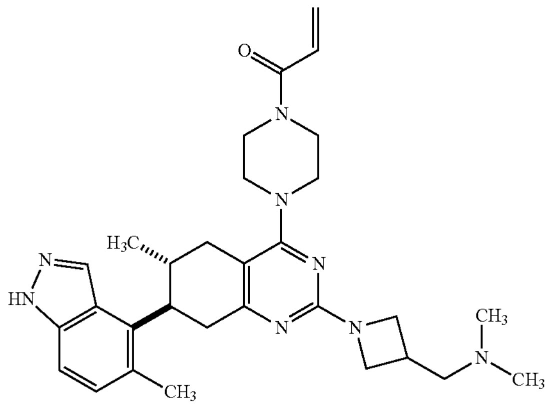 | 1-{4-[(6R,7R)-rel-7-(5-chloro-1H-indazol-4-yl)-2-{3-[(dimethyl-amino)methyl]azetidin-1-yl}-6-methyl-5,6,7,8-tetrahydroquinazolin-4-yl]piperazin-1-yl}prop-2-en-1-one | 529 (M + H) | $^1$H NMR (400 MHz, MeOD) δ 8.00 (s, 1H), 7.32 (d, J = 8.5 Hz, 1H), 7.24 (d, J = 8.5 Hz, 1H), 6.81 (dd, J = 16.8, 10.6 Hz, 1H), 6.24 (dd, J = 16.8, 1.8 Hz, 1H), 5.78 (dd, J = 10.6, 1.8 Hz, 1H), 4.17 (t, J = 8.2 Hz, 2H), 3.87 (dd, J = 9.9, 7.1 Hz, 2H), 3.72 (m, 4H), 3.67-3.53 (m, 3H), 3.37 (s, 3H), 3.16 (dd, J = 18.2, 11.5 Hz, 2H), 2.98 (d, J = 6.5 Hz, 1H), 2.91 (dd, J = 15.9, 6.7 Hz, 2H), 2.75 (d, J = 12.4 Hz, 1H), 2.72-2.63 (m, 2H), 2.46 (d, J = 6.7 Hz, 3H), 2.44-2.36 (m, 2H), 2.30 (s, 6H), 1.29 (m, 3H), 0.79 (d, J = 5.7 Hz, 3H). |
| F12 | 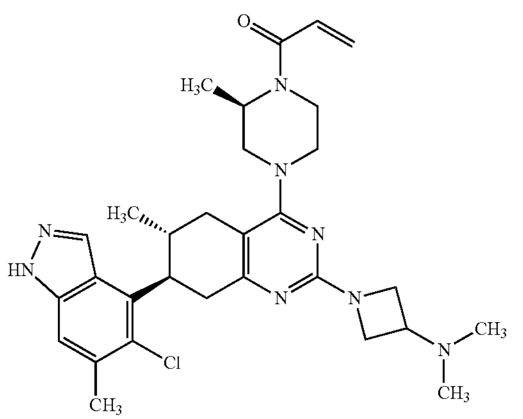 [SMILES: C=CC(=O)N1CCN(c2nc(N3CC(N(C)C)C3)nc3c2C[C@@H](C)[C@H](c2c(Cl)c(C)cc4[nH]ncc24)C3)C[C@H]1C] | 1-[(2R)-4-{(6R,7R)-7-(5-chloro-6-methyl-1H-indazol-4-yl)-2-[3-(dimethyl-amino)azetidin-1-yl]-6-methyl-5,6,7,8-tetrahydroquinazolin-4-yl}-2-methylpiperazin-1-yl]prop-2-en-1-one | 563 (M + H) | $^1$H NMR (400 MHz, DMSO) δ 13.14 (s, 1H), 8.17 (s, 1H), 7.43 (s, 1H), 6.83 (dd, J = 16.7, 10.5 Hz, 1H), 6.14 (d, J = 16.2 Hz, 1H), 5.71 (d, J = 12.3 Hz, 1H), 3.94 (t, J = 7.8 Hz, 2H), 3.84-3.65 (m, 6H), 3.30-3.23 (m, 1H), 3.08-2.98 (m, 2H), 2.89 (s, 2H), 2.74 (ddd, J = 27.1, 16.8, 4.0 Hz, 4H), 2.48 (s, 3H), 2.45 (s, 1H), 2.07 (s, 6H), 1.35 (s, 3H), 0.70 (d, J = 5.2 Hz, 3H). |
| F13 | 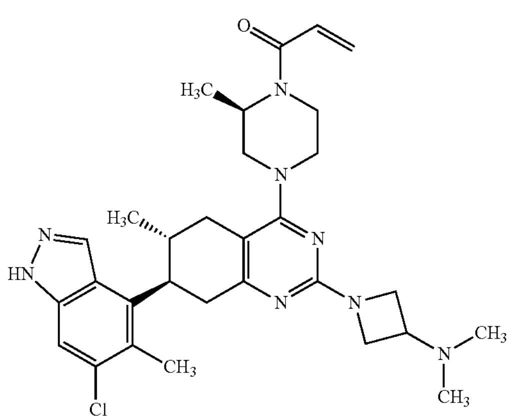 [SMILES: C=CC(=O)N1CCN(c2nc(N3CC(N(C)C)C3)nc3c2C[C@@H](C)[C@H](c2c(C)c(Cl)cc4[nH]ncc24)C3)C[C@H]1C] | 1-[(2R)-4-{(6R,7R)-7-(6-chloro-5-methyl-1H-indazol-4-yl)-2-[3-(dimethyl-amino)azetidin-1-yl]-6-methyl-5,6,7,8-tetrahydroquinazolin-4-yl}-2-methylpiperazin-1-yl]prop-2-en-1-one | 563 (M + H) | $^1$H NMR (400 MHz, MeOD) δ 8.07 (s, 1H), 7.54 (s, 1H), 6.80 (dd, J = 16.7, 10.7 Hz, 1H), 6.24 (dd, J = 16.7 Hz, 1H), 5.78 (dd, J = 10.7, 1.7 Hz, 1H), 4.46 (s, 1H), 4.11 (t, J = 8.0 Hz, 2H), 3.97 (d, J = 12.9 Hz, 1H), 3.88 (m, J = 8.5, 6.0, 3.3 Hz, 3H), 3.52 (m, J = 6.4 Hz, 1H), 3.19 (m, J = 12.5, 5.8 Hz, 2H), 3.08-2.82 (m, 5H), 2.54 (s, 3H), 2.49 (d, J = 14.1 Hz, 2H), 2.22 (s, 6H), 1.30 (d, J = 12.6, 5.4 Hz, 3H), 0.90 (m, 1H), 0.79 (d, J = 5.7 Hz, 3H). |

Example G1 (Scheme G)
1-(4-(7-(5-(trifluoromethyl)-1H-indazol-4-yl)-5,6,7,8-tetrahydroquinazolin-4-yl)piperazin-1-yl)prop-2-en-1-one
Scheme G:
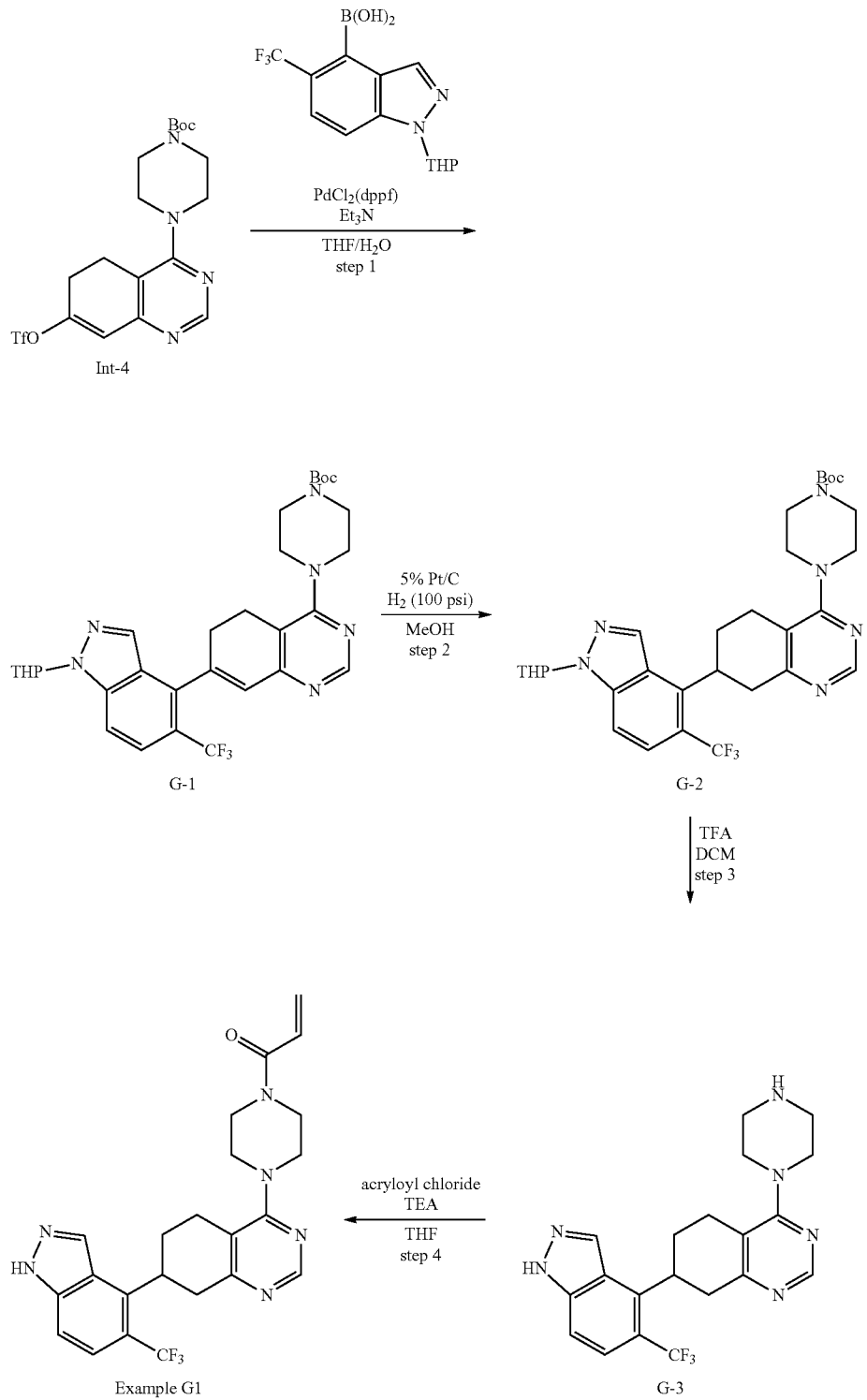

Step 1: Synthesis of tert-butyl 4-(7-(1-(tetrahydro-2H-pyran-2-yl)-5-(trifluoromethyl)-1H-indazol-4-yl)-5,6-dihydroquinazolin-4-yl)piperazine-1-carboxylate (G-1)

To a 25 mL flask equipped with a magnetic stir bar was added tert-butyl 4-(7-{[(trifluoromethyl)sulfonyl]oxy}-5,6-dihydroquinazolin-4-yl)piperazine-1-carboxylate (Int-4) (186 mg, 0.4 mmol). The material was dissolved in THF/H$_2$O (9:1, 5 mL). [1-(tetrahydro-2H-pyran-2-yl)-5-(trifluoromethyl)-1H-indazol-4-yl]boronic acid (151 mg, 0.48 mmol, 1.2 eq) and PdCl$_2$(dppf) (29.3 mg, 0.04 mmol, 0.1 eq) were added. The flask was evacuated and backfilled with nitrogen (3×), and then triethylamine (0.56 mL, 4.0 mmol, 10 eq) was added. The mixture was heated to 60° C. for 2 h. LCMS analysis indicated formation of the desired product and complete consumption of starting material. The mixture was diluted with EtOAc, washed with brine, and dried over anhydrous MgSO$_4$. The mixture was concentrated to dryness and the residue was purified by ISCO (0-50% acetone/heptanes) to provide tert-butyl 4-(7-(1-(tetrahydro-2H-pyran-2-yl)-5-(trifluoromethyl)-1H-indazol-4-yl)-5,6-dihydroquinazolin-4-yl)piperazine-1-carboxylate (G-1) (200.0 mg, 85% yieldyield) as an off-white/light yellow solid. $^1$H NMR (400 MHz, CDCl$_3$) δ=8.67 (s, 1H), 7.98 (s, 1H), 7.70 (s, 2H), 6.67-6.59 (m, 1H), 5.81-5.71 (m, 1H), 4.04 (d, J=11.3 Hz, 1H), 3.84-3.72 (m, 1H), 3.59 (br s, 4H), 3.37 (br s, 4H), 3.00-2.85 (m, 2H), 2.70 (br s, 2H), 2.61-2.47 (m, 1H), 2.17 (s, 1H), 1.88-1.62 (m, 4H), 1.50 (s, 9H). LCMS (ESI) m/z 585.7 (M+H).

Step 2: Synthesis of 4-(piperazin-1-yl)-7-[5-(trifluoromethyl)-1H-indazol-4-yl]-5,6,7,8-tetrahydroquinazoline (G-2)

A 50-mL tube equipped with a magnetic stir bar was charged with tert-butyl 4-(7-(1-(tetrahydro-2H-pyran-2-yl)-5-(trifluoromethyl)-1H-indazol-4-yl)-5,6-dihydroquinazolin-4-yl)piperazine-1-carboxylate (G-1) (30 mg, 0.051 mmol, 1.0 eq), MeOH (5 mL), and Pt/C (5% loading, 70 mg). The mixture was pressurized with H$_2$ (100 psi) and then heated to 60° C. for 3 d. LCMS analysis indicated formation of the desired product and almost complete consumption of starting material. The mixture was filtered through a pad of celite. The filtrate was concentrated and the crude was purified by flash chromatography (SiO$_2$, 0-70%, acetone/heptanes) to provide 4-(piperazin-1-yl)-7-[5-(trifluoromethyl)-1H-indazol-4-yl]-5,6,7,8-tetrahydroquinazoline (G-2) (17.0 mg, 56% yield) as a yellow solid. $^1$H NMR (400 MHz, CDCl$_3$) δ 8.63 (d, J=2.3 Hz, 1H), 8.14 (d, J=2.3 Hz, 1H), 7.73-7.65 (m, 1H), 7.62-7.51 (m, 1H), 5.83-5.66 (m, 1H), 4.10-3.97 (m, 1H), 3.90-3.73 (m, 2H), 3.71-3.60 (m, 2H), 3.51 (d, J=9.8 Hz, 4H), 3.43-3.18 (m, 4H), 2.80 (br. s., 1H), 2.64-2.47 (m, 1H), 2.17 (m, 4H), 1.87-1.63 (m, 4H), 1.50 (s, 9H). LCMS (ESI) m/z 587.6 (M+H).

Step 3: Synthesis of 4-(piperazin-1-yl)-7-[5-(trifluoromethyl)-1H-indazol-4-yl]-5,6,7,8-tetrahydroquinazoline (G-3)

To a 8 mL vial equipped with a magnetic stir bar was added tert-butyl 4-{7-[1-(tetrahydro-2H-pyran-2-yl)-5-(trifluoromethyl)-1H-indazol-4-yl]-5,6,7,8-tetrahydroquinazolin-4-yl}piperazine-1-carboxylate (G-2) (6 mg, 0.01 mmol, 1.0 eq), DCM (0.4 mL) and TFA (0.2 mL). The reaction was left to stir 15 min. LCMS analysis indicated formation of the fully de-protected product. The reaction was concentrated to dryness to provide 4-(piperazin-1-yl)-7-[5-(trifluoromethyl)-1H-indazol-4-yl]-5,6,7,8-tetrahydroquinazoline (G-3) (6 mg, 100% yield) as a brown residue, which was taken onto the next step without further purification. LCMS (ESI) m/z 403.3 (M+H).

Step 4: Synthesis of 1-(4-{7-[5-(trifluoromethyl)-1H-indazol-4-yl]-5,6,7,8-tetrahydroquinazolin-4-yl}piperazin-1-yl)prop-2-en-1-one (Example G1)

4-(piperazin-1-yl)-7-[5-(trifluoromethyl)-1H-indazol-4-yl]-5,6,7,8-tetrahydroquinazoline (G-3) was dissolved in THF (1 mL) and cooled to 0° C. The mixture was treated with acryloyl chloride (0.945 mg, 0.01 mmol, 0.85 uL, 1.0 eq) and triethylamine (7.13 uL, 0.05 mmol, 10.0 eq). The mixture was stirred at 0° C. for 15 min. LCMS analysis indicated formation of the desired product and complete consumption of starting material. The solvent was removed under reduced pressure and the residue was purified by HPLC to provide 1-(4-{7-[5-(trifluoromethyl)-1H-indazol-4-yl]-5,6,7,8-tetrahydroquinazolin-4-yl}piperazin-1-yl)prop-2-en-1-one (Example G1) (3.0 mg, 40% yield) as an off-white solid. $^1$H NMR (400 MHz, CDCl$_3$) δ 8.61 (s, 1H), 8.16-8.10 (m, 1H), 7.65-7.57 (m, 1H), 7.52-7.41 (m, 1H), 6.62-6.50 (m, 1H), 6.34-6.22 (m, 1H), 5.82-5.66 (m, 1H), 4.14-3.59 (m, 8H), 3.53-3.39 (m, 2H), 3.12-2.60 (m, 3H), 2.36-2.08 (m, 2H). LCMS (ESI) m/z 457.5 (M+H).

The intermediate G-4 detailed in the following preparation afford Examples G2 and G3 according to method G. However, this example fall outside of the synthetic scope of the preceding examples due a required deprotection step and this chemistry is included below for completeness. Subsequent chemistry to afford final examples is similar to the Method G examples, with minimal additions or changes that one skilled in the art can appreciate.

Step 5: Synthesis of 1-{4-[(7R)-7-(3-hydroxynaphthalen-1-yl)-5,6,7,8-tetrahydroquinazolin-4-yl]piperazin-1-yl}prop-2-en-1-one (Example G2) and 1-{4-[(7S)-7-(3-hydroxynaphthalen-1-yl)-5,6,7,8-tetrahydroquinazolin-4-yl]piperazin-1-yl}prop-2-en-1-one (Example G3)

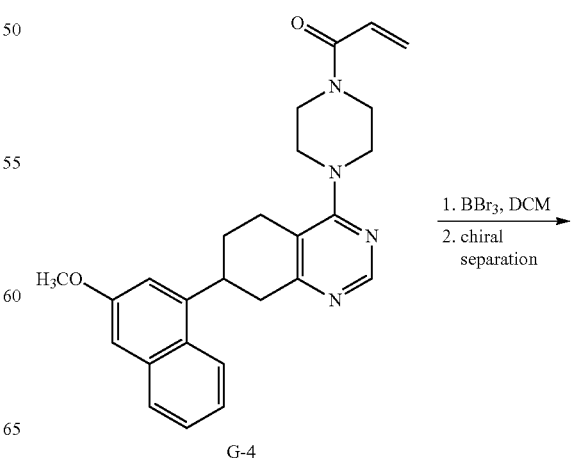

G-4

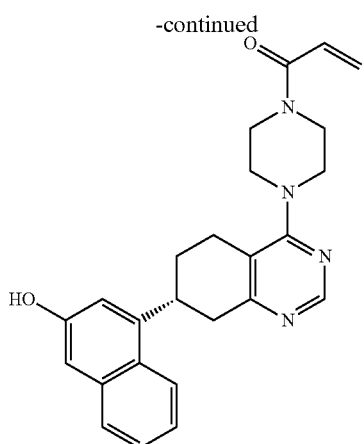

Example G2

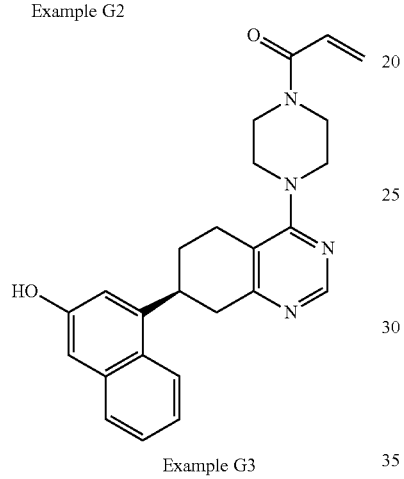

Example G3

A solution of 1-{4-[7-(3-methoxpaphthalen-1-yl)-5,6,7,8-tetrahydroquinazolin-4-yl]piperazin-1-yl}prop-2-en-1-one (G-4) (166 mg, 0.387 mmol) in DCM (10 mL) under nitrogen was cooled to 0° C. with an ice bath. The mixture was treated dropwise with a solution of boron tribromide (1.0 M, 1.94 mL, 1.94 mmol, 5.0 eq) to provide a pink suspension, which was slowly warmed to room temperature and stirred for a further 4 hours. The suspension was cooled with an ice bath and carefully quenched with sat. aq. NaHCO$_3$ (10 mL). The layers were separated and the aqueous layer was extracted with DCM:MeOH (95:5, 4×). The combined organics were dried over anhydrous sodium sulfate and concentrated. The crude material was purified by preparative SFC on a Chiralpak AD-3 (4.6×100 mm) column, which was eluted with 40% IPA in CO$_2$ at 120 bar. A flow rate of 4 mL/min gave Rt$_{(Peak\ 1)}$=2.83 min, and Rt$_{(Peak\ 2)}$=3.49 min. 1-{4-[(7R)-7-(3-hydroxynaphthalen-1-yl)-5,6,7,8-tetrahydroquinazolin-4-yl]piperazin-1-yl}prop-2-en-1-one (Peak 1) (Example G2): 23 mg, >99% ee, 32% yield. $^1$H NMR (400 MHz, DMSO-d$_6$)=9.66 (s, 1H), 8.52 (s, 1H), 8.08 (d, J=8.4 Hz, 1H), 7.71 (d, J=8.2 Hz, 1H), 7.40 (t, J=7.3 Hz, 1H), 7.35-7.27 (m,1H), 7.05-6.97 (m, 2H), 6.84 (dd, J=10.4, 16.6 Hz, 1H), 6.15 (dd, J=2.3, 16.8 Hz, 1H), 5.77-5.65 (m, 1H), 3.92 (d, J=2.9 Hz, 1H), 3.84-3.58 (m, 4H), 3.50 (td, J=3.5, 13.0 Hz, 2H), 3.29-3.25 (m, 2H), 3.17 (dd, J=5.0, 18.1 Hz, 1H), 3.01 (t, J=11.4 Hz, 1H), 2.85 (dd, J=11.0, 18.2 Hz, 1H), 2.64 (d, J=16.0 Hz, 1H), 2.15 (d, J=12.7 Hz, 1H), 1.87 (dd, J=3.3, 11.5 Hz, 1H). [α]$_d^{22}$=27.7° (C=0.1, MeOH); LCMS (ESI) m/z 415 (M+H). 1-{4-[(7S)-7-(3-hydroxynaphthalen-1-yl)-5,6,7,8-tetrahydroquinazolin-4-yl]piperazin-1-yl}prop-2-en-1-one (Peak 2) (Example G3): 27 mg, ~99% ee, 37% yield. $^1$H NMR (400 MHz, DMSO-d$_6$) δ 9.66 (s, 1H), 8.52 (s, 1H), 8.08 (d, J=8.4 Hz, 1H), 7.71 (d, J=7.9 Hz, 1H), 7.40 (t, J=7.2 Hz, 1H), 7.35-7.27 (m,1H), 7.07-6.97 (m, 2H), 6.84 (dd, J=10.5, 16.6 Hz, 1H), 6.15 (dd, J=2.3, 16.8 Hz, 1H), 5.79-5.64 (m, 1H), 3.92 (d, J=3.8 Hz, 1H), 3.83-3.58 (m, 4H), 3.55-3.44 (m, 2H), 3.29-3.25 (m, 2H), 3.17 (dd, J=4.8, 18.3 Hz, 1H), 3.00 (d, J=11.5 Hz, 1H), 2.85 (dd, J=11.1, 18.2 Hz, 1H), 2.71-2.59 (m, 1H), 2.15 (d, J=12.7 Hz, 1H), 1.87 (dd, J=3.8, 12.0 Hz, 1H). [α]$_d^{22}$=−24.8° (C=0.1, MeOH); LCMS (ESI) m/z 415 (M+H).

Example H1 (Scheme H)

Synthesis of 1-(4-{(6R,7R)-7-(6-chloro-5-methyl-1H-indazol-4-yl)-6-methyl-2-[3-(methylamino)azetidin-1-yl]-5,6,7,8-tetrahydroquinazolin-4-yl}piperazin-1-yl)prop-2-en-1-one (Example H1)

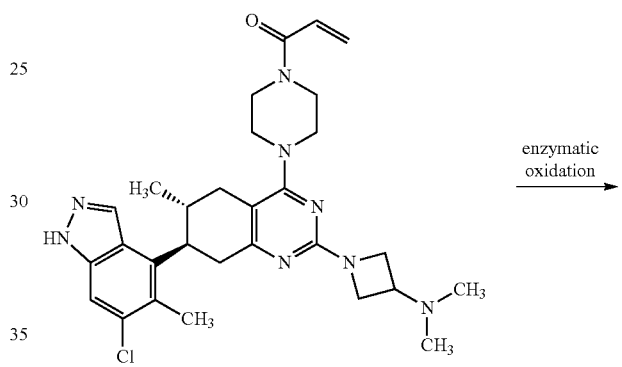

Example F14

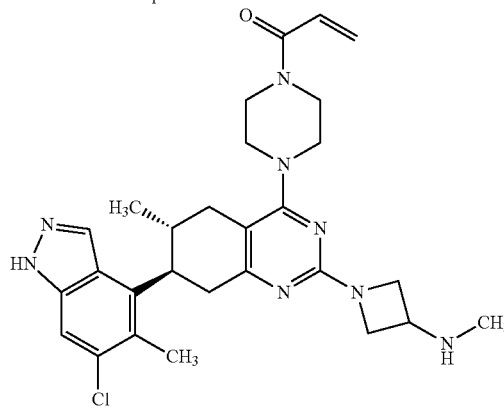

Example G1

A 500 mL Erlenmeyer flask was charged with de-ionized H$_2$O (27.04 mL) and treated with 1.0 M potassium phosphate buffer solution at pH 7.5 (4.0 mL), 0.165 M MgCl solution (0.8 mL, 132 μmop and a 0.005 M solution of 1-(4-{(6R,7R)-7-(6-chloro-5-methyl-1H-indazol-4-yl)-2-[3-(dimethylamino)azetidin-1-yl]-6-methyl-5,6,7,8-tetrahydroquinazolin-4-yl}piperazin-1-yl)prop-2-en-1-one (Example F14) (0.16 mL, 0.8 μmol) in MeCN/H$_2$O (1:1). The mixture was treated with dexamethasone-induced male rat liver microsomes (prepared fresh, 2 mg/mL), followed by the addition of a freshly prepared 0.013 M aqueous solution of NADPH (4.0 mL, 52 μmol). The uncapped Erlenmeyer flask was shaken using a Thermo Scientific Precision shaker with a 1" throw at 37° C. for 1 h. The reaction mixture was divided into equal portions (20 mL each) and poured into two 50 mL Falcon conical centrifuge tubes. The solutions were quenched by addition of MeCN (20 ml) to each Falcon tube. The Falcon tubes were vortexed and centrifuged at 3000 rpm for 5 min using a Cetrifuge CT422 instrument. The supernatant was decanted and transferred in equal portions (20 ml each) to two 50 ml Falcon conical centrifuge tubes and the solvent was evaporated using an EZ-2 Plus Genevac (1 h HPLC setting, 34° C./238 mbar to 41° C./7 mbar). The remaining aqueous solutions were combined (~20 mL) into a 50 mL Falcon conical centrifuge tube and treated with MeCN (0.5 ml) and neat formic acid (0.5 ml) and charged with de-ionized $H_2O$ to a final volume of 50 ml. The solution was divided into equal portions (25 mL each) and poured into two high speed centrifuge tubes and centrifuged at 40,000 G for 30 min using a Beckman Coulter Allegra 64R (26200 speed, 24° C.) instrument. The supernatant was decanted into a 50 mL glass conical tube and the clear solution was absorbed onto a C18 HPLC column (Zorbax Polaris, C18-A, 250×4.6 mm, 5 µm particle size) using a JASCO PU-1580 HPLC pump at a flow rate of 0.8 ml/min over ~60 min. The HPLC column was transferred to a Thermo LTQ Velos mass spectrometer in-line with a Waters Acquity UHPLC instrument comprised of a quaternary pump, autosampler, and photodiode array UV/vis detector. A gradient (MeCN/$H_2O$+0.1% formic acid) was applied to separate the products of interest. After passing through the PDA detector the eluent was split at a ratio of ~15:1 with the larger portion going to a fraction detector (Collect PAL, Leap Technologies) and the smaller portion going to the mass spectrometer (fractions were collected every 20 s). Fractions containing peaks of interest were analyzed by UHPLC-UV-HRMS using a Thermo Orbitrap Elite high-resolution ion trap mass spectrometer in line with a Thermo Accelar UHPLC and diode array UV/vis detector with a CTC Analytics Leap autoinjector (Thermo-Fisher). Samples were injected (2 µL) onto a C18 UHPLC column (Phenomenex Kinetex, C18, 50×2.1 mm, 1.7 µm particle size) and a MeCN/$H_2O$ +0.1% formic acid gradient was applied at a flow rate of 0.4 mL/min, maintained at 45° C. After UHPLC-UV-HRMS analysis fractions were pooled and the solvent was removed using an EZ-2 Plus Genevac (3 h HPLC setting 34° C./238 mbar to 41° C./7 mbar) to afford 1-(4-{(6R,7R)-7-(6-chloro-5-methyl-1H-indazol-4-yl)-6-methyl-2-[3-(methylamino)azetidin-1-yl]-5,6,7,8-tetrahydroquinazolin-4-yl}piperazin-1-yl)prop-2-en-1-one (Example G1) (32 µg, 60 nmol, 7.5% yield). The dried samples were analyzed by NMR spectroscopy and quantified by external calibration against the $^1$H NMR spectrum of 5.0 mM benzoic acid standard solution in DMSO-$d_6$ using the ERETIC2 function with Topspin V3.2. $^1$H NMR (600 MHz, DMSO-$d_6$) δ 13.12 (br. s, 1H), 8.12 (s, 1H), 7.54 (s, 1H), 6.85 (dd, J=16.7, 10.4 Hz, 1H), 6.15 (dd, J=16.7, 2.3, 1H), 5.72 (dd, J=10.4, 2.3 Hz, 1H), 4.03 (t, J=7.8 Hz, 2H), 3.87-3.77 (m, 1H), 3.77-3.67 (m, 1H), 3.65-3.56 (m, 4H), 3.50-3.40 (m, 4H), 3.24-3.15 (m, 2H), 3.04-2.96 (m, 1H), 2.89-2.81 (m, 1H), 2.64-2.61 (m, 1H), 2.49-2.47 (m, 4H), 2.43-2.39 (m, 1H), 2.22 (s, 3H), 0.68 (d, J=6.3 Hz, 3H). HRMS (ESI-TOF) calculated for $C_{28}H_{36}ClN_8O$[M+H]: m/z=535.2701, found 535.2700 (0.2 ppm)

Biological Examples and Biochemical Assay Methods

Mass Spectrometry Reactivity Assay (MSRA)

Compounds presented in the present invention covalently bind to kRas G12C using MSRA to detect a covalent adduct of the exemplary compound and kRas G12C. GDP-loaded kRas (1-169) G12C, C51S, C80L, C118S were diluted in the protein assay buffer 25 mM Hepes pH7.5, 200 mM NaCl, 5% glycerol to concentration of 5 µM and 20 µl of protein was transferred into 96-well plate. Initial compound stocks were generated at concentrations 100-fold higher that their desired assay concentrations. See *K-Ras(G12C) inhibitors allosterically control GTP affinity and effector interactions;* Ostrem J M, Peters U, Sos M L, Wells J A, Shokat K M; Nature. 2013, Nov. 28; 503(7477):548-51.

Exemplary compounds dissolved in DMSO were diluted 100-fold into solution containing 20 µl of 5 µM KRas protein in the 96-well plate to initiate the reaction. Mosquito (TPP Lab tech) liquid handling robot was used to add compounds to protein solution. Typical final concentration of the compounds was 10 µM. The plates were placed on a shaker for 1 min at RT, sealed and incubated at room temperature for specified time period. 5 µl of reaction mix was added to 10 µl of 0.2% formic acid stop solution and mixed well. Typical end points were 30, 120, 600 and 1440 min.

Data were collected using Waters Acquity H-class UPLC system/Xevo G2-XS TOF mass spectrometer. The protein was injected in their liquid phase onto a Bruker Microtrap protein column TR1/15109/03. The following buffers were used to set LC gradient: Buffer A: 0.2% formic acid H20; B: 0.2% formic acid CAN. The protein was eluted from the column using the following LC Gradient: 0-0.4 min, 10% B to 30% B; 0.4 min-2.4 min, to 90% B, 2.5 min, 10% B, 3 min, 10% B. Initial data analysis was performed using MaxEnt software right after data acquisition.

The standard auto processing function was used to define percentage of unmodified and modified kRas protein using MexEnt software right after data acquisition. The highest peak was defined as 100% while smaller peak as assigned the number defined by autoprocessing function. The percent of modification corresponding to modified with exemplary compound and unmodified KRas GDP-loaded kRas (1-169) G12C, C51S, C80L, C118S were exported to Xcel data analysis software.

The percent of modified protein at the defined concentration of exemplary compound was calculated using the following formula: % mod=Num of modified peak/Sum of modified+unmodified. The resultant value defined as Percent Modification (PM) and an increase in PM reflects that the specific compound is better than other compounds at specified compound concentration at a given time point.

MiaPaCa2 Cell Activity Assay

Compounds presented in the present invention lead to the accumulation of the GDP bound Ras upon treatment of human cancer cell line.

The accumulation of the GDP-bound KRAS G12C in cellular environment was measured based on the principle that KRAS G12C only binds to its downstream kinase; Raf-1 (MAP Kinase Kinase Kinase), when in its active-GTP bound state. In this state, Ras binded to a domain of Raf-1 kinase referred to as the Ras Binding Domain (RBD).

MiaPaCa2 cells were grown in DMEM medium (Gibco 11995) supplemented with 10% fetal bovine serum and 1% penicillin/streptomycin. Cells were seeded in 96-well tissue culture plates at a density of 40,000 cells/well and allowed to attach for 16-24 hours. Test compounds were prepared as a 10 mM stock in DMSO and serially diluted in 100% DMSO using a 3-fold dilution scheme. An intermediate 5× concentrated plate in complete growth medium was made and 25 µl/well was added to the 100 µl of cells for a final concentration of 0.1% DMSO. Each concentration of exemplary compound was tested in duplicate. The negative control wells were cells with control inhibitor at 10 µM, and the positive control wells were cells without drugs, DMSO only. Plates were incubated for 6 hours at 37° C., 5% $CO_2$. Following treatment, cells were washed 3× with ice-cold PBS and 100 µl/well ice-cold 1× Assay/Lysis. Buffer with protease inhibitors was added (25 mM HEPES, pH 7.5, 150 mM NaCl, 1% NP-40, 10 mM $MgCl_2$, 1 mM EDTA, 2% Glycerol). Following lysis samples were frozen at −80° C.

Raf-1 RBD (LJIC-1988A1) was diluted to 100 ng/well in PBS and 5 µl/well was spot coated onto MSD high bind SECTOR plates (L15XB). Plates were incubated at room temperature for 1 hour on an orbital shaker. Plates were washed with PBS/0.05% Tween-20 and 50 µl/well of thawed lysate samples were added, followed by 50 µl of 1% MSD Blocker A in PBS/0.05% Tween-20 (R93BA). Plates were incubated for 1 hour on an orbital shaker and washed with PBS/0.05% Tween-20. 25 µl/well of Anti-pan-Ras Antibody (Cell Biolabs 244003) diluted 1:3000 was added in 1% MSD Blocker A solution and plates were incubated for 1 hour on an orbital shaker and washed with PBS/0.05% Tween-20. SULFO-TAG goat anti-mouse secondary antibody (MSD R32AC) was diluted 1:500 in MSD Blocker A solution and added at 25 µL/well. Plates were incubated for 1 hour on an orbital shaker and washed with PBS/0.05% Tween-20. 150 µl/well of Read Buffer T (MSD R92TC) diluted 1:3 in $H_2O$ was added and plates were read on a Meso Scale Discovery Sector Imager S600.

KRAS signal was normalized to maximum inhibition and DMSO control values, and IC50 values were generated using a 4 parameter fit of the dose response curve. The decrease in IC50 reflects that the exemplary compound lead to a higher level of accumulation of GDP-bound KRAS G12C than another exemplary compounds at specific time-point of treatment of cancer cell line.

H358 Cell Activity Assay

Compounds presented in the present invention lead to the accumulation of the GDP bound Ras upon treatment of human cancer cell line.

The accumulation of the GDP-bound KRAS G12C in cellular environment was measured based on the principle that KRAS G12C only binds to its downstream kinase; Raf-1 (MAP Kinase Kinase Kinase), when in its active-GTP bound state. In this state, Ras binded to a domain of Raf-1 kinase referred to as the Ras Binding Domain (RBD).

H358 cells were grown in RPMI 1640 medium (Gibco 11875) supplemented with 10% fetal bovine serum and 1% penicillin/streptomycin. Cells were seeded in 96-well tissue culture plates at a density of 40,000 cells/well and allowed to attach for 16-24 hours. Test compounds were prepared as a 10 mM stock in DMSO and serially diluted in 100% DMSO using a 3-fold dilution scheme. An intermediate 5× concentrated plate in complete growth medium was made and 25 µl/well was added to the 100 µl of cells for a final concentration of 0.1% DMSO. Each concentration of exemplary compound was tested in duplicate. The negative control wells were cells with control inhibitor at 10 µM, and the positive control wells were cells without drugs, DMSO only. Plates were incubated for 6 hours at 37° C., 5% $CO_2$. Following treatment, cells were washed 3× with ice-cold PBS and 100 µl/well ice-cold 1× Assay/Lysis. Buffer with protease inhibitors was added (25 mM HEPES, pH 7.5, 150 mM NaCl, 1% NP-40, 10 mM $MgCl_2$, 1 mM EDTA, 2% Glycerol). Following lysis samples were frozen at −80° C.

Raf-1 RBD (LJIC-1988A1) was diluted to 100 ng/well in PBS and 5 µl/well was spot coated onto MSD high bind SECTOR plates (L15XB). Plates were incubated at room temperature for 1 hour on an orbital shaker. Plates were washed with PBS/0.05% Tween-20 and 50 µl/well of thawed lysate samples were added, followed by 50 µl of 1% MSD Blocker A in PBS/0.05% Tween-20 (R93BA). Plates were incubated for 1 hour on an orbital shaker and washed with PBS/0.05% Tween-20. 25 µl/well of Anti-pan-Ras Antibody (Cell Biolabs 244003) diluted 1:3000 was added in 1% MSD Blocker A solution and plates were incubated for 1 hour on an orbital shaker and washed with PBS/0.05% Tween-20. SULFO-TAG goat anti-mouse secondary antibody (MSD R32AC) was diluted 1:500 in MSD Blocker A solution and added at 25 µL/well. Plates were incubated for 1 hour on an orbital shaker and washed with PBS/0.05% Tween-20. 150 µl/well of Read Buffer T (MSD R92TC) diluted 1:3 in $H_2O$ was added and plates were read on a Meso Scale Discovery Sector Imager S600.

KRAS signal was normalized to maximum inhibition and DMSO control values, and IC50 values were generated using a 4 parameter fit of the dose response curve. The decrease in IC50 reflects that the exemplary compound lead to a higher level of accumulation of GDP-bound KRAS G12C than another exemplary compounds at specific time-point of treatment of cancer cell line.

MSRA Data and MIAPaCa-2 Cell Activity Assay Data

| Example number | % Modification (0.5 h) | $IC_{50}$ (µM)* MIAPaCa-2 | $IC_{50}$ (µM) H358 |
|---|---|---|---|
| A1 | 14 | 7.86 | Not Tested |
| A2 | 0 | Not Tested | Not Tested |
| A3 | 39 | 4.15 | Not Tested |
| A4 | 53 | 1.30 | Not Tested |
| A5 | 77 | 0.640 | 0.78 |
| A6 | 3 | Not Tested | Not Tested |
| A7 | 11 | 29.3 | Not Tested |
| A8 | 54 | 0.462 | Not Tested |
| A9 | 77 | 0.155 | Not Tested |
| B1 | 9 | 18.7 | Not Tested |
| B2 | 13 | 4.86 | Not Tested |
| B3 | 7 | 28.4 | Not Tested |
| C1 | 19 | 9.84 | Not Tested |
| C2 | 22 | Not Tested | Not Tested |
| C3 | 15 | 12.0 | Not Tested |
| C4 | 34 | 3.61 | Not Tested |
| C5 | 74 | 0.214 | 0.468 |
| C6 | 66 | 0.260 | 0.521 |
| C7 | 73 | 0.088 | 0.106 |
| C8 | 65 | 0.140 | 0.116 |
| C9 | 74 | 0.382 | 0.270 |
| C10 | 80 | 0.236 | 0.129 |
| D1 | 12 | Not Tested | Not Tested |
| E1 | 40 | Not Tested | Not Tested |
| F1 | 59 | 0.429 | 0.360 |
| F2 | 79 | 0.285 | 0.277 |
| F3 | 0 | Not Tested | Not Tested |
| F4 | 22 | 4.29 | Not Tested |
| F5 | 72 | 0.154 | 0.145 |
| F6 | 83 | 0.126 | 0.116 |
| F7 | 82 | 0.108 | 0.062 |
| F8 | 12 | 22.9 | Not Tested |
| F9 | 32 | 1.00 | Not Tested |
| F10 | 85 | 0.169 | 0.395 |
| F11 | 8 | Not Tested | Not Tested |
| F12 | 84 | 0.060 | 0.064 |
| F13 | 79 | 0.113 | Not Tested |
| F14 | 72 | 0.068 | 0.102 |
| G1 | 16 | Not Tested | Not Tested |
| G2 | 0 | Not Tested | Not Tested |
| G3 | 73 | 1.11 | Not Tested |
| H1 | Not Tested | 0.178 | Not Tested |

*Assay limit is 30.0 µM

We claim:
1. A compound of Formula (I):

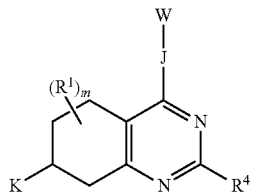

or a pharmaceutically acceptable salt thereof; wherein:
J is a heterocycle having 3-12 ring atoms, where J is optionally substituted with 1, 2, 3, 4, 5 or 6 $R^2$;
K is $C_6$-$C_{12}$ aryl, or K is heteroaryl having 5-12 ring atoms, where K is optionally substituted with 1, 2, 3, 4, 5, 6 or 7 $R^3$;
W is selected from the group consisting of:

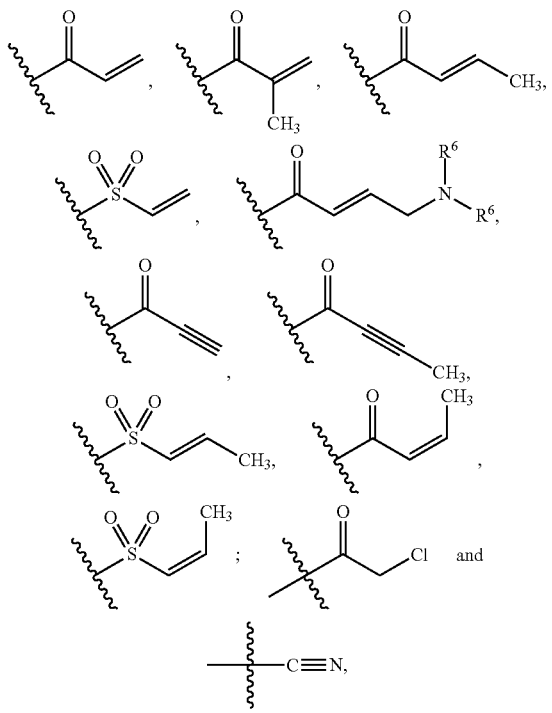

where W is optionally substituted with 1, 2 or 3 $R^5$;
each $R^1$ is independently selected from the group consisting of $C_1$-$C_6$ alkyl, $C_3$-$C_6$ cycloalkyl, $C_1$-$C_6$ alkyl-hydroxy, $C_1$-$C_6$ alkoxy, $C_1$-$C_6$ alkyl-$C_1$-$C_6$alkoxy, hydroxy, $C_2$-$C_6$ alkenyl, $C_2$-$C_6$ alkynyl, halogen, $C_1$-$C_6$ haloalkyl, cyano and —$N(R^6)_2$, or two $R^1$ optionally join to form a heterocycle having 3-12 ring atoms or a $C_3$-$C_6$ cycloalkyl;
each $R^2$ is independently selected from the group consisting of $C_1$-$C_6$ alkyl, $C_3$-$C_6$ cycloalkyl, hydroxy, $C_1$-$C_6$ alkyl-hydroxy, $C_1$-$C_6$ alkoxy, halogen, $C_1$-$C_6$ haloalkyl, cyano, $C_1$-$C_6$ alkyl-cyano and oxo, or two $R^2$ optionally join to form a heterocycle having 3-12 ring atoms or a $C_3$-$C_6$ cycloalkyl;
each $R^3$ is independently selected from the group consisting of $C_1$-$C_6$ alkyl, $C_3$-$C_6$ cycloalkyl, hydroxy, $C_1$-$C_6$ alkoxy, $C_1$-$C_6$ alkyl-hydroxy, halogen, $C_1$-$C_6$ haloalkyl, $N(R^6)_2$, oxo and cyano, or two $R^3$ optionally join to form a heterocycle having 3-12 ring atoms or $C_3$-$C_6$ cycloalkyl;
$R^4$ is —X—Y—Z where:
X is absent or is selected from the group consisting of oxygen, sulfur and —$NR^6$—,
Y is absent or $C_1$-$C_6$ alkylenlyl, and
Z is selected from H, —$N(R^6)_2$, —C(O)—$N(R^6)_2$, —$OR^6$, heterocycle having 3-12 ring atoms, heteroaryl having 5-12 ring atoms, and $C_3$-$C_6$ cycloalkyl,
where $R^4$ is optionally substituted with one or more $R^7$;
each $R^5$ is independently selected from the group consisting of: $C_1$-$C_6$ alkyl, hydroxy, $C_1$-$C_6$ alkoxy, halogen and —$N(R^6)_2$;
each $R^6$ is independently selected from the group consisting of hydrogen, hydroxyl, $C_1$-$C_6$ alkoxy and $C_1$-$C_6$ alkyl, or two $R^6$ optionally join to form heterocycle having 3-12 ring atoms or $C_3$-$C_6$ cycloalkyl;
each $R^7$ is independently $R^{7'}$ or $C_1$-$C_6$ alkyl-$R^{7'}$, where each $R^{7'}$ is independently selected from the group consisting of: $C_1$-$C_6$ alkyl, hydroxy, $C_1$-$C_6$ alkoxy, halogen, —$N(R^6)_2$, heterocycle having 3-12 ring atoms and oxo; and
m is 0, 1, 2, 3, 4, 5, 6 or 7.
2. The compound or salt of claim 1, wherein:
J is selected from the group consisting of:

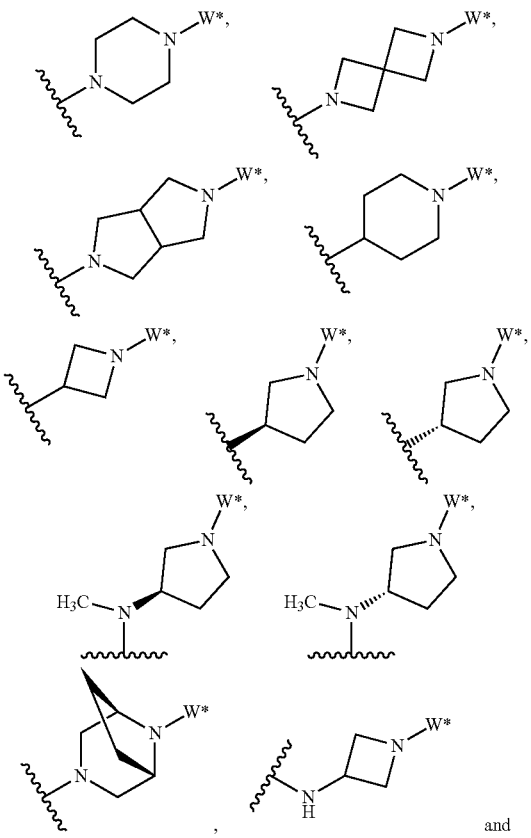

-continued

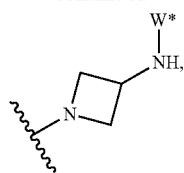

where W* represents the point of attachment to W, and where J is optionally substituted with 1, 2, 3, 4, 5 or 6 R²;

K is selected from the group consisting of:

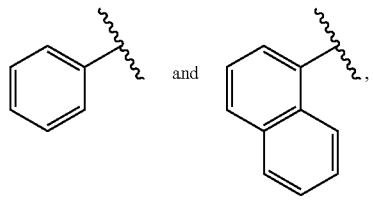 [SMILES: *c1ccccc1 ; *c1cccc2ccccc12]

or

K is selected from the group consisting of:

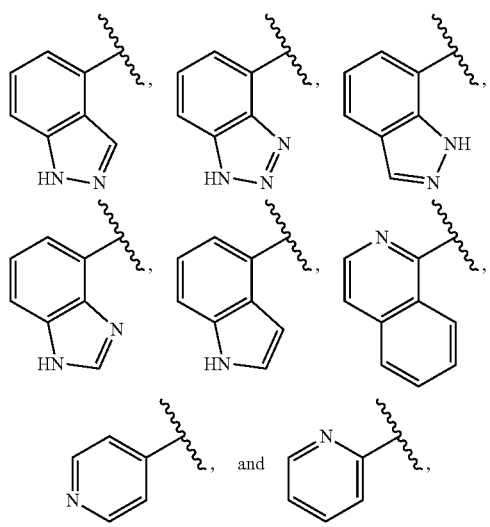

where K is optionally substituted with 1, 2, 3, 4, 5, 6 or 7 R³;

W is selected from the group consisting of:

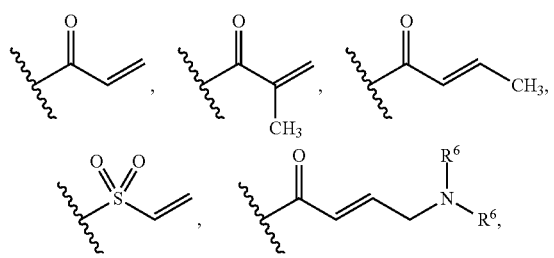

-continued

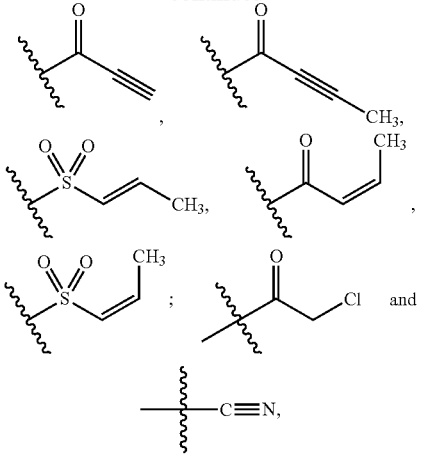

where W is optionally substituted with 1, 2 or 3 R⁵;

each R¹ is independently selected from the group consisting of $C_1$-$C_6$ alkyl, $C_3$-$C_6$ cycloalkyl, $C_1$-$C_6$ alkyl-hydroxy, $C_1$-$C_6$ alkoxy, $C_1$-$C_6$ alkyl-$C_1$-$C_6$alkoxy, hydroxy, $C_2$-$C_6$ alkenyl, $C_2$-$C_6$ alkynyl, halogen, $C_1$-$C_6$ haloalkyl, cyano and —N(R⁶)₂, or two R¹ optionally join to form a heterocycle having 3-12 ring atoms or a $C_3$-$C_6$ cycloalkyl;

each R² is independently selected from the group consisting of $C_1$-$C_6$ alkyl, $C_3$-$C_6$ cycloalkyl, hydroxy, $C_1$-$C_6$ alkyl-hydroxy, $C_1$-$C_6$ alkoxy, halogen, $C_1$-$C_6$ haloalkyl, cyano, $C_1$-$C_6$ alkyl-cyano and oxo, or two R² optionally join to form a heterocycle having 3-12 ring atoms or a $C_3$-$C_6$ cycloalkyl;

each R³ is independently selected from the group consisting of $C_1$-$C_6$ alkyl, $C_3$-$C_6$ cycloalkyl, hydroxy, $C_1$-$C_6$ alkoxy, $C_1$-$C_6$ alkyl-hydroxy, halogen, $C_1$-$C_6$ haloalkyl, N(R⁶)₂, oxo and cyano, or two R³ optionally join to form a heterocycle having 3-12 ring atoms or $C_3$-$C_6$ cycloalkyl;

R⁴ is —X—Y—Z where:

X is absent or is selected from the group consisting of oxygen, sulfur and —NR⁶—, Y is absent or $C_1$-$C_6$ alkylenlyl, and Z is selected from H, —N(R⁶)₂, —C(O)—N(R⁶)₂, —OR⁶, heterocycle having 3-12 ring atoms, heteroaryl having 5-12 ring atoms, and $C_3$-$C_6$ cycloalkyl, where R⁴ is optionally substituted with one or more R⁷;

each R⁵ is independently selected from the group consisting of: $C_1$-$C_6$ alkyl, hydroxy, $C_1$-$C_6$ alkoxy, halogen and —N(R⁶)₂;

each R⁶ is independently selected from the group consisting of hydrogen, hydroxyl, $C_1$-$C_6$ alkoxy and $C_1$-$C_6$ alkyl, or two R⁶ optionally join to form heterocycle having 3-12 ring atoms or $C_3$-$C_6$ cycloalkyl;

each R⁷ is independently R⁷' or $C_1$-$C_6$ alkyl-R⁷', where each R⁷' is independently selected from the group consisting of: $C_1$-$C_6$ alkyl, hydroxy, $C_1$-$C_6$ alkoxy, halogen, —N(R⁶)₂, heterocycle having 3-12 ring atoms and oxo; and m is 0, 1, 2, 3, 4, 5, 6 or 7.

3. The compound or salt of claim 2, wherein:

J is selected from the group consisting of:

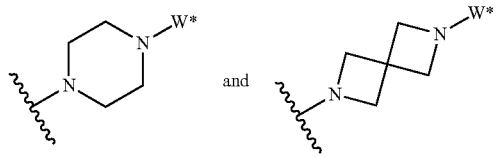

and where W* represents the point of attachment to W, and where J is optionally substituted with $R^2$;

K is selected from the group consisting of:

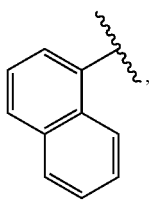 [SMILES: *c1cccc2ccccc12]

or

K is selected from the group consisting of:

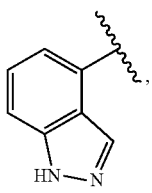

where K is optionally substituted with 1 or 2 $R^3$;

W is selected from the group consisting of:

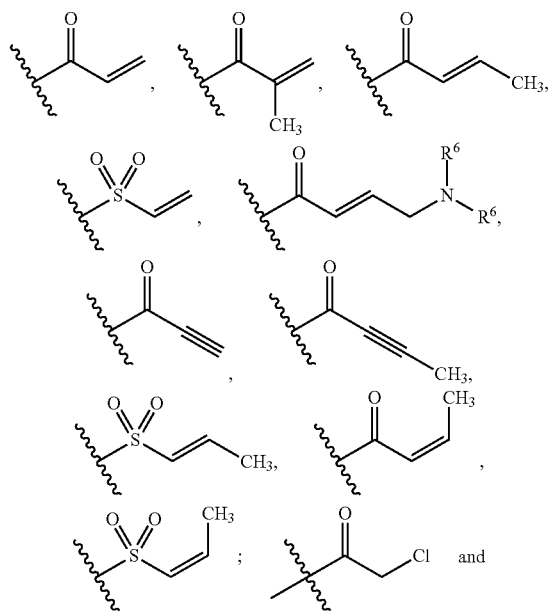

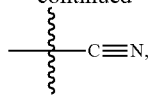

where W is optionally substituted with 1, 2 or 3 $R^5$;

$R^1$ is independently selected from the group consisting of $C_1$-$C_6$ alkyl and $C_1$-$C_6$ alkyl-$C_1$-$C_6$alkoxy;

$R^2$ is $C_1$-$C_6$ alkyl;

each $R^3$ is independently selected from the group consisting of $C_1$-$C_6$ alkyl, hydroxy, halogen, $C_1$-$C_6$ halo-alkyl and $C_1$-$C_6$ alkyl-hydroxy;

$R^4$ is —X—Y—Z where:
  X is absent or is oxygen,
  Y is absent or $C_1$-$C_6$ alkylenlyl, and
  Z is selected from H, —N($R^6$)$_2$, —O$R^6$ and heterocycle having 3-12 ring atoms, where $R^4$ is optionally substituted with one or more $R^7$;

each $R^5$ is independently selected from the group consisting of: $C_1$-$C_6$ alkyl, hydroxy, $C_1$-$C_6$ alkoxy, halogen and —N($R^6$)$_2$;

each $R^6$ is independently selected from the group consisting of hydrogen and $C_1$-$C_6$ alkyl;

each $R^7$ is independently $R^{7'}$ or $C_1$-$C_6$ alkyl-$R^{7'}$, where each $R^{7'}$ is independently selected from the group consisting of: $C_1$-$C_6$ alkyl and —N($R^6$)$_2$;

m is 0 or 1.

4. The compound or salt of claim 2, wherein K is selected from the group consisting of:

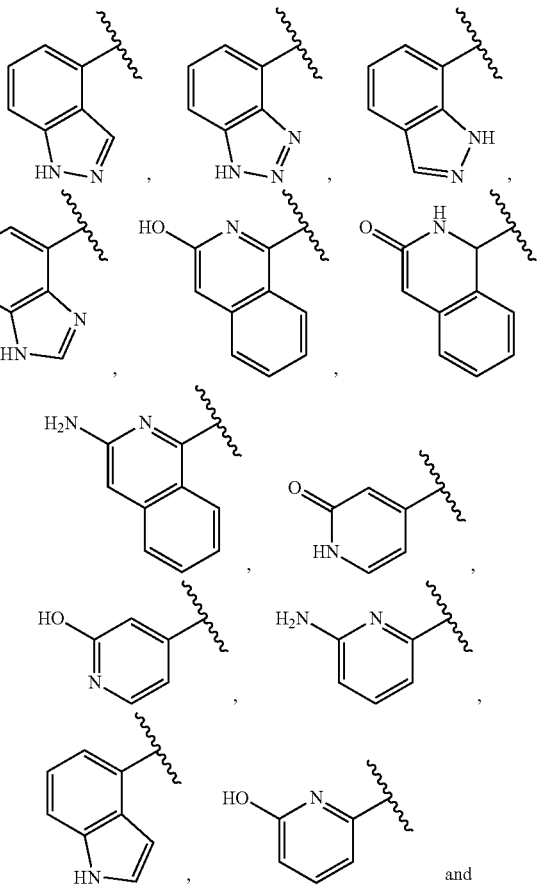

and

-continued

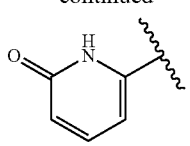

5. The compound or salt of claim 2, wherein K is selected from the group consisting of:

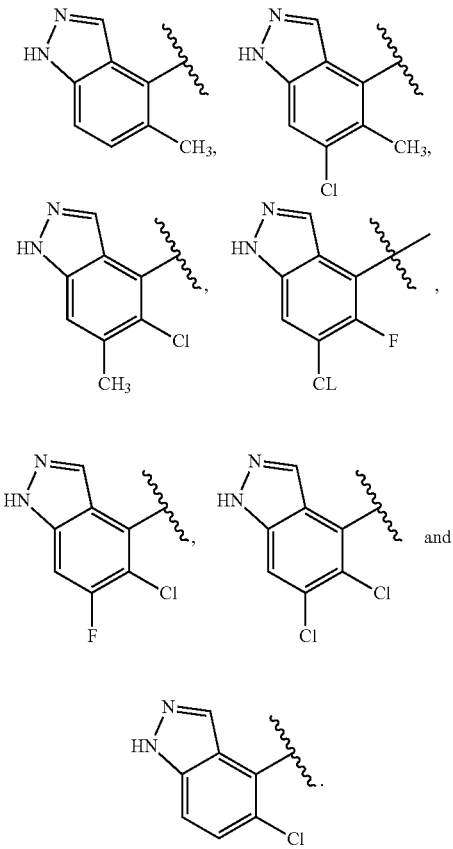

6. The compound or salt of claim 2, wherein K is:

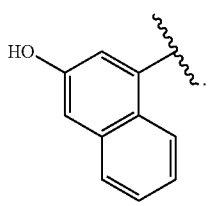 [SMILES: *c1cc(O)cc2ccccc12]

7. The compound or salt of claim 2, wherein W is:

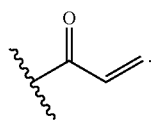 [SMILES: *C(=O)C=C]

8. The compound or salt of claim 2, wherein J is optionally substituted:

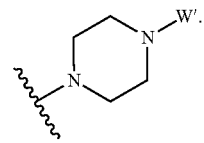

9. The compound or salt of claim 2, wherein J is selected from the group consisting of:

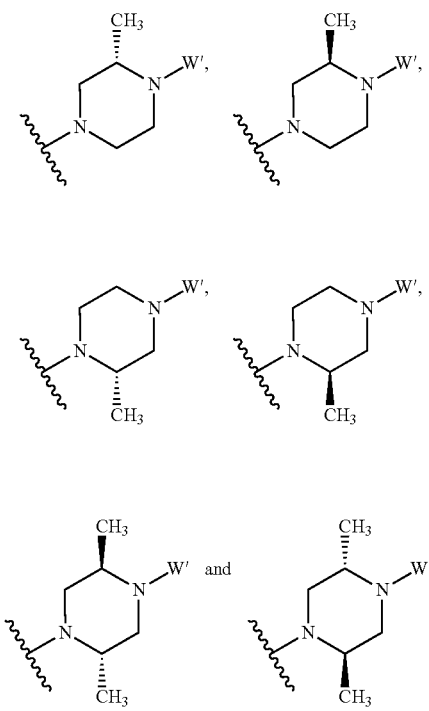

10. The compound or salt of claim 2, wherein $R^4$ is selected from the group consisting of:

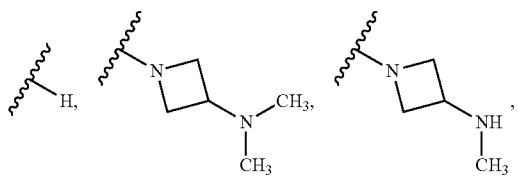

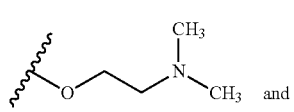

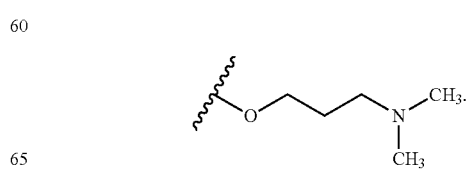

11. A compound selected from the group consisting of:
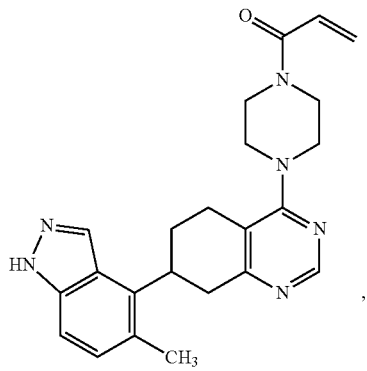
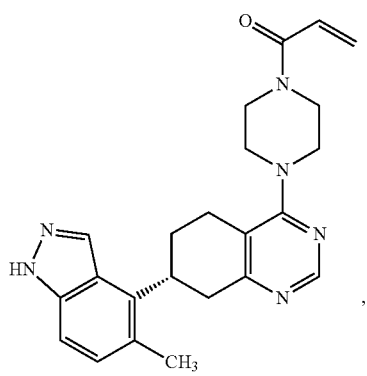
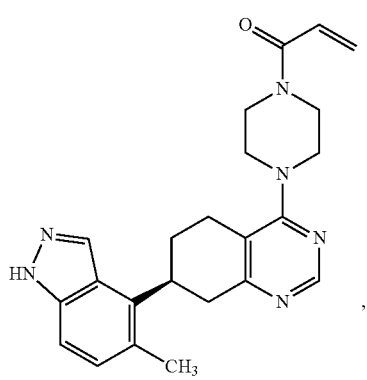
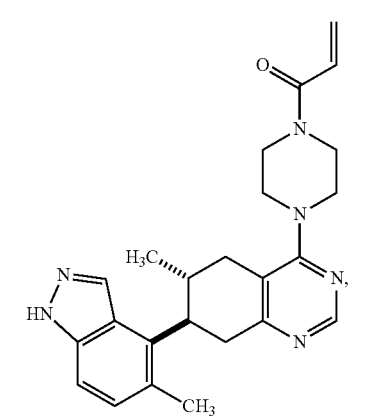
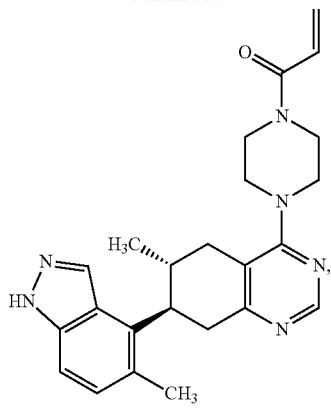
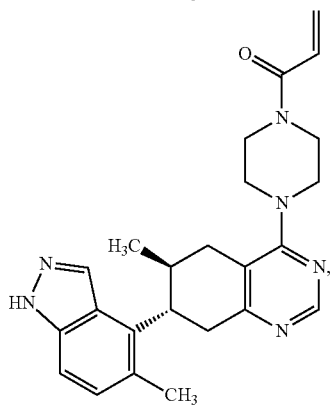
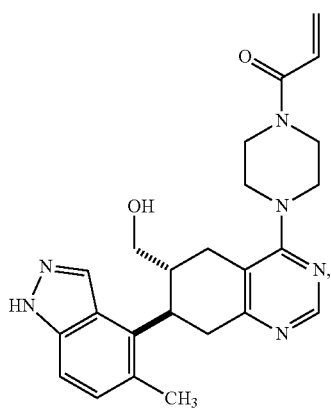
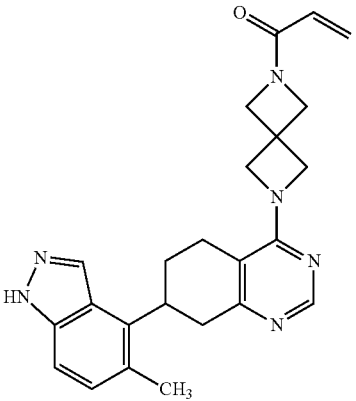

141
-continued
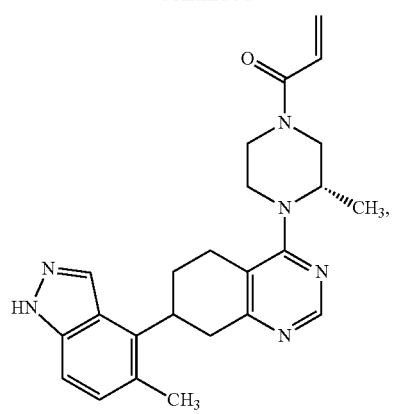
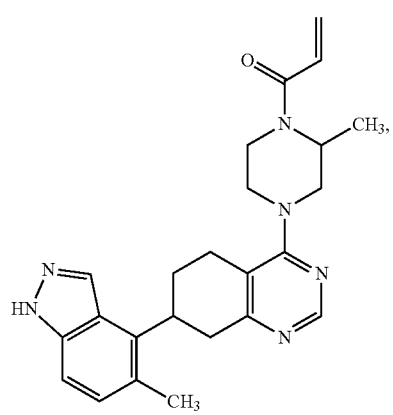
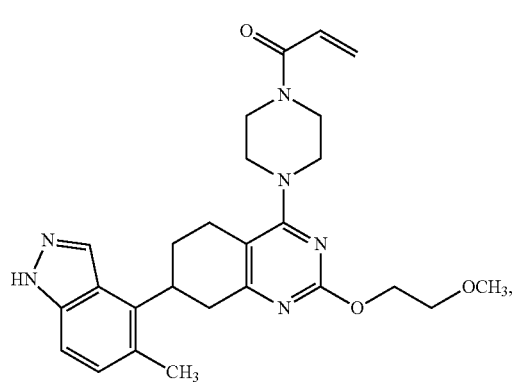
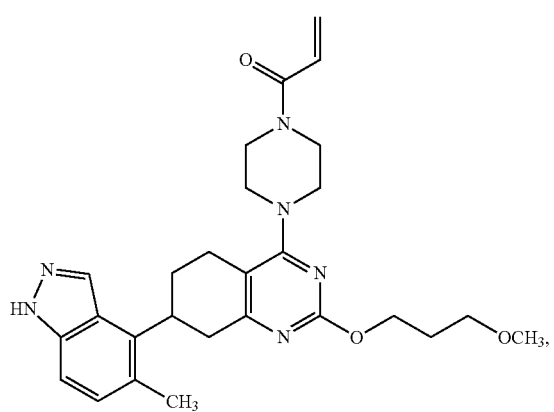
142
-continued
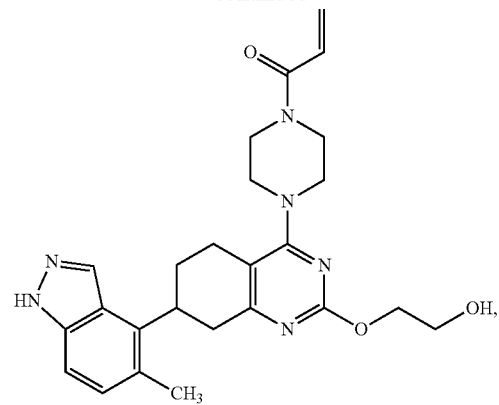
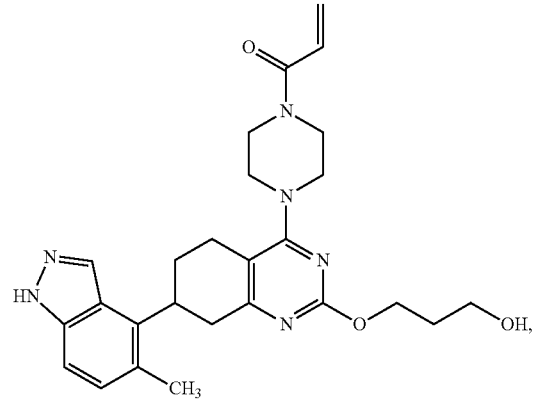
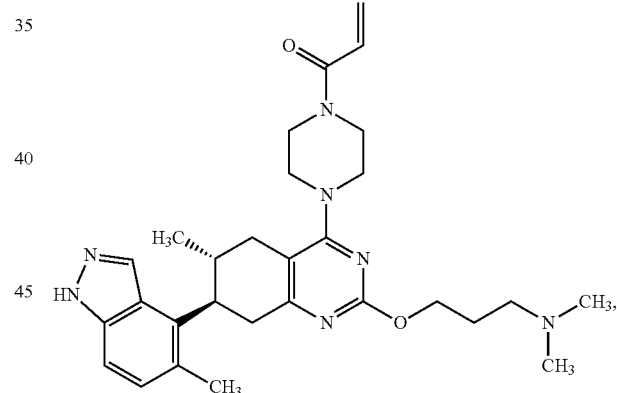
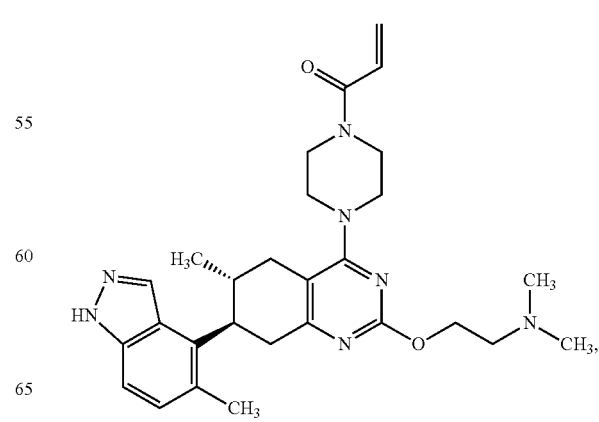

143
-continued
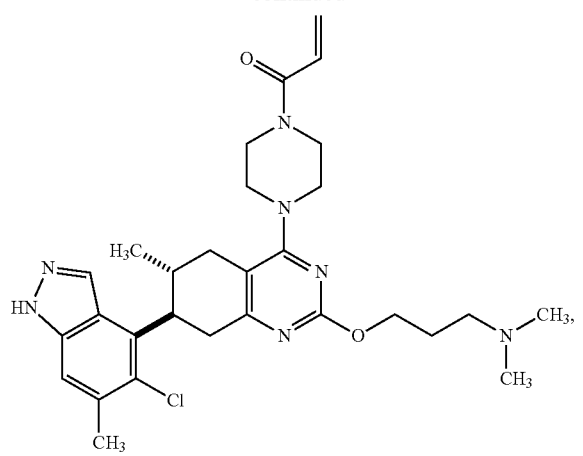
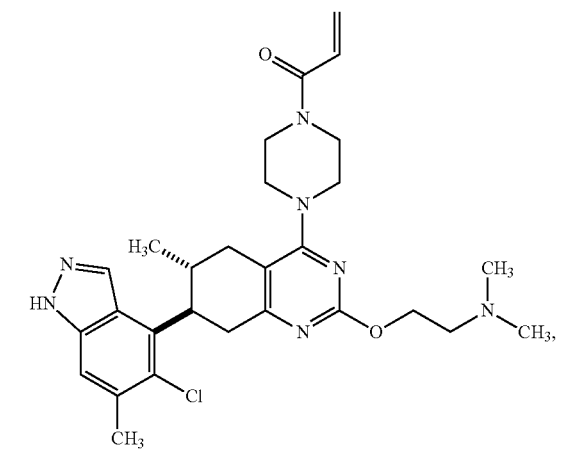
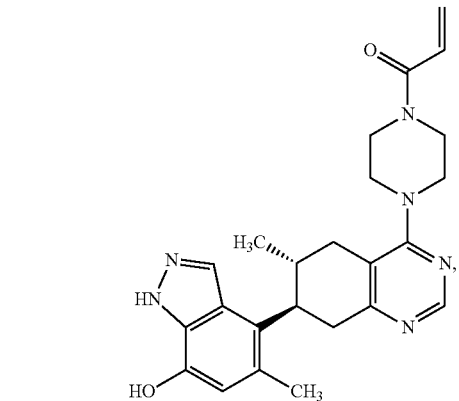
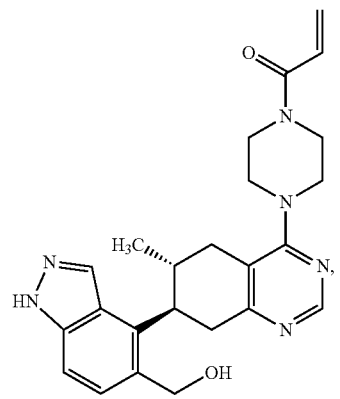
144
-continued
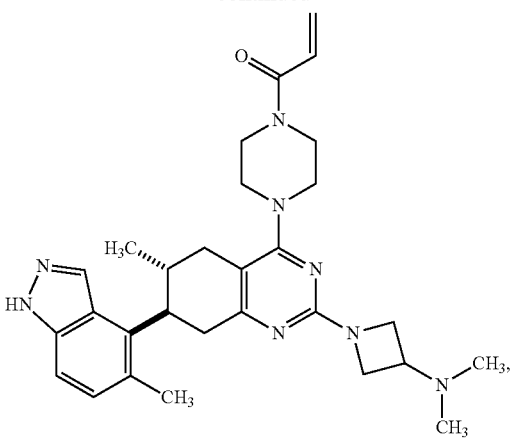
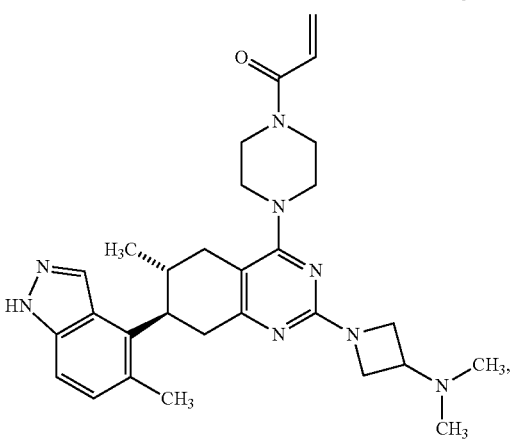
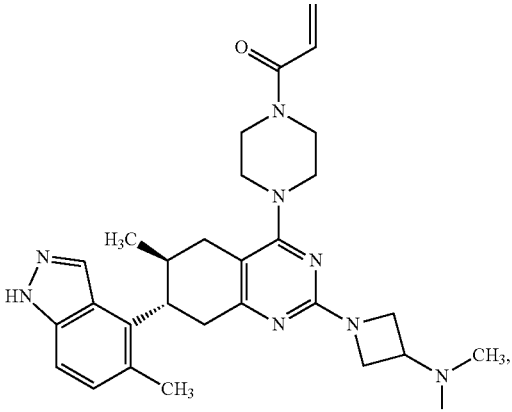
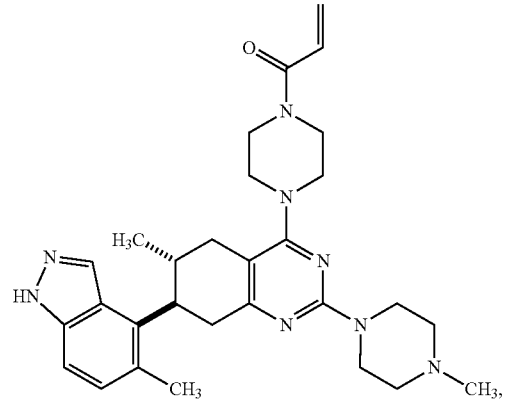

145
-continued
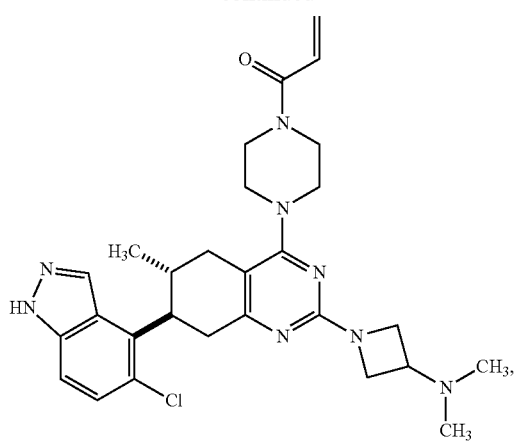
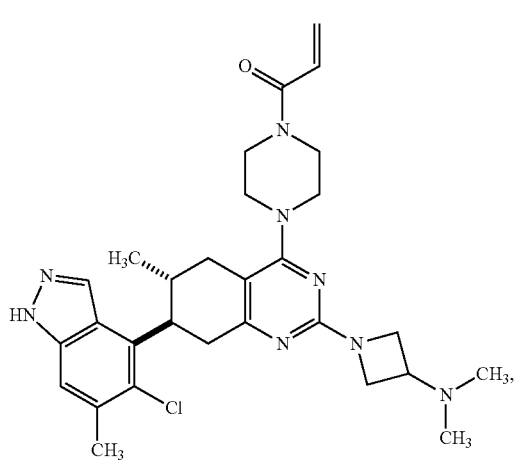
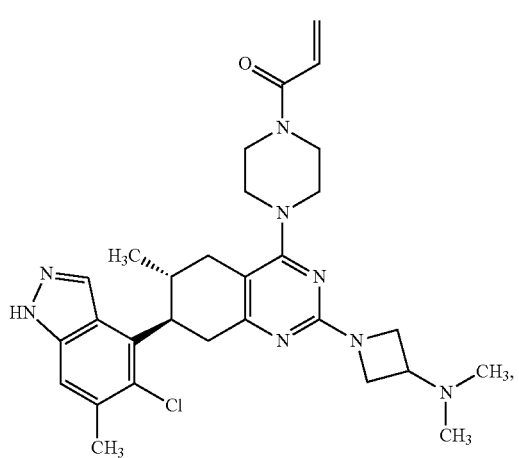
146
-continued
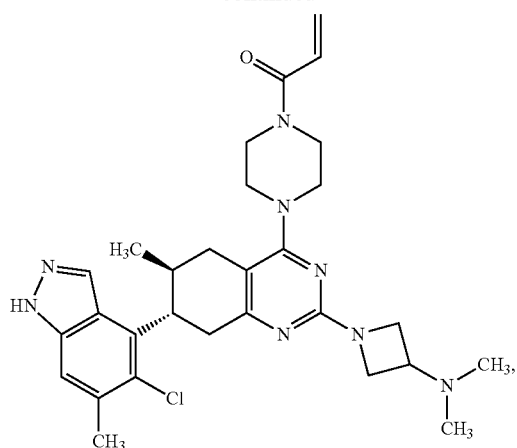
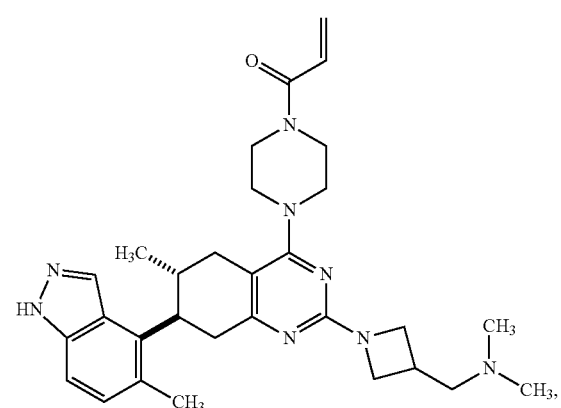
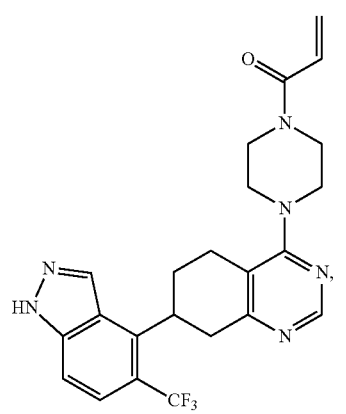
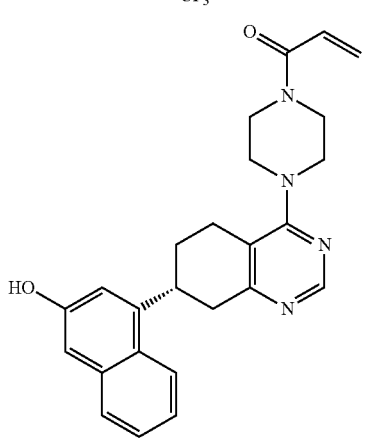

147
-continued
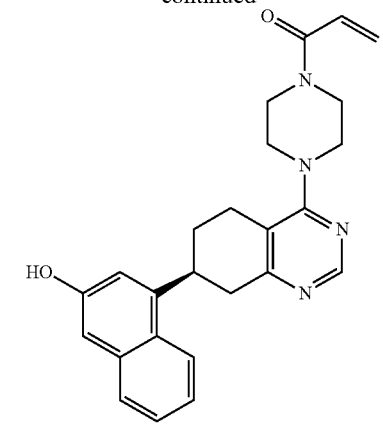
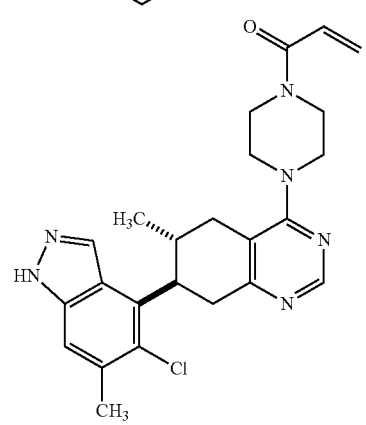
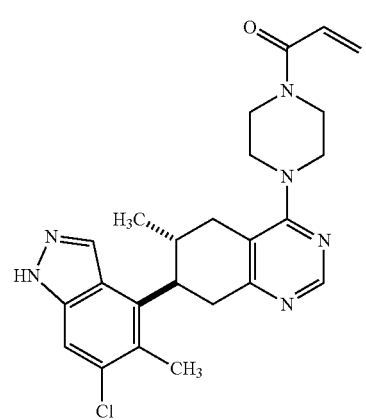
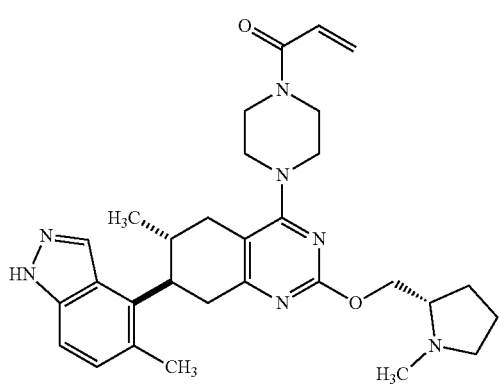
148
-continued
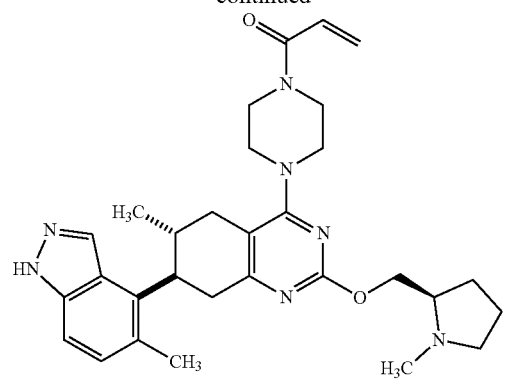
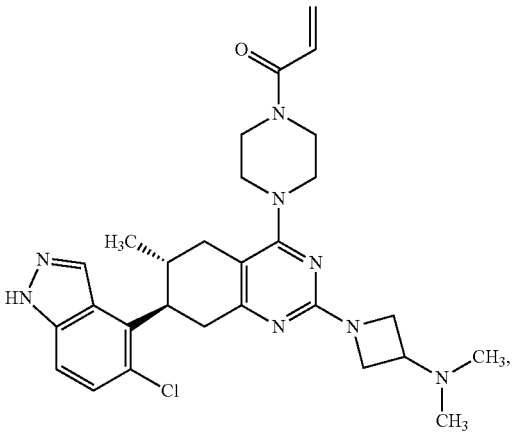
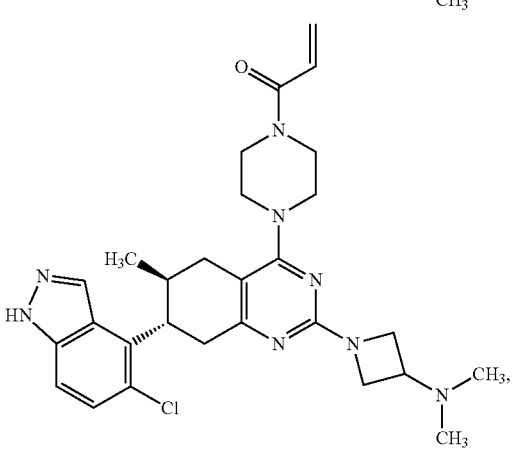
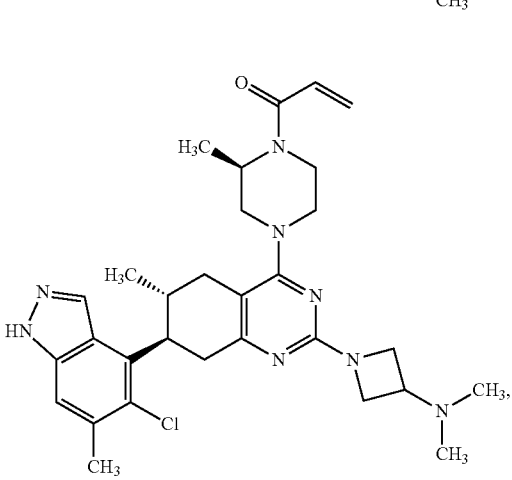

-continued
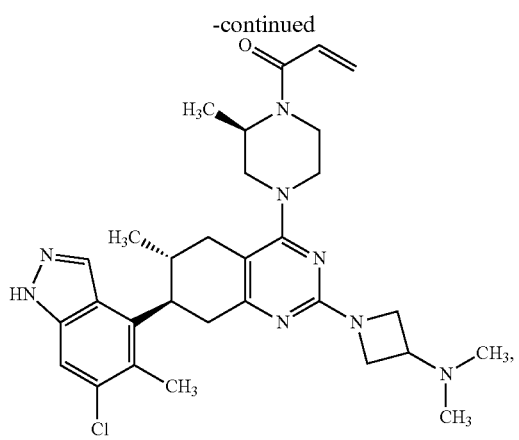
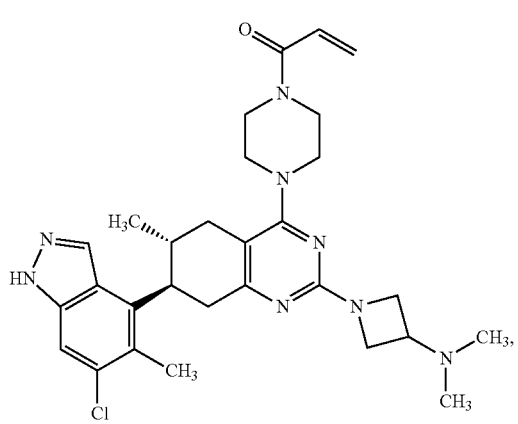
or a pharmaceutically acceptable salt thereof.
12. A compound selected from the group consisting of:
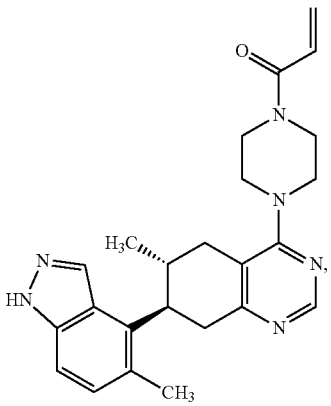
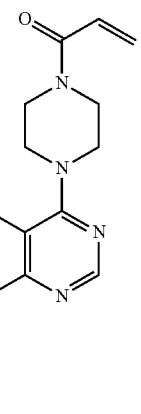
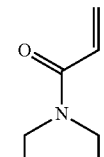
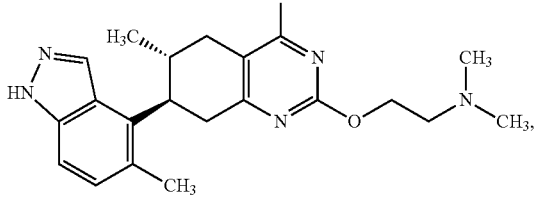

151
-continued
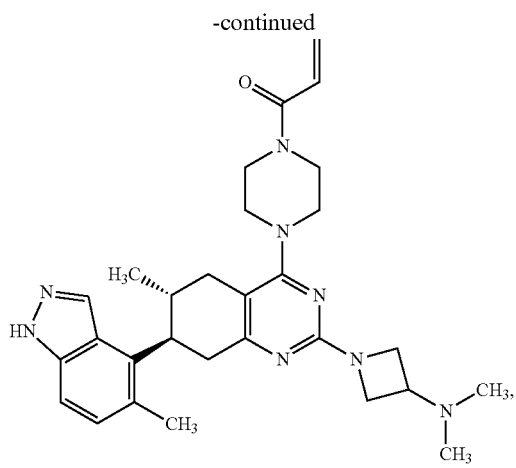
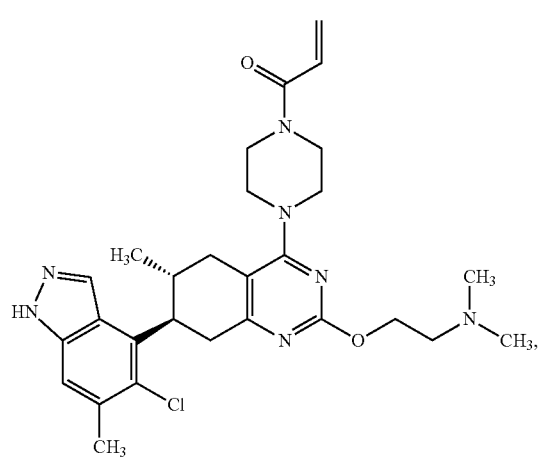
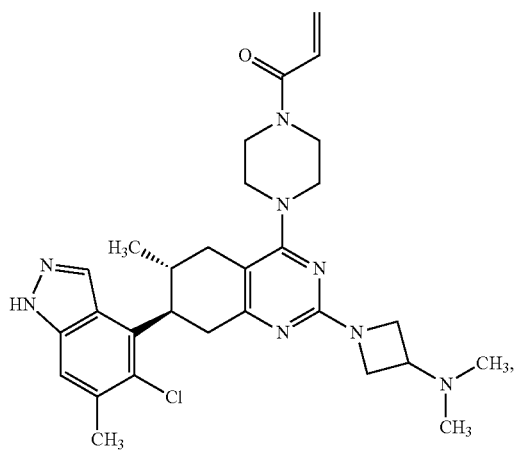
152
-continued
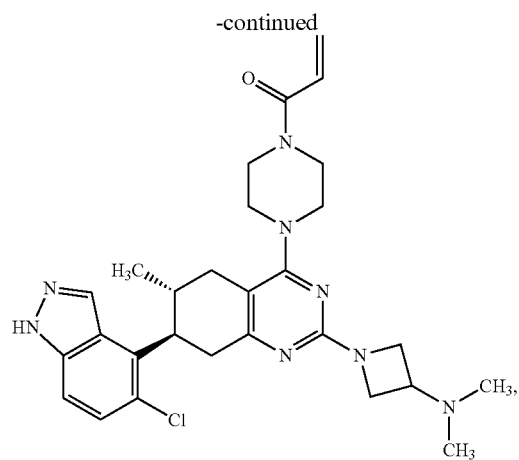
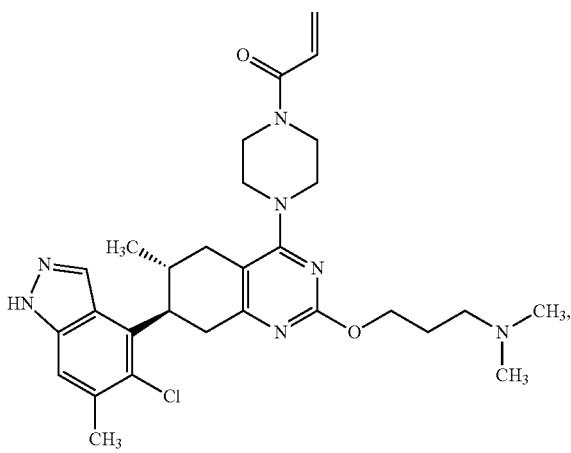
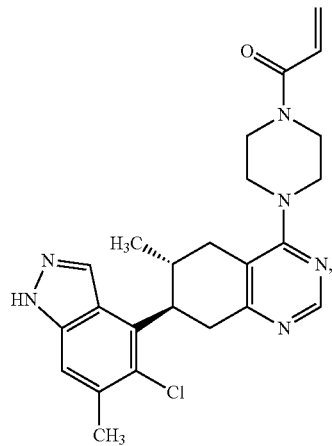

153
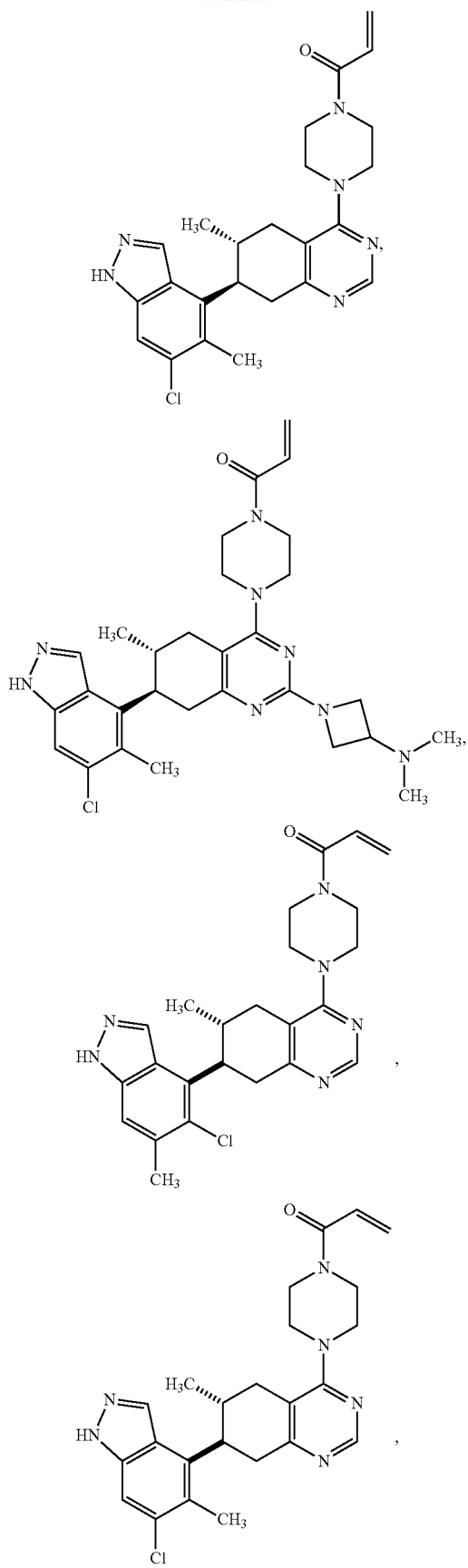
154
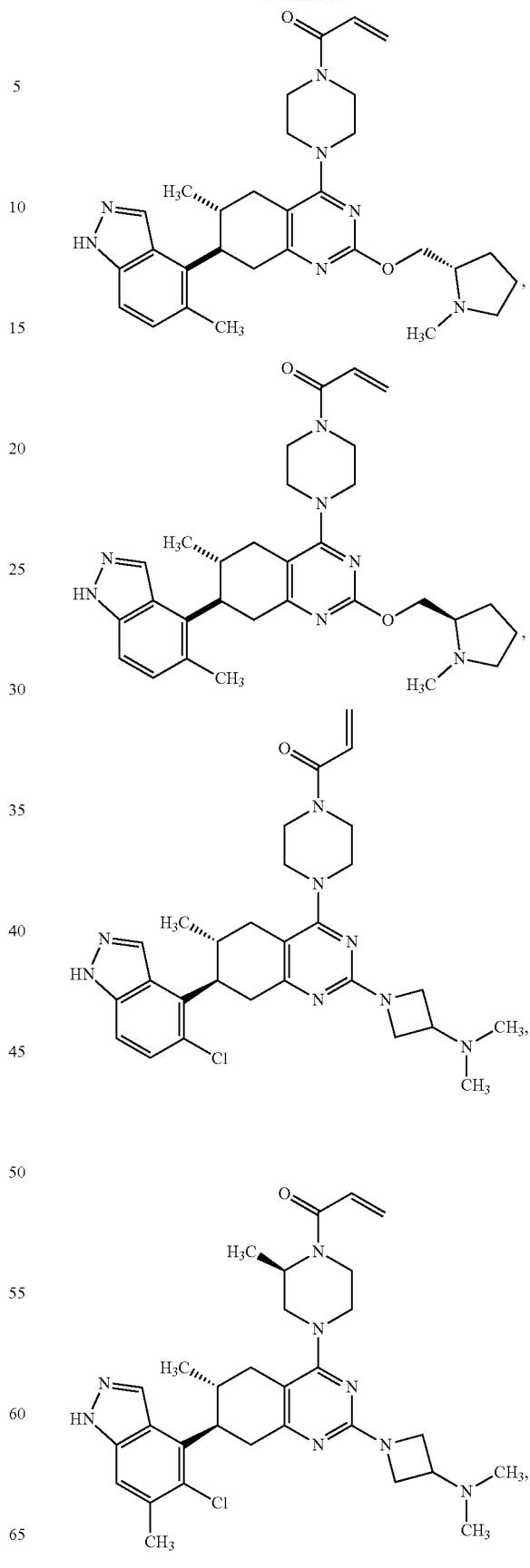

-continued

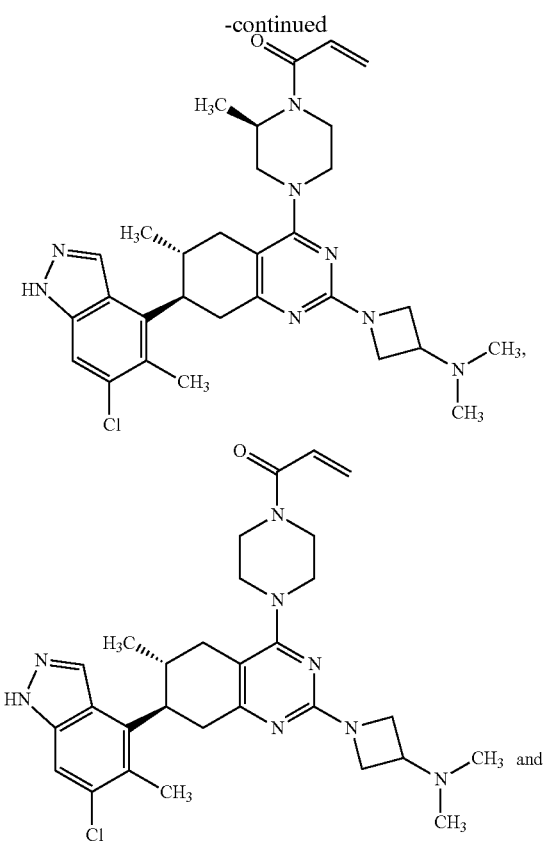

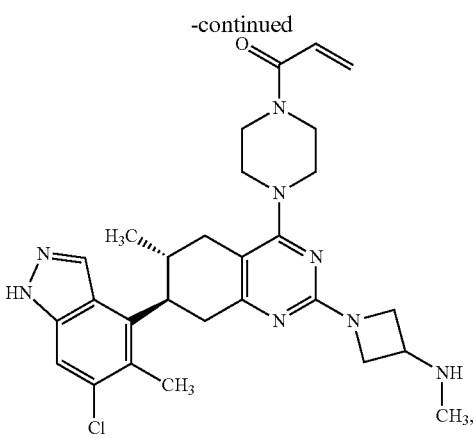

or a pharmaceutically acceptable salt thereof.

13. A compound or pharmaceutically acceptable salt of according to any one of claims 2, 11 and 12, wherein one or more hydrogen atoms are replaced with deuterium atoms.

14. A pharmaceutical composition, comprising a therapeutically effective amount of a compound according to any one of claims 2, 11 and 12 or pharmaceutically acceptable salt thereof, and a pharmaceutically acceptable excipient.

* * * * *